(12) United States Patent
Pedersen et al.

(10) Patent No.: US 11,466,081 B2
(45) Date of Patent: *Oct. 11, 2022

(54) OLIGONUCLEOTIDES FOR REDUCTION OF PD-L1 EXPRESSION

(71) Applicant: HOFFMANN-LA ROCHE INC., Little Falls, NJ (US)

(72) Inventors: Lykke Pedersen, Horsholm (DK); Hassan Javanbakht, Basel (CH); Malene Jackerott, Horsholm (DK); Søren Ottosen, Horsholm (DK); Souphalone Luangsay, Basel (CH)

(73) Assignee: HOFFMANN-LA ROCHE INC., Little Falls, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/000,203

(22) Filed: Aug. 21, 2020

(65) Prior Publication Data

US 2021/0147535 A1 May 20, 2021

Related U.S. Application Data

(63) Continuation of application No. 16/839,025, filed on Apr. 2, 2020, now Pat. No. 10,829,555, which is a continuation of application No. 16/664,749, filed on Oct. 25, 2019, now Pat. No. 10,745,480, which is a continuation of application No. 15/458,800, filed on Mar. 14, 2017, now abandoned.

(30) Foreign Application Priority Data

Mar. 14, 2016 (EP) .................. 16160149

(51) Int. Cl.
| | |
|---|---|
| *C12N 15/11* | (2006.01) |
| *C07K 16/28* | (2006.01) |
| *C12N 15/113* | (2010.01) |
| *A61K 38/17* | (2006.01) |
| *A61K 39/39* | (2006.01) |
| *A61K 39/395* | (2006.01) |
| *A61K 45/06* | (2006.01) |
| *A61K 39/00* | (2006.01) |

(52) U.S. Cl.
CPC .......... *C07K 16/28* (2013.01); *A61K 38/1709* (2013.01); *A61K 39/39* (2013.01); *A61K 39/39558* (2013.01); *C12N 15/1138* (2013.01); *A61K 45/06* (2013.01); *A61K 2039/505* (2013.01); *A61K 2039/55516* (2013.01); *A61K 2039/572* (2013.01); *C07K 2317/70* (2013.01); *C12N 2310/11* (2013.01); *C12N 2310/315* (2013.01); *C12N 2310/3231* (2013.01); *C12N 2310/341* (2013.01); *C12N 2310/346* (2013.01); *C12N 2310/351* (2013.01); *G01N 2800/26* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,587,044 A | 5/1986 | Miller et al. | |
| 4,667,025 A | 5/1987 | Miyoshi et al. | |
| 4,948,882 A | 8/1990 | Ruth | |
| 5,112,963 A | 5/1992 | Pieles et al. | |
| 5,245,022 A | 9/1993 | Weis et al. | |
| 5,254,469 A | 10/1993 | Warren, III et al. | |
| 5,391,723 A | 2/1995 | Priest | |
| 5,486,603 A | 1/1996 | Buhr | |
| 5,510,475 A | 4/1996 | Agrawal et al. | |
| 5,512,667 A | 4/1996 | Reed et al. | |
| 5,525,465 A | 6/1996 | Haralambidis et al. | |
| 5,541,313 A | 7/1996 | Ruth | |
| 5,545,730 A | 8/1996 | Urdea et al. | |
| 5,552,538 A | 9/1996 | Urdea et al. | |
| 5,574,142 A | 11/1996 | Meyer, Jr. et al. | |
| 5,580,731 A | 12/1996 | Chang et al. | |
| 5,608,046 A | 3/1997 | Cook et al. | |
| 5,684,142 A | 11/1997 | Mishra et al. | |
| 5,770,716 A | 6/1998 | Khan et al. | |
| 5,885,968 A | 3/1999 | Biessen et al. | |
| 5,994,517 A | 11/1999 | Ts'o et al. | |
| 6,096,875 A | 8/2000 | Khan et al. | |

(Continued)

FOREIGN PATENT DOCUMENTS

| | | |
|---|---|---|
| CN | 101084438 A | 12/2007 |
| CN | 104955952 A | 9/2015 |

(Continued)

OTHER PUBLICATIONS

Berge et al, Pharmaceutical Salts, Journal of Pharmaceutical Sciences, 1977, vol. 66, No. 1, pp. 1-19 (Year: 1977).*

(Continued)

*Primary Examiner* — Ekaterina Poliakova-Georgantas
(74) *Attorney, Agent, or Firm* — Holland & Hart LLP

(57) ABSTRACT

The present invention relates to antisense oligonucleotides that are capable of reducing expression of PD-L1 in a target cell. The oligonucleotides hybridize to PD-L1 mRNA. The present invention further relates to conjugates of the oligonucleotide and pharmaceutical compositions and methods for treatment of viral liver infections such as HBV, HCV and HDV; parasite infections such as malaria, toxoplasmosis, leishmaniasis and trypanosomiasis or liver cancer or metastases in the liver using the oligonucleotide.

22 Claims, 17 Drawing Sheets

Specification includes a Sequence Listing.

(56) References Cited

U.S. PATENT DOCUMENTS

| | | |
|---|---|---|
| 6,335,432 B1 | 1/2002 | Segev |
| 6,335,437 B1 | 1/2002 | Manoharan |
| 8,507,663 B2 | 8/2013 | Defougerolles et al. |
| 10,745,480 B2 | 8/2020 | Pedersen et al. |
| 10,829,555 B2 | 11/2020 | Pedersen et al. |
| 10,982,215 B2 | 4/2021 | Hinkle |
| 2002/0147332 A1 | 10/2002 | Kaneko et al. |
| 2007/0083334 A1 | 4/2007 | Mintz et al. |
| 2011/0251259 A1 | 10/2011 | Defougerolles |
| 2012/0122801 A1 | 5/2012 | Platenburg |
| 2014/0288153 A1 | 9/2014 | Collard et al. |
| 2015/0197540 A1 | 7/2015 | Shimizu |
| 2015/0232836 A1 | 8/2015 | Krieg et al. |
| 2017/0283496 A1 | 10/2017 | Pedersen et al. |

FOREIGN PATENT DOCUMENTS

| | | |
|---|---|---|
| EP | 1495769 A1 | 1/2005 |
| EP | 1537878 A1 | 6/2005 |
| EP | 2361921 A2 | 8/2011 |
| EP | 2734208 B1 | 1/2017 |
| EP | 3377510 B1 | 2/2020 |
| EP | 3430141 B1 | 3/2020 |
| JP | 2014210793 A | 11/2014 |
| RU | 2123528 C1 | 12/1998 |
| WO | 1993007883 A1 | 4/1993 |
| WO | 1996011205 A1 | 4/1996 |
| WO | 1998039352 A1 | 9/1998 |
| WO | 1998052614 A2 | 11/1998 |
| WO | 1999014226 A2 | 3/1999 |
| WO | 1999065925 A1 | 12/1999 |
| WO | 2000047599 A1 | 8/2000 |
| WO | 2000066604 A2 | 11/2000 |
| WO | 2001023613 A1 | 4/2001 |
| WO | 2004046160 A2 | 6/2004 |
| WO | 2005007855 A2 | 1/2005 |
| WO | 2005014806 A2 | 2/2005 |
| WO | 2006042237 A2 | 4/2006 |
| WO | 2007031091 A2 | 3/2007 |
| WO | 2007084865 A2 | 7/2007 |
| WO | 2007090071 A2 | 8/2007 |
| WO | 2007134181 A2 | 11/2007 |
| WO | 2007146511 A2 | 12/2007 |
| WO | 2008113832 A2 | 9/2008 |
| WO | 2008150729 A2 | 12/2008 |
| WO | 2008154401 A2 | 12/2008 |
| WO | 2009006478 A2 | 1/2009 |
| WO | 2009067647 A1 | 5/2009 |
| WO | 2009090182 A1 | 7/2009 |
| WO | 2009124238 A1 | 10/2009 |
| WO | 2009126933 A2 | 10/2009 |
| WO | 2010036698 A1 | 4/2010 |
| WO | 2010077578 A1 | 7/2010 |
| WO | 2010129799 A1 | 11/2010 |
| WO | 2011017521 A4 | 2/2011 |
| WO | 2011127180 A1 | 10/2011 |
| WO | 2011156202 A1 | 12/2011 |
| WO | 2012024170 A2 | 2/2012 |
| WO | 2012055362 A1 | 5/2012 |
| WO | 2012083046 A2 | 6/2012 |
| WO | 2012089352 A1 | 7/2012 |
| WO | 2012145697 A1 | 10/2012 |
| WO | 2013003520 A1 | 1/2013 |
| WO | 2013012758 A1 | 1/2013 |
| WO | 2013033230 A1 | 3/2013 |
| WO | 2013036868 A1 | 3/2013 |
| WO | 2013049307 A2 | 4/2013 |
| WO | 2013154798 A1 | 10/2013 |
| WO | 2013159109 A1 | 10/2013 |
| WO | WO-2013173598 A1 * | 11/2013 ............ C07H 21/04 |
| WO | 2014076195 A1 | 5/2014 |
| WO | 2014076196 A1 | 5/2014 |
| WO | 2014083178 A1 | 6/2014 |
| WO | 2014118267 A1 | 8/2014 |
| WO | 2014118272 A1 | 8/2014 |
| WO | 2014179620 A1 | 11/2014 |
| WO | 2014179629 A1 | 11/2014 |
| WO | 2014207232 A1 | 12/2014 |
| WO | 2015114146 | 8/2015 |
| WO | 2016025647 A1 | 2/2016 |
| WO | 2016055601 A1 | 4/2016 |
| WO | 2016138278 A2 | 9/2016 |
| WO | 2016/180784 A1 | 11/2016 |
| WO | 2017055423 A1 | 4/2017 |
| WO | 2017084987 A1 | 5/2017 |
| WO | 2017100587 A1 | 6/2017 |

OTHER PUBLICATIONS

Rehermann et al., "The Cytotoxic T Lymphocyte Response to Multiple Hepatitis B Virus Polymerase Epitopes During and After Acute Viral Hepatitis," Journal of Experimental Medicine, 1995, 181(3), pp. 1047-1058, 12 pages.

Rukov, JL et al., "Dissecting the target specificity of RNase H recruiting oligonucleotides using massively parallel reporter analysis of short RNA motifs," Nucl. Acids Res, 2015, 43(17), pp. 8476-8487, 12 pages.

Salem et al., "Programmed death-1/programmed death-L1 signaling pathway and its blockade in hepatitis C virus immunotherapy," World J Hepatol, 2015, 7(23), pp. 2449-2458, 11 pages.

Santa Lucia, JJr., "A unified view of polymer, dumbbell, and oligonucleotide DNA nearest-neighborthermodynamics," Proc Natl Acad Sci USA, 1998, 95(4), pp. 1460-1465, 6 pages.

Seth, PP et al., "Synthesis and Biophysical Evaluation of 2',4'-Constrained 2'O-Methoxyethyl and 2',4'-Constrained 2' O-Ethyl Nucleic Acid Analogues," J. Org. Chem., 2010, vol. 75, No. 5, pp. 1569-1581, 7 pages.

Sette, A et al., "The Relationship Between Class I Binding Affinity and Immunogenicity of Potential Cytotoxic T Cell Epitopes," Journal of Immunology, 1994, pp. 5586-5592, 7 pages.

Sugimoto, N et al., "Thermodynamic Parameters to Predict Stability of RNA/DNA Hybrid Duplexes," Biochemistry, 1995, vol. 34(35), pp. 11211-11216, 6 pages.

Tupin E et al., "Activation of Natural Killer T Cells by Glycolipids," Methods in Enzymol., 2006, vol. 417, pp. 185-201, 17 pages.

Uhlmann E, "Recent advances in the medicinal chemistry of antisense olignonucleotides," Current Opinion in Drug Development, 2000, vol. 3(2), pp. 203-213, 12 pages.

Vester B et al., "Chemically modified oligonucleotides with efficient RNase H response," Bioorganic & Medicinal Chemistry Letters, 2008, vol. 18, pp. 2296-2300, 5 pages.

Wykes MN et al., "Malaria drives T cells to exhaustion," Frontiers in Microbiology, 2014, vol. 5, article 249, pp. 1-5, 5 pages.

Xu, Y et al., "Effective small interfering RNAs and phosphorothioate antisense DNAs have different preferences for target sites in the luciferase mRNAs," Biochem. Biophys. Res. Comm., 2003, 306(3), pp. 712-717 6 pages.

Yang, N et al., "HPMA Polymer-Based Site-Specific Delivery of Oligonucleotides to Hepatic Stellate Cells," Bioconjug Chem, 2009, 20(2), pp. 213-221, 9 pages.

Yang, D et al., "A mouse model for HBV immunotolerance and immunotherapy," Cellular & Molecular Immunology, 2014, 11(1), pp. 71-78, 8 pages.

Yi, JS et al., "T-cell exhaustion: characteristics, causes and conversion," Immunology, 2010, 129(4), pp. 474-481, 8 pages.

Yu, RZ et al., "Disposition and Pharmacology of a GalNAc3-conjugated ASO Targeting Human Lipoprotein (a) in Mice," Molecular Therapy—Nucleic Acids, 2016, vol. 5, e317, pp. 1-10, 10 pages.

Zatsepin et al., "Synthesis and Applications of Oligonucleotide-Carbohydrate Conjugates," Chemistry and Biodiversity, 2004, 1(10), pp. 1401-1417, 17 pages.

Dull, RJ et al., "Intrabody Tissue-Specific Delivery of Antisense Conjugates in Animals: Ligand-Linker-Antisense Oligomer Conjugates," Methods Enzymol, 2000, 313, pp. 297-321, 25 pages.

Krieg, AM et al., "Uptake of Oligodeoxyribonucleotides by Lymphoid Cells is Heterogeneous and Inducible," Antisense Research and Development, 1991, vol. 1, pp. 161-171, 11 pages.

(56) References Cited

OTHER PUBLICATIONS

Manoharan, M., "Oligonucleotide Conjugates as Potential Antisense Drugs with Improved Uptake, Biodistribution, Targeted Delivery, and Mechanism of Action," Antisense and Nucleic Acid Drug Development, 2004, 12(2), pp. 103-128, 26 pages.
International Search Report and Written Opinion for International Application No. PCT/EP2017/055925, dated Jun. 8, 2017, 12 pages.
Biessen et al., "Targeted delivery of oligodeoxynucleotides to parenchymal liver cells in vivo," Biochem J., 1999, vol. 340, pp. 783-792, 10 pages.
Asseline et al., "Nucleic acid-binding molecules with high affinity and base sequence specificity: Intercalating agents covalently linked to oligodeoxynucleotides," Proc Natl Acad. Sci USA, 1984, 81, pp. 3297-3301, 5 pages.
Barber et al., "Restoring function in exhausted CD8 T cells during chronic viral infection," Nature, 2006,439, pp. 682-687, 6 pages.
Bergstrom DE, "Unnatural Nucleosides with Unusual Base Pairing Properties," Current Protocols in Nucleic Acid Chemistry, 2001, Suppl. 5, pp. 1.4.1-1.4.13, 13 pages.
Bertoletti et al., "Different Cytokine Profiles of Intrahepatic T Cells in Chronic Hepatitis B and Hepatitis C Virus Infections," Gastroenterology, 1997, 112(1), pp. 193-199, 7 pages.
Bhadra et al., "Control of Toxoplasma reactivation by rescue of dysfunctional CD8+ T-cell response via PD-1-PDL-1 blockade," Proc Natl Acad Sci USA, 2011, vol. 108, No. 22, pp. 9196-9201, 6 pages.
Bhadra R et al., "PD-1-Mediated Attrition of Polyfunctional Memory CD8+ T Cells in Chronic Toxoplasma Infection," J Infect Dis, 2012, vol. 206, pp. 125-134, 125 pages.
Biessen et al., "Synthesis of Cluster Galactosides with High Affinity for the Hepatic Asialoglycoprotein Receptor," J. Med. Chem., 1995, vol. 38, pp. 1538-1546, 9 pages.
Breton et al., "siRNA knockdown of PD-L1 and PD-L2 in monocyte-derived dendritic cells only modestly improves proliferative responses to Gag by CD8(+) T cells from HIV-1-infected individuals.", J Clin Immunol, (Sep. 2009), vol. 29, No. 5, pp. 637-645.
Glen Research Catalogue No. 10-1920-xx downloaded Mar. 21, 2018, 2 pgs.
Glen Research Catalogue No. 10-1922-xx downloaded Mar. 21, 2018, 2 pgs.
Glen Research Catalogue No. 10-1925-xx downloaded Mar. 21, 2018, 2 pgs.
Official Letter issued in Colombia Patent Application No. NC2020/0010348 dated May 3, 2021, 7 pgs.
Notice of Allowance issued in Korean Patent Application No. 10-2018-7026546, dated Jun. 20, 2021, 3 pgs.
Chilean Patent Application No. 201802570, abstract, 3 pages.
European Patent Application No. 15194811.4 filed Nov. 16, 2015, 44 pgs.
Office Action issued in Russian Patent Application No. 2018134379, dated Jun. 23, 2020, 6 pgs.
Inquiry under Substantive Examination issued in Russian Patent Application No. 2018134379, dated Jun. 22, 2020, 8 pgs.
Office Action issued in Argentine Patent Application No. 20170100626 dated Oct. 7, 2020, 5 pgs.
Office Action issued in Chilean Patent Application No. 201802570 dated Sep. 24, 2020, 23 pgs.
Specification and Claims of Chilean Patent Application No. 202001127, filed Apr. 28, 2020, 684 pgs.
Specification and Claims of Chilean Patent Application No. 202001126, filed Apr. 28, 2020, 685 pgs.
Chilean Patent Application No. 20200865 filed Mar. 31, 2020, 685 pgs.
Claims of Chilean Patent Application No. 20200865, filed Jun. 10, 2020, 5 pgs.
Biessen, Eal et al., "Receptro-Dependent Cell Specific Delivery of Antisense Oligonucleotides," Developments in Cardiovascular Medicine, 1999, vol. 24, pp. 285-299, 15 pages.
Caruthers, MH et al., "Chemical Synthesis of Deoxyoligonucleotides by the Phosphoramidite Method," Methods in Enzymology, 1987, vol. 154:15, pp. 287-313, 27 pages.
Deleavey, GE et al., "Designing Chemically Modified Oligonucleotides for Targeted Gene Silencing," Chemistry and Biology, 2012, vol. 19(8), pp. 937-954, 18 pages.
Dion et al., "Adeno-Associated Virus-Mediated Gene Transfer Leads to Persistent Hepatitis B Virus Replication in Mice Expressing HLA-A2 and HLA-DRI Molecules," Journal of Virology, 2013, vol. 87, No. 10, pp. 5554-5563, 10 pages.
Dolina et al., "Lipidoid Nanoparticles Containing PD-LI siRNA Delivered In Vivo Enter Kupffer Cells and Enhance NK and CD8+T Cell-mediated Hepatic Antiviral Immunity," Molecular Therapy-Nucleic Acids, 2013, 2:e72, pp. 1-14, 14 pages.
Esch, KJ et al., "Programmed Death 1-Mediated T Cell Exhaustion during Visceral Leishmaniasis Impairs Phagocyte Function," Journal of Immunology, 2013, 191, pp. 5542-5550, 10 pages.
Fluiter, K et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Molecular Biosystems, 2009, vol. 5, issue 8, pp. 838-843, 6 pages.
Freeman et al., "A new therapeutic strategy for malaria: targeting T cell exhaustion," Nature Immunology, 2012, vol. 13(2), pp. 113-115, 3 pages.
Freier et al., "The ups and downs of nucleic acid duplex stability: structure-stability studies on chemically-modified DNA:RNA duplexes," Nucleic Acids Ressearch, 1997, vol. 25(22), pp. 4429-4443, 15 pages.
GenBank Accession No. XM_005581779.2, "Predicted: Macaca fascicularis CD274 molecule (CD274), transcript variant XI, mRNA," Sep. 19, 2013, 2 pages.
GenBank Accession No. NM_021893.3, "Mus musculus CD274 antigen (Cd274), mRNA," Feb. 15, 2015, 5 pages.
GenBankAccession No. NM_014143.4, "*Homo sapiens* CD274 molecule (CD274), transcript variant 1, mRNA," Mar. 15, 2015, 5 pages.
Gennaro, AR et al., "Remington's Pharmaceutical Sciences," Mack Publishing Company, 17th ed., 1985, 9 pages.
Gutierrez, FRS et al., "Regulation of Trypanosoma cruzi-lnduced Myocarditis by Programmed Death Cell Receptor 1," Infection and Immunity, 2011, 79(5), pp. 1873-1881, 9 pages.
Hangeland, JJ et al., "Cell-Type Specific and Ligand Specific Enhancement of Cellular Uptake of Oligodeoxynucleoside Methylphosphonates Covalently Linked with a Neoglycopeptide, YEE(ah-GalNAc)3," Bioconjugate Chem., 1995, 6(6), pp. 95-701, 7 pages.
Hansen, LD et al., Entropy Titration. A Calorimetric Method for the Determination of $\Delta G°(K)$, $\Delta H°$ and $\Delta S°$, Chemical Communications, 1965, pp. 36-38, 3 pages.
Hirao, I et al., "Natural versus Arlilicial Creation of Base Pairs in DNA: Origin of Nucleobases from the Perspectives of Unnatural Base Pair Studies," Accounts of Chemical Research, 2012, vol. 45, No. 12, pp. 2055-2065, 11 pages.
Holdgate, GA et al., "Measurements of binding thermodynamics in drug discovery," Drug Discovery Today, 2005, vol. 10, No. 22, pp. 1543-1550, 8 pages.
Jobst, ST et al., "Selective Sugar Binding to the Carbohydrate Recognition Domains of the Rat Hepatic and Macrophage Asialoglycoprotein Receptors," Journal of Biological Chemistry, 1996, 271(12), pp. 6686-6693, 9 pages.
Joshi, T et al., "B7-HI Blockade Increases Survival of Dysfunctional CD8+ T Cells and Confers Protection against Leishmania donovani Infections," PLoS Pathogens, 2009, 5(5), e1000431, pp. 1-14, 14 pages.
Kapoor, R et al., "Strategies to eliminate HBV infection," Future Virology, 2014, 9(6), pp. 565-585, 21 pages.
Langer, R, "New Methods of Drug Delivery," Science, 1990, vol. 249, pp. 1527-1533, 7 pages.
Liang, S et al., "PD-LI and PD-L2 have distinct roles in regulating host immunity to cutaneous leishmaniasis," Eur J Immunol, 2006, 36(1), pp. 58-64, 7 pages.

(56) References Cited

OTHER PUBLICATIONS

Loirat, D et al., "Multiepitopic HLA-A*0201-Restricted Immune Response Against Hepatitis B Surface Antigen After DNA-Based Immunization," Journal of Immunology, 2000, 165(8), pp. 4748-4755, 9 pages.
Maier al., "Synthesis of Antisense Oligonucleotides Conjugated to a Multivalent Carbohydrate Cluster for Cellular Targeting," Bioconjug Chem, 2003, 14, pp. 18-29, 13 pages.
Maier, H et al., "PD-1:PD-L1 Interactions Contribute to the Functional Suppression of Virus-Specific CD8+ T Lymphocytes in the Liver," J. Immunol., 2007, 178(5), pp. 2714-2720, 8 pages.
Mangos, MM et al., "Efficient RNase H-Directed Cleavage of RNA Promoted by Antisense DNA or 2'F-ANA Constructs Containing Acyclic Nucleotide Inserts," J. Am. Chem. Soc., 2003, 125(3), pp. 654-661, 8 pages.
Manoharan, M., "Designer Antisense Oligonucleotides: Conjugation Chemistry and Functionality Placement," CRC Press, Inc., 1993, Ch. 17, pp. 303-350, 49 pages.
Manoharan, M., "Oligonucleotide Conjugates in Antisense Technology," Antisense Drug Technology, Marcel Dekker, Inc , 2001, Ch. 16, pp. 391-469, 81 pages.
Matsuda, S et al., siRNA Conjugates Carring Sequentially Assembled Trivalent N-Acetylgalactosamine Linked Through Nucleosides Elicit Robust Gene Silencing In Vivo in Hepatocytes, ACS Chem Biol 2015, vol. 10, No. 5, pp. 1181-1187, 7 pages.
McTigue, PM et al., "Sequence-Dependent Thermodynamic Parameters for Locked Nucleic Acid (LNA)—DNA Duplex Formation," Biochemistry, 2004, vol. 43(18), pp. 5388-5405, 18 pages.
Mergny, JL et al., "Analysis of Thermal Melting Curves," Oligonucleotides, 2003, vol. 13, pp. 515-537, 23 pages.
Michel, ML et al., "DNA-mediated immunization to the hepatitis B surface antigen in mice: aspects of the humoral response mimic hepatitis B viral infection in humans," Proc Natl Acad Sci USA, 1995, vol. 92, pp. 5307-5311, 5 pages.
Mitsuoka, Y et al., "A bridged nucleic acid, 2',4'-BNA COC: synthesis of fully modified oligonucleotides bearing thymine, 5-methylcytosine, adenine and guanine 2',4'-BNA COC monomers and RNA-selective nucleic-acid recognition," Nucleic Acids Research, 2009, 37(4), pp. 1225-1238, 14 pages.
Mizukoshi et al., "Cellular Immune Responses to the Hepatitis B Virus Polymerase," Journal of Immunology, 2004, 173, pp. 5863-5871, 10 pages.
Morita K et al.,"2'-O,4'-C-Ethylene-Bridged Nucleic Acids (ENA): Highly Nuclease-Resistant and Thermodynamically Stable Oligonucleotides for Antisense Drug," Bioorganic & Medicinal Chemistry Letters, 2002, vol. 12, pp. 73-76, 4 pages.
Nayersina R et al., "HLA A2 restricted cytotoxic T lymphocyte responses to multiple hepatitis B surface antigen epitopes during hepatitis B virus infection," Journal of Immunology, (1993), vol. 150(10), pp. 4659-4671, 14 pages.
Pajot A et al., "A mouse model of human adaptive immune functions: HLA-A2.1-/HLA-DR1-transgenic H-2 class I-/class II-knockout mice," Eur Journal of Immunology, 2004, vol. 34, pp. 3060-3069, 10 pages.
Pajot, A et al., "Identification of novel HLA-DRl-restricted epitopes from the hepatitis B virus envelope protein in mice expressing HLA-DRI and vaccinated human subjects," Microbes Infect, 2006, 8, pp. 2783-2790, 8 pages.
Prakash, TP et al., Targeted delivery of antisense oligonucleotides to hepatocytes using triantennary N-acetyl galactosamine improves potency 10-fold in mice, Nucleic Acids Research, 2014, vol. 42, issue 13, pp. 8796-8807, 12 pages.
Manoharan: Antisense Drug Technology, Prinoiples, Strategies, and Applications. Macrel Dekker Inc., 2001.
Manoharan: Oligonucleotide Conjugates as Potential Antisense Drugs with Improved Uptake, Biodistribution, Targeted Delivery, and Mechanism of Action, 2002, 103, 26 pgs.
Biessen: Receptor-Dependent Cell Specific Delivery of Antisense Oligonucleotides, British Library Feb. 13, 2020, 16 pgs.
Bergstrom DE, "Unnatural nucleosides with unusual base pairing properties", Current Protocols in Nucleic Acid Chemistry, 2009, Suppl. 37 1.4.1, 32 pgs.
Gutierrez et al. "Regulation of Trypanosoma cmzi-induced myocarditis by programmed death cell receptor I," InfectImmun, May 2011, 79(5):1873-1881.
Office Action received for Taiwan Patent Application No. 109135755, dated Oct. 25, 2021, 6 pages (3 pages of English Translation and 3 pages of Original Document).
SantaLucia, Jr., "A unified view of polymer, dumbbell, and oligonucleotide DNA nearest-neighbor thermodynamics," Proc Natl Acad Sci USA, Feb. 17, 1998, 95(4):1460-1465.
Wykes et al., "Malaria drives T cells to exhaustion," Front Microbiol, May 27, 2014, 5:249.

* cited by examiner

CMP ID NO 766_2

CMP ID NO 767_2

CMP ID NO 768_2

CMP ID NO 769_2

CMP ID NO 770_2

OLIGONUCLEOTIDES FOR REDUCTION OF PD-L1 EXPRESSION

RELATED APPLICATIONS

The present application is a continuation of U.S. patent application Ser. No. 16/839,025 filed Apr. 2, 2020, now U.S. Pat. No. 10,829,555, entitled "OLIGONUCLEOTIDES FOR REDUCTION OF PD-L1 EXPRESSION," which is a continuation of U.S. Pat. No. 10,745,480 issued Aug. 18, 2020, entitled "OLIGONUCLEOTIDES FOR REDUCTION OF PD-L1 EXPRESSION," which is a continuation of U.S. patent application Ser. No. 15/458,800, entitled "OLIGONUCLEOTIDES FOR REDUCTION OF PD-L1 EXPRESSION," filed on 14 Mar. 2017, and claims priority to EP 16160149.7, entitled "OLIGONUCLEOTIDES FOR REDUCTION OF PD-L1 EXPRESSION," filed on 14 Mar. 2016, the contents of each of which is incorporated herein by reference.

FIELD OF INVENTION

The present invention relates to oligonucleotides (oligomers) that are complementary to programmed death ligand-1 (PD-L1), leading to reduction of the expression of PD-L1 the liver.

The present invention also relates to a method of alleviating the T cell exhaustion caused by an infection of the liver or cancer in the liver. Relevant infections are chronic HBV, HCV and HDV and parasite infections like malaria and toxoplasmosis (e.g. caused by protozoa of the *Plasmodium*, in particular of the species *P. vivax, P. malariae* and *P. falciparum*).

BACKGROUND

The costimulatory pathway consisting of the programmed death-1 (PD-1) receptor and its ligand, PD-L1 (or B7-H1 or CD274) is known to contribute directly to T cell exhaustion resulting in lack of viral control during chronic infections of the liver. The PD-1 pathway also plays a role in autoimmunity as mice disrupted in this pathway develop autoimmune diseases.

It has been shown that antibodies that block the interaction between PD-1 and PD-L1 enhance T cell responses, in particular the response of CD8+ cytotoxic T cells (see Barber et al 2006 Nature Vol 439 p 682 and Maier et al 2007 J. Immunol. Vol 178 p 2714).

WO 2006/042237 describes a method of diagnosing cancer by assessing PD-L1 (B7-H1) expression in tumors and suggests delivering an agent, which interferes with the PD-1/PD-L1 interaction, to a patient. Interfering agents can be antibodies, antibody fragments, siRNA or antisense oligonucleotides. There are no specific examples of such interfering agents nor is there any mentioning of chronic liver infections.

RNA interference mediated inhibition of PD-L1 using double stranded RNA (dsRNA, RNAi or siRNA) molecules have also been disclosed in for example WO 2005/007855, WO 2007/084865 and U.S. Pat. No. 8,507,663. None of these describes targeted delivery to the liver. Dolina et al. 2013 Molecular Therapy-Nucleic Acids, 2 e72 describes in vivo delivery of PD-L1 targeting siRNA molecules to Kupffer cells thereby enhancing NK and CD8+ T cell clearance in MCMV infected mice. This paper concludes that PD-L1 targeting siRNA molecules delivered to hepatocytes are not effective in relation to enhancing CD8+ T cell effector function.

The siRNA approach is significantly different from the single stranded antisense oligonucleotide approach since the biodistribution and the mode of actions is quite different. As described in Xu et al 2003 Biochem. Biophys. Res. Comm. Vol 306 page 712-717, antisense oligonucleotides and siRNAs have different preferences for target sites in the mRNA.

WO2016/138278 describes inhibition of immune checkpoints including PD-L1, using two or more single stranded antisense oligonucleotides that are linked at their 5' ends. The application does not mention HBV or targeted delivery to the liver.

OBJECTIVE OF THE INVENTION

The present invention identifies novel oligonucleotides and oligonucleotide conjugates which reduce PD-L1 mRNA very efficiently in liver cells, both in parenchymal cells (e.g. hepatocytes) and in non-parenchymal cells such as Kupffer cells and liver sinusoidal endothelial cells (LSECs). By reducing or silencing PD-L1, the oligonucleotides and oligonucleotide conjugates decrease PD-1-mediated inhibition and thereby promote immunostimulation of exhausted T cells. Alleviation of the T cell exhaustion in a chronic pathogenic infection of the liver will result in regained immune control and reduced levels of viral antigens in the blood during a chronic pathogenic infection of the liver. Natural killer (NK) cells and natural killer T (NKT) cells may also be activated by the oligonucleotides and oligonucleotide conjugates of the present invention.

The oligonucleotide conjugates secures local reduction of PD-L1 in liver cells and therefore reduces the risk of autoimmune side effects, such as pneumonitis, non-viral hepatitis and colitis associated with systemic depletion of PD-L1.

SUMMARY OF INVENTION

The present invention relates to oligonucleotides or conjugates thereof targeting a nucleic acid capable of modulating the expression of PD-L1 and to treat or prevent diseases related to the functioning of the PD-L1. The oligonucleotides or oligonucleotide conjugates may in particular be used to treat diseases where the immune response against an infectious agent has been exhausted.

Accordingly, in a first aspect the invention provides oligonucleotides which comprise a contiguous nucleotide sequence of 10 to 30 nucleotides in length with at least 90% complementarity to a PD-L1 target nucleic acid. The oligonucleotide can be an antisense oligonucleotide, preferably with a gapmer design. Preferably, the oligonucleotide is capable of inhibiting the expression of PD-L1 by cleavage of a target nucleic acid. The cleavage is preferably achieved via nuclease recruitment.

In a further aspect, the oligonucleotide is conjugated to at least one asialoglycoprotein receptor targeting conjugate moiety, such as a conjugate moiety comprising at least one N-Acetylgalactosamine (GalNAc) moiety. The conjugation moiety and the oligonucleotide may be linked together by a linker, in particular a biocleavable linker.

In a further aspect, the invention provides pharmaceutical compositions comprising the oligonucleotides or oligonucleotide conjugates of the invention and pharmaceutically acceptable diluents, carriers, salts and/or adjuvants.

In a further aspect, the invention provides methods for in vivo or in vitro method for reduction of PD-L1 expression in a target cell which is expressing PD-L1, by administering an oligonucleotide or composition of the invention in an effective amount to said cell.

In a further aspect, the invention provides oligonucleotides, oligonucleotide conjugates or pharmaceutical compositions for use in restoration of immunity against a virus or parasite.

In a further aspect, the invention provides oligonucleotides, oligonucleotide conjugates or pharmaceutical compositions for use as a medicament.

In a further aspect the invention provides methods for treating or preventing a disease, disorder or dysfunction by administering a therapeutically or prophylactically effective amount of the oligonucleotide of the invention to a subject suffering from or susceptible to the disease, disorder or dysfunction, in particular diseases selected from viral liver infections or parasite infections.

In a further aspect the oligonucleotide, oligonucleotide conjugates or pharmaceutical composition of the invention is used in the treatment or prevention of viral liver infections such as HBV, HCV and HDV or a parasite infections such as malaria, toxoplasmosis, leishmaniasis and trypanosomiasis or liver cancer or metastases in the liver.

DEFINITIONS

Oligonucleotide

Figure 1:
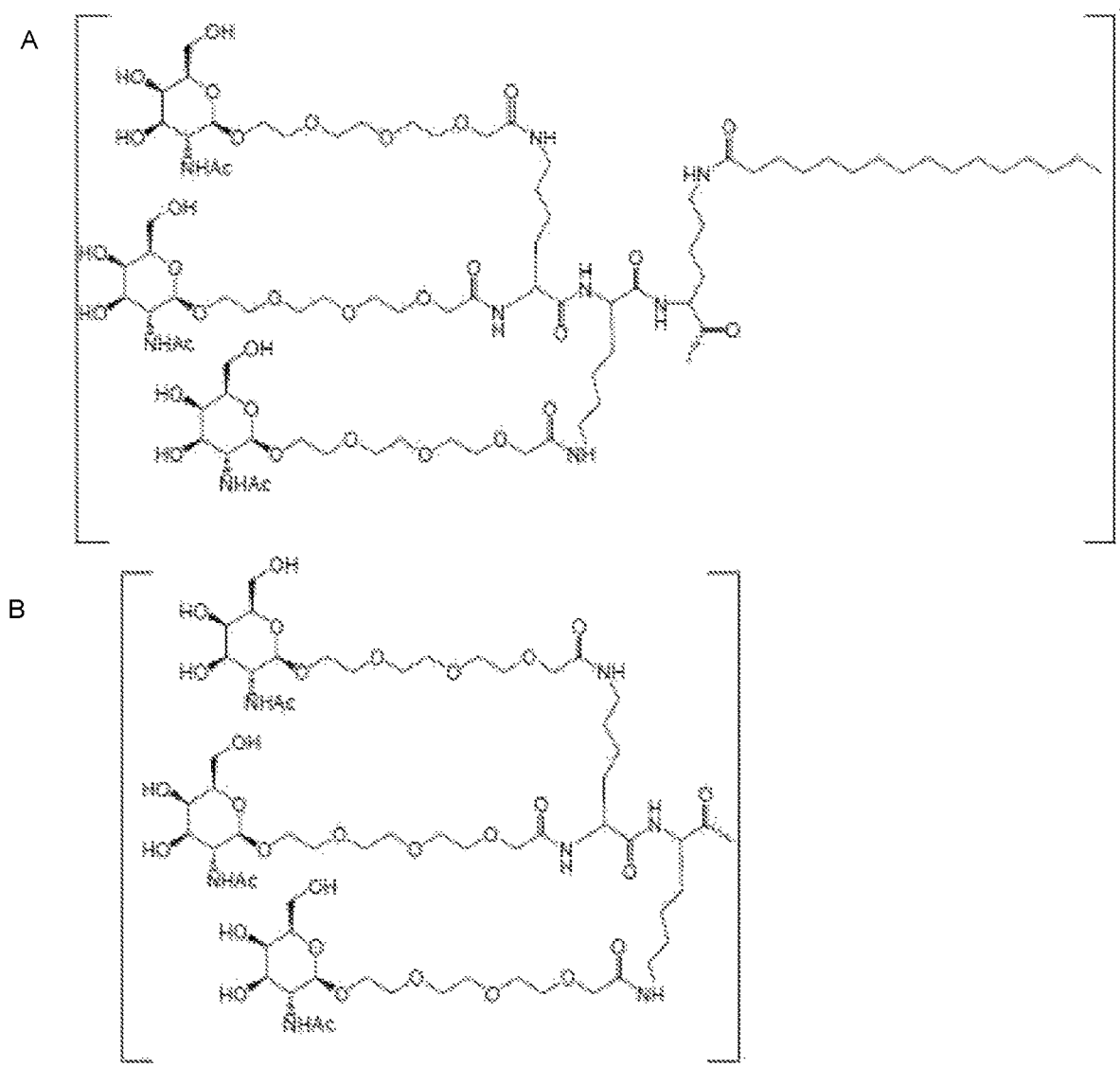
FIG. 1: Illustrates exemplary antisense oligonucleotide conjugates, where the oligonucleotide either is represented as a wavy line (A-D) or as "oligonucleotide" (E-H) or as $T_2$ (I) and the asialoglycoprotein receptor targeting conjugate moieties are trivalent N-acetylgalactosamine moieties. Compounds A to D comprise a di-lysine brancher molecule a PEG3 spacer and three terminal GalNAc carbohydrate moieties. In compound A and B the oligonucleotide is attached directly to the asialoglycoprotein receptor targeting conjugate moiety without a linker. In compound C and D the oligonucleotide is attached directly to the asialoglycoprotein receptor targeting conjugate moiety via a C6 linker. Compounds E-I comprise a trebler brancher molecule and spacers of varying length and structure and three terminal GalNAc carbohydrate moieties.
Figure 1:
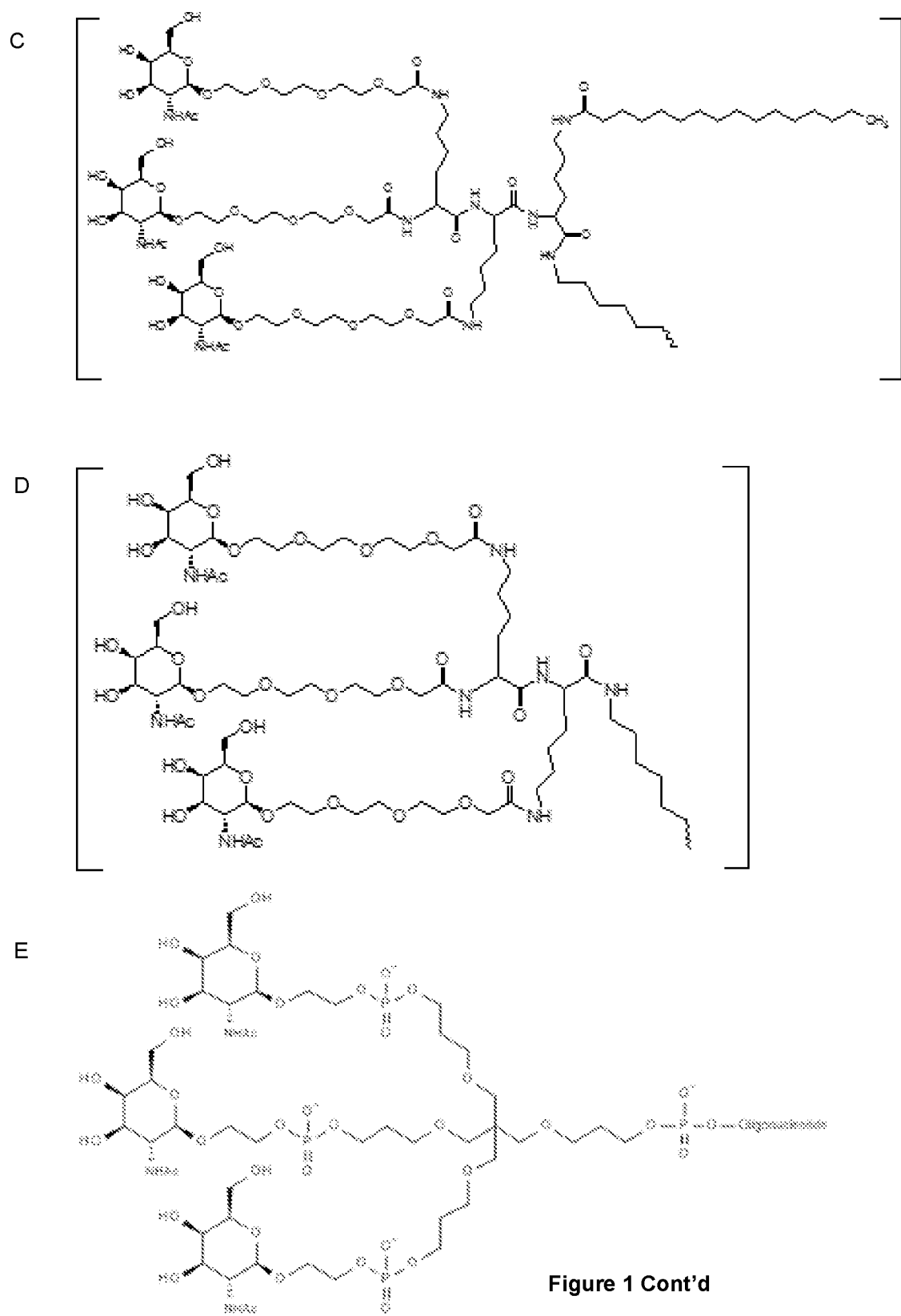
Figure 1:
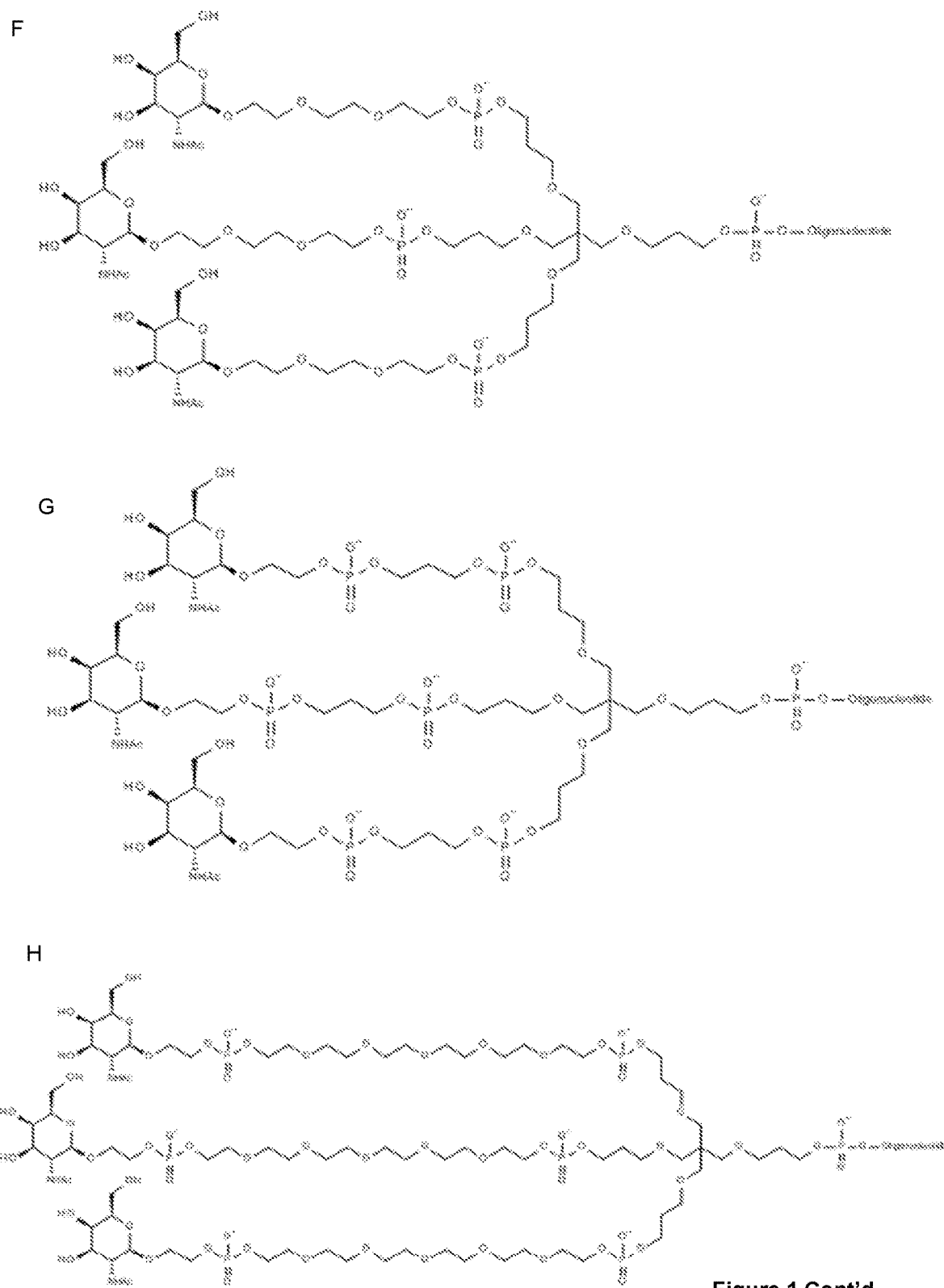
Figure 1:
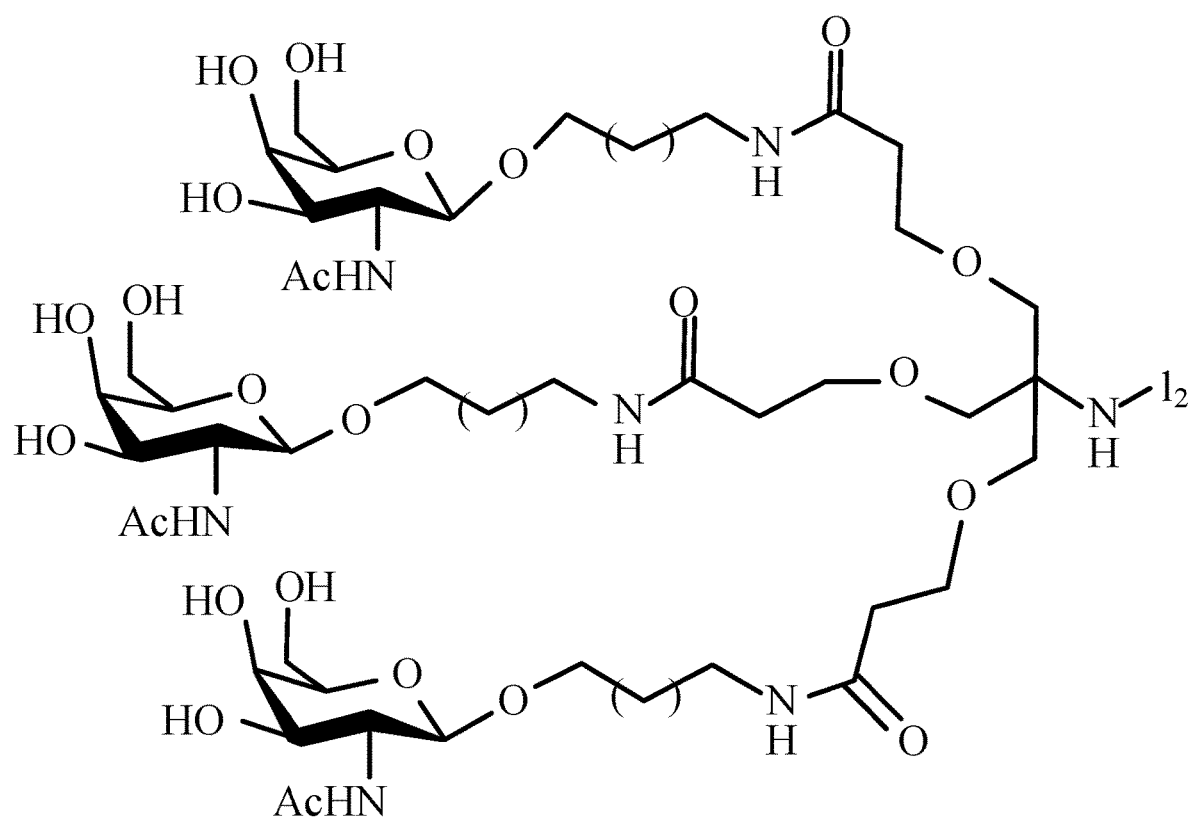

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs. Preferably, the antisense oligonucleotides of the present invention are single stranded.

Contiguous Nucleotide Sequence

The term "contiguous nucleotide sequence" refers to the region of the oligonucleotide which is complementary to the target nucleic acid. The term is used interchangeably herein with the term "contiguous nucleobase sequence" and the term "oligonucleotide motif sequence". In some embodiments all the nucleotides of the oligonucleotide constitute the contiguous nucleotide sequence. In some embodiments the oligonucleotide comprises the contiguous nucleotide sequence and may optionally comprise further nucleotide(s), for example a nucleotide linker region which may be used to attach a functional group to the contiguous nucleotide sequence. The nucleotide linker region may or may not be complementary to the target nucleic acid.

Nucleotides

Nucleotides are the building blocks of oligonucleotides and polynucleotides and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprise a modified sugar moiety. The term modified nucleoside may also be used herein interchangeably with the term "nucleoside analogue" or modified "units" or modified "monomers".

Modified Internucleoside Linkage

The term "modified internucleoside linkage" is defined as generally understood by the skilled person as linkages other than phosphodiester (PO) linkages, that covalently couples two nucleosides together. Nucleotides with modified internucleoside linkage are also termed "modified nucleotides". In some embodiments, the modified internucleoside linkage increases the nuclease resistance of the oligonucleotide compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides for in vivo use, and may serve to protect against nuclease cleavage at regions of DNA or RNA nucleosides in the oligonucleotide of the invention, for example within the gap region of a gapmer oligonucleotide, as well as in regions of modified nucleosides.

In an embodiment, the oligonucleotide comprises one or more internucleoside linkages modified from the natural phosphodiester to a linkage that is for example more resistant to nuclease attack. Nuclease resistance may be determined by incubating the oligonucleotide in blood serum or by using a nuclease resistance assay (e.g. snake venom phosphodiesterase (SVPD)), both are well known in the art. Internucleoside linkages which are capable of enhancing the nuclease resistance of an oligonucleotide are referred to as nuclease resistant internucleoside linkages. In some embodiments at least 50% of the internucleoside linkages in the oligonucleotide, or contiguous nucleotide sequence thereof, are modified, such as at least 60%, such as at least 70%, such as at least 80 or such as at least 90% of the internucleoside linkages in the oligonucleotide, or contiguous nucleotide sequence thereof, are modified. In some embodiments all of the internucleoside linkages of the oligonucleotide, or contiguous nucleotide sequence thereof, are modified. It will be recognized that, in some embodiments the nucleosides which link the oligonucleotide of the invention to a non-nucleotide functional group, such as a conjugate, may be phosphodiester. In some embodiments all of the internucleoside linkages of the oligonucleotide, or contiguous nucleotide sequence thereof, are nuclease resistant internucleoside linkages.

Modified internucleoside linkages may be selected from the group comprising phosphorothioate, diphosphorothioate and boranophosphate. In some embodiments, the modified internucleoside linkages are compatible with the RNaseH recruitment of the oligonucleotide of the invention, for example phosphorothioate, diphosphorothioate or boranophosphate.

In some embodiments the internucleoside linkage comprises sulphur (S), such as a phosphorothioate internucleoside linkage.

A phosphorothioate internucleoside linkage is particularly useful due to nuclease resistance, beneficial pharmakokinetics and ease of manufacture. In some embodiments at least 50% of the internucleoside linkages in the oligonucleotide, or contiguous nucleotide sequence thereof, are phosphorothioate, such as at least 60%, such as at least 70%, such as at least 80 or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

In some embodiments, the oligonucleotide comprises one or more neutral internucleoside linkage, particularly a internucleoside linkage selected from phosphotriester, methylphosphonate, MMI, amide-3, formacetal or thioformacetal.

Further internucleoside linkages are disclosed in WO2009/124238 (incorporated herein by reference). In an embodiment the internucleoside linkage is selected from linkers disclosed in WO2007/031091 (incorporated herein by reference). Particularly, the internucleoside linkage may be selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—

O—, —NR$^H$—CO—O—, —NR$^H$—CO—NR$^H$—, and/or the internucleoside linker may be selected form the group consisting of: —O—CO—O—, —O—CO—NR$^H$—, —NR$^H$—CO—CH$_2$—, —O—CH$_2$—CO—NR$^H$—, —O—CH$_2$—CH$_2$—NR$^H$, —CO—NR$^H$—CH$_2$—, —CH$_2$—NR$^H$CO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—, —CH$_2$—NCH$_3$—O—CH$_2$—, where R$^H$ is selected from hydrogen and C1-4-alkyl.

Nuclease resistant linkages, such as phosphothioate linkages, are particularly useful in oligonucleotide regions capable of recruiting nuclease when forming a duplex with the target nucleic acid, such as region G for gapmers, or the non-modified nucleoside region of headmers and tailmers. Phosphorothioate linkages may, however, also be useful in non-nuclease recruiting regions and/or affinity enhancing regions such as regions F and F' for gapmers, or the modified nucleoside region of headmers and tailmers.

Each of the design regions may however comprise internucleoside linkages other than phosphorothioate, such as phosphodiester linkages, in particularly in regions where modified nucleosides, such as LNA, protect the linkage against nuclease degradation. Inclusion of phosphodiester linkages, such as one or two linkages, particularly between or adjacent to modified nucleoside units (typically in the non-nuclease recruiting regions) can modify the bioavailability and/or bio-distribution of an oligonucleotide—see WO2008/113832, incorporated herein by reference.

In an embodiment all the internucleoside linkages in the oligonucleotide are phosphorothioate and/or boranophosphate linkages. Preferably, all the internucleoside linkages in the oligonucleotide are phosphorothioate linkages.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In a some embodiments the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide describes an oligonucleotide comprising one or more sugar-modified nucleosides and/or modified internucleoside linkages. The term chimeric" oligonucleotide is a term that has been used in the literature to describe oligonucleotides with modified nucleosides.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the number of nucleotides in percent of a contiguous nucleotide sequence in a nucleic acid molecule (e.g. oligonucleotide) which, at a given position, are complementary to (i.e. form Watson Crick base pairs with) a contiguous nucleotide sequence, at a given position of a separate nucleic acid molecule (e.g. the target nucleic acid). The percentage is calculated by counting the number of aligned bases that form pairs between the two sequences (when aligned with the target sequence 5'-3' and the oligonucleotide sequence from 3'-5'), dividing by the total number of nucleotides in the oligonucleotide and multiplying by 100. In such a comparison a nucleobase/nucleotide which does not align (form a base pair) is termed a mismatch.

The term "fully complementary", refers to 100% complementarity.

The following is an example of an oligonucleotide (SEQ ID NO: 5) that is fully complementary to the target nucleic acid (SEQ ID NO: 772).

(SEQ ID NO: 772)
5'gcagtagagccaatta3'

(SEQ ID NO: 5)
3'cgtcatctcggttaat5'

Identity

The term "Identity" as used herein, refers to the number of nucleotides in percent of a contiguous nucleotide sequence in a nucleic acid molecule (e.g. oligonucleotide) which, at a given position, are identical to (i.e. in their ability to form Watson Crick base pairs with the complementary nucleoside) a contiguous nucleotide sequence, at a given position of a separate nucleic acid molecule (e.g. the target nucleic acid). The percentage is calculated by counting the number of aligned bases that are identical between the two sequences, including gaps, dividing by the total number of nucleotides in the oligonucleotide and multiplying by 100.

Percent Identity=(Matches×100)/Length of aligned region (with gaps).

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, Oligonucleotides 13:515-537). The standard state Gibbs free energy $\Delta G°$ is a more accurate representation of binding affinity and is related to the dissociation constant ($K_d$) of the reaction by $\Delta G°=-RT \ln(K_d)$, where R is the gas constant and T is the absolute temperature. Therefore, a very low $\Delta G°$ of the reaction between an oligonucleotide and the target nucleic acid reflects a strong hybridization between the oligonucleotide and target nucleic acid. $\Delta G°$ is the energy associated with a reaction where aqueous concentrations are 1M, the pH is 7, and the temperature is 37° C. The hybridization of oligonucleotides to a target nucleic acid is a spontaneous reaction and for spontaneous reactions $\Delta G°$ is less than zero. $\Delta G°$ can be measured experimentally, for example, by use of the isothermal titration calorimetry (ITC) method as described in Hansen et al., 1965, *Chem. Comm.* 36-38 and Holdgate et al., 2005, *Drug Discov Today*. The skilled person will know that commercial equipment is available for $\Delta G°$ measurements. $\Delta G°$ can also be estimated numerically by using the nearest neighbor model as described by SantaLucia, 1998, *Proc Natl Acad Sci USA*, 95: 1460-1465 using appropriately derived thermodynamic parameters described by Sugimoto et al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated $\Delta G°$ values below –10 kcal for oligonucleotides that are 10-30 nucleotides in length. In some embodiments the degree or strength of hybridization is measured by the standard state Gibbs free energy $\Delta G°$. The oligonucleotides may hybridize to a target nucleic acid with estimated $\Delta G°$ values below the range of –10 kcal, such as below –15 kcal, such as below –20 kcal and such as below –25 kcal for oligonucleotides that are 8-30 nucleotides in length. In some embodiments the oligonucleotides hybridize to a target nucleic acid with an estimated $\Delta G°$ value of –10 to –60 kcal, such as –12 to –40, such as from –15 to –30 kcal or –16 to –27 kcal such as –18 to –25 kcal.

Target Nucleic Acid

According to the present invention, the target nucleic acid is a nucleic acid which encodes mammalian PD-L1 and may for example be a gene, a RNA, a mRNA, and pre-mRNA, a mature mRNA or a cDNA sequence. The target may therefore be referred to as a PD-L1 target nucleic acid. The oligonucleotide of the invention may for example target exon regions of a mammalian PD-L1, or may for example target intron region in the PD-L1 pre-mRNA (see Table 1).

TABLE 1 human PD-L1 Exons and Introns

| Exonic regions in the human PD-L1 premRNA (SEQ ID NO 1) | | | Intronic regions in the human PD-L1 premRNA (SEQ ID NO 1) | | |
|---|---|---|---|---|---|
| ID | start | end | ID | start | end |
| e1 | 1 | 94 | i1 | 95 | 5597 |
| e2 | 5598 | 5663 | i2 | 5664 | 6576 |
| e3 | 6577 | 6918 | i3 | 6919 | 12331 |
| e4 | 12332 | 12736 | i4 | 12737 | 14996 |
| e5 | 14997 | 15410 | i5 | 15411 | 16267 |
| e6 | 16268 | 16327 | i6 | 16328 | 17337 |
| e7 | 17338 | 20064 | | | |

Suitably, the target nucleic acid encodes a PD-L1 protein, in particular mammalian PD-L1, such as human PD-L1 (See for example tables 2 and 3, which provide reference to the mRNA and pre-mRNA sequences for human, monkey, and mouse PD-L1). In the context of the present invention pre-mRNA is also considered as a nucleic acid that encodes a protein.

In some embodiments, the target nucleic acid is selected from the group consisting of SEQ ID NO: 1, 2 and 3 or naturally occurring variants thereof (e.g. sequences encoding a mammalian PD-L1 protein).

If employing the oligonucleotide of the invention in research or diagnostics the target nucleic acid may be a cDNA or a synthetic nucleic acid derived from DNA or RNA.

For in vivo or in vitro application, the oligonucleotide of the invention is typically capable of inhibiting the expression of the PD-L1 target nucleic acid in a cell which is expressing the PD-L1 target nucleic acid. The contiguous sequence of nucleobases of the oligonucleotide of the invention is typically complementary to the PD-L1 target nucleic acid, as measured across the length of the oligonucleotide, optionally with the exception of one or two mismatches, and optionally excluding nucleotide based linker regions which may link the oligonucleotide to an optional functional group such as a conjugate, or other non-complementary terminal nucleotides (e.g. region D' or D"). The target nucleic acid may, in some embodiments, be a RNA or DNA, such as a messenger RNA, such as a mature mRNA or a pre-mRNA. In some embodiments the target nucleic acid is a RNA or DNA which encodes mammalian PD-L1 protein, such as human PD-L1, e.g. the human PD-L1 premRNA sequence, such as that disclosed as SEQ ID NO 1 or the human mRNA sequence with NCBI reference number NM_014143. Further information on exemplary target nucleic acids is provided in tables 2 and 3.

TABLE 2

Genome and assembly information for PD-L1 across species.

| Species | Chr. | Strand | Genomic coordinates | | | NCBI reference sequence* accession number for mRNA |
|---|---|---|---|---|---|---|
| | | | Start | End | Assembly | |
| Human | 9 | fwd | 5450503 | 5470566 | GRCh38: CM000671.2 | NM_014143 |
| Cynomolgus monkey | 15 | | 73560846 | 73581371 | GCF_000364345.1 | XM_005581779 |
| Mouse | 19 | fwd | 29367455 | 29388095 | GRCm38: CM001012.2 | NM_021893 |

Fwd = forward strand. The genome coordinates provide the pre-mRNA sequence (genomic sequence).
The NCBI reference provides the mRNA sequence (cDNA sequence).
*The National Center for Biotechnology Information reference sequence database is a comprehensive, integrated, non-redundant, well-annotated set of reference sequences including genomic, transcript, and protein. It is hosted at www.ncbi.nlm.nih.gov/refseq.

TABLE 3

Sequence details for PD-L1 across species.

| Species | RNA type | Length (nt) | SEQ ID NO |
|---|---|---|---|
| Human | premRNA | 20064 | 1 |
| Monkey Cyno | premRNA GCF ref | 20261 | 2 |
| Monkey Cyno | premRNA Internal | 20340 | 3 |
| Mouse | premRNA | 20641 | 4 |

Target Sequence

The term "target sequence" as used herein refers to a sequence of nucleotides present in the target nucleic acid which comprises the nucleobase sequence which is complementary to the oligonucleotide of the invention. In some embodiments, the target sequence consists of a region on the target nucleic acid which is complementary to the contiguous nucleotide sequence of the oligonucleotide of the invention. In some embodiments the target sequence is longer than the complementary sequence of a single oligonucleotide, and may, for example represent a preferred region of the target nucleic acid which may be targeted by several oligonucleotides of the invention.

The target sequence may be a sub-sequence of the target nucleic acid.

In some embodiments the sub-sequence is a sequence selected from the group consisting of a1-a149 (see tables 4). In some embodiments the sub-sequence is a sequence selected from the group consisting of a human PD-L1 mRNA exon, such as a PD-L1 human mRNA exon selected from the group consisting of e1, e2, e3, e4, e5, e6, and e7 (see table 1 above).

In some embodiments the sub-sequence is a sequence selected from the group consisting of a human PD-L1 mRNA intron, such as a PD-L1 human mRNA intron selected from the group consisting of i1, i2, i3, i4, i5 and i6 (see table 1 above).

The oligonucleotide of the invention comprises a contiguous nucleotide sequence which is complementary to or hybridizes to the target nucleic acid, such as a sub-sequence of the target nucleic acid, such as a target sequence described herein.

The oligonucleotide comprises a contiguous nucleotide sequence of at least 8 nucleotides which is complementary to or hybridizes to a target sequence present in the target nucleic acid molecule. The contiguous nucleotide sequence (and therefore the target sequence) comprises of at least 8 contiguous nucleotides, such as 9, 10, 11, 12, 13, 14, 15, 16, 17, 18, 19, 20, 21, 22, 23, 24, 25, 26, 27, 28, 29 or 30 contiguous nucleotides, such as from 12-25, such as from 14-18 contiguous nucleotides.

Target Cell

The term a "target cell" as used herein refers to a cell which is expressing the target nucleic acid. In some embodiments the target cell may be in vivo or in vitro. In some embodiments the target cell is a mammalian cell such as a rodent cell, such as a mouse cell or a rat cell, or a primate cell such as a monkey cell or a human cell.

In preferred embodiments the target cell expresses PD-L1 mRNA, such as the PD-L1 pre-mRNA or PD-L1 mature mRNA. The poly A tail of PD-L1 mRNA is typically disregarded for antisense oligonucleotide targeting.

Naturally Occurring Variant

The term "naturally occurring variant" refers to variants of PD-L1 gene or transcripts which originate from the same genetic loci as the target nucleic acid, but may differ for example, by virtue of degeneracy of the genetic code causing a multiplicity of codons encoding the same amino acid, or due to alternative splicing of pre-mRNA, or the presence of polymorphisms, such as single nucleotide polymorphisms, and allelic variants. Based on the presence of the sufficient complementary sequence to the oligonucleotide, the oligonucleotide of the invention may therefore target the target nucleic acid and naturally occurring variants thereof.

In some embodiments, the naturally occurring variants have at least 95% such as at least 98% or at least 99% homology to a mammalian PD-L1 target nucleic acid, such as a target nucleic acid selected form the group consisting of SEQ ID NO 1, 2 and 3.

Numerous single nucleotide polymorphisms are known in the PD-L1 gene, for example those disclosed in the following table (human premRNA start/reference sequence is SEQ ID NO 2)

| Variant name | Variant alleles | minor allele | Minor allele frequency | Start on SEQ ID NO: 1 |
|---|---|---|---|---|
| rs73397192 | G/A | A | 0.10 | 2591 |
| rs12342381 | A/G | G | 0.12 | 308 |
| rs16923173 | G/A | A | 0.13 | 14760 |
| rs2890658 | C/A | A | 0.16 | 14628 |
| rs2890657 | G/C | C | 0.21 | 2058 |
| rs3780395 | A/G | A | 0.21 | 14050 |
| rs147367592 | AG/— | — | 0.21 | 13425 |
| rs7023227 | T/C | T | 0.22 | 6048 |
| rs2297137 | G/A | A | 0.23 | 15230 |
| rs1329946 | G/A | A | 0.23 | 2910 |
| rs5896124 | —/G | G | 0.23 | 2420 |
| rs61061063 | T/C | C | 0.23 | 11709 |
| rs1411263 | T/C | C | 0.23 | 8601 |
| rs59906468 | A/G | G | 0.23 | 15583 |
| rs6476976 | T/C | T | 0.24 | 21012 |
| rs35744625 | C/A | A | 0.24 | 3557 |
| rs17804441 | T/C | C | 0.24 | 7231 |
| rs148602745 | C/T | T | 0.25 | 22548 |
| rs4742099 | G/A | A | 0.25 | 20311 |
| rs10815228 | T/C | C | 0.25 | 21877 |
| rs58817806 | A/G | G | 0.26 | 20769 |
| rs822342 | T/C | T | 0.27 | 3471 |
| rs10481593 | G/A | A | 0.27 | 7593 |
| rs822339 | A/G | A | 0.28 | 2670 |
| rs860290 | A/C | A | 0.28 | 2696 |
| rs822340 | A/G | A | 0.28 | 2758 |
| rs822341 | T/C | T | 0.28 | 2894 |
| rs12002985 | C/G | C | 0.28 | 6085 |
| rs822338 | C/T | C | 0.28 | 1055 |
| rs866066 | C/T | T | 0.28 | 451 |
| rs6651524 | A/T | T | 0.28 | 8073 |
| rs6415794 | A/T | A | 0.28 | 8200 |
| rs4143815 | G/C | C | 0.28 | 17755 |
| rs111423622 | G/A | A | 0.28 | 24096 |
| rs6651525 | C/A | A | 0.29 | 8345 |
| rs4742098 | A/G | G | 0.29 | 19995 |
| rs10975123 | C/T | T | 0.30 | 10877 |
| rs2282055 | T/G | G | 0.30 | 5230 |
| rs4742100 | A/C | C | 0.30 | 20452 |
| rs60520638 | —/TC | TC | 0.30 | 9502 |
| rs17742278 | T/C | C | 0.30 | 6021 |
| rs7048841 | T/C | T | 0.30 | 10299 |
| rs10815229 | T/G | G | 0.31 | 22143 |
| rs10122089 | C/T | T | 0.32 | 13278 |
| rs1970000 | C/A | C | 0.32 | 14534 |
| rs112071324 | AGAGAG/— | AGAGAG | 0.33 | 16701 |
| rs2297136 | G/A | G | 0.33 | 17453 |
| rs10815226 | A/T | T | 0.33 | 9203 |
| rs10123377 | A/G | A | 0.36 | 10892 |
| rs10123444 | A/G | A | 0.36 | 11139 |
| rs7042084 | G/T | G | 0.36 | 7533 |
| rs10114060 | G/A | A | 0.36 | 11227 |
| rs7028894 | G/A | G | 0.36 | 10408 |

| Variant name | Variant alleles | minor allele | Minor allele frequency | Start on SEQ ID NO: 1 |
|---|---|---|---|---|
| rs4742097 | C/T | C | 0.37 | 5130 |
| rs1536926 | G/T | G | 0.37 | 13486 |
| rs1411262 | C/T | T | 0.39 | 8917 |
| rs7041009 | G/A | A | 0.45 | 12741 |

Modulation of Expression

The term "modulation of expression" as used herein is to be understood as an overall term for an oligonucleotide's ability to alter the amount of PD-L1 when compared to the amount of PD-L1 before administration of the oligonucleotide. Alternatively modulation of expression may be determined by reference to a control experiment. It is generally understood that the control is an individual or target cell treated with a saline composition or an individual or target cell treated with a non-targeting oligonucleotide (mock). It may however also be an individual treated with the standard of care.

One type of modulation is an oligonucleotide's ability to inhibit, down-regulate, reduce, suppress, remove, stop, block, prevent, lessen, lower, avoid or terminate expression of PD-L1, e.g. by degradation of mRNA or blockage of transcription. Another type of modulation is an oligonucleotide's ability to restore, increase or enhance expression of PD-L1, e.g. by repair of splice sites or prevention of splicing or removal or blockage of inhibitory mechanisms such as microRNA repression.

High Affinity Modified Nucleosides

A high affinity modified nucleoside is a modified nucleotide which, when incorporated into the oligonucleotide enhances the affinity of the oligonucleotide for its complementary target, for example as measured by the melting temperature ($T^m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The oligomer of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions. Nucleosides with modified sugar moieties also include 2' modified nucleosides, such as 2' substituted nucleosides. Indeed, much focus has been spent on developing 2' substituted nucleosides, and numerous 2' substituted nucleosides have been found to have beneficial properties when incorporated into oligonucleotides, such as enhanced nucleoside resistance and enhanced affinity.

2' Modified Nucleosides.

A 2' sugar modified nucleoside is a nucleoside which has a substituent other than H or —OH at the 2' position (2' substituted nucleoside) or comprises a 2' linked biradicle, and includes 2' substituted nucleosides and LNA (2'-4' biradicle bridged) nucleosides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

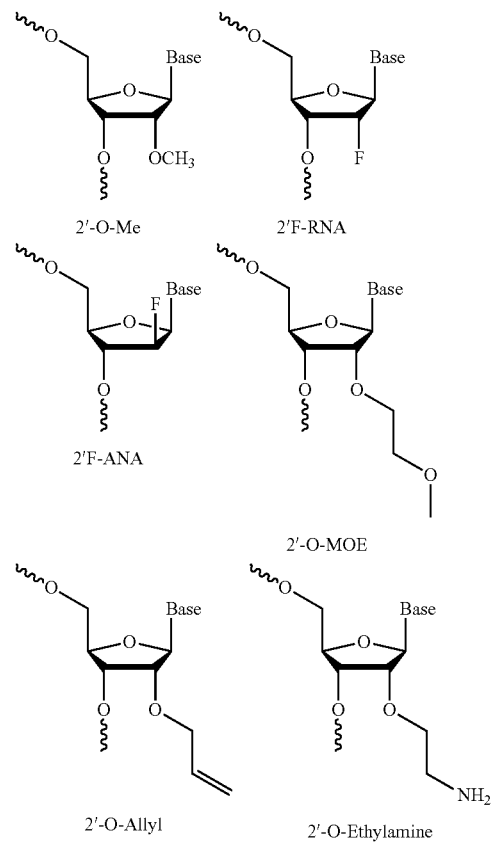

Locked Nucleic Acid Nucleosides (LNA).

LNA nucleosides are modified nucleosides which comprise a linker group (referred to as a biradicle or a bridge)

between C2' and C4' of the ribose sugar ring of a nucleotide. These nucleosides are also termed bridged nucleic acid or bicyclic nucleic acid (BNA) in the literature. In some embodiments, the modified nucleoside or the LNA nucleosides of the oligomer of the invention has a general structure of the formula I or II:

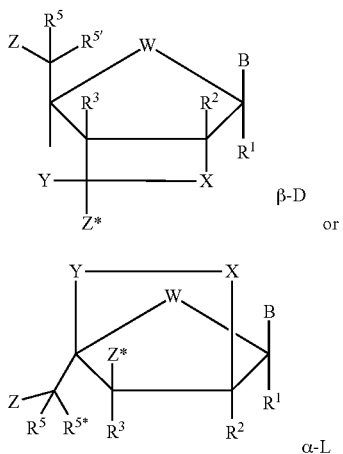

Formula I β-D or

Formula II α-L wherein W is selected from —O—, —S—, —N($R^a$)—, —C($R^a R^b$)—, such as, in some embodiments —O—;

B designates a nucleobase or modified nucleobase moiety;

Z designates an internucleoside linkage to an adjacent nucleoside, or a 5'-terminal group;

Z* designates an internucleoside linkage to an adjacent nucleoside, or a 3'-terminal group;

X designates a group selected from the list consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, X is selected from the group consisting of: —O—, —S—, NH—, N$R^a R^b$, —CH$_2$—, C$R^a R^b$, —C(=CH$_2$)—, and —C(=C$R^a R^b$)—

In some embodiments, X is —O—

Y designates a group selected from the group consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z In some embodiments, Y is selected from the group consisting of: —CH$_2$—, —C($R^a R^b$)—, —CH$_2$CH$_2$—, —C($R^a R^b$)—C($R^a R^b$)—, —CH$_2$CH$_2$CH$_2$—, —C($R^a R^b$)C($R^a R^b$)C($R^a R^b$)—, —C($R^a$)=C($R^b$)—, and —C($R^a$)=N—

In some embodiments, Y is selected from the group consisting of: —CH$_2$—, —CH$R^a$—, —CHCH$_3$—, C$R^a R^b$— or —X—Y— together designate a bivalent linker group (also referred to as a radicle) together designate a bivalent linker group consisting of 1, 2, 3 or 4 groups/atoms selected from the group consisting of —C($R^a R^b$)—, —C($R^a$)=C($R^b$)—, —C($R^a$)=N—, —O—, —Si($R^a$)$_2$—, —S—, —SO$_2$—, —N($R^a$)—, and >C=Z, In some embodiments, —X—Y— designates a biradicle selected from the groups consisting of: —X—CH$_2$—, —X—C$R^a R^b$—, —X—CH$R^a$—, —X—C(HCH$_3$)—, —O—Y—, —O—CH$_2$—, —S—CH$_2$—, —NH—CH$_2$—, —O—CHCH$_3$—, —CH$_2$—O—CH$_2$—, —O—CH(CH$_3$CH$_3$)—, —O—CH$_2$—CH$_2$—, OCH$_2$—CH$_2$—CH$_2$—, —O—CH$_2$OCH$_2$—, —O—NCH$_2$—, —C(=CH$_2$)—CH$_2$—, —N$R^a$—CH$_2$—, NO—CH$_2$, —S—C$R^a R^b$— and —S—CH$R^a$—.

In some embodiments —X—Y— designates —O—CH$_2$— or —O—CH(CH$_3$)—.

wherein Z is selected from —O—, —S—, and —N($R^a$)—, and $R^a$ and, when present $R^b$, each is independently selected from hydrogen, optionally substituted C$_{1-6}$-alkyl, optionally substituted C$_{2-6}$-alkenyl, optionally substituted C$_{2-6}$-alkynyl, hydroxy, optionally substituted C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation.

wherein $R^1$, $R^2$, $R^3$, $R^5$ and $R^{5*}$ are independently selected from the group consisting of: hydrogen, optionally substituted C$_{1-6}$-alkyl, optionally substituted C$_{2-6}$-alkenyl, optionally substituted C$_{2-6}$-alkynyl, hydroxy, C$_{1-6}$-alkoxy, C$_{2-6}$-alkoxyalkyl, C$_{2-6}$-alkenyloxy, carboxy, C$_{1-6}$-alkoxycarbonyl, C$_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di(C$_{1-6}$-alkyl)amino, carbamoyl, mono- and di(C$_{1-6}$-alkyl)-amino-carbonyl, amino-C$_{1-6}$-alkyl-aminocarbonyl, mono- and di(C$_{1-6}$-alkyl)amino-C$_{1-6}$-alkyl-aminocarbonyl, C$_{1-6}$-alkyl-carbonylamino, carbamido, C$_{1-6}$-alkanoyloxy, sulphono, C$_{1-6}$-alkylsulphonyloxy, nitro, azido, sulphanyl, C$_{1-6}$-alkylthio, halogen, where aryl and heteroaryl may be optionally substituted, and where two geminal substituents together may designate oxo, thioxo, imino, or optionally substituted methylene.

In some embodiments $R^1$, $R^2$, $R^3$, $R^5$ and $R^{5*}$ are independently selected from C$_{1-6}$ alkyl, such as methyl, and hydrogen.

In some embodiments $R^1$, $R^2$, $R^3$, $R^5$ and $R^{5*}$ are all hydrogen.

In some embodiments $R^1$, $R^2$, $R^3$, are all hydrogen, and either $R^5$ and $R^{5*}$ is also hydrogen and the other of $R^5$ and $R^{5*}$ is other than hydrogen, such as C$_{1-6}$ alkyl such as methyl.

In some embodiments, $R^a$ is either hydrogen or methyl. In some embodiments, when present, $R^b$ is either hydrogen or methyl.

In some embodiments, one or both of $R^a$ and $R^b$ is hydrogen

In some embodiments, one of $R^a$ and $R^b$ is hydrogen and the other is other than hydrogen In some embodiments, one of $R^a$ and $R^b$ is methyl and the other is hydrogen In some embodiments, both of $R^a$ and $R^b$ are methyl.

In some embodiments, the biradicle —X—Y— is —O—CH$_2$—, W is O, and all of $R^1$, $R^2$, $R^3$, $R^5$ and $R^{5*}$ are all hydrogen. Such LNA nucleosides are disclosed in WO99/014226, WO00/66604, WO98/039352 and WO2004/046160 which are all hereby incorporated by reference, and include what are commonly known as beta-D-oxy LNA and alpha-L-oxy LNA nucleosides.

In some embodiments, the biradicle —X—Y— is —S—CH$_2$—, W is O, and all of R$^1$, R$^2$, R$^3$, R$^5$ and R$^{5*}$ are all hydrogen. Such thio LNA nucleosides are disclosed in WO99/014226 and WO2004/046160 which are hereby incorporated by reference.

In some embodiments, the biradicle —X—Y— is —NH—CH$_2$—, W is O, and all of R$^1$, R$^2$, R$^3$, R$^5$ and R$^{5*}$ are all hydrogen. Such amino LNA nucleosides are disclosed in WO99/014226 and WO2004/046160 which are hereby incorporated by reference.

In some embodiments, the biradicle —X—Y— is —O—CH$_2$—CH$_2$— or —O—CH$_2$—CH$_2$—CH$_2$—, W is O, and all of R$^1$, R$^2$, R$^3$, R$^5$ and R$^{5*}$ are all hydrogen. Such LNA nucleosides are disclosed in WO00/047599 and Morita et al, Bioorganic & Med. Chem. Lett. 12 73-76, which are hereby incorporated by reference, and include what are commonly known as 2'-O-4'C-ethylene bridged nucleic acids (ENA).

In some embodiments, the biradicle —X—Y— is —O—CH$_2$—, W is O, and all of R$^1$, R$^2$, R$^3$, and one of R$^5$ and R$^{5*}$ are hydrogen, and the other of R$^5$ and R$^{5*}$ is other than hydrogen such as C$_{1-6}$ alkyl, such as methyl. Such 5' substituted LNA nucleosides are disclosed in WO2007/134181 which is hereby incorporated by reference.

In some embodiments, the biradicle —X—Y— is —O—CR$^a$R$^b$—, wherein one or both of R$^a$ and R$^b$ are other than hydrogen, such as methyl, W is O, and all of R$^1$, R$^2$, R$^3$, and one of R$^5$ and R$^{5*}$ are hydrogen, and the other of R$^5$ and R$^{5*}$ is other than hydrogen such as C$_{1-6}$ alkyl, such as methyl.

Such bis modified LNA nucleosides are disclosed in WO2010/077578 which is hereby incorporated by reference.

In some embodiments, the biradicle —X—Y— designate the bivalent linker group —O—CH(CH$_2$OCH$_3$)— (2' O-methoxyethyl bicyclic nucleic acid—Seth at al., 2010, J. Org. Chem. Vol 75(5) pp. 1569-81). In some embodiments, the biradicle —X—Y— designate the bivalent linker group —O—CH(CH$_2$CH$_3$)— (2'O-ethyl bicyclic nucleic acid—Seth at al., 2010, J. Org. Chem. Vol 75(5) pp. 1569-81). In some embodiments, the biradicle —X—Y— is —O—CHR$^a$—, W is O, and all of R$^1$, R$^2$, R$^3$, R$^5$ and R$^{5*}$ are all hydrogen. Such 6' substituted LNA nucleosides are disclosed in WO10036698 and WO07090071 which are both hereby incorporated by reference.

In some embodiments, the biradicle —X—Y— is —O—CH(CH$_2$OCH$_3$)—, W is O, and all of R$^1$, R$^2$, R$^3$, R$^5$ and R$^{5*}$ are all hydrogen. Such LNA nucleosides are also known as cyclic MOEs in the art (cMOE) and are disclosed in WO07090071.

In some embodiments, the biradicle —X—Y— designate the bivalent linker group —O—CH(CH$_3$)—. —in either the R- or S-configuration. In some embodiments, the biradicle —X—Y— together designate the bivalent linker group —O—CH$_2$—O—CH$_2$— (Seth at al., 2010, J. Org. Chem). In some embodiments, the biradicle —X—Y— is —O—CH(CH$_3$)—, W is O, and all of R$^1$, R$^2$, R$^3$, R$^5$ and R$^{5*}$ are all hydrogen. Such 6' methyl LNA nucleosides are also known as cET nucleosides in the art, and may be either (S)cET or (R)cET stereoisomers, as disclosed in WO07090071 (beta-D) and WO2010/036698 (alpha-L) which are both hereby incorporated by reference).

In some embodiments, the biradicle —X—Y— is —O—CR$^a$R$^b$—, wherein in neither R$^a$ or R$^b$ is hydrogen, W is O, and all of R$^1$, R$^2$, R$^3$, R$^5$ and R$^{5*}$ are all hydrogen. In some embodiments, R$^a$ and R$^b$ are both methyl. Such 6' di-substituted LNA nucleosides are disclosed in WO 2009006478 which is hereby incorporated by reference.

In some embodiments, the biradicle —X—Y— is —S—CHR$^a$—, W is O, and all of R$^1$, R$^2$, R$^3$, R$^5$ and R$^{5*}$ are all hydrogen. Such 6' substituted thio LNA nucleosides are disclosed in WO11156202 which is hereby incorporated by reference. In some 6' substituted thio LNA embodiments R$^a$ is methyl.

In some embodiments, the biradicle —X—Y— is —C(=CH$_2$)—C(R$^a$R$^b$)—, such as —C(=CH$_2$)—CH$_2$—, or —C(=CH$_2$)—CH(CH$_3$)—W is O, and all of R$^1$, R$^2$, R$^3$, R$^5$ and R$^{5*}$ are all hydrogen. Such vinyl carbo LNA nucleosides are disclosed in WO08154401 and WO09067647 which are both hereby incorporated by reference.

In some embodiments the biradicle —X—Y— is —N(—OR$^a$)—, W is O, and all of R$^1$, R$^2$, R$^3$, R$^5$ and R$^{5*}$ are all hydrogen. In some embodiments R$^a$ is C$_{1-6}$ alkyl such as methyl. Such LNA nucleosides are also known as N substituted LNAs and are disclosed in WO2008/150729, which is hereby incorporated by reference. In some embodiments, the biradicle —X—Y— together designate the bivalent linker group —O—NR$^a$—CH$_3$— (Seth at al., 2010, J. Org. Chem). In some embodiments the biradicle —X—Y— is —N(R$^a$)—, W is O, and all of R$^1$, R$^2$, R$^3$, R$^5$ and R$^{5*}$ are all hydrogen. In some embodiments R$^a$ is C$_{1-6}$ alkyl such as methyl.

In some embodiments, one or both of R$^5$ and R$^{5*}$ is hydrogen and, when substituted the other of R$^5$ and R$^{5*}$ is C$_{1-6}$ alkyl such as methyl. In such an embodiment, R$^1$, R$^2$, R$^3$, may all be hydrogen, and the biradicle —X—Y— may be selected from —O—CH$_2$— or —O—C(HCR$^a$)—, such as —O—C(HCH3)—.

In some embodiments, the biradicle is —CR$^a$R$^b$—O—CR$^a$R$^b$—, such as CH$_2$—O—CH$_2$—, W is O and all of R$^1$, R$^2$, R$^3$, R$^5$ and R$^{5*}$ are all hydrogen. In some embodiments R$^a$ is C$_{1-6}$ alkyl such as methyl. Such LNA nucleosides are also known as conformationally restricted nucleotides (CRNs) and are disclosed in WO2013036868 which is hereby incorporated by reference.

In some embodiments, the biradicle is —O—CR$^a$R$^b$—O—CR$^a$R$^b$—, such as O—CH$_2$—O—CH$_2$—, W is O and all of R$^1$, R$^2$, R$^3$, R$^5$ and R$^{5*}$ are all hydrogen. In some embodiments R$^a$ is C$_{1-6}$ alkyl such as methyl. Such LNA nucleosides are also known as COC nucleotides and are disclosed in Mitsuoka et al., Nucleic Acids Research 2009 37(4), 1225-1238, which is hereby incorporated by reference.

It will be recognized than, unless specified, the LNA nucleosides may be in the beta-D or alpha-L stereoisoform.

Certain examples of LNA nucleosides are presented in Scheme 1.

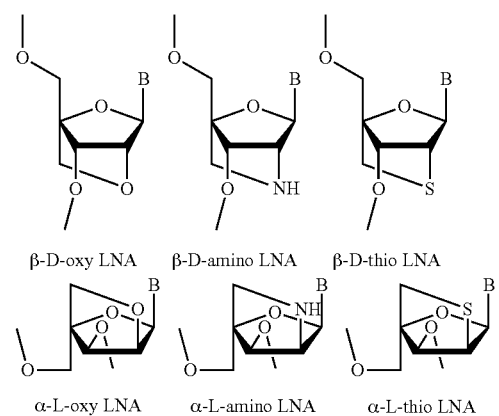

Scheme 1

β-D-oxy LNA   β-D-amino LNA   β-D-thio LNA

α-L-oxy LNA   α-L-amino LNA   α-L-thio LNA

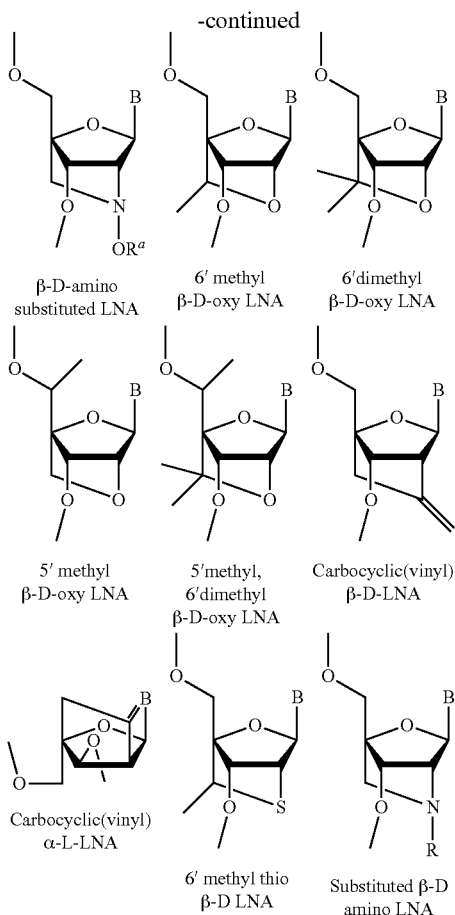

As illustrated in the examples, in some embodiments of the invention the LNA nucleosides in the oligonucleotides are beta-D-oxy-LNA nucleosides.

Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the invention are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 DNA nucleosides and are flanked on one side or both sides by affinity enhancing nucleosides, for example gapmers, headmers and tailmers.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference).

Gapmer

The term gapmer as used herein refers to an antisense oligonucleotide which comprises a region of RNase H recruiting oligonucleotides (gap) which is flanked 5' and 3' by regions which comprise one or more affinity enhancing modified nucleosides (flanks or wings). Various gapmer designs are described herein and a characterized by their ability to recruit RNaseH. Headmers and tailmers are oligonucleotides capable of recruiting RNase H where one of the flanks is missing, i.e. only one of the ends of the oligonucleotide comprises affinity enhancing modified nucleosides. For headmers the 3' flank is missing (i.e. the 5' flank comprises affinity enhancing modified nucleosides) and for tailmers the 5' flank is missing (i.e. the 3' flank comprises affinity enhancing modified nucleosides).

LNA Gapmer

The term LNA gapmer is a gapmer oligonucleotide wherein at least one of the affinity enhancing modified nucleosides is an LNA nucleoside.

Mixed Wing Gapmer

The term mixed wing gapmer or mixed flank gapmer refers to a LNA gapmer wherein at least one of the flank regions comprise at least one LNA nucleoside and at least one non-LNA modified nucleoside, such as at least one 2' substituted modified nucleoside, such as, for example, 2'-O-alkyl-RNA, 2'-O-methyl-RNA, 2'-alkoxy-RNA, 2'-O-methoxyethyl-RNA (MOE), 2'-amino-DNA, 2'-Fluoro-RNA and 2'-F-ANA nucleoside(s). In some embodiments the mixed wing gapmer has one flank which comprises only LNA nucleosides (e.g. 5' or 3') and the other flank (3' or 5' respectfully) comprises 2' substituted modified nucleoside(s) and optionally LNA nucleosides.

Gapbreaker

The term "gapbreaker oligonucleotide" is used in relation to a gapmer capable of maintaining RNAseH recruitment even though the gap region is disrupted by a non-RNaseH recruiting nucleoside (a gap-breaker nucleoside, E) such that the gap region comprise less than 5 consecutive DNA nucleosides. Non-RNaseH recruiting nucleosides are for example nucleosides in the 3' endo conformation, such as LNA's where the bridge between C2' and C4' of the ribose sugar ring of a nucleoside is in the beta conformation, such as beta-D-oxy LNA or ScET nucleoside. The ability of gapbreaker oligonucleotide to recruit RNaseH is typically sequence or even compound specific—see Rukov et al. 2015 Nucl. Acids Res. Vol. 43 pp. 8476-8487, which discloses "gapbreaker" oligonucleotides which recruit RNaseH which in some instances provide a more specific cleavage of the target RNA.

In some embodiments, the oligonucleotide of the invention is a gapbreaker oligonucleotide. In some embodiments the gapbreaker oligonucleotide comprise a 5'-flank (F), a gap (G) and a 3'-flank (F'), wherein the gap is disrupted by a non-RNaseH recruiting nucleoside (a gap-breaker nucleoside, E) such that the gap contain at least 3 or 4 consecutive DNA nucleosides. In some embodiments the gapbreaker nucleoside (E) is an LNA nucleoside where the bridge between C2' and C4' of the ribose sugar ring of a nucleoside is in the beta conformation and is placed within the gap region such that the gap-breaker LNA nucleoside is flanked 5' and 3' by at least 3 (5') and 3 (3') or at least 3 (5') and 4

(3') or at least 4(5') and 3(3') DNA nucleosides, and wherein the oligonucleotide is capable of recruiting RNaseH.

The gapbreaker oligonucleotide can be represented by the following formulae:

F-G-E-G-F'; in particular $F_{1-7}-G_{3-4}-E_1-G_{3-4}-F'_{1-7}$
D'-F-G-F', in particular $D'_{1-3}-F_{1-7}-G_{3-4}-E_1-G_{3-4}-F'_{1-7}$
F-G-F'-D", in particular $F_{1-7}-G_{3-4}-E_1-G_{3-4}-F'_{1-7}-D''_{1-3}$
D'-F-G-F'-D", in particular $D'_{1-3}-F_{1-7}-G_{3-4}-E_1-G_{3-4}-F'_{1-7}-D''_{1-3}$ Where region D' and D" are as described in the section "Gapmer design".

In some embodiments the gapbreaker nucleoside (E) is a beta-D-oxy LNA or ScET or another beta-LNA nucleosides shown in Scheme 1).

Conjugate

The term conjugate as used herein refers to an oligonucleotide which is covalently linked to a non-nucleotide moiety (conjugate moiety or region C or third region), also termed a oligonucleotide conjugate.

Conjugation of the oligonucleotides of the invention to one or more non-nucleotide moieties may improve the pharmacology of the oligonucleotide, e.g. by affecting the activity, cellular distribution, cellular uptake or stability of the oligonucleotide. In some embodiments the conjugate moiety targets the oligonucleotide to the liver. A the same time the conjugate serve to reduce activity of the oligonucleotide in non-target cell types, tissues or organs, e.g. off target activity or activity in non-target cell types, tissues or organs. In one embodiment of the invention the oligonucleotide conjugate of the invention display improved inhibition of PD-L1 in the target cell when compared to an unconjugated oligonucleotide. In another embodiment the oligonucleotide conjugate of the invention has improved cellular distribution between liver and other organs, such as spleen or kidney (i.e. more conjugated oligonucleotide goes to the liver than the spleen or kidney) when compared to an unconjugated oligonucleotide. In another embodiment the oligonucleotide conjugate of the invention show improved cellular uptake into the liver of the conjugate oligonucleotide when compared to an unconjugated oligonucleotide.

WO 93/07883 and WO2013/033230 provides suitable conjugate moieties, which are hereby incorporated by reference. Further suitable conjugate moieties are those capable of binding to the asialoglycoprotein receptor (ASGPr). In particular tri-valent N-acetylgalactosamine conjugate moieties are suitable for binding to the ASGPr, see for example WO 2014/076196, WO 2014/207232 and WO 2014/179620 (hereby incorporated by reference). The conjugate moiety is essentially the part of the antisense oligonucleotides conjugates which is not composed of nucleic acids.

Oligonucleotide conjugates and their synthesis has also been reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103, each of which is incorporated herein by reference in its entirety.

In an embodiment, the non-nucleotide moiety (conjugate moiety) is selected from the group consisting of carbohydrates, cell surface receptor ligands, drug substances, hormones, lipophilic substances, polymers, proteins, peptides, toxins (e.g. bacterial toxins), vitamins, viral proteins (e.g. capsids) or combinations thereof.

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety (Region C), to a first region, e.g. an oligonucleotide or contiguous nucleotide sequence complementary to the target nucleic acid (region A).

In some embodiments of the invention the conjugate or oligonucleotide conjugate of the invention may optionally, comprise a linker region (second region or region B and/or region Y) which is positioned between the oligonucleotide or contiguous nucleotide sequence complementary to the target nucleic acid (region A or first region) and the conjugate moiety (region C or third region).

Region B refers to biocleavable linkers comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. In a preferred embodiment the nuclease susceptible linker comprises between 1 and 10 nucleosides, such as 1, 2, 3, 4, 5, 6, 7, 8, 9 or 10 nucleosides, more preferably between 2 and 6 nucleosides and most preferably between 2 and 4 linked nucleosides comprising at least two consecutive phosphodiester linkages, such as at least 3 or 4 or 5 consecutive phosphodiester linkages. Preferably the nucleosides are DNA or RNA. Phosphodiester containing biocleavable linkers are described in more detail in WO 2014/076195 (hereby incorporated by reference).

Region Y refers to linkers that are not necessarily biocleavable but primarily serve to covalently connect a conjugate moiety (region C or third region), to an oligonucleotide or contiguous nucleotide sequence complementary to the target nucleic acid (region A or first region). The region Y linkers may comprise a chain structure or an oligomer of repeating units such as ethylene glycol, amino acid units or amino alkyl groups The oligonucleotide conjugates of the present invention can be constructed of the following regional elements A-C, A-B-C, A-B-Y-C, A-Y-B-C or A-Y-C. In some embodiments the linker (region Y) is an amino alkyl, such as a C2-C36 amino alkyl group, including, for example C6 to C12 amino alkyl groups. In a preferred embodiment the linker (region Y) is a C6 amino alkyl group.

Treatment

The term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic.

Restoration of Immune Response Against Pathogens

The immune response is divided into the innate and adaptive immune response. The innate immune system provides an immediate, but non-specific response. The adaptive immune response is activated by innate immune response and is highly specific to a particular pathogen. Upon presentation of a pathogen-derived antigen on the surface of antigen-presenting cells, immune cells of the adaptive immune response (i.e. T and B lymphocytes) are activated through their antigen-specific receptors leading to a pathogenic-specific immune response and development of immunological memory. Chronic viral infections, such as HBV and HCV, are associated with T cell exhaustion characterized by unresponsiveness of the viral-specific T cells. T cell exhaustion is well studied, for a review see for example Yi et al 2010 Immunology 129, 474-481. Chronic viral infections are also associated with reduced function of NK cells that are innate immune cells. Enhancing viral immune response is important for clearance of chronic infection. Restoration of immune response against pathogens, mediated by T cells and NK cells, can be assessed by measurement of proliferation, cytokine secretion and cytolytic function (Dolina et al. 2013 Molecular Therapy-Nucleic Acids, 2 e72 and Example 6 herein).

DETAILED DESCRIPTION OF THE INVENTION

The present invention relates to the use of antisense oligonucleotides and conjugates thereof and pharmaceutical compositions comprising these to restore immune response against pathogens that have infected an animal, in particular a human. The antisense oligonucleotide conjugates of the present invention are particular useful against pathogens that have infected the liver, in particular chronic liver infections like HBV. The conjugates allow targeted distribution of the oligonucleotides and prevents systemic knockdown of the target nucleic acid.

The Oligonucleotides of the Invention

The invention relates to oligonucleotides capable of modulating expression of PD-L1. The modulation is may achieved by hybridizing to a target nucleic acid encoding PD-L1 or which is involved in the regulation of PD-L1. The target nucleic acid may be a mammalian PD-L1 sequence, such as a sequence selected from the group consisting of SEQ ID NO: 1, SEQ ID NO: 2 and/or SEQ ID NO: 3. The target nucleic acid may be a pre-mRNA, an mRNA or any RNA sequence expressed from a mammalian cell that supports the expression or regulation of PD-L1.

The oligonucleotide of the invention is an antisense oligonucleotide which targets PD-L1.

In one aspect of the invention the oligonucleotides of the invention are conjugated to a conjugate moiety, in particular an asialoglycoprotein receptor targeting conjugate moiety.

In some embodiments the antisense oligonucleotide of the invention is capable of modulating the expression of the target by inhibiting or down-regulating it. Preferably, such modulation produces an inhibition of expression of at least 20% compared to the normal expression level of the target, more preferably at least 30%, 40%, 50%, 60%, 70%, 80%, or 90% inhibition compared to the normal expression level of the target. Preferably, such modulation produces an inhibition of expression of at least 20% compared to the expression level when the cell or organism is challenged by an infectious agent, or treated with an agent simulating the challenge by an infectious agent (eg poly I:C or LPS), more preferably at least 30%, 40%, 50%, 60%, 70%, 80%, or 90% inhibition compared to the expression level when the cell or organism is challenged by an infectious agent, or treated with an agent simulating the challenge by an infectious agent (eg poly I:C or LPS). In some embodiments oligonucleotides of the invention may be capable of inhibiting expression levels of PD-L1 mRNA by at least 60% or 70% in vitro using KARPAS-299 or THP1 cells. In some embodiments compounds of the invention may be capable of inhibiting expression levels of PD-L1 protein by at least 50% in vitro using KARPAS-299 or THP1 cells. Suitably, the examples provide assays which may be used to measure PD-L1 RNA (e.g. example 1). The target modulation is triggered by the hybridization between a contiguous nucleotide sequence of the oligonucleotide and the target nucleic acid. In some embodiments the oligonucleotide of the invention comprises mismatches between the oligonucleotide and the target nucleic acid. Despite mismatches, hybridization to the target nucleic acid may still be sufficient to show a desired modulation of PD-L1 expression. Reduced binding affinity resulting from mismatches may advantageously be compensated by increased number of nucleotides in the oligonucleotide and/or an increased number of modified nucleosides capable of increasing the binding affinity to the target, such as 2' modified nucleosides, including LNA, present within the oligonucleotide sequence.

In some embodiments the antisense oligonucleotide of the invention is capable of restoring pathogen-specific T cells. In some embodiments, oligonucleotides of the invention are capable of increasing the pathogen-specific T cells by at least 40%, 50%, 60% or 70% when compared to untreated controls or controls treated with standard of care. In one embodiment the antisense oligonucleotide or conjugate of the invention is capable increasing HBV-specific T cells when compared to untreated controls or controls treated with standard of care. Suitably, the examples provide assays which may be used to measure the HBV-specific T cells (e.g. T cell proliferation, cytokine secretion and cytolytic activity). In another embodiment the antisense oligonucleotide or conjugate of the invention is capable increasing HCV-specific T cells when compared to untreated controls or controls treated with standard of care. In another embodiment the antisense oligonucleotide or conjugate of the invention is capable increasing HDV-specific T cells when compared to untreated controls or controls treated with standard of care.

In some embodiments the antisense oligonucleotide of the invention is capable reducing HBsAg levels in an animal or human. In some embodiments, oligonucleotides of the invention are capable of reducing the HBsAg levels by at least 40%, 50%, 60% or 70%, more preferably by at least 80%, 90% or 95% when compared to the level prior to treatment. Most preferably oligonucleotides of the invention are capable of achieving seroconversion of HBsAg in an animal or human infected with HBV.

An aspect of the present invention relates to an antisense oligonucleotide which comprises a contiguous nucleotide sequence of 10 to 30 nucleotides in length with at least 90% complementarity to a PD-L1 target nucleic acid.

In some embodiments, the oligonucleotide comprises a contiguous sequence which is at least 90% complementary, such as at least 91%, such as at least 92%, such as at least 93%, such as at least 94%, such as at least 95%, such as at least 96%, such as at least 97%, such as at least 98%, or 100% complementary with a region of the target nucleic acid.

In a preferred embodiment the oligonucleotide of the invention, or contiguous nucleotide sequence thereof is fully complementary (100% complementary) to a region of the target nucleic acid, or in some embodiments may comprise one or two mismatches between the oligonucleotide and the target nucleic acid.

In some embodiments the oligonucleotide comprises a contiguous nucleotide sequence of 10 to 30 nucleotides in length with at least 90% complementary, such as fully (or 100%) complementary, to a region target nucleic acid region present in SEQ ID NO: 1 or SEQ ID NO: 2. In some embodiments the oligonucleotide sequence is 100% complementary to a corresponding target nucleic acid region present SEQ ID NO: 1 and SEQ ID NO: 2. In some embodiments the oligonucleotide sequence is 100% complementary to a corresponding target nucleic acid region present SEQ ID NO: 1 and SEQ ID NO: 3.

In some embodiments, the oligonucleotide or oligonucleotide conjugate comprises a contiguous nucleotide sequence of 10 to 30 nucleotides in length with at least 90% complementary, such as 100% complementarity, to a corresponding target nucleic acid region wherein the contiguous nucleotide sequence is complementary to a sub-sequence of the target nucleic acid selected from the group consisting of position 371-3068, 5467-12107 and 15317-19511 on SEQ ID NO: 1. In a further embodiment the sub-sequence of the target nucleic acid is selected from the group consisting of position 371-510, 822-1090, 1992-3068, 5467-5606, 6470-12107, 15317-15720, 15317-18083, 18881-19494 and 1881-19494 on SEQ ID NO: 1. In a preferred embodiment the sub-sequence of the target nucleic acid is selected from the group consisting of position 7300-7333, 8028-8072, 9812-9859, 11787-11873 and 15690-15735 on SEQ ID NO: 1.

In some embodiments, the oligonucleotide or oligonucleotide conjugate comprises a contiguous nucleotide sequence of 10 to 30 nucleotides in length with at least 90% complementary, such as 100% complementarity, to a corresponding target nucleic acid region present in SEQ ID NO: 1, wherein the target nucleic acid region is selected from the group consisting of region a1 to a449 in table 4.

TABLE 4

Regions of SEQ ID NO 1 which may be targeted using oligonucleotide of the invention Position in SEQ ID NO 1

| Reg. a | from | to | Length |
|---|---|---|---|
| a1 | 51 | 82 | 32 |
| a2 | 87 | 116 | 30 |
| a3 | 118 | 133 | 16 |
| a4 | 173 | 206 | 34 |
| a5 | 221 | 287 | 67 |
| a6 | 304 | 350 | 47 |
| a7 | 354 | 387 | 34 |
| a8 | 389 | 423 | 35 |
| a9 | 425 | 440 | 16 |
| a10 | 452 | 468 | 17 |
| a11 | 470 | 484 | 15 |
| a12 | 486 | 500 | 15 |
| a13 | 503 | 529 | 27 |
| a14 | 540 | 574 | 35 |
| a15 | 576 | 649 | 74 |
| a16 | 652 | 698 | 47 |
| a17 | 700 | 750 | 51 |
| a18 | 744 | 758 | 15 |
| a19 | 774 | 801 | 28 |
| a20 | 805 | 820 | 16 |
| a21 | 827 | 891 | 65 |
| a22 | 915 | 943 | 29 |
| a23 | 950 | 982 | 33 |
| a24 | 984 | 1000 | 17 |
| a25 | 1002 | 1054 | 53 |
| a26 | 1060 | 1118 | 59 |
| a27 | 1124 | 1205 | 82 |
| a28 | 1207 | 1255 | 49 |
| a29 | 1334 | 1349 | 16 |
| a30 | 1399 | 1425 | 27 |
| a31 | 1437 | 1458 | 22 |
| a32 | 1460 | 1504 | 45 |
| a33 | 1548 | 1567 | 20 |
| a34 | 1569 | 1586 | 18 |
| a35 | 1608 | 1662 | 55 |
| a36 | 1677 | 1700 | 24 |
| a37 | 1702 | 1721 | 20 |

TABLE 4-continued

Regions of SEQ ID NO 1 which may be targeted using oligonucleotide of the invention Position in SEQ ID NO 1

| Reg. a | from | to | Length |
|---|---|---|---|
| a38 | 1723 | 1745 | 23 |
| a39 | 1768 | 1794 | 27 |
| a40 | 1820 | 1835 | 16 |
| a41 | 1842 | 1874 | 33 |
| a42 | 1889 | 1979 | 91 |
| a43 | 1991 | 2011 | 21 |
| a44 | 2013 | 2038 | 26 |
| a45 | 2044 | 2073 | 30 |
| a46 | 2075 | 2155 | 81 |
| a47 | 2205 | 2228 | 24 |
| a48 | 2253 | 2273 | 21 |
| a49 | 2275 | 2303 | 29 |
| a50 | 2302 | 2333 | 32 |
| a51 | 2335 | 2366 | 32 |
| a52 | 2368 | 2392 | 25 |
| a53 | 2394 | 2431 | 38 |
| a54 | 2441 | 2455 | 15 |
| a55 | 2457 | 2494 | 38 |
| a56 | 2531 | 2579 | 49 |
| a57 | 2711 | 2732 | 22 |
| a58 | 2734 | 2757 | 24 |
| a59 | 2772 | 2786 | 15 |
| a60 | 2788 | 2819 | 32 |
| a61 | 2835 | 2851 | 17 |
| a62 | 2851 | 2879 | 29 |
| a63 | 2896 | 2912 | 17 |
| a64 | 2915 | 2940 | 26 |
| a65 | 2944 | 2973 | 30 |
| a66 | 2973 | 2992 | 20 |
| a67 | 2998 | 3016 | 19 |
| a68 | 3018 | 3033 | 16 |
| a69 | 3036 | 3051 | 16 |
| a70 | 3114 | 3139 | 26 |
| a71 | 3152 | 3173 | 22 |
| a72 | 3181 | 3203 | 23 |
| a73 | 3250 | 3271 | 22 |
| a74 | 3305 | 3335 | 31 |
| a75 | 3346 | 3363 | 18 |
| a76 | 3391 | 3446 | 56 |
| a77 | 3448 | 3470 | 23 |
| a78 | 3479 | 3497 | 19 |
| a79 | 3538 | 3554 | 17 |
| a80 | 3576 | 3597 | 22 |
| a81 | 3603 | 3639 | 37 |
| a82 | 3663 | 3679 | 17 |
| a83 | 3727 | 3812 | 86 |
| a84 | 3843 | 3869 | 27 |
| a85 | 3874 | 3904 | 31 |
| a86 | 3926 | 3955 | 30 |
| a87 | 3974 | 3993 | 20 |
| a88 | 3995 | 4042 | 48 |
| a89 | 4053 | 4073 | 21 |
| a90 | 4075 | 4123 | 49 |
| a91 | 4133 | 4157 | 25 |
| a92 | 4158 | 4188 | 31 |
| a93 | 4218 | 4250 | 33 |
| a94 | 4277 | 4336 | 60 |
| a95 | 4353 | 4375 | 23 |
| a96 | 4383 | 4398 | 16 |
| a97 | 4405 | 4446 | 42 |
| a98 | 4448 | 4464 | 17 |
| a99 | 4466 | 4493 | 28 |
| a100 | 4495 | 4558 | 64 |
| a101 | 4571 | 4613 | 43 |
| a102 | 4624 | 4683 | 60 |
| a103 | 4743 | 4759 | 17 |
| a104 | 4761 | 4785 | 25 |
| a105 | 4811 | 4858 | 48 |
| a106 | 4873 | 4932 | 60 |
| a107 | 4934 | 4948 | 15 |
| a108 | 4955 | 4974 | 20 |
| a109 | 4979 | 5010 | 32 |
| a110 | 5012 | 5052 | 41 |

TABLE 4-continued

Regions of SEQ ID NO 1 which may be targeted using oligonucleotide of the invention Position in SEQ ID NO 1

| Reg. a | from | to | Length |
|---|---|---|---|
| a111 | 5055 | 5115 | 61 |
| a112 | 5138 | 5166 | 29 |
| a113 | 5168 | 5198 | 31 |
| a114 | 5200 | 5222 | 23 |
| a115 | 5224 | 5284 | 61 |
| a116 | 5286 | 5302 | 17 |
| a117 | 5317 | 5332 | 16 |
| a118 | 5349 | 5436 | 88 |
| a119 | 5460 | 5512 | 53 |
| a120 | 5514 | 5534 | 21 |
| a121 | 5548 | 5563 | 16 |
| a122 | 5565 | 5579 | 15 |
| a123 | 5581 | 5597 | 17 |
| a124 | 5600 | 5639 | 40 |
| a125 | 5644 | 5661 | 18 |
| a126 | 5663 | 5735 | 73 |
| a127 | 5737 | 5770 | 34 |
| a128 | 5778 | 5801 | 24 |
| a129 | 5852 | 5958 | 107 |
| a130 | 6007 | 6041 | 35 |
| a131 | 6049 | 6063 | 15 |
| a132 | 6065 | 6084 | 20 |
| a133 | 6086 | 6101 | 16 |
| a134 | 6119 | 6186 | 68 |
| a135 | 6189 | 6234 | 46 |
| a136 | 6236 | 6278 | 43 |
| a137 | 6291 | 6312 | 22 |
| a138 | 6314 | 6373 | 60 |
| a139 | 6404 | 6447 | 44 |
| a140 | 6449 | 6482 | 34 |
| a141 | 6533 | 6555 | 23 |
| a142 | 6562 | 6622 | 61 |
| a143 | 6624 | 6674 | 51 |
| a144 | 6679 | 6762 | 84 |
| a145 | 6764 | 6780 | 17 |
| a146 | 6782 | 6822 | 41 |
| a147 | 6824 | 6856 | 33 |
| a148 | 6858 | 6898 | 41 |
| a149 | 6906 | 6954 | 49 |
| a150 | 6969 | 6992 | 24 |
| a151 | 6994 | 7020 | 27 |
| a152 | 7033 | 7048 | 16 |
| a153 | 7050 | 7066 | 17 |
| a154 | 7078 | 7094 | 17 |
| a155 | 7106 | 7122 | 17 |
| a156 | 7123 | 7144 | 22 |
| a157 | 7146 | 7166 | 21 |
| a158 | 7173 | 7193 | 21 |
| a159 | 7233 | 7291 | 59 |
| a160 | 7300 | 7333 | 34 |
| a161 | 7336 | 7351 | 16 |
| a162 | 7353 | 7373 | 21 |
| a163 | 7375 | 7412 | 38 |
| a164 | 7414 | 7429 | 16 |
| a165 | 7431 | 7451 | 21 |
| a166 | 7453 | 7472 | 20 |
| a167 | 7474 | 7497 | 24 |
| a168 | 7517 | 7532 | 16 |
| a169 | 7547 | 7601 | 55 |
| a170 | 7603 | 7617 | 15 |
| a171 | 7632 | 7647 | 16 |
| a172 | 7649 | 7666 | 18 |
| a173 | 7668 | 7729 | 62 |
| a174 | 7731 | 7764 | 34 |
| a175 | 7767 | 7817 | 51 |
| a176 | 7838 | 7860 | 23 |
| a177 | 7862 | 7876 | 15 |
| a178 | 7880 | 7944 | 65 |
| a179 | 7964 | 8012 | 49 |
| a180 | 8028 | 8072 | 45 |
| a181 | 8086 | 8100 | 15 |
| a182 | 8102 | 8123 | 22 |
| a183 | 8125 | 8149 | 25 |
| a184 | 8151 | 8199 | 49 |
| a185 | 8218 | 8235 | 18 |
| a186 | 8237 | 8276 | 40 |
| a187 | 8299 | 8344 | 46 |
| a188 | 8346 | 8436 | 91 |
| a189 | 8438 | 8470 | 33 |
| a190 | 8472 | 8499 | 28 |
| a191 | 8505 | 8529 | 25 |
| a192 | 8538 | 8559 | 22 |
| a193 | 8562 | 8579 | 18 |
| a194 | 8581 | 8685 | 105 |
| a195 | 8688 | 8729 | 42 |
| a196 | 8730 | 8751 | 22 |
| a197 | 8777 | 8800 | 24 |
| a198 | 8825 | 8865 | 41 |
| a199 | 8862 | 8894 | 33 |
| a200 | 8896 | 8911 | 16 |
| a201 | 8938 | 8982 | 45 |
| a202 | 8996 | 9045 | 50 |
| a203 | 9048 | 9070 | 23 |
| a204 | 9072 | 9139 | 68 |
| a205 | 9150 | 9168 | 19 |
| a206 | 9170 | 9186 | 17 |
| a207 | 9188 | 9202 | 15 |
| a208 | 9204 | 9236 | 33 |
| a209 | 9252 | 9283 | 32 |
| a210 | 9300 | 9331 | 32 |
| a211 | 9339 | 9354 | 16 |
| a212 | 9370 | 9398 | 29 |
| a213 | 9400 | 9488 | 89 |
| a214 | 9490 | 9537 | 48 |
| a215 | 9611 | 9695 | 85 |
| a216 | 9706 | 9721 | 16 |
| a217 | 9723 | 9746 | 24 |
| a218 | 9748 | 9765 | 18 |
| a219 | 9767 | 9788 | 22 |
| a220 | 9794 | 9808 | 15 |
| a221 | 9812 | 9859 | 48 |
| a222 | 9880 | 9913 | 34 |
| a223 | 9923 | 9955 | 33 |
| a224 | 9966 | 10007 | 42 |
| a225 | 10009 | 10051 | 43 |
| a226 | 10053 | 10088 | 36 |
| a227 | 10098 | 10119 | 22 |
| a228 | 10133 | 10163 | 31 |
| a229 | 10214 | 10240 | 27 |
| a230 | 10257 | 10272 | 16 |
| a231 | 10281 | 10298 | 18 |
| a232 | 10300 | 10318 | 19 |
| a233 | 10339 | 10363 | 25 |
| a234 | 10409 | 10426 | 18 |
| a235 | 10447 | 10497 | 51 |
| a236 | 10499 | 10529 | 31 |
| a237 | 10531 | 10546 | 16 |
| a238 | 10560 | 10580 | 21 |
| a239 | 10582 | 10596 | 15 |
| a240 | 10600 | 10621 | 22 |
| a241 | 10623 | 10664 | 42 |
| a242 | 10666 | 10685 | 20 |
| a243 | 10717 | 10773 | 57 |
| a244 | 10775 | 10792 | 18 |
| a245 | 10794 | 10858 | 65 |
| a246 | 10874 | 10888 | 15 |
| a247 | 10893 | 10972 | 80 |
| a248 | 10974 | 10994 | 21 |
| a249 | 10996 | 11012 | 17 |
| a250 | 11075 | 11097 | 23 |
| a251 | 11099 | 11124 | 26 |
| a252 | 11140 | 11157 | 18 |
| a253 | 11159 | 11192 | 34 |
| a254 | 11195 | 11226 | 32 |
| a255 | 11235 | 11261 | 27 |
| a256 | 11279 | 11337 | 59 |

TABLE 4-continued

Regions of SEQ ID NO 1 which may be targeted using oligonucleotide of the invention Position in SEQ ID NO 1

| Reg. a | from | to | Length |
|---|---|---|---|
| a257 | 11344 | 11381 | 38 |
| a258 | 11387 | 11411 | 25 |
| a259 | 11427 | 11494 | 68 |
| a260 | 11496 | 11510 | 15 |
| a261 | 11512 | 11526 | 15 |
| a262 | 11528 | 11551 | 24 |
| a263 | 11570 | 11592 | 23 |
| a264 | 11594 | 11634 | 41 |
| a265 | 11664 | 11684 | 21 |
| a266 | 11699 | 11719 | 21 |
| a267 | 11721 | 11746 | 26 |
| a268 | 11753 | 11771 | 19 |
| a269 | 11787 | 11873 | 87 |
| a270 | 11873 | 11905 | 33 |
| a271 | 11927 | 11942 | 16 |
| a272 | 11946 | 11973 | 28 |
| a273 | 11975 | 11993 | 19 |
| a274 | 12019 | 12114 | 96 |
| a275 | 12116 | 12135 | 20 |
| a276 | 12137 | 12158 | 22 |
| a277 | 12165 | 12192 | 28 |
| a278 | 12194 | 12216 | 23 |
| a279 | 12218 | 12246 | 29 |
| a280 | 12262 | 12277 | 16 |
| a281 | 12283 | 12319 | 37 |
| a282 | 12334 | 12368 | 35 |
| a283 | 12370 | 12395 | 26 |
| a284 | 12397 | 12434 | 38 |
| a285 | 12436 | 12509 | 74 |
| a286 | 12511 | 12543 | 33 |
| a287 | 12545 | 12565 | 21 |
| a288 | 12567 | 12675 | 109 |
| a289 | 12677 | 12706 | 30 |
| a290 | 12708 | 12724 | 17 |
| a291 | 12753 | 12768 | 16 |
| a292 | 12785 | 12809 | 25 |
| a293 | 12830 | 12859 | 30 |
| a294 | 12864 | 12885 | 22 |
| a295 | 12886 | 12916 | 31 |
| a296 | 12922 | 12946 | 25 |
| a297 | 12948 | 12970 | 23 |
| a298 | 12983 | 13003 | 21 |
| a299 | 13018 | 13051 | 34 |
| a300 | 13070 | 13090 | 21 |
| a301 | 13092 | 13115 | 24 |
| a302 | 13117 | 13134 | 18 |
| a303 | 13136 | 13169 | 34 |
| a304 | 13229 | 13249 | 21 |
| a305 | 13295 | 13328 | 34 |
| a306 | 13330 | 13372 | 43 |
| a307 | 13388 | 13406 | 19 |
| a308 | 13408 | 13426 | 19 |
| a309 | 13437 | 13453 | 17 |
| a310 | 13455 | 13471 | 17 |
| a311 | 13518 | 13547 | 30 |
| a312 | 13565 | 13597 | 33 |
| a313 | 13603 | 13620 | 18 |
| a314 | 13630 | 13663 | 34 |
| a315 | 13665 | 13679 | 15 |
| a316 | 13706 | 13725 | 20 |
| a317 | 13727 | 13774 | 48 |
| a318 | 13784 | 13821 | 38 |
| a319 | 13831 | 13878 | 48 |
| a320 | 13881 | 13940 | 60 |
| a321 | 13959 | 14013 | 55 |
| a322 | 14015 | 14031 | 17 |
| a323 | 14034 | 14049 | 16 |
| a324 | 14064 | 14114 | 51 |
| a325 | 14116 | 14226 | 111 |
| a326 | 14229 | 14276 | 48 |
| a327 | 14292 | 14306 | 15 |
| a328 | 14313 | 14384 | 72 |
| a329 | 14386 | 14408 | 23 |
| a330 | 14462 | 14481 | 20 |
| a331 | 14494 | 14519 | 26 |
| a332 | 14557 | 14577 | 21 |
| a333 | 14608 | 14628 | 21 |
| a334 | 14646 | 14668 | 23 |
| a335 | 14680 | 14767 | 88 |
| a336 | 14765 | 14779 | 15 |
| a337 | 14815 | 14844 | 30 |
| a338 | 14848 | 14925 | 78 |
| a339 | 14934 | 14976 | 43 |
| a340 | 14978 | 15009 | 32 |
| a341 | 15013 | 15057 | 45 |
| a342 | 15064 | 15091 | 28 |
| a343 | 15094 | 15140 | 47 |
| a344 | 15149 | 15165 | 17 |
| a345 | 15162 | 15182 | 21 |
| a346 | 15184 | 15198 | 15 |
| a347 | 15200 | 15221 | 22 |
| a348 | 15232 | 15247 | 16 |
| a349 | 15250 | 15271 | 22 |
| a350 | 15290 | 15334 | 45 |
| a351 | 15336 | 15369 | 34 |
| a352 | 15394 | 15416 | 23 |
| a353 | 15433 | 15451 | 19 |
| a354 | 15453 | 15491 | 39 |
| a355 | 15496 | 15511 | 16 |
| a356 | 15520 | 15553 | 34 |
| a357 | 15555 | 15626 | 72 |
| a358 | 15634 | 15652 | 19 |
| a359 | 15655 | 15688 | 34 |
| a360 | 15690 | 15735 | 46 |
| a361 | 15734 | 15764 | 31 |
| a362 | 15766 | 15787 | 22 |
| a363 | 15803 | 15819 | 17 |
| a364 | 15846 | 15899 | 54 |
| a365 | 15901 | 15934 | 34 |
| a366 | 15936 | 15962 | 27 |
| a367 | 15964 | 15985 | 22 |
| a368 | 15987 | 16023 | 37 |
| a369 | 16025 | 16061 | 37 |
| a370 | 16102 | 16122 | 21 |
| a371 | 16134 | 16183 | 50 |
| a372 | 16185 | 16281 | 97 |
| a373 | 16283 | 16298 | 16 |
| a374 | 16305 | 16323 | 19 |
| a375 | 16325 | 16356 | 32 |
| a376 | 16362 | 16404 | 43 |
| a377 | 16406 | 16456 | 51 |
| a378 | 16494 | 16523 | 30 |
| a379 | 16536 | 16562 | 27 |
| a380 | 16564 | 16580 | 17 |
| a381 | 16582 | 16637 | 56 |
| a382 | 16631 | 16649 | 19 |
| a383 | 16655 | 16701 | 47 |
| a384 | 16737 | 16781 | 45 |
| a385 | 16783 | 16804 | 22 |
| a386 | 16832 | 16907 | 76 |
| a387 | 16934 | 16965 | 32 |
| a388 | 16972 | 17035 | 64 |
| a389 | 17039 | 17069 | 31 |
| a390 | 17072 | 17109 | 38 |
| a391 | 17135 | 17150 | 16 |
| a392 | 17167 | 17209 | 43 |
| a393 | 17211 | 17242 | 32 |
| a394 | 17244 | 17299 | 56 |
| a395 | 17304 | 17344 | 41 |
| a396 | 17346 | 17400 | 55 |
| a397 | 17447 | 17466 | 20 |
| a398 | 17474 | 17539 | 66 |
| a399 | 17561 | 17604 | 44 |
| a400 | 17610 | 17663 | 54 |
| a401 | 17681 | 17763 | 83 |
| a402 | 17793 | 17810 | 18 |

TABLE 4-continued

Regions of SEQ ID NO 1 which may be targeted using oligonucleotide of the invention

| | Position in SEQ ID NO 1 | | |
|---|---|---|---|
| Reg. a | from | to | Length |
| a403 | 17812 | 17852 | 41 |
| a404 | 17854 | 17928 | 75 |
| a405 | 17941 | 18005 | 65 |
| a406 | 18007 | 18035 | 29 |
| a407 | 18041 | 18077 | 37 |
| a408 | 18085 | 18146 | 62 |
| a409 | 18163 | 18177 | 15 |
| a410 | 18179 | 18207 | 29 |
| a411 | 18209 | 18228 | 20 |
| a412 | 18230 | 18266 | 37 |
| a413 | 18268 | 18285 | 18 |
| a414 | 18287 | 18351 | 65 |
| a415 | 18365 | 18395 | 31 |
| a416 | 18402 | 18432 | 31 |
| a417 | 18434 | 18456 | 23 |
| a418 | 18502 | 18530 | 29 |
| a419 | 18545 | 18590 | 46 |
| a420 | 18603 | 18621 | 19 |
| a421 | 18623 | 18645 | 23 |
| a422 | 18651 | 18708 | 58 |
| a423 | 18710 | 18729 | 20 |
| a424 | 18731 | 18758 | 28 |
| a425 | 18760 | 18788 | 29 |
| a426 | 18799 | 18859 | 61 |
| a427 | 18861 | 18926 | 66 |
| a428 | 18928 | 18980 | 53 |
| a429 | 19001 | 19018 | 18 |
| a430 | 19034 | 19054 | 21 |
| a431 | 19070 | 19092 | 23 |
| a432 | 19111 | 19154 | 44 |
| a433 | 19191 | 19213 | 23 |
| a434 | 19215 | 19240 | 26 |
| a435 | 19255 | 19356 | 102 |
| a436 | 19358 | 19446 | 89 |
| a437 | 19450 | 19468 | 19 |
| a438 | 19470 | 19512 | 43 |
| a439 | 19514 | 19541 | 28 |
| a440 | 19543 | 19568 | 26 |
| a441 | 19570 | 19586 | 17 |
| a442 | 19588 | 19619 | 32 |
| a443 | 19683 | 19739 | 57 |
| a444 | 19741 | 19777 | 37 |
| a445 | 19779 | 19820 | 42 |
| a446 | 19822 | 19836 | 15 |
| a447 | 19838 | 19911 | 74 |
| a448 | 19913 | 19966 | 54 |
| a449 | 19968 | 20026 | 59 |

In some embodiment the oligonucleotide or contiguous nucleotide sequence is complementary to a region of the target nucleic acid, wherein the target nucleic acid region is selected from the group consisting of a7, a26, a43, a119, a142, a159, a160, a163, a169, a178, a179, a180, a189, a201, a202, a204, a214, a221, a224, a226, a243, a254, a258, 269, a274, a350, a360, a364, a365, a370, a372, a381, a383, a386, a389, a400, a427, a435 and a438.

In a preferred embodiment the oligonucleotide or contiguous nucleotide sequence is complementary to a region of the target nucleic acid, wherein the target nucleic acid region is selected from the group consisting of a160, a180, a221, a269 and a360.

In some embodiments, the oligonucleotide of the invention comprises or consists of 8 to 35 nucleotides in length, such as from 9 to 30, such as 10 to 22, such as from 11 to 20, such as from 12 to 18, such as from 13 to 17 or 14 to 16 contiguous nucleotides in length. In a preferred embodiment, the oligonucleotide comprises or consists of 16 to 20 nucleotides in length. It is to be understood that any range given herein includes the range endpoints. Accordingly, if an oligonucleotide is said to include from 10 to 30 nucleotides, both 10 and 30 nucleotides are included.

In some embodiments, the contiguous nucleotide sequence comprises or consists of 8, 9, 10, 11, 12, 13, 14, 15, 16, 17, 18, 19, 20, 21, 22, 23, 24, 25, 26, 27, 28, 29 or 30 contiguous nucleotides in length. In a preferred embodiment, the oligonucleotide comprises or consists of 16, 17, 18, 19 or 20 nucleotides in length.

In some embodiments, the oligonucleotide or contiguous nucleotide sequence comprises or consists of a sequence selected from the group consisting of sequences listed in table 5.

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 5 to 743 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 5 to 743 and 771.

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 6, 8, 9, 13, 41, 42, 58, 77, 92, 111, 128, 151, 164, 166, 169, 171, 222, 233, 245, 246, 250, 251, 252, 256, 272, 273, 287, 292, 303, 314, 318, 320, 324, 336, 342, 343, 344, 345, 346, 349, 359, 360, 374, 408, 409, 415, 417, 424, 429, 430, 458, 464, 466, 474, 490, 493, 512, 519, 519, 529, 533, 534, 547, 566, 567, 578, 582, 601, 619, 620, 636, 637, 638, 640, 645, 650, 651, 652, 653, 658, 659, 660, 665, 678, 679, 680, 682, 683, 684, 687, 694, 706, 716, 728, 733, 734, and 735.

In some embodiments, the antisense oligonucleotide or contiguous nucleotide sequence comprises or consists of 10 to 30 nucleotides in length with at least 90% identity, preferably 100% identity, to SEQ ID NO: 287.

In some embodiments, the antisense oligonucleotide or contiguous nucleotide sequence comprises or consists of 10 to 30 nucleotides in length with at least 90% identity, preferably 100% identity, to SEQ ID NO: 342.

In some embodiments, the antisense oligonucleotide or contiguous nucleotide sequence comprises or consists of 10 to 30 nucleotides in length with at least 90% identity, preferably 100% identity, to SEQ ID NO: 640.

In some embodiments, the antisense oligonucleotide or contiguous nucleotide sequence comprises or consists of 10 to 30 nucleotides in length with at least 90% identity, preferably 100% identity, to SEQ ID NO: 466.

In some embodiments, the antisense oligonucleotide or contiguous nucleotide sequence comprises or consists of 10 to 30 nucleotides in length with at least 90% identity, preferably 100% identity, to SEQ ID NO: 566.

In embodiments where the oligonucleotide is longer than the contiguous nucleotide sequence (which is complementary to the target nucleic acid), the motif sequences in table 5 form the contiguous nucleotide sequence part of the antisense oligonucleotides of the invention. In some embodiments the sequence of the oligonucleotide is equivalent to the contiguous nucleotide sequence (e.g. if no biocleavable linkers are added).

It is understood that the contiguous nucleobase sequences (motif sequence) can be modified to for example increase nuclease resistance and/or binding affinity to the target nucleic acid.

Modifications are described in the definitions and in the "Oligonucleotide design" section. Table 5 lists preferred designs of each motif sequence.

Oligonucleotide Design

Oligonucleotide design refers to the pattern of nucleoside sugar modifications in the oligonucleotide sequence. The oligonucleotides of the invention comprise sugar-modified nucleosides and may also comprise DNA or RNA nucleosides. In some embodiments, the oligonucleotide comprises sugar-modified nucleosides and DNA nucleosides. Incorporation of modified nucleosides into the oligonucleotide of the invention may enhance the affinity of the oligonucleotide for the target nucleic acid. In that case, the modified nucleosides can be referred to as affinity enhancing modified nucleotides, the modified nucleosides may also be termed units.

In an embodiment, the oligonucleotide comprises at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides. In an embodiment the oligonucleotide comprises from 1 to 10 modified nucleosides, such as from 2 to 8 modified nucleosides, such as from 3 to 7 modified nucleosides, such as from 4 to 6 modified nucleosides, such as 3, 4, 5, 6 or 7 modified nucleosides.

In an embodiment, the oligonucleotide comprises one or more sugar modified nucleosides, such as 2' sugar modified nucleosides. Preferably the oligonucleotide of the invention comprise the one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. Even more preferably the one or more modified nucleoside is a locked nucleic acid (LNA).

In a further embodiment the oligonucleotide comprises at least one modified internucleoside linkage. In a preferred embodiment all the internucleoside linkages within the contiguous nucleotide sequence are phosphorothioate or boranophosphate internucleoside linkages. In some embodiments all the internucleotide linkages in the contiguous sequence of the oligonucleotide are phosphorothioate linkages.

In some embodiments, the oligonucleotide of the invention comprises at least one LNA nucleoside, such as 1, 2, 3, 4, 5, 6, 7, or 8 LNA nucleosides, such as from 2 to 6 LNA nucleosides, such as from 3 to 7 LNA nucleosides, 4 to 6 LNA nucleosides or 3, 4, 5, 6 or 7 LNA nucleosides. In some embodiments, at least 75% of the modified nucleosides in the oligonucleotide are LNA nucleosides, such as 80%, such as 85%, such as 90% of the modified nucleosides are LNA nucleosides. In a still further embodiment all the modified nucleosides in the oligonucleotide are LNA nucleosides. In a further embodiment, the oligonucleotide may comprise both beta-D-oxy-LNA, and one or more of the following LNA nucleosides: thio-LNA, amino-LNA, oxy-LNA, and/or ENA in either the beta-D or alpha-L configurations or combinations thereof. In a further embodiment, all LNA cytosine units are 5-methyl-cytosine. In a preferred embodiment the oligonucleotide or contiguous nucleotide sequence has at least 1 LNA nucleoside at the 5' end and at least 2 LNA nucleosides at the 3' end of the nucleotide sequence.

In some embodiments, the oligonucleotide of the invention comprises at least one modified nucleoside which is a 2'-MOE-RNA nucleoside, such as 2, 3, 4, 5, 6, 7, 8, 9 or 10 2'-MOE-RNA nucleosides. In some embodiments, at least one of said modified nucleoside is 2'-fluoro DNA, such as 2, 3, 4, 5, 6, 7, 8, 9 or 10 2'-fluoro-DNA nucleosides.

In some embodiments, the oligonucleotide of the invention comprises at least one LNA nucleoside and at least one 2' substituted modified nucleoside.

In some embodiments of the invention, the oligonucleotide comprise both 2' sugar modified nucleosides and DNA units. Preferably the oligonucleotide comprises both LNA and DNA nucleosides (units). Preferably, the combined total of LNA and DNA units is 8-30, such as 10-25, preferably 12-22, such as 12-18, even more preferably 11-16. In some embodiments of the invention, the nucleotide sequence of the oligonucleotide, such as the contiguous nucleotide sequence consists of at least one or two LNA nucleosides and the remaining nucleosides are DNA units. In some embodiments the oligonucleotide comprises only LNA nucleosides and naturally occurring nucleosides (such as RNA or DNA, most preferably DNA nucleosides), optionally with modified internucleoside linkages such as phosphorothioate.

In an embodiment of the invention the oligonucleotide of the invention is capable of recruiting RNase H.

The structural design of the oligonucleotide of the invention may be selected from gapmers, gapbreakers, headmers and tailmers.

Gapmer Design

In a preferred embodiment the oligonucleotide of the invention has a gapmer design or structure also referred herein merely as "Gapmer". In a gapmer structure the oligonucleotide comprises at least three distinct structural regions a 5'-flank, a gap and a 3'-flank, F-G-F' in '5→3' orientation. In this design, flanking regions F and F' (also termed wing regions) comprise a contiguous stretch of modified nucleosides, which are complementary to the PD-L1 target nucleic acid, while the gap region, G, comprises a contiguous stretch of nucleotides which are capable of recruiting a nuclease, preferably an endonuclease such as RNase, for example RNase H, when the oligonucleotide is in duplex with the target nucleic acid. Nucleosides which are capable of recruiting a nuclease, in particular RNase H, can be selected from the group consisting of DNA, alpha-L-oxy-LNA, 2'-Flouro-ANA and UNA. Regions F and F', flanking the 5' and 3' ends of region G, preferably comprise non-nuclease recruiting nucleosides (nucleosides with a 3' endo structure), more preferably one or more affinity enhancing modified nucleosides. In some embodiments, the 3' flank comprises at least one LNA nucleoside, preferably at least 2 LNA nucleosides. In some embodiments, the 5' flank comprises at least one LNA nucleoside. In some embodiments both the 5' and 3' flanking regions comprise a LNA nucleoside. In some embodiments all the nucleosides in the flanking regions are LNA nucleosides. In other embodiments, the flanking regions may comprise both LNA nucleosides and other nucleosides (mixed flanks), such as DNA nucleosides and/or non-LNA modified nucleosides, such as 2' substituted nucleosides. In this case the gap is defined as a contiguous sequence of at least 5 RNase H recruiting nucleosides (nucleosides with a 2' endo structure, preferably DNA) flanked at the 5' and 3' end by an affinity enhancing modified nucleoside, preferably LNA, such as beta-D-oxy-LNA. Consequently, the nucleosides of the 5' flanking region and the 3' flanking region which are adjacent to the gap region are modified nucleosides, preferably non-nuclease recruiting nucleosides.

Region F

Region F (5' flank or 5' wing) attached to the '5 end of region G comprises, contains or consists of at least one modified nucleoside such as at least 2, at least 3, at least 4, at least 5, at least 6, at least 7 modified nucleosides. In an embodiment region F comprises or consists of from 1 to 7 modified nucleosides, such as from 2 to 6 modified nucleosides, such as from 2 to 5 modified nucleosides, such as from 2 to 4 modified nucleosides, such as from 1 to 3 modified nucleosides, such as 1, 2, 3 or 4 modified nucleosides. The F region is defined by having at least on modified nucleoside at the 5' end and at the 3' end of the region.

In some embodiments, the modified nucleosides in region F have a 3' endo structure.

In an embodiment, one or more of the modified nucleosides in region F are 2' modified nucleosides. In one embodiment all the nucleosides in Region F are 2' modified nucleosides.

In another embodiment region F comprises DNA and/or RNA in addition to the 2' modified nucleosides. Flanks comprising DNA and/or RNA are characterized by having a 2' modified nucleoside in the 5' end and the 3' end (adjacent to the G region) of the F region. In one embodiment the region F comprise DNA nucleosides, such as from 1 to 3 contiguous DNA nucleosides, such as 1 to 3 or 1 to 2 contiguous DNA nucleosides. The DNA nucleosides in the flanks should preferably not be able to recruit RNase H. In some embodiments the 2' modified nucleosides and DNA and/or RNA nucleosides in the F region alternate with 1 to 3 2' modified nucleosides and 1 to 3 DNA and/or RNA nucleosides. Such flanks can also be termed alternating flanks. The length of the 5' flank (region F) in oligonucleotides with alternating flanks may be 4 to 10 nucleosides, such as 4 to 8, such as 4 to 6 nucleosides, such as 4, 5, 6 or 7 modified nucleosides. In some embodiments only the 5' flank of the oligonucleotide is alternating. Specific examples of region F with alternating nucleosides are

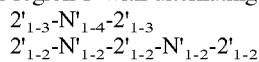

Where 2' indicates a modified nucleoside and N' is a RNA or DNA. In some embodiments all the modified nucleosides in the alternating flanks are LNA and the N' is DNA. In a further embodiment one or more of the 2' modified nucleosides in region F are selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In some embodiments the F region comprises both LNA and a 2' substituted modified nucleoside. These are often termed mixed wing or mixed flank oligonucleotides.

In one embodiment of the invention all the modified nucleosides in region F are LNA nucleosides. In a further embodiment all the nucleosides in Region F are LNA nucleosides. In a further embodiment the LNA nucleosides in region F are independently selected from the group consisting of oxy-LNA, thio-LNA, amino-LNA, cET, and/or ENA, in either the beta-D or alpha-L configurations or combinations thereof. In a preferred embodiment region F comprise at least 1 beta-D-oxy LNA unit, at the 5' end of the contiguous sequence.

Region G

Region G (gap region) preferably comprise, contain or consist of at least 4, such as at least 5, such as at least 6, at least 7, at least 8, at least 9, at least 10, at least 11, at least 12, at least 13, at least 14, at least 15 or at least 16 consecutive nucleosides capable of recruiting the aforementioned nuclease, in particular RNaseH. In a further embodiment region G comprise, contain or consist of from 5 to 12, or from 6 to 10 or from 7 to 9, such as 8 consecutive nucleotide units capable of recruiting aforementioned nuclease.

The nucleoside units in region G, which are capable of recruiting nuclease are in an embodiment selected from the group consisting of DNA, alpha-L-LNA, C4' alkylated DNA (as described in PCT/EP2009/050349 and Vester et al., Bioorg. Med. Chem. Lett. 18 (2008) 2296-2300, both incorporated herein by reference), arabinose derived nucleosides like ANA and 2'F-ANA (Mangos et al. 2003 J. AM. CHEM. SOC. 125, 654-661), UNA (unlocked nucleic acid) (as described in Fluiter et al., Mol. Biosyst., 2009, 10, 1039 incorporated herein by reference). UNA is unlocked nucleic acid, typically where the bond between C2 and C3 of the ribose has been removed, forming an unlocked "sugar" residue.

In a still further embodiment at least one nucleoside unit in region G is a DNA nucleoside unit, such as from 1 to 18 DNA units, such as 2, 3, 4, 5, 6, 7, 8, 9, 10, 11, 12, 13, 14, 15, 16 or 17 DNA units, preferably from 2 to 17 DNA units, such as from 3 to 16 DNA units, such as from 4 to 15 DNA units. such as from 5 to 14 DNA units, such as from 6 to 13 DNA units, such as from 7 to 12 DNA units, such as from 8 to 11 DNA units, more preferably from units 8 to 17 DNA units, or from 9 to 16 DNA units, 10 to 15 DNA units or 11 to 13 DNA units, such as 8, 9, 10, 11, 12, 13, 14, 154, 16, 17 DNA units. In some embodiments, region G consists of 100% DNA units.

In further embodiments the region G may consist of a mixture of DNA and other nucleosides capable of mediating RNase H cleavage. Region G may consist of at least 50% DNA, more preferably 60%, 70% or 80% DNA, and even more preferred 90% or 95% DNA.

In a still further embodiment at least one nucleoside unit in region G is an alpha-L-LNA nucleoside unit, such as at least one alpha-L-LNA, such as 2, 3, 4, 5, 6, 7, 8 or 9 alpha-L-LNA.

In a further embodiment, region G comprises the least one alpha-L-LNA is alpha-L-oxy-LNA. In a further embodiment region G comprises a combination of DNA and alpha-L-LNA nucleoside units.

In some embodiments, nucleosides in region G have a 2' endo structure.

In some embodiments region G may comprise a gapbreaker nucleoside, leading to a gapbreaker oligonucleotide, which is capable of recruiting RNase H.

Region F'

Region F' (3' flank or 3' wing) attached to the '3 end of region G comprises, contains or consists of at least one modified nucleoside such as at least 2, at least 3, at least 4, at least 5, at least 6, at least 7 modified nucleosides. In an embodiment region F' comprise or consist of from 1 to 7 modified nucleosides, such as from 2 to 6 modified nucleoside, such as from 2 to 4 modified nucleosides, such as from 1 to 3 modified nucleosides, such as 1, 2, 3 or 4 modified nucleosides. The F' region is defined by having at least on modified nucleoside at the 5' end and at the 3' end of the region.

In some embodiments, the modified nucleosides in region F' have a 3' endo structure.

In an embodiment, one or more of the modified nucleosides in region F' are 2' modified nucleosides. In one embodiment all the nucleosides in Region F' are 2' modified nucleosides.

In an embodiment, one or more of the modified nucleosides in region F' are 2' modified nucleosides.

In one embodiment all the nucleosides in Region F' are 2' modified nucleosides. In another embodiment region F' comprises DNA or RNA in addition to the 2' modified nucleosides. Flanks comprising DNA or RNA are characterized by having a 2' modified nucleoside in the 5' end (adjacent to the G region) and the 3' end of the F' region. In one embodiment the region F' comprises DNA nucleosides, such as from 1 to 4 contiguous DNA nucleosides, such as 1 to 3 or 1 to 2 contiguous DNA nucleosides. The DNA nucleosides in the flanks should preferably not be able to recruit RNase H. In some embodiments the 2' modified nucleosides and DNA and/or RNA nucleosides in the F' region alternate with 1 to 3 2' modified nucleosides and 1 to 3 DNA and/or RNA nucleosides, such flanks can also be termed alternating flanks. The length of the 3' flank (region F') in oligonucleotides with alternating flanks may be 4 to 10 nucleosides, such as 4 to 8, such as 4 to 6 nucleosides, such as 4, 5, 6 or 7 modified nucleosides. In some embodiments only the 3' flank of the oligonucleotide is alternating. Specific examples of region F' with alternating nucleosides are $2'_{1-2}$-N$'_{1-4}$-$2'_{1-4}$
$2'_{1-2}$-N$'_{1-2}$-$2'_{1-2}$-N$'_{1-2}$-$2'_{1-2}$ Where 2' indicates a modified nucleoside and N' is a RNA or DNA. In some embodiments all the modified nucleosides in the alternating flanks are LNA and the N' is DNA. In a further embodiment modified nucleosides in region F' are selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In some embodiments the F' region comprises both LNA and a 2' substituted modified nucleoside. These are often termed mixed wing or mixed flank oligonucleotides.

In one embodiment of the invention all the modified nucleosides in region F' are LNA nucleosides. In a further embodiment all the nucleosides in Region F' are LNA nucleosides. In a further embodiment the LNA nucleosides in region F' are independently selected from the group consisting of oxy-LNA, thio-LNA, amino-LNA, cET and/or ENA, in either the beta-D or alpha-L configurations or combinations thereof. In a preferred embodiment region F' has at least 2 beta-D-oxy LNA unit, at the 3' end of the contiguous sequence.

Region D' and D"

Region D' and D" can be attached to the 5' end of region F or the 3' end of region F', respectively. Region D' or D" are optional.

Region D' or D" may independently comprise 0 to 5, such as 1 to 5, such as 2 to 4, such as 0, 1, 2, 3, 4 or 5 additional nucleotides, which may be complementary or non-complementary to the target nucleic acid. In this respect the oligonucleotide of the invention, may in some embodiments comprise a contiguous nucleotide sequence capable of modulating the target which is flanked at the 5' and/or 3' end by additional nucleotides. Such additional nucleotides may serve as a nuclease susceptible biocleavable linker (see definition of linkers). In some embodiments the additional 5' and/or 3' end nucleosides are linked with phosphodiester linkages, and may be DNA or RNA. In another embodiment, the additional 5' and/or 3' end nucleosides are modified nucleosides which may for example be included to enhance nuclease stability or for ease of synthesis. In one embodiment, the oligonucleotide of the invention, comprises a region D' and/or D" at the 5' or 3' end of the contiguous nucleotide sequence. In a further embodiment the D' and/or D" region is composed of 1 to 5 phosphodiester linked DNA or RNA nucleosides which are not complementary to the target nucleic acid.

The gapmer oligonucleotide of the present invention can be represented by the following formulae:

5'-F-G-F'-3'; in particular $F_{1-7}$-$G_{4-12}$-$F'_{1-7}$
5'-D'-F-G-F'-3', in particular $D'_{1-3}$-$F_{1-7}$-$G_{4-12}$-$F'_{1-7}$
5'-F-G-F'-D"-3', in particular $F_{1-7}$-$G_{4-12}$-$F'_{1-7}$-$D"_{1-3}$
5'-D'-F-G-F'-D'-3", in particular $D'_{1-3}$-$F_{1-7}$-$G_{4-12}$-$F'_{1-7}$-$D"_{1-3}$ The preferred number and types of nucleosides in regions F, G and F', D' and D" have been described above. The oligonucleotide conjugates of the present invention have a region C covalently attached to either the 5' or 3' end of the oligonucleotide, in particular the gapmer oligonucleotides presented above.

In one embodiment the oligonucleotide conjugate of the invention comprises a oligonucleotide with the formula 5'-D'-F-G-F'-3' or 5'-F-G-F'-D"-3', where region F and F' independently comprise 1-7 modified nucleosides, G is a region between 6 and 16 nucleosides which are capable of recruiting RNaseH and region D' or D" comprise 1-5 phosphodiester linked nucleosides. Preferably region D' or D" is present in the end of the oligonucleotide where conjugation to a conjugate moiety is contemplated.

Examples of oligonucleotides with alternating flanks can be represented by the following formulae:

$2'_{1-3}$-N$'_{1-4}$-$2'_{1-3}$-Ge$_{6-12}$-$2'_{1-2}$-N$'_{1-4}$-$2'_{1-4}$
$2'_{1-2}$-N$'_{1-2}$-$2'_{1-2}$-N$'_{1-2}$-$2'_{1-2}$-G$_{6-12}$-$2'_{1-2}$-N$'_{1-2}$-$2'_{1-2}$-N$'_{1-2}$-$2'_{1-2}$
F-G$_{6-12}$-$2'_{1-2}$-N$'_{1-4}$-$2'_{1-4}$
F-G$_{6-12}$-$2'_{1-2}$-N$'_{1-2}$-$2'_{1-2}$-N$'_{1-2}$-$2'_{1-2}$
$2'_{1-3}$-N$'_{1-4}$-$2'_{1-3}$-G$_{6-12}$-F'
$2'_{1-2}$-N$'_{1-2}$-$2'_{1-2}$-N$_{1-2}$-$2'_{1-2}$-Ge$_{6-12}$-F'

Where a flank is indicated by F or F' it only contains 2' modified nucleosides, such as LNA nucleosides. The preferred number and types of nucleosides in the alternating regions, and region F, G and F', D' and D" have been described above.

In some embodiments the oligonucleotide is a gapmer consisting of 16, 17, 18, 19, 20, 21, 22 nucleotides in length, wherein each of regions F and F' independently consists of 1, 2, 3 or 4 modified nucleoside units complementary to the PD-L1 target nucleic acid and region G consists of 8, 9, 10, 11, 12, 13, 14, 15, 16, 17 nucleoside units, capable of recruiting nuclease when in duplex with the PD-L1 target nucleic acid and region D' consists of 2 phosphodiester linked DNAs.

In a further embodiments, the oligonucleotide is a gapmer wherein each of regions F and F' independently consists of 3, 4, 5 or 6 modified nucleoside units, such as nucleoside units containing a 2'-O-methoxyethyl-ribose sugar (2'-MOE) or nucleoside units containing a 2'-fluoro-deoxyribose sugar and/or LNA units, and region G consists of 8, 9, 10, 11, 12, 13, 14, 15, 16 or 17 nucleoside units, such as DNA units or other nuclease recruiting nucleosides such as alpha-L-LNA or a mixture of DNA and nuclease recruiting nucleosides.

In a further specific embodiment, the oligonucleotide is a gapmer wherein each of regions F and F' region consists of two LNA units each, and region G consists of 12, 13, 14 nucleoside units, preferably DNA units. Specific gapmer designs of this nature include 2-12-2, 2-13-2 and 2-14-2.

In a further specific embodiment, the oligonucleotide is a gapmer wherein each of regions F and F' independently consists of three LNA units, and region G consists of 8, 9, 10, 11, 12, 13 or 14 nucleoside units, preferably DNA units. Specific gapmer designs of this nature include 3-8-3, 3-9-3 3-10-3, 3-11-3, 3-12-3, 3-13-3 and 3-14-3.

In a further specific embodiment, the oligonucleotide is a gapmer wherein each of regions F and F' consists of four LNA units each, and region G consists of 8 or 9, 10, 11 or 12 nucleoside units, preferably DNA units. Specific gapmer designs of this nature include 4-8-4, 4-9-4, 4-10-4, 4-11-4 and 4-12-4.

Specific gapmer designs of this nature include F-G-F' designs selected from a group consisting of a gap with 6 nucleosides and independently 1 to 4 modified nucleosides in the wings including 1-6-1, 1-6-2, 2-6-1, 1-6-3, 3-6-1, 1-6-4, 4-6-1, 2-6-2, 2-6-3, 3-6-2 2-6-4, 4-6-2, 3-6-3, 3-6-4 and 4-6-3 gapmers.

Specific gapmer designs of this nature include F-G-F' designs selected from a group consisting of a gap with 7 nucleosides and independently 1 to 4 modified nucleosides in the wings including 1-7-1, 2-7-1, 1-7-2, 1-7-3, 3-7-1, 1-7-4, 4-7-1, 2-7-2, 2-7-3, 3-7-2, 2-7-4, 4-7-2, 3-7-3, 3-7-4, 4-7-3 and 4-7-4 gapmers.

Specific gapmer designs of this nature include F-G-F' designs selected from a group consisting of a gap with 8 nucleosides and independently 1 to 4 modified nucleosides in the wings including 1-8-1, 1-8-2, 1-8-3, 3-8-1, 1-8-4, 4-8-1, 2-8-1, 2-8-2, 2-8-3, 3-8-2, 2-8-4, 4-8-2, 3-8-3, 3-8-4, 4-8-3 and 4-8-4 gapmers.

Specific gapmer designs of this nature include F-G-F' designs selected from a group consisting of a gap with 9 nucleosides and independently 1 to 4 modified nucleosides in the wings including, 1-9-1, 2-9-1, 1-9-2, 1-9-3, 3-9-1, 1-9-4, 4-9-1, 2-9-2, 2-9-3, 3-9-2, 2-9-4, 4-9-2, 3-9-3, 3-9-4, 4-9-3 and 4-9-4 gapmers.

Specific gapmer designs of this nature include F-G-F' designs selected from a group consisting of a gap with 10 nucleosides including, 1-10-1, 2-10-1, 1-10-2, 1-10-3, 3-10-1, 1-10-4, 4-10-1, 2-10-2, 2-10-3, 3-10-2, 2-10-4, 4-10-2, 3-10-3, 3-10-4, 4-10-3 and 4-10-4 gapmers.

Specific gapmer designs of this nature include F-G-F' designs selected from a group consisting of a gap with 11 nucleosides including, 1-11-1, 2-11-1, 1-11-2, 1-11-3, 3-11-1, 1-11-4, 4-11-1, 2-11-2, 2-11-3, 3-11-2, 2-11-4, 4-11-2, 3-11-3, 3-11-4, 4-11-3 and 4-11-4 gapmers.

Specific gapmer designs of this nature include F-G-F' designs selected from a group consisting of a gap with 12 nucleosides including, 1-12-1, 2-12-1, 1-12-2, 1-12-3, 3-12-1, 1-12-4, 4-12-1, 2-12-2, 2-12-3, 3-12-2, 2-12-4, 4-12-2, 3-12-3, 3-12-4, 4-12-3 and 4-12-4 gapmers.

Specific gapmer designs of this nature include F-G-F' designs selected from a group consisting of a gap with 13 nucleosides including, 1-13-1, 2-13-1, 1-13-2, 1-13-3, 3-13-1, 1-13-4, 4-13-1, 2-13-2, 2-13-3, 3-13-2, 2-13-4, 4-13-2, 3-13-3, 3-13-4, 4-13-3 and 4-13-4 gapmers.

Specific gapmer designs of this nature include F-G-F' designs selected from a group consisting of a gap with 14 nucleosides including, 1-14-1, 2-14-1, 1-14-2, 1-14-3, 3-14-1, 1-14-4, 4-14-1, 2-14-2, 2-14-3, 3-14-2, 2-14-4, 4-14-2, 3-14-3, 3-14-4, 4-14-3 and 4-14-4 gapmers.

Specific gapmer designs of this nature include F-G-F' designs selected from a group consisting of a gap with 15 nucleosides including, 1-15-1, 2-15-1, 1-15-2, 1-15-3, 3-15-1, 1-15-4, 4-15-1, 2-15-2, 2-15-3, 3-15-2, 2-15-4, 4-15-2 and 3-15-3 gapmers.

Specific gapmer designs of this nature include F-G-F' designs selected from a group consisting of a gap with 16 nucleosides including, 1-16-1, 2-16-1, 1-16-2, 1-16-3, 3-16-1, 1-16-4, 4-16-1, 2-16-2, 2-16-3, 3-16-2, 2-16-4, 4-16-2 and 3-16-3 gapmers.

Specific gapmer designs of this nature include F-G-F' designs selected from a group consisting of a gap with 17 nucleosides including, 1-17-1, 2-17-1, 1-17-2, 1-17-3, 3-17-1, 1-17-4, 4-17-1, 2-17-2, 2-17-3 and 3-17-2 gapmers.

In all instances the F-G-F' design may further include region D' and/or D", which may have 1, 2 or 3 nucleoside units, such as DNA units, such as 2 phosphodiester linked DNA units.

Preferably, the nucleosides in region F and F' are modified nucleosides, while nucleotides in region G are preferably unmodified nucleosides.

In each design, the preferred modified nucleoside is LNA.

In another embodiment all the internucleoside linkages in the gap in a gapmer are phosphorothioate and/or boranophosphate linkages. In another embodiment all the internucleoside linkages in the flanks (F and F' region) in a gapmer are phosphorothioate and/or boranophosphate linkages. In another preferred embodiment all the internucleoside linkages in the D' and D" region in a gapmer are phosphodiester linkages.

For specific gapmers as disclosed herein, when the cytosine (C) residues are annotated as 5-methyl-cytosine, in various embodiments, one or more of the Cs present in the oligonucleotide may be unmodified C residues.

In a particular embodiment, the gapmer is a so-called shortmer as described in WO2008/113832 incorporated herein by reference.

Further gapmer designs are disclosed in WO2004/046160, WO2007/146511 and incorporated by reference.

For certain embodiments of the invention, the oligonucleotide is selected from the group of oligonucleotide compounds with CMP-ID-NO: 5_1 to 743_1 and 771_1.

For certain embodiments of the invention, the oligonucleotide is selected from the group of oligonucleotide compounds with CMP-ID-NO 6_1, 8_1, 9_1, 13_1, 41_1, 42_1, 58_1, 77_1, 92_1, 111_1, 128_1, 151_1, 164_1, 166_1, 169_1, 171_1, 222_1, 233_1, 245_1, 246_1, 250_1, 251_1, 252_1, 256_1, 272_1, 273_1, 287_1, 292_1, 303_1, 314_1, 318_1, 320_1, 324_1, 336_1, 342_1, 343_1, 344_1, 345_1, 346_1, 349_1, 359_1, 360_1, 374_1, 408_1, 409_1, 415_1, 417_1, 424_1, 429_1, 430_1, 458_1, 464_1, 466_1, 474_1, 490_1, 493_1, 512_1, 519_1, 519_1, 529_1, 533_1, 534_1, 547_1, 566_1, 567_1, 578_1, 582_1, 601_1, 619_1, 620_1, 636_1, 637_1, 638_1, 640_1, 645_1, 650_1, 651_1, 652_1, 653_1, 658_1, 659_1, 660_1, 665_1, 678_1, 679_1, 680_1, 682_1, 683_1, 684_1, 687_1, 694_1, 706_1, 716_1, 728_1, 733_1, 734_1, and 735_1.

In one preferred embodiment of the invention, the oligonucleotide is CMP-ID-NO: 287_1.

In another preferred embodiment of the invention, the oligonucleotide is CMP-ID-NO: 342_1.

In another preferred embodiment of the invention, the oligonucleotide is CMP-ID-NO: 640_1.

In another preferred embodiment of the invention, the oligonucleotide is CMP-ID-NO: 466_1.

In another preferred embodiment of the invention, the oligonucleotide is CMP-ID-NO: 566_1.

In a further embodiment of the invention the contiguous nucleotide sequence of the oligonucleotide motifs and oligonucleotide compounds of the invention comprise two to four additional phosphodiester linked nucleosides at the 5' end of the contiguous nucleotide sequence (e.g. region D').

In one embodiment the nucleosides serve as a biocleavable linker (see section on biocleavable linkers). In a preferred embodiment a ca (cytidine-adenosine) dinucleotide is linked to the 5' end of contiguous nucleotide sequence (i.e. any one of the motif sequences or oligonucleotide compounds listed in table 5) via a phosphodiester linkage. In a preferred embodiment the ca di nucleotide is not complementary to the target sequence at the position where the reminder of the contiguous nucleotide is complementary.

In some embodiments of the invention the oligonucleotide or contiguous nucleotide sequence is selected from the group consisting of the nucleotide motif sequences with SEQ ID NO: 766, 767, 768, 769 and 770.

In some embodiments of the invention the oligonucleotide is selected from the group consisting of the oligonucleotide compounds with CMP-ID-NO 766_1, 767_1, 768_1, 769_1 and 770_1.

Carbohydrate Conjugate Moieties

Carbohydrate conjugate moieties include but are not limited to galactose, lactose, n-acetylgalactosamine, mannose and mannose-6-phosphate. Carbohydrate conjugates may be used to enhance delivery or activity in a range of tissues, such as liver and/or muscle. See, for example, EP1495769, WO99/65925, Yang et al., Bioconjug Chem (2009) 20(2): 213-21. Zatsepin & Oretskaya Chem Biodivers. (2004) 1(10): 1401-17.

In some embodiments the carbohydrate conjugate moiety is multivalent, such as, for example 2, 3 or 4 identical or non-identical carbohydrate moieties may be covalently joined to the oligonucleotide, optionally via a linker or linkers. In some embodiments the invention provides a conjugate comprising the oligonucleotide of the invention and a carbohydrate conjugate moiety.

In some embodiments, the conjugate moiety is or may comprise mannose or mannose-6-phosphate. This is particular useful for targeting muscle cells, see for example US 2012/122801.

Conjugate moieties capable of binding to the asialoglycoprotein receptor (ASGPr) are particular useful for targeting hepatocytes in liver. In some embodiments the invention provides a oligonucleotide conjugate comprising the oligonucleotide of the invention and an asialoglycoprotein receptor targeting conjugate moiety. The asialoglycoprotein receptor targeting conjugate moiety comprises one or more carbohydrate moieties capable of binding to the asialoglycoprotein receptor (ASGPr binding carbohydrate moieties) with affinity equal to or greater than that of galactose. The affinities of numerous galactose derivatives for the asialoglycoprotein receptor have been studied (see for example: Jobst, S. T. and Drickamer, K. JB. C. 1996, 271, 6686) or are readily determined using methods typical in the art.

One aspect of the present invention is an antisense oligonucleotide conjugate comprising a) an oligonucleotide (Region A) comprising a contiguous nucleotide sequence of 10 to 30 nucleotides in length with at least 90% complementarity to a PD-L1 target nucleic acid; and b) at least one asialoglycoprotein receptor targeting conjugate moiety (Region C) covalently attached to the oligonucleotide in a). The oligonucleotide or a contiguous nucleotide sequence can be as described in any of the sections "oligonucleotides of the invention", "oligonucleotide design and "gapmer design".

In some embodiments asialoglycoprotein receptor targeting conjugate moiety comprises at least one ASPGr binding carbohydrate moiety selected from the group consisting of galactose, galactosamine, N-formyl-galactosamine, N-acetylgalactosamine, N-propionyl-galactosamine, N-n-butanoyl-galactosamine and N-isobutanoylgalactosamine.

In some embodiments, the asialoglycoprotein receptor targeting conjugate moiety is mono-valent, di-valent, tri-valent or tetra-valent (i.e. containing 1, 2, 3 or 4 terminal carbohydrate moieties capable of binding to the asialoglycoprotein receptor). Preferably, the asialoglycoprotein receptor targeting conjugate moiety is di-valent, even more preferred it is trivalent. In a preferred embodiment the asialoglycoprotein receptor targeting conjugate moiety comprises 1 to 3 N-acetylgalactosamine (GalNAc) moieties (also termed a GalNAc conjugate). In some embodiments the oligonucleotide conjugate comprises a asialoglycoprotein receptor targeting conjugate moiety that is a tri-valent N-acetylgalactosamine (GalNAc) moiety. GalNAc conjugates have been used with phosphodiester, methylphosphonate and PNA antisense oligonucleotides (e.g. U.S. Pat. No. 5,994, 517 and Hangeland et al., Bioconjug Chem. 1995 November-December; 6(6):695-701, Biessen et al 1999 Biochem J. 340, 783-792 and Maier et al 2003 Bioconjug Chem 14, 18-29) and siRNAs (e.g. WO 2009/126933, WO 2012/089352 & WO 2012/083046) and with LNA and 2'-MOE modified nucleosides WO 2014/076196 WO 2014/207232 and WO 2014/179620 (hereby incorporated by reference).

To generate the asialoglycoprotein receptor targeting conjugate moiety the ASPGr binding carbohydrate moieties (preferably GalNAc) are attached to a brancher molecule through the C-I carbons of the saccharides. The ASPGr binding carbohydrate moieties are preferably linked to the brancher molecule via spacers. A preferred spacer is a flexible hydrophilic spacer (U.S. Pat. No. 5,885,968; Biessen et al. J. Med. Chern. 1995 Vol. 39 p. 1538-1546). A preferred flexible hydrophilic spacer is a PEG spacer. A preferred PEG spacer is a PEG3 spacer (three ethylene units). The brancher molecule can be any small molecule which permits attachment of two or three terminal ASPGr binding carbohydrate moieties and further permits attachment of the branch point to the oligonucleotide. An exemplary brancher molecule is a di-lysine. A di-lysine molecule contains three amine groups through which three ASPGr binding carbohydrate moieties may be attached and a carboxyl reactive group through which the di-lysine may be attached to the oligonucleotide. Alternative brancher molecules may be a doubler or trebler such as those supplied by Glen Research. In some embodiments the brancher may be selected from the from the group consisting of 1,3-bis-[5-(4,4'-dimethoxytrityloxy)pentylamido]propyl-2-[(2-cyanoethyl)-(N,N-diisopropyl)] phosphoramidite (Glen Research Catalogue Number: 10-1920-xx), tris-2,2,2-[3-(4,4'-dimethoxytrityloxy)propyloxymethyl]ethyl-[(2-cyanoethyl)-(N, N-diisopropyl)]-phosphoramidite (Glen Research Catalogue Number: 10-1922-xx), tris-2,2,2-[3-(4,4'-dimethoxytrityloxy)propyloxymethyl]methyleneoxypropyl-[(2-cyanoethyl)-(N,N-diisopropyl)]-phosphoramidite and 1-[5-(4,4'-dimethoxy-trityloxy)pentylamido]-3-[5-fluorenomethoxy-carbonyl-oxy-pentylamido]-propyl-2-[(2-cyanoethyl)-(N, N-diisopropyl)]-phosphoramidite (Glen Research Catalogue Number: 10-1925-xx). WO 2014/179620 and PCT application No. PCT/EP2015/073331 describes the generation of various GalNAc conjugate moieties (hereby incorporated by reference). One or more linkers may be inserted between the brancher molecule and the oligonucleotide. In a preferred embodiment the linker is a biocleavable linker. The linker may be selected from the linkers described in the section "Linkers" and its subsections.

The asialoglycoprotein receptor targeting conjugate moiety, in particular the GalNAc conjugate moiety, may be attached to the 3'- or 5'-end of the oligonucleotide using methods known in the art. In preferred embodiments the asialoglycoprotein receptor targeting conjugate moiety is linked to the 5'-end of the oligonucleotide.

Pharmacokinetic modulators in relation to siRNAs delivery has been described in WO 2012/083046 (hereby incorporated by reference). In some embodiments the carbohydrate conjugate moiety comprises a pharmacokinetic modulator selected from the group consisting of a hydrophobic group having 16 or more carbon atoms, hydrophobic group having 16-20 carbon atoms, palmitoyl, hexadec-8-enoyl, oleyl, (9E,12E)-octadeca-9,12dienoyl, dioctanoyl, and C16-C20 acyl, and cholesterol. In a preferred embodiment the pharmacokinetic modulator containing carbohydrate conjugate moiety is a GalNAc conjugate.

Figure 3:
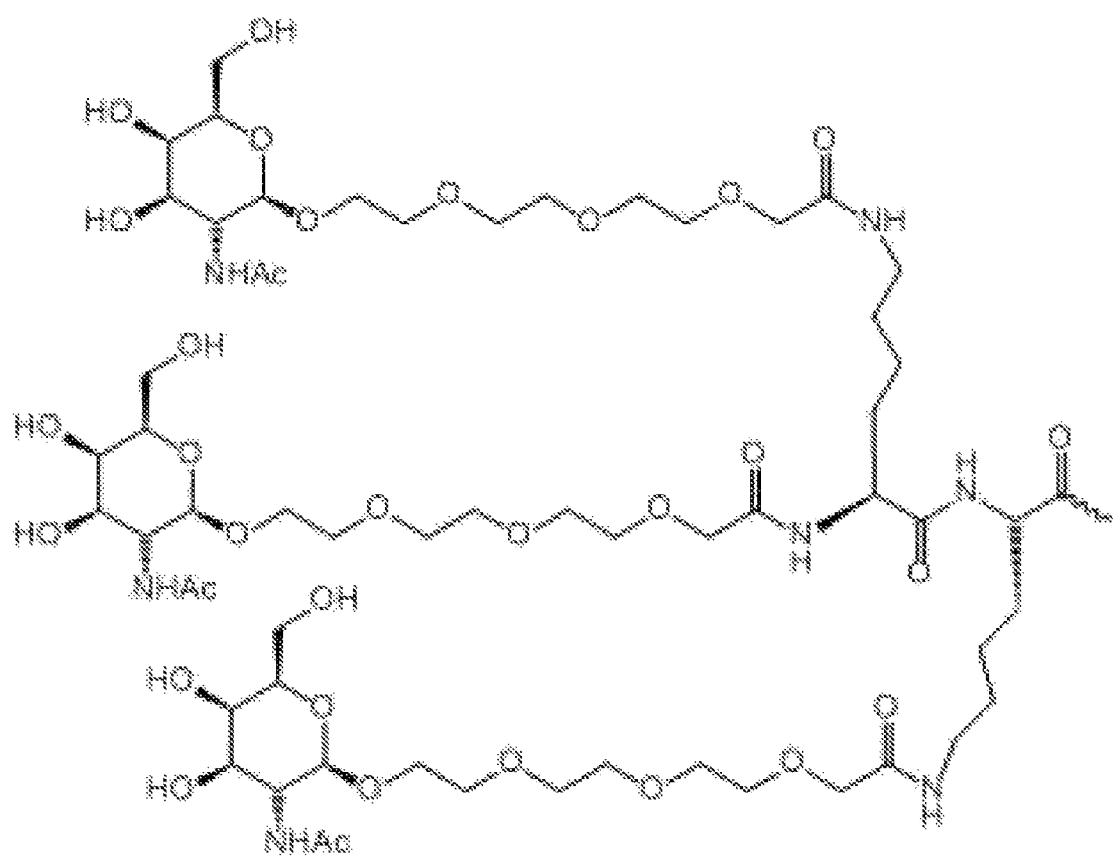
FIG. 3: Structural formula of the trivalent GalNAc cluster (GN2). GN2 is useful as conjugation moiety in the present invention. The wavy line illustrates the site of conjugation of the cluster to e.g. a C6 amino linker or directly to the oligonucleotide.

Preferred carbohydrate conjugate moieties comprises one to three terminal ASPGr binding carbohydrate moieties, preferably N-acetylgalactosamine moiety(s). In some embodiments the carbohydrate conjugate moiety comprises three ASPGr binding carbohydrate moieties, preferably N-acetylgalactosamine moieties, linked via a spacer to a brancher molecule. The spacer molecule can be between 8 and 30 atoms long. A preferred carbohydrate conjugate moiety comprises three terminal GalNAc moieties linked via a PEG spacer to a di-lysine brancher molecule. Preferably the PEG spacer is a 3PEG spacer. Suitable asialoglycoprotein receptor targeting conjugate moieties are shown in FIG. 1. A preferred asialoglycoprotein receptor targeting conjugate moiety is shown in FIG. 3.

Other GalNAc conjugate moieties can include, for example, small peptides with GalNAc moieties attached such as Tyr-Glu-Glu-(aminohexyl GalNAc)3 (YEE(ahGalNAc)3; a glycotripeptide that binds to asialoglycoprotein receptor on hepatocytes, see, e.g., Duff, et al., Methods Enzymol, 2000, 313, 297); lysine-based galactose clusters (e.g., L3G4; Biessen, et al., Cardovasc. Med., 1999, 214); and cholane-based galactose clusters (e.g., carbohydrate recognition motif for asialoglycoprotein receptor).

In some embodiments of the invention the antisense oligonucleotide conjugate is selected from the group consisting of the following CPM ID NO: 766_2, 767_2, 768_2, 769_2 and 770_2.

Figure 4:
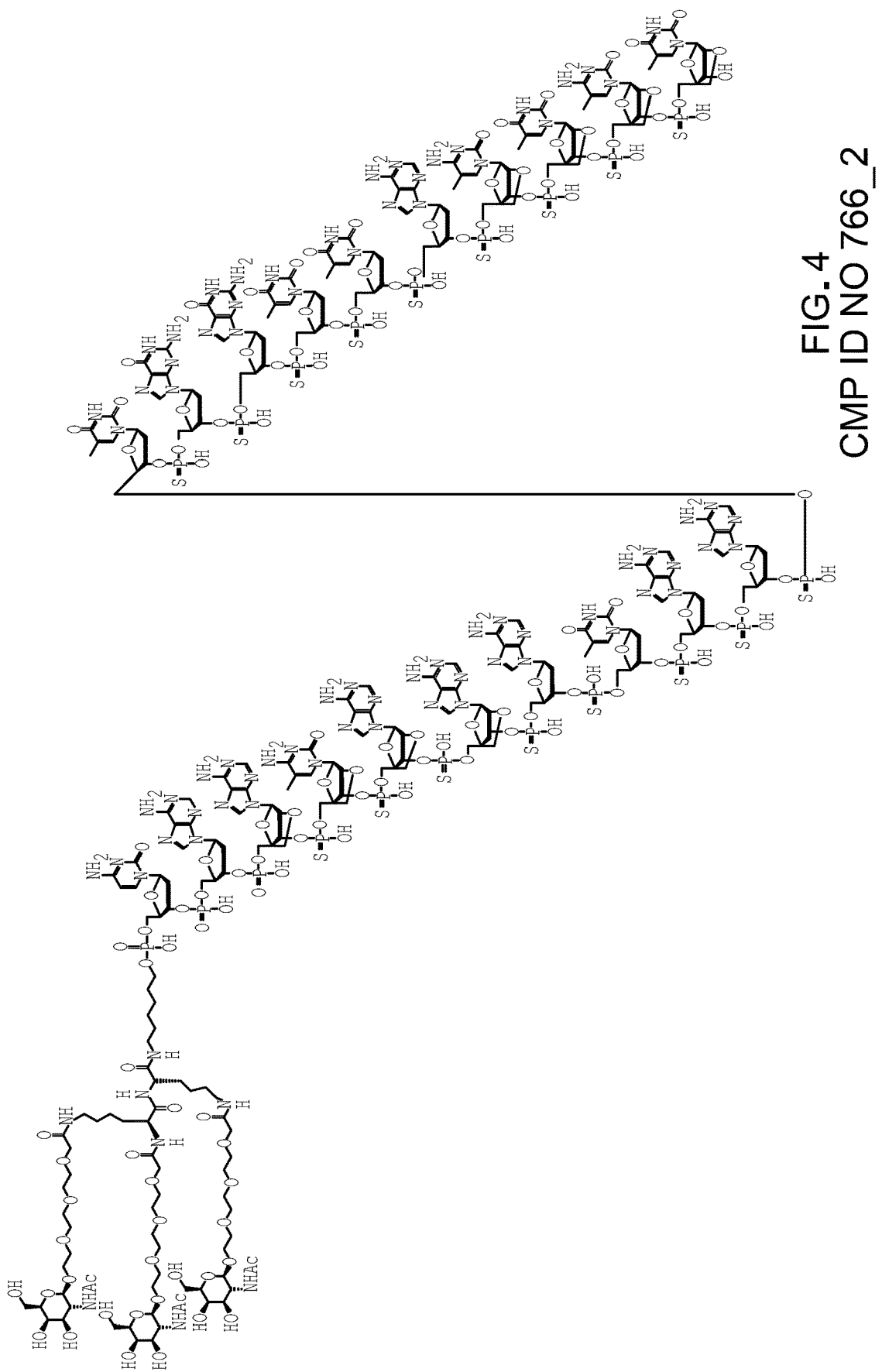
FIG. 4: Structural formula of CMP ID NO 766_2.

In a preferred embodiment the antisense oligonucleotide conjugate corresponds to the compound represented in FIG. 4.

Figure 5:
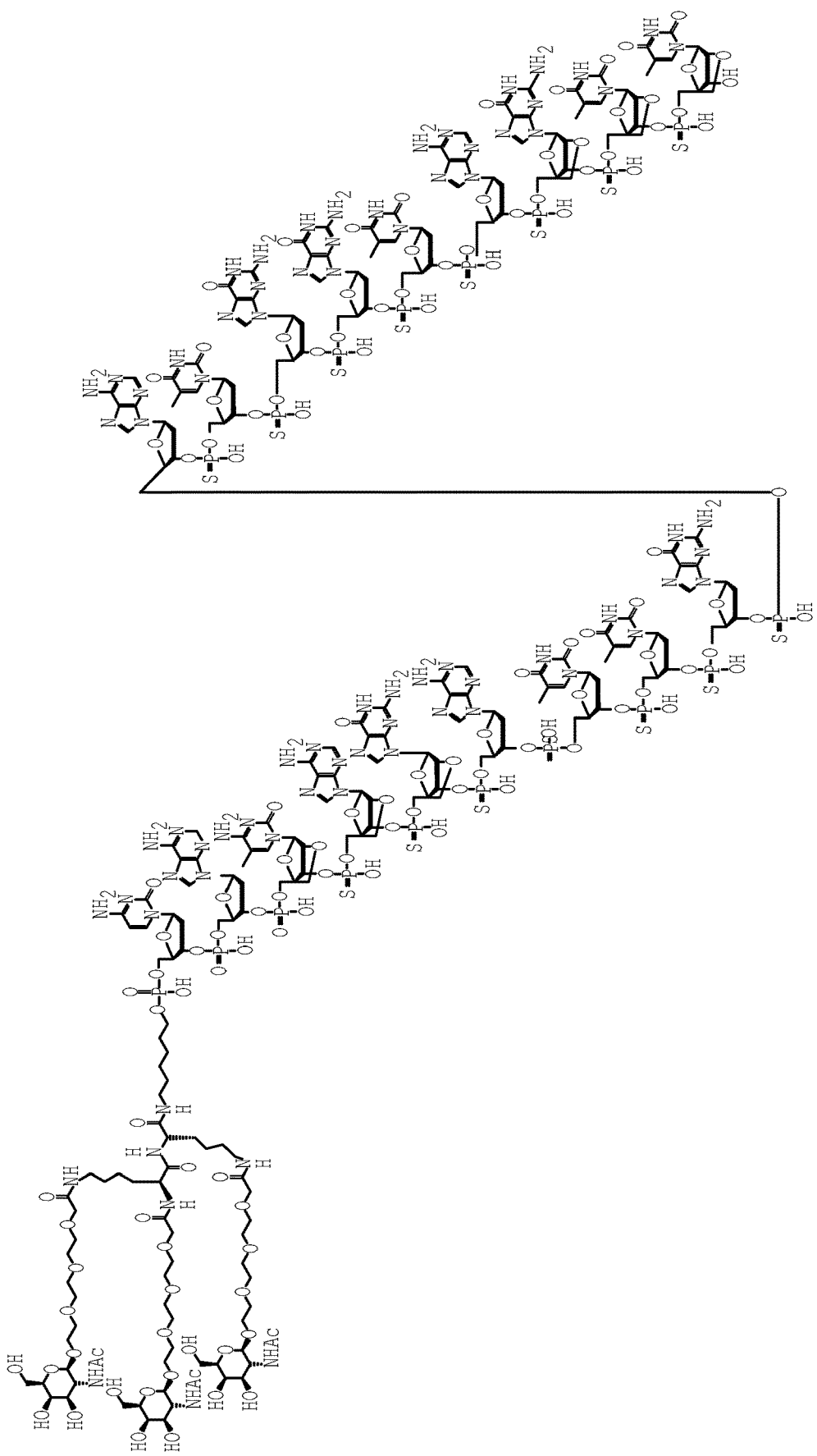
FIG. 5: Structural formula of CMP ID NO 767_2.

In another preferred embodiment the antisense oligonucleotide conjugate corresponds to the compound represented in FIG. 5.

Figure 6:
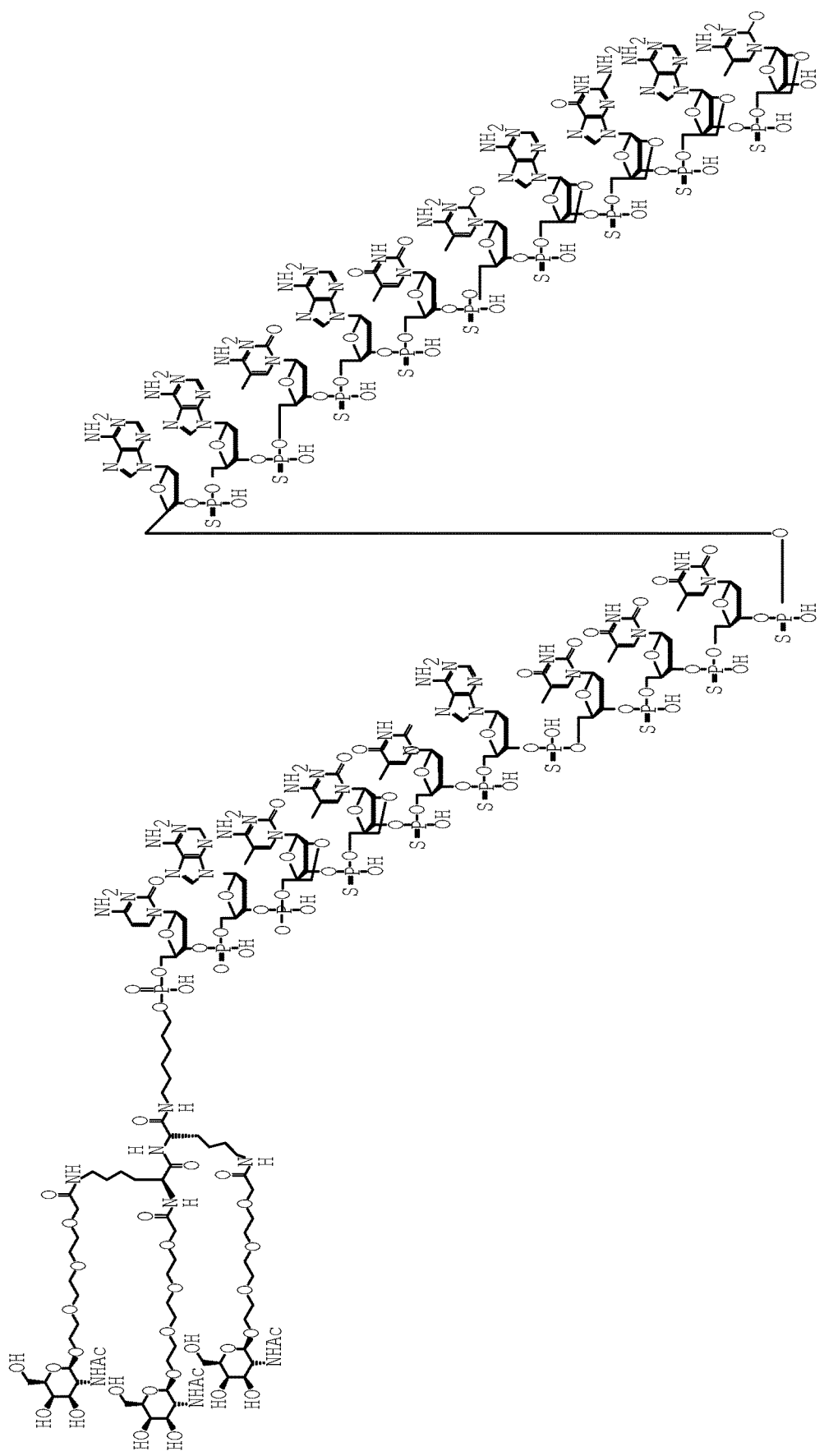
FIG. 6: Structural formula of CMP ID NO 768_2.

In another preferred embodiment the antisense oligonucleotide conjugate corresponds to the compound represented in FIG. 6.

Figure 7:
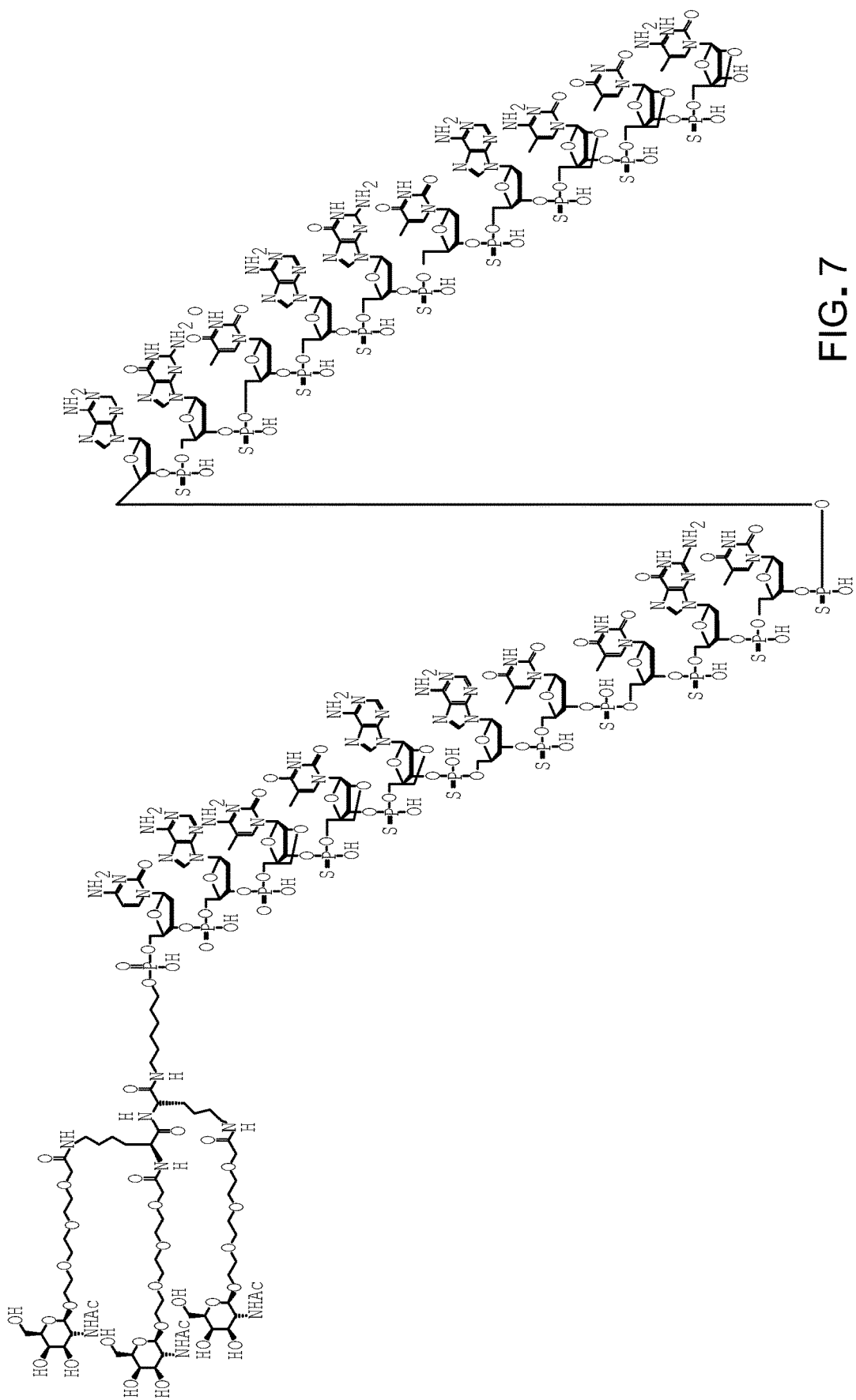
FIG. 7: Structural formula of CMP ID NO 769_2.

In another preferred embodiment the antisense oligonucleotide conjugate corresponds to the compound represented in FIG. 7.

Figure 8:
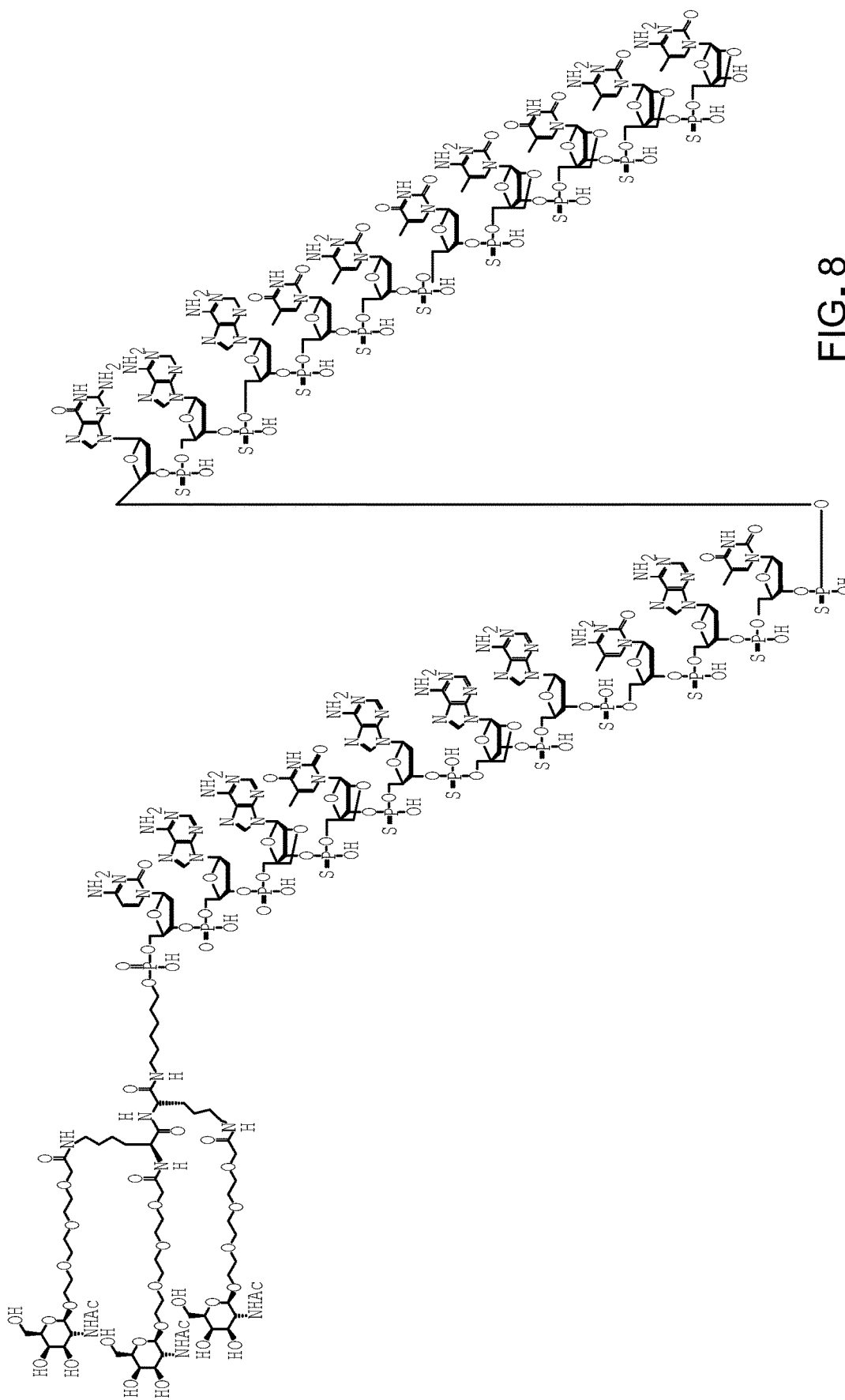
FIG. 8: Structural formula of CMP ID NO 770_2.

In another preferred embodiment the antisense oligonucleotide conjugate corresponds to the compound represented in FIG. 8.

Linkers

Biocleavable Linkers (Region B)

The use of a conjugate is often associated with enhanced pharmacokinetic or pharmeodynamic dynamic properties. However, the presence of a conjugate moiety may interfere with the activity of the oligonucleotide against its intended target, for example via steric hindrance preventing hybridization or nuclease recruitment (e.g. RNAseH). The use of a physiologically labile bond (biocleavable linker) between the oligonucleotide (region A or first region) and the conjugate moiety (region C or third region), allows for the improved properties due to the presence of the conjugate moiety, whilst ensuring that once at the target tissue, the conjugate group does not prevent effective activity of the oligonucleotide.

Cleavage of the physiologically labile bond occurs spontaneously when a molecule containing the labile bond reaches an appropriate intra- and/or extra-cellular environment. For example, a pH labile bond may be cleaved when the molecule enters an acidified endosome. Thus, a pH labile bond may be considered to be an endosomal cleavable bond. Enzyme cleavable bonds may be cleaved when exposed to enzymes such as those present in an endosome or lysosome or in the cytoplasm. A disulfide bond may be cleaved when the molecule enters the more reducing environment of the cell cytoplasm. Thus, a disulfide may be considered to be a cytoplasmic cleavable bond. As used herein, a pH-labile bond is a labile bond that is selectively broken under acidic conditions (pH<7). Such bonds may also be termed endosomally labile bonds, since cell endosomes and lysosomes have a pH less than 7.

For biocleavable linkers associated with a conjugate moiety for targeted delivery it is preferred that, the cleavage rate seen in the target tissue (for example muscle, liver, kidney or a tumor) is greater than that found in blood serum. Suitable methods for determining the level (%) of cleavage in target tissue versus serum or cleavage by S1 nuclease are described in the "Materials and methods" section. In some embodiments, the biocleavable linker (also referred to as the physiologically labile linker, or nuclease susceptible linker or region B), in a conjugate of the invention, is at least about 20% cleaved, such as at least about 30% cleaved, such as at least about 40% cleaved, such as at least about 50% cleaved, such as at least about 60% cleaved, such as at least about 70% cleaved, such as at least about 75% cleaved when compared against a standard.

In some embodiments, the oligonucleotide conjugate of the invention comprises three regions: i) a first region (region A), which comprises 10-25 contiguous nucleotides complementary to the target nucleic acid; ii) a second region (region B) which comprises a biocleavable linker and iii) a third region (region C) which comprises a conjugate moiety, such as an asialoglycoprotein receptor targeting conjugate moiety, wherein the third region is covalent linked to the second region which is covalently linked to the first region.

In one embodiment of the present invention the oligonucleotide conjugate comprises a biocleavable linker (Region B) between the contiguous nucleotide sequence (region A) and the asialoglycoprotein receptor targeting conjugate moiety (region C).

In some embodiments, the biocleavable linker may be situated either at the 5' end and/or the 3'-end of the contiguous nucleotides complementary to the target nucleic acid (region A). In a preferred embodiment the biocleavable linker is at the 5'-end.

In some embodiments, the cleavable linker is susceptible to nuclease(s) which may for example, be expressed in the target cell. In some embodiments the biocleavable linker is composed of 2 to 5 consecutive phosphodiester linkages. The linker may be a short region (e.g. 1-10 as detailed in the definition of linkers) phosphodiester linked nucleosides. In some embodiments, the nucleosides in the biocleavable linker region B is (optionally independently) selected from the group consisting of DNA and RNA or modifications thereof which do not interfere with nuclease cleavage. Modifications of DNA and RNA nucleosides which do not interfere with nuclease cleavage may be non-naturally occurring nucleobases. Certain sugar-modified nucleosides may also allow nuclease cleavage such as an alpha-L-oxy- LNA. In some embodiments, all the nucleosides of region B comprise (optionally independently) either a 2'-OH ribose sugar (RNA) or a 2'-H sugar—i.e. RNA or DNA. In a preferred embodiment, at least two consecutive nucleosides of region B are DNA or RNA nucleosides (such as at least 3 or 4 or 5 consecutive DNA or RNA nucleosides). In an even more preferred embodiment, the nucleosides of region B are DNA nucleosides Preferably region B consists of between 1 to 5, or 1 to 4, such as 2, 3, 4 consecutive phosphodiester linked DNA nucleosides. In preferred embodiments region B is so short that it does not recruit RNAseH. In some embodiments, region B comprises no more than 3 or no more than 4 consecutive phospodiester linked DNA and/or RNA nucleosides (such as DNA nucleosides).

Where region B is composed of phosphodiester linked nucleosides, region A and B may together form the oligonucleotide that is linked to region C. In this context region A can be differentiated from region B in that Region A starts with at least one, preferably at least two, modified nucleosides with increased binding affinity to the target nucleic acid (e.g. LNA or nucleosides with a 2' substituted sugar moiety) and region A on its own is capable of modulation of the expression the target nucleic acid in a relevant cell line. Furthermore, if region A comprises DNA or RNA nucleosides these are linked with nuclease resistant internucleoside linkage, such phosphorothioate or boranophosphate. Region B on the other hand comprises phophodiester linkages between DNA or RNA nucleosides. In some embodiments region B is not complementary to or comprises at least 50% mismatches to the target nucleic acid.

In some embodiments, region B is not complementary to the target nucleic acid sequence or to the contiguous nucleotides complementary to the target nucleic acid in region A.

In some embodiments, region B is complementary with the target nucleic acid sequence. In this respect region A and B together may form a single contiguous sequence which is complementary to the target sequence.

In some aspects of the invention the internucleoside linkage between the first (region A) and the second region (region B) may be considered part of the second region.

In some embodiments, the sequence of bases in region B is selected to provide an optimal endonuclease cleavage site, based upon the predominant endonuclease cleavage enzymes present in the target tissue or cell or sub-cellular compartment. In this respect, by isolating cell extracts from target tissues and non-target tissues, endonuclease cleavage sequences for use in region B may be selected based upon a preferential cleavage activity in the desired target cell (e.g. liver/hepatocytes) as compared to a non-target cell (e.g. kidney). In this respect, the potency of the compound for target down-regulation may be optimized for the desired tissue/cell.

In some embodiments region B comprises a dinucleotide of sequence AA, AT, AC, AG, TA, TT, TC, TG, CA, CT, CC, CG, GA, GT, GC, or GG, wherein C may be 5-methylcytosine, and/or T may be replaced with U. Preferably, the internucleoside linkage is a phosphodiester linkage. In some embodiments region B comprises a trinucleotide of sequence AAA, AAT, AAC, AAG, ATA, ATT, ATC, ATG, ACA, ACT, ACC, ACG, AGA, AGT, AGC, AGG, TAA, TAT, TAC, TAG, TTA, TTT, TTC, TAG, TCA, TCT, TCC, TCG, TGA, TGT, TGC, TGG, CAA, CAT, CAC, CAG, CTA, CTG, CTC, CTT, CCA, CCT, CCC, CCG, CGA, CGT, CGC, CGG, GAA, GAT, GAC, CAG, GTA, GTT, GTC, GTG, GCA, GCT, GCC, GCG, GGA, GGT, GGC, and GGG wherein C may be 5-methylcytosine and/or T may be replaced with U. Preferably, the internucleoside linkages are phosphodiester linkages. In some embodiments region B comprises a trinucleotide of sequence AAAX, AATX, AACX, AAGX, ATAX, ATTX, ATCX, ATGX, ACAX, ACTX, ACCX, ACGX, AGAX, AGTX, AGCX, AGGX, TAAX, TATX, TACX, TAGX, TTAX, TTTX, TTCX, TAGX, TCAX, TCTX, TCCX, TCGX, TGAX, TGTX, TGCX, TGGX, CAAX, CATX, CACX, CAGX, CTAX, CTGX, CTCX, CTTX, CCAX, CCTX, CCCX, CCGX, CGAX, CGTX, CGCX, CGGX, GAAX, GATX, GACX, CAGX, GTAX, GTTX, GTCX, GTGX, GCAX, GCTX, GCCX, GCGX, GGAX, GGTX, GGCX, and GGGX, wherein X may be selected from the group consisting of A, T, U, G, C and analogues thereof, wherein C may be 5-methylcytosine and/or T may be replaced with U. Preferably, the internucleoside linkages are phosphodiester linkages. It will be recognized that when referring to (naturally occurring) nucleobases A, T, U, G, C, these may be substituted with nucleobase analogues which function as the equivalent natural nucleobase (e.g. base pair with the complementary nucleoside).

Other Linkers (Region Y)

The linker can have at least two functionalities, one for attaching to the oligonucleotide and the other for attaching to the conjugate moiety. Example linker functionalities can be electrophilic for reacting with nucleophilic groups on the oligonucleotide or conjugate moiety, or nucleophilic for reacting with electrophilic groups. In some embodiments, linker functionalities include amino, hydroxyl, carboxylic acid, thiol, phosphoramidate, phosphorothioate, phosphate, phosphite, unsaturations (e.g., double or triple bonds), and the like. Some example linkers (region Y) include 8-amino-3,6-dioxaoctanoic acid (ADO), succinimidyl 4-(N-maleimidomethyl)cyclohexane-1-carboxylate (SMCC), 6-aminohexanoic acid (AHEX or AHA), 6-aminohexyloxy, 4-aminobutyric acid, 4-aminocyclohexylcarboxylic acid, succinimidyl 4-(N-maleimidomethyl)cyclohexane-I-carboxy-(6-amido-caproate) (LCSMCC), succinimidyl m-maleimido-benzoylate (MBS), succinimidyl N-e-maleimido-caproylate (EMCS), succinimidyl 6-(beta-maleimido-propionamido) hexanoate (SMPH), succinimidyl N-(a-maleimido acetate) (AMAS), succinimidyl 4-(p-maleimidophenyl)butyrate (SMPB), beta-alanine (beta-ALA), phenylglycine (PHG), 4-aminocyclohexanoic acid (ACHC), beta-(cyclopropyl) alanine (beta-CYPR), amino dodecanoic acid (ADC), alylene diols, polyethylene glycols, amino acids, and the like. In some embodiments the linker (region Y) is an amino alkyl, such as a C2-C36 amino alkyl group, including, for example C6 to C12 amino alkyl groups. In a preferred embodiment the linker (region Y) is a C6 amino alkyl group. The amino alkyl group may be added to the oligonucleotide (region A or region A-B) as part of standard oligonucleotide synthesis, for example using a (e.g. protected) amino alkyl phosphoramidite. The linkage group between the amino alkyl and the oligonucleotide may for example be a phosphorothioate or a phosphodiester, or one of the other nucleoside linkage groups referred to herein. The amino alkyl group is covalently linked to the 5' or 3'-end of the oligonucleotide. Commercially available amino alkyl linkers are for example 3'-Amino-Modifier reagent for linkage at the 3'-end of the oligonucleotide and for linkage at the 5'-end of an oligonucleotide 5'-Amino-Modifier C6 is available. These reagents are available from Glen Research Corporation (Sterling, Va.). These compounds or similar ones were utilized by Krieg, et al, Antisense Research and Development 1991, 1, 161 to link fluorescein to the 5'-terminus of an oligonucleotide. A wide variety of further linker groups are known in the art and can be useful in the attachment of conjugate moieties to oligonucleotides. A review of many of the useful linker groups can be found in, for example, Antisense Research and Applications, S. T. Crooke and B. Lebleu, Eds., CRC Press, Boca Raton, Fla., 1993, p. 303-350. Other compounds such as acridine have been attached to the 3'-terminal phosphate group of an oligonucleotide via a polymethylene linkage (Asseline, et al., *Proc. Natl. Acad. Sci. USA* 1984, 81, 3297). Any of the above groups can be used as a single linker (region Y) or in combination with one or more further linkers (region Y-Y' or region Y-B or B-Y).

Linkers and their use in preparation of conjugates of oligonucleotides are provided throughout the art such as in WO 96/11205 and WO 98/52614 and U.S. Pat. Nos. 4,948,882; 5,525,465; 5,541,313; 5,545,730; 5,552,538; 5,580,731; 5,486,603; 5,608,046; 4,587,044; 4,667,025; 5,254,469; 5,245,022; 5,112,963; 5,391,723; 5,510,475; 5,512,667; 5,574,142; 5,684,142; 5,770,716; 6,096,875; 6,335,432; and 6,335,437, WO 2012/083046 each of which is incorporated by reference in its entirety.

Method of Manufacture

In a further aspect, the invention provides methods for manufacturing the oligonucleotides of the invention comprising reacting nucleotide units and thereby forming covalently linked contiguous nucleotide units comprised in the oligonucleotide. Preferably, the method uses phophoramidite chemistry (see for example Caruthers et al, 1987, Methods in Enzymology vol. 154, pages 287-313). In a further embodiment the method further comprises reacting the contiguous nucleotide sequence with a conjugating moiety (ligand). In a further aspect a method is provided for manufacturing the composition of the invention, comprising mixing the oligonucleotide or conjugated oligonucleotide of the invention with a pharmaceutically acceptable diluent, solvent, carrier, salt and/or adjuvant.

Pharmaceutical Composition

In a further aspect, the invention provides pharmaceutical compositions comprising any of the aforementioned oligonucleotides and/or oligonucleotide conjugates and a pharmaceutically acceptable diluent, solvent, carrier, salt and/or adjuvant. A pharmaceutically acceptable diluent includes phosphate-buffered saline (PBS) and pharmaceutically acceptable salts include, but are not limited to, sodium and potassium salts. In some embodiments the pharmaceutically acceptable diluent is sterile phosphate buffered saline. In some embodiments the oligonucleotide is used in the pharmaceutically acceptable diluent at a concentration of 50-300 µM solution.

Suitable formulations for use in the present invention are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990). WO 2007/031091 provides further suitable and preferred examples of pharmaceutically acceptable diluents, carriers and adjuvants (hereby incorporated by reference). Suitable dosages, formulations, administration routes, compositions, dosage forms, combinations with other therapeutic agents, pro-drug formulations are also provided in WO2007/031091.

Oligonucleotides or oligonucleotide conjugates of the invention may be mixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

In some embodiments, the oligonucleotide or oligonucleotide conjugate of the invention is a prodrug. In particular with respect to oligonucleotide conjugates the conjugate moiety is cleaved of the oligonucleotide once the prodrug is delivered to the site of action, e.g. the target cell.

Applications

The oligonucleotides or oligonucleotide conjugates of the present invention may be utilized as research reagents for, for example, diagnostics, therapeutics and prophylaxis.

In research, such oligonucleotides or oligonucleotide conjugates may be used to specifically modulate the synthesis of PD-L1 protein in cells (e.g. in vitro cell cultures) and experimental animals thereby facilitating functional analysis of the target or an appraisal of its usefulness as a target for therapeutic intervention. Typically the target modulation is achieved by degrading or inhibiting the mRNA producing the protein, thereby prevent protein formation or by degrading or inhibiting a modulator of the gene or mRNA producing the protein.

If employing the oligonucleotide of the invention in research or diagnostics the target nucleic acid may be a cDNA or a synthetic nucleic acid derived from DNA or RNA.

The present invention provides an in vivo or in vitro method for modulating PD-L1 expression in a target cell which is expressing PD-L1, said method comprising administering an oligonucleotide or oligonucleotide conjugate of the invention in an effective amount to said cell.

In some embodiments, the target cell, is a mammalian cell in particular a human cell. The target cell may be an in vitro cell culture or an in vivo cell forming part of a tissue in a mammal. In preferred embodiments the target cell is present in the liver. Liver target cell can be selected from parenchymal cells (e.g. hepatocytes) and non-parenchymal cells such as Kupffer cells, LSECs, stellate cells (or Ito cells), cholangiocytes and liver-associated leukocytes (including T cells and NK cells). In some embodiments the target cell is an antigen-presenting cell. Antigen-presenting cells displays foreign antigens complexed with major histocompatibility complex (MHC) class I or class II on their surfaces. In some embodiments the antigen-presenting cell expresses MHC class II (i.e. professional antigen-presenting cells such as dendritic cells, macrophages and B cells).

In diagnostics the oligonucleotides may be used to detect and quantitate PD-L1 expression in cell and tissues by northern blotting, in-situ hybridisation or similar techniques.

For therapeutics oligonucleotides or oligonucleotide conjugates of the present invention or pharmaceutical compositions thereof may be administered to an animal or a human, suspected of having a disease or disorder, which can be alleviated or treated by reduction of the expression of PD-L1, in particular by reduction of the expression of PD-L1 in liver target cells.

The invention provides methods for treating or preventing a disease, comprising administering a therapeutically or prophylactically effective amount of an oligonucleotide, an oligonucleotide conjugate or a pharmaceutical composition of the invention to a subject suffering from or susceptible to the disease.

The invention also relates to an oligonucleotide, oligonucleotide conjugate or a pharmaceutical composition according to the invention for use as a medicament.

The oligonucleotide, oligonucleotide conjugate or a pharmaceutical composition according to the invention is typically administered in an effective amount.

The invention also provides for the use of the oligonucleotide or oligonucleotide conjugate or pharmaceutical composition of the invention as described for the manufacture of a medicament for the treatment of a disease or disorder as referred to herein. In one embodiment the disease is selected from a) viral liver infections such as HBV, HCV and HDV; b) parasite infections such as malaria, toxoplasmosis, leishmaniasis and trypanosomiasis and c) liver cancer or metastases in the liver.

In one embodiment, the invention relates to oligonucleotides, oligonucleotide conjugates or pharmaceutical compositions for use in the treatment of diseases or disorders selected from viral or parasitic infections. In a further embodiment the disease is selected from a) viral liver infections such as HBV, HCV and HDV; b) parasite infections such as malaria, toxoplasmosis, leishmaniasis and trypanosomiasis and c) liver cancer or metastases in the liver.

The disease or disorder, as referred to herein, is associated with immune exhaustion. In particular the disease or disorder is associated with exhaustion of virus-specific T-cell responses. In some embodiments disease or disorder may be alleviated or treated by reduction of PD-L1 expression.

The methods of the invention are preferably employed for treatment or prophylaxis against diseases associated with immune exhaustion.

In one embodiment of the invention the oligonucleotide, oligonucleotide conjugate or pharmaceutical compositions of the invention are used in restoration of immune response against a liver cancer or metastases in the liver.

In one embodiment of the invention the oligonucleotide, oligonucleotide conjugate or pharmaceutical compositions of the invention are used in restoration of immune response against a pathogen. In some embodiments the pathogen can be found in the liver. The pathogens can be a virus or a parasite, in particular those described herein. In a preferred embodiment the pathogen is HBV.

The invention further relates to use of an oligonucleotide, oligonucleotide conjugate or a pharmaceutical composition as defined herein for the manufacture of a medicament for the restoration of immunity against a viral or parasite infection as mentioned herein.

Oligonucleotides or oligonucleotide conjugates or pharmaceutical compositions of the present invention can be used in the treatment of viral infections, in particular viral infections in the liver where the PD-1 pathway is affected (see for example Kapoor and Kottilil 2014 Future Virol Vol. 9 pp. 565-585 and Salem and El-Badawy 2015 World J Hepatol Vol. 7 pp. 2449-2458). Viral liver infections can be selected from the group consisting of hepatitis viruses, in particular HBV, HCV and HDV, in particular chronic forms of these infections. In one embodiment the oligonucleotides or oligonucleotide conjugates or pharmaceutical compositions of the present invention are used to treat HBV, in particular chronic HBV. Indicators of chronic HBV infections are high levels of viral load (HBV DNA) and even higher levels of empty HBsAg particles (>100-fold in excess of virions) in the circulation.

Oligonucleotides or oligonucleotide conjugates of the present invention can also be used to treat viral liver infections that occur as co-infections with HIV. Other viral infections which can be treated with the oligonucleotides or oligonucleotide conjugates or pharmaceutical compositions of the present invention are lcmv (Lymphocytic Choriomeningitis Virus), and HIV as a mono infection, HSV-1 and -2, and other herpesviruses. These viruses are not hepatotrophic, however they may be sensitive to PDL1 down regulation.

In some embodiments the restoration of immunity or immune response involves improvement of the T-cell and/or NK cell response and/or alleviation of the T-cell exhaustion, in particular the HBV-specific T-cell response, the HCV-specific T-cell response and or the HDV-specific T-cell response is restored. An improvement of the T cell response can for example be assessed as an increase in T cells in the liver, in particular an increase in CD8+ and/or CD4+ T cells when compared to a control (e.g. the level prior to treatment or the level in a vehicle treated subject) In a further embodiment it is the virus specific CD8+ T cells that are restored or increased when compared to control), in particular HBV specific CD8+ T cells or HCV specific CD8+ T cells or HDV specific CD8+ T cells are restored or increased when compared to control. In a preferred embodiment CD8+ T cells specific for HBV s antigen (HBsAg) and/or CD8+ T cells specific for HBV e antigen (HBeAg) and/or CD8+ T cells specific for HBV core antigen (HBcAg) are increased in subjects treated with an oligonucleotide, oligonucleotide conjugate or pharmaceutical composition of the present invention compared to control. Preferably the HBV antigen specific CD8+ T cells produce one or more cytokines, such as interferon-gamma (IFN-γ) or tumor necrosis factor alpha (TNF-α). The increase in CD8+ T cells described above is in particular observed in the liver. The increase described herein should be statistically significant when compared to a control. Preferably the increase is at least 20%, such as 25%, such as 50% such as 75% when compared to control. In another embodiment natural killer (NK) cells and/or natural killer T (NKT) cells are activated by the oligonucleotides or oligonucleotide conjugates of the present invention.

Oligonucleotides or oligonucleotide conjugates or pharmaceutical compositions of the present invention can be used in the treatment parasite infections, in particular parasite infections where the PD-1 pathway is affected (see for example Bhadra et al. 2012 J Infect Dis vol 206 pp. 125-134; Bhadra et al. 2011 Proc Natl Acad Sci USA Vol. 108 pp. 9196-9201; Esch et al. J Immunol vol 191 pp 5542-5550; Freeman and Sharpe 2012 Nat Immunol Vol 13 pp. 113-115; Gutierrez et al. 2011 Infect Immun Vol 79 pp. 1873-1881; Joshi et al. 2009 PLoS Pathog Vol 5 e1000431; Liang et al. 2006 Eur J Immunol Vol. 36 pp 58-64; Wykes et al. 2014 Front Microbiol Vol 5 pp 249). Parasite infections can be selected from the group consisting of malaria, toxoplasmosis, leishmaniasis and trypanosomiasis. Malaria infection is caused by protozoa of the genus *Plasmodium*, in particular of the species *P. vivax, P. malariae* and *P. falciparum*. Toxoplasmosis is a parasitic disease caused by *Toxoplasma gondii*. Leishmaniasis is a disease caused by protozoan parasites of the genus *Leishmania*. Trypanosomiasis is caused by the protozoan of the genus *Trypanosoma*. Chaga disease which is the tropical form caused by the species *Trypanosoma cruzi*, and sleeping disease is caused by the species *Trypanosoma brucei*.

In some embodiments the restoration of immunity involves restoration of a parasite-specific T cell and NK cell response, in particular a *Plasmodium*-specific T-cell response, a *Toxoplasma gondii*-specific T-cell and NK cell response, a *Leishmania*-specific T-cell and NK cell response, a *Trypanosoma cruzi*-specific T-cell and NK cell response or a *Trypanosoma brucei*-specific T-cell and NK cell response. In a further embodiment it is the parasite-specific CD8+ T cell and NK cell response that is restored.

Administration

The oligonucleotides or pharmaceutical compositions of the present invention may be administered topical (such as, to the skin, inhalation, ophthalmic or otic) or enteral (such as, orally or through the gastrointestinal tract) or parenteral (such as, intravenous, subcutaneous, intra-muscular, intracerebral, intracerebroventricular or intrathecal).

In a preferred embodiment the oligonucleotide or pharmaceutical compositions of the present invention are administered by a parenteral route including intravenous, intraarterial, subcutaneous, intraperitoneal or intramuscular injection or infusion, intrathecal or intracranial, e.g. intracerebral or intraventricular, intravitreal administration. In one embodiment the active oligonucleotide or oligonucleotide conjugate is administered intravenously. In another embodiment the active oligonucleotide or oligonucleotide conjugate is administered subcutaneously.

In some embodiments, the oligonucleotide, oligonucleotide conjugate or pharmaceutical composition of the invention is administered at a dose of 0.1-15 mg/kg, such as from 0.1-10 mg/kg, such as from 0.2-10 mg/kg, such as from 0.25-10 mg/kg, such as from 0.1-5 mg/kg, such as from 0.2-5 mg/kg, such as from 0.25-5 mg/kg. The administration can be once a week, every $2^{nd}$ week, every third week or even once a month.

Combination Therapies

In some embodiments the oligonucleotide, oligonucleotide conjugate or pharmaceutical composition of the invention is for use in a combination treatment with another therapeutic agent. The therapeutic agent can for example be the standard of care for the diseases or disorders described above.

For the treatment of chronic HBV infections a combination of antiviral drugs and immune system modulators is recommended as standard of care. The antiviral drugs effective against HBV are for example nucleos(t)ide analogs. There are five nucleos(t)ide analogs licensed for therapy of HBV namely lamivudine (Epivir), adefovir (Hepsera), tenofovir (Viread), telbivudine (Tyzeka), entecavir (Baraclude) these are effective in suppressing viral replication (HBV DNA) but have no effect on HBsAg levels. Other antiviral drugs include ribavirin and an HBV antibody therapy (monoclonal or polyclonal). The immune system modulators can for example be interferon alpha-2a and PEGylated interferon alpha-2a (Pegasys) or TLR7 agonists (e.g. GS-9620) or therapeutic vaccines. IFN-α treatment show only very modest effect in reducing viral load, but result in some HBsAg decline, albeit very inefficiently (<10% after 48 week therapy).

The oligonucleotide or oligonucleotide conjugates of the present invention may also be combined with other antiviral drugs effective against HBV such as the antisense oligonucleotides described in WO2012/145697 and WO 2014/179629 or the siRNA molecules described in WO 2005/014806, WO 2012/024170, WO 2012/2055362, WO 2013/003520 and WO 2013/159109.

When the oligonucleotides or oligonucleotide conjugates of this invention are administered in combination therapies with other agents, they may be administered sequentially or concurrently to an individual. Alternatively, pharmaceutical compositions according to the present invention may be comprised of a combination of an oligonucleotide or oligonucleotide conjugate of the present invention in association with a pharmaceutically acceptable excipient, as described herein, and another therapeutic or prophylactic agent known in the art.

EMBODIMENTS

The following embodiments of the present invention may be used in combination with any other embodiments described herein.

1. An antisense oligonucleotide which comprises or consists of a contiguous nucleotide sequence of 10 to 30 nucleotides in length capable of reducing the expression of PD-1.

2. The oligonucleotide of embodiment 1, wherein the contiguous nucleotide sequence is at least 90% complementarity to a PD-L1 target nucleic acid.

3. The oligonucleotide of embodiment 1 or 2, wherein the contiguous nucleotide sequence is complementary to a target nucleic acid selected from the group consisting of SEQ ID NO: 1, SEQ ID NO: 2 and/or SEQ ID NO: 3.

4. The oligonucleotide of embodiment 1 to 3, wherein the contiguous nucleotide sequence is complementary to a region within position 1 and 15720 on SEQ ID NO: 1.

5. The oligonucleotide of embodiment 1 to 4, wherein the oligonucleotide is capable of hybridizing to a target nucleic acid of selected from the group consisting of SEQ ID NO: 1, SEQ ID NO: 2 and/or SEQ ID NO: 3 with a ΔG° below −10 kcal.

6. The oligonucleotide of embodiment 1 to 5, wherein the contiguous nucleotide sequence is complementary to a sub-sequence of the target nucleic acid, wherein the sub-sequence is selected from the group consisting of position 371-3068, 5467-12107, 15317-15720, 15317-18083, 15317-19511 and 18881-19494 on SEQ ID NO: 1.

7. The oligonucleotide of embodiment 6, wherein the sub-sequence is selected from the group consisting of position 7300-7333, 8028-8072, 9812-9859, 11787-11873 and 15690-15735 on SEQ ID NO: 1.

8. The oligonucleotide of embodiment 2 to 7, wherein the target nucleic acid is RNA.

9. The oligonucleotide of embodiment 8, wherein the RNA is mRNA.

10. The oligonucleotide of embodiment 9, wherein the mRNA is pre-mRNA or mature mRNA.

11. The oligonucleotide of embodiment 1-10, wherein the contiguous nucleotide sequence comprises or consists of at least 14 contiguous nucleotides, particularly 15, 16, 17, 18, 19, 20, 21, 22, 23 or 24 contiguous nucleotides.

12. The oligonucleotide of embodiment 1-10, wherein the contiguous nucleotide sequence comprises or consists of from 16 to 20 nucleotides.

13. The oligonucleotide of embodiment 1-10, wherein the oligonucleotide comprises or consists of 14 to 35 nucleotides in length.

14. The oligonucleotide of embodiment 13, wherein the oligonucleotide comprises or consists of 18 to 22 nucleotides in length.

15. The oligonucleotide of embodiment 1-14, wherein the oligonucleotide or contiguous nucleotide sequence is single stranded.

16. The oligonucleotide of embodiment 1-15, wherein the contiguous nucleotide sequence is complementary to a subsequence of the target nucleic acid, wherein the subsequence is selected from the group consisting of A7, A26, A43, A119, A142, A159, A160, A163, A169, A178, A179, A180, A189, A201, A202, A204, A214, A221, A224, A226, A243, A254, A258, 269, A274, A350, A360, A364, A365, A370, A372, A381, A383, A386, A389, A400, A427, A435 and A438.

17. The oligonucleotide of embodiment 16, wherein the subsequence is selected from the group consisting of A221, A360, A180, A160 and A269.

18. The oligonucleotide of embodiment 1-17, wherein the oligonucleotide is not siRNA and is not self-complementary.

19. The oligonucleotide of embodiment 1-18, wherein the contiguous nucleotide sequence comprises or consists of a sequence selected from SEQ ID NO: 5 to 743 or 771.

20. The oligonucleotide of embodiment 1-19, wherein the contiguous nucleotide sequence comprises or consists of a sequence selected from SEQ ID NO: 6, 8, 9, 13, 41, 42, 58, 77, 92, 111, 128, 151, 164, 166, 169, 171, 222, 233, 245, 246, 250, 251, 252, 256, 272, 273, 287, 292, 303, 314, 318, 320, 324, 336, 342, 343, 344, 345, 346, 349, 359, 360, 374, 408, 409, 415, 417, 424, 429, 430, 458, 464, 466, 474, 490, 493, 512, 519, 519, 529, 533, 534, 547, 566, 567, 578, 582, 601, 619, 620, 636, 637, 638, 640, 645, 650, 651, 652, 653, 658, 659, 660, 665, 678, 679, 680, 682, 683, 684, 687, 694, 706, 716, 728, 733, 734, and 735.

21. The oligonucleotide of embodiment 1-20, wherein the contiguous nucleotide sequence comprises or consists of a sequence selected from SEQ ID NO: 466, 640, 342, 287 and 566.

22. The oligonucleotide of embodiment 1-21 wherein the contiguous nucleotide sequence has zero to three mismatches compared to the target nucleic acid it is complementary to.

23. The oligonucleotide of embodiment 22, wherein the contiguous nucleotide sequence has one mismatch compared to the target nucleic acid.

24. The oligonucleotide of embodiment 22, wherein the contiguous nucleotide sequence has two mismatches compared to the target nucleic acid.

25. The oligonucleotide of embodiment 22, wherein the contiguous nucleotide sequence is fully complementary to the target nucleic acid sequence.

26. The oligonucleotide of embodiment 1-25, comprising one or more modified nucleosides.

27. The oligonucleotide of embodiment 26, wherein the one or more modified nucleoside is a high-affinity modified nucleosides.

28. The oligonucleotide of embodiment 26 or 27, wherein the one or more modified nucleoside is a 2' sugar modified nucleoside.

29. The oligonucleotide of embodiment 28, wherein the one or more 2' sugar modified nucleoside is independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, 2'-fluoro-ANA and LNA nucleosides.

30. The oligonucleotide of embodiment 28, wherein the one or more modified nucleoside is a LNA nucleoside.

31. The oligonucleotide of embodiment 30, wherein the modified LNA nucleoside is oxy-LNA.

32. The oligonucleotide of embodiment 31, wherein the modified nucleoside is beta-D-oxy-LNA.

33. The oligonucleotide of embodiment 30, wherein the modified nucleoside is thio-LNA.

34. The oligonucleotide of embodiment 30, wherein the modified nucleoside is amino-LNA.

35. The oligonucleotide of embodiment 30, wherein the modified nucleoside is cET.

36. The oligonucleotide of embodiment 30, wherein the modified nucleoside is ENA.

37. The oligonucleotide of embodiment 30, wherein the modified LNA nucleoside is selected from beta-D-oxy-LNA, alpha-L-oxy-LNA, beta-D-amino-LNA, alpha-L-amino-LNA, beta-D-thio-LNA, alpha-L-thio-LNA, (S)cET, (R)cET beta-D-ENA and alpha-L-ENA.

38. The oligonucleotide of embodiment 30-37, wherein there in addition to the modified LNA nucleoside is at least one 2' substituted modified nucleoside.

39. The oligonucleotide of embodiment 38, wherein the 2' substituted modified nucleoside is selected from the group consisting of 2'-O-alkyl-RNA, 2'-O-methyl-RNA, 2'-alkoxy-RNA, 2'-O-methoxyethyl-RNA (MOE), 2'-amino-DNA, 2'-fluoro-DNA, 2'-fluoro-ANA.

40. The oligonucleotide of any one of embodiments 1-39, wherein the oligonucleotide comprises at least one modified internucleoside linkage.

41. The oligonucleotide of embodiment 40, wherein the modified internucleoside linkage is nuclease resistant.

42. The oligonucleotide of embodiment 40 or 41, wherein at least 50% of the internucleoside linkages within the contiguous nucleotide sequence are phosphorothioate internucleoside linkages or boranophosphate internucleoside linkages.

43. The oligonucleotide of embodiment 40 or 41, wherein all the internucleoside linkages within the contiguous nucleotide sequence are phosphorothioate internucleoside linkages.

44. The oligonucleotide of embodiment 1-43, wherein the oligonucleotide is capable of recruiting RNase H.

45. The oligonucleotide of embodiment 44, wherein the oligonucleotide is a gapmer.

46. The oligonucleotide of embodiment 44 or 45, wherein the oligonucleotide is a gapmer of formula 5'-F-G-F'-3', where region F and F' independently comprise or consist of 1-7 modified nucleosides and G is a region between 6 and 16 nucleosides which are capable of recruiting RNaseH.

47. The oligonucleotide of embodiment 44 or 45, wherein the gapmer has formula 5'-D'-F-G-F'-3' or 5'-F-G-F'-D''-3', where region F and F' independently comprise 1-7 modified nucleosides, G is a region between 6 and 16 nucleosides which are capable of recruiting RNaseH and region D' or D'' comprise 1-5 phosphodiester linked nucleosides.

48. The oligonucleotide of embodiment 47, wherein D' or D'' are optional.

49. The oligonucleotide of embodiment 47, wherein region D' consist of two phosphodiester linked nucleosides.

50. The oligonucleotide of embodiment 49, wherein the phosphodiester linked nucleosides are ca (cytidine-adenosine).

51. The oligonucleotide of embodiment 46 or 47, wherein the modified nucleoside is a 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

52. The oligonucleotide of embodiments 46 to 51, wherein one or more of the modified nucleosides in region F and F' is a LNA nucleoside.

53. The oligonucleotide of embodiment 52, wherein all the modified nucleosides in region F and F' are LNA nucleosides.

54. The oligonucleotide of embodiment 53, wherein region F and F' consist of LNA nucleosides.

55. The oligonucleotide of embodiment 52-54, wherein all the modified nucleosides in region F and F' are oxy-LNA nucleosides.

56. The oligonucleotide of embodiment 52, wherein at least one of region F or F' further comprises at least one 2' substituted modified nucleoside independently selected from the group consisting of 2'-O-alkyl-RNA, 2'-O-methyl-RNA, 2'-alkoxy-RNA, 2'-O-methoxyethyl-RNA, 2'-amino-DNA and 2'-fluoro-DNA.

57. The oligonucleotide of embodiment 46-56, wherein the RNaseH recruiting nucleosides in region G are independently selected from DNA, alpha-L-LNA, C4' alkylated DNA, ANA and 2'F-ANA and UNA.

58. The oligonucleotide of embodiment 57, wherein the nucleosides in region G is DNA and/or alpha-L-LNA nucleosides.

59. The oligonucleotide of embodiment 57 or 58, wherein region G consists of at least 75% DNA nucleosides.

60. The oligonucleotide of embodiment 1-59, wherein the oligonucleotide is selected from any one of the CMP ID NO: 5_1 to 743_1 and 771_1 (table 5).

61. The oligonucleotide of embodiment 1-60, wherein the oligonucleotide is selected from the group consisting of CMP ID NO: 6_1, 8_1, 9_1, 13_1, 41_1, 42_1, 58_1, 77_1, 92_1, 111_1, 128_1, 151_1, 164_1, 166_1, 169_1, 171_1, 222_1, 233_1, 245_1, 246_1, 250_1, 251_1, 252_1, 256_1, 272_1, 273_1, 287_1, 292_1, 303_1, 314_1, 318_1, 320_1, 324_1, 336_1, 342_1, 343_1, 344_1, 345_1, 346_1, 349_1, 359_1, 360_1, 374_1, 408_1, 409_1, 415_1, 417_1, 424_1, 429_1, 430_1, 458_1, 464_1, 466_1, 474_1, 490_1, 493_1, 512_1, 519_1, 519_1, 529_1, 533_1, 534_1, 547_1, 566_1, 567_1, 578_1, 582_1, 601_1, 619_1, 620_1, 636_1, 637_1, 638_1, 640_1, 645_1, 650_1, 651_1, 652_1, 653_1, 658_1, 659_1, 660_1, 665_1, 678_1, 679_1, 680_1, 682_1, 683_1, 684_1, 687_1, 694_1, 706_1, 716_1, 728_1, 733_1, 734_1, and 735_1.

62. The oligonucleotide of embodiment 1-61, wherein the oligonucleotide is selected from the group consisting of CMP ID NO: 287_1, 342_1, 466_1, 640_1, 566_1, 766_1, 767_1, 768_1, 769_1 and 770_1.

63. An antisense oligonucleotide conjugate comprising
a. an oligonucleotide according to any one of claims 1-62 (Region A); and
b. at least one at least one conjugate moiety (Region C) covalently attached to said oligonucleotide.

64. The oligonucleotide conjugate of embodiment 63, wherein the conjugate moiety is selected from carbohydrates, cell surface receptor ligands, drug substances, hormones, lipophilic substances, polymers, proteins, peptides, toxins, vitamins, viral proteins or combinations thereof.

65. The oligonucleotide conjugate of embodiment 63 or 64, wherein the conjugate moiety is a carbohydrate containing moiety.

66. The oligonucleotide conjugate of embodiment 65, wherein the carbohydrate conjugate moiety comprises at least one asialoglycoprotein receptor targeting moiety covalently attached to an oligonucleotide according to any one of claims 1-62.

67. The oligonucleotide conjugate of embodiment 66, wherein the asialoglycoprotein receptor targeting conjugate moiety comprises at least one carbohydrate moiety selected from group consisting of galactose, galactosamine, N-formyl-galactosamine, N-acetylgalactosamine, N-propionyl-galactosamine, N-n-butanoyl-galactosamine and N-isobutanoylgalactosamine.

68. The oligonucleotide conjugate of embodiment 66 or 67, wherein the asialoglycoprotein receptor targeting conjugate moiety is mono-valent, di-valent, tri-valent or tetravalent.

69. The oligomer conjugate of embodiment 68, wherein the asialoglycoprotein receptor targeting conjugate moiety consists of two to four terminal GalNAc moieties, a PEG spacer linking each GalNAc moiety to a brancher molecule.

70. The oligonucleotide conjugate of embodiment 66 to 69, wherein the asialoglycoprotein receptor targeting conjugate moiety is a tri-valent N-acetylgalactosamine (GalNAc) moiety.

71. The oligonucleotide conjugate of embodiment 66 to 70, wherein the conjugate moiety is selected from one of the trivalent GalNAc moieties in FIG. 1.

72. The oligonucleotide conjugate of embodiment 71, wherein the conjugate moiety is the trivalent GalNAc moiety in FIG. 3.

73. The oligonucleotide conjugate of embodiment 63-72, where a linker is present between the oligonucleotide or contiguous oligonucleotide sequence and the conjugate moiety.

74. The oligonucleotide conjugate of embodiment 73, wherein the linker is a physiologically labile linker (region B).

75. The oligonucleotide conjugate of embodiment 74, wherein the physiologically labile linker is nuclease susceptible linker.

76. The oligonucleotide conjugate of embodiment 74 or 75, wherein the physiologically labile linker is composed of 2 to 5 consecutive phosphodiester linkages.

77. The oligonucleotide conjugate of embodiment 76, wherein the physiologically labile linker is equivalent to region D' or D" presented in embodiment 47 to 50.

78. The oligonucleotide conjugate of any one of embodiments 63-77, wherein the oligonucleotide conjugate is selected from CMP ID NO: 766_2, 767_2, 768_2, 769_2 and 770_2.

79. The oligonucleotide conjugate of embodiment 78, wherein the oligonucleotide conjugate is selected from the oligonucleotide conjugated represented in FIGS. 4, 5, 6, 7 and 8.

80. The oligonucleotide conjugate of embodiment 63-76, which display improved inhibition of PD-L1 in the target cell, or improved cellular distribution between liver and the spleen or improved cellular uptake into the liver of the conjugate oligonucleotide as compared to an unconjugated oligonucleotide.

81. A pharmaceutical composition comprising the oligonucleotide of embodiment 1-62 or a conjugate of embodiment 63-80 and a pharmaceutically acceptable diluent, carrier, salt and/or adjuvant.

82. A method for manufacturing the oligonucleotide of embodiment 1-62, comprising reacting nucleotide units thereby forming covalently linked contiguous nucleotide units comprised in the oligonucleotide.

83. The method of embodiment 82, further comprising reacting the contiguous nucleotide sequence with a non-nucleotide conjugation moiety.

84. A method for manufacturing the composition of embodiment 81, comprising mixing the oligonucleotide with a pharmaceutically acceptable diluent, carrier, salt and/or adjuvant.

85. An in vivo or in vitro method for modulating PD-L1 expression in a target cell which is expressing PD-L1, said method comprising administering an oligonucleotide of embodiment 1-62 or a conjugate of embodiment 63-80 or the pharmaceutical composition of embodiment 81 in an effective amount to said cell.

86. A method for treating or preventing a disease comprising administering a therapeutically or prophylactically effective amount of an oligonucleotide of embodiment 1-62 or a conjugate of embodiment 63-80 or the pharmaceutical composition of embodiment 81 to a subject suffering from or susceptible to the disease.

87. A method for restoration of immunity against a virus or parasite comprising administering a therapeutically or prophylactically effective amount of an oligonucleotide conjugate of embodiment 63-80 or the oligonucleotide of embodiment 1-62 or the pharmaceutical composition of embodiment 81 to a subject infected with a virus or parasite.

88. The method of embodiment 87, the restoration of immunity is an increase in the liver of CD8+ T cells specific to one or more HBV antigens when compared to a control.

89. The oligonucleotide of embodiment 1-62 or a conjugate of embodiment 63-80 or the pharmaceutical composition of embodiment 81, for use as a medicament for treatment or prevention of a disease in a subject.

90. Use of the oligonucleotide of oligonucleotide of embodiment 1-62 or a conjugate of embodiment 63-80 for the preparation of a medicament for treatment or prevention of a disease in a subject.

91. The oligonucleotide of embodiment 1-62 or a conjugate of embodiment 63-80 or the pharmaceutical composition of embodiment 81, for use in restoration of immunity against a virus or parasite.

92. The use of embodiment 91, wherein the restoration of immunity is an increase in the liver of CD8+ T cells specific to one or more HBV antigens when compared to a control.

93. The use of embodiment 92, wherein the HBV antigen is the HBsAg.

94. The method, the oligonucleotide or the use of embodiments 86-93, wherein the disease is associated with in vivo activity of PD-1.

95. The method, the oligonucleotide or the use of embodiments 86-94, wherein the disease is associated with increased expression of PD-L1 in an antigen presenting cell.

96. The method, the oligonucleotide or the use of embodiments 95, wherein the PD-L1 is reduced by at least 30%, or at least or at least 40%, or at least 50%, or at least 60%, or at least 70%, or at least 80%, or at least 90%, or at least 95% compared to the expression without or before treatment with the oligonucleotide of embodiment 1-62 or a conjugate of embodiment 63-80 or the pharmaceutical composition of embodiment 81.

97. The method, the oligonucleotide or the use of embodiments 86-95, wherein the disease is selected from a viral liver infection or a parasite infections.

98. The method, the oligonucleotide or the use of embodiment 98, wherein the viral infection is HBV, HCV or HDV.

99. The method, the oligonucleotide or the use of embodiment 86-95, wherein the disease is chronic HBV.

100. The method, the oligonucleotide or the use of embodiment 98, wherein the parasite infection is malaria, toxoplasmosis, leishmaniasis or trypanosomiasis.

101. The method, the oligonucleotide or the use of embodiments 86-100, wherein the subject is a mammal.

102. The method, the oligonucleotide or the use of embodiment 101, wherein the mammal is human.

EXAMPLES

Materials and Methods
Motif Sequences and Oligonucleotide Compounds

TABLE 5 list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 5 | taattggctctactgc | 2-11-3 | TAattggctctacTGC | 5_1 | 236 | -20 |
| 6 | tcgcataagaatgact | 4-10-2 | TCGCataagaatgaCT | 6_1 | 371 | -19 |
| 7 | tgaacacacagtcgca | 2-12-2 | TGaacacacagtcgCA | 7_1 | 382 | -19 |
| 8 | ctgaacacacagtcgc | 3-10-3 | CTGaacacacagtCGC | 8_1 | 383 | -22 |
| 9 | tctgaacacacagtcg | 3-11-2 | TCTgaacacacagtCG | 9_1 | 384 | -19 |
| 10 | ttctgaacacacagtc | 3-11-2 | TTCtgaacacacagTC | 10_1 | 385 | -17 |
| 11 | acaagtcatgttacta | 2-11-3 | ACaagtcatgttaCTA | 11_1 | 463 | -16 |
| 12 | acacaagtcatgttac | 2-12-2 | ACacaagtcatgttAC | 12_1 | 465 | -14 |
| 13 | cttacttagatgctgc | 2-11-3 | CTtacttagatgcTGC | 13_1 | 495 | -20 |
| 14 | acttacttagatgctg | 2-11-3 | ACttacttagatgCTG | 14_1 | 496 | -18 |
| 15 | gacttacttagatgct | 3-11-2 | GACttacttagatgCT | 15_1 | 497 | -19 |
| 16 | agacttacttagatgc | 2-11-3 | AGacttacttagaTGC | 16_1 | 498 | -18 |
| 17 | gcaggaagagacttac | 3-10-3 | GCAggaagagactTAC | 17_1 | 506 | -20 |
| 18 | aataaattccgttcagg | 4-9-4 | AATAaattccgttCAGG | 18_1 | 541 | -22 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 19 | gcaaataaattccgtt | 3-10-3 | GCAaataaattccGTT | 19_2 | 545 | -18 |
| 19 | gcaaataaattccgtt | 4-8-4 | GCAAataaattcCGTT | 19_1 | 545 | -20 |
| 20 | agcaaataaattccgt | 4-9-3 | AGCAaataaattcCGT | 20_1 | 546 | -20 |
| 21 | cagagcaaataaattcc | 4-10-3 | CAGAgcaaataaatTCC | 21_1 | 548 | -21 |
| 22 | tggacagagcaaataaat | 4-11-3 | TGGAcagagcaaataAAT | 22_1 | 551 | -19 |
| 23 | atggacagagcaaata | 4-8-4 | ATGGacagagcaAATA | 23_1 | 554 | -20 |
| 24 | cagaatggacagagca | 2-11-3 | CAgaatggacagaGCA | 24_1 | 558 | -21 |
| 25 | ttctcagaatggacag | 3-11-2 | TTCtcagaatggacAG | 25_1 | 562 | -17 |
| 26 | ctgaactttgacatag | 4-8-4 | CTGAactttgacATAG | 26_1 | 663 | -20 |
| 27 | aagacaaacccagactga | 2-13-3 | AAgacaaacccagacTGA | 27_1 | 675 | -21 |
| 28 | tataagacaaacccagac | 4-10-4 | TATAagacaaacccAGAC | 28_1 | 678 | -22 |
| 29 | ttataagacaaacccaga | 4-10-4 | TTATaagacaaaccCAGA | 29_1 | 679 | -23 |
| 30 | tgttataagacaaaccc | 4-10-3 | TGTTataagacaaaCCC | 30_1 | 682 | -22 |
| 31 | tagaacaatggtacttt | 4-9-4 | TAGAacaatggtaCTTT | 31_1 | 708 | -20 |
| 32 | gtagaacaatggtact | 4-10-2 | GTAGaacaatggtaCT | 32_1 | 710 | -19 |
| 33 | aggtagaacaatggta | 3-10-3 | AGGtagaacaatgGTA | 33_1 | 712 | -19 |
| 34 | aagaggtagaacaatgg | 4-9-4 | AAGAggtagaacaATGG | 34_1 | 714 | -21 |
| 35 | gcatccacagtaaatt | 2-12-2 | GCatccacagtaaaTT | 35_1 | 749 | -17 |
| 36 | gaaggttatttaattc | 2-11-3 | GAaggttatttaaTTC | 36_1 | 773 | -13 |
| 37 | ctaatcgaatgcagca | 4-9-3 | CTAAtcgaatgcaGCA | 37_1 | 805 | -22 |
| 38 | tacccaatctaatcga | 3-10-3 | TACccaatctaatCGA | 38_1 | 813 | -20 |
| 39 | tagttacccaatctaa | 3-10-3 | TAGttacccaatcTAA | 39_1 | 817 | -19 |
| 40 | catttagttacccaat | 3-10-3 | CATttagttacccAAT | 40_1 | 821 | -18 |
| 41 | tcatttagttacccaa | 3-10-3 | TCAtttagttaccCAA | 41_1 | 822 | -19 |
| 42 | ttcatttagttaccca | 2-10-4 | TTcatttagttaCCCA | 42_1 | 823 | -22 |
| 43 | gaattaatttcatttagt | 4-10-4 | GAATtaatttcattTAGT | 43_1 | 829 | -19 |
| 44 | cagtgaggaattaattt | 4-9-4 | CAGTgaggaattaATTT | 44_1 | 837 | -20 |
| 45 | ccaacagtgaggaatt | 4-8-4 | CCAAcagtgaggAATT | 45_1 | 842 | -21 |
| 46 | cccaacagtgaggaat | 3-10-3 | CCCaacagtgaggAAT | 46_1 | 843 | -22 |
| 47 | tatacccaacagtgagg | 2-12-3 | TAtacccaacagtgAGG | 47_1 | 846 | -21 |
| 48 | ttatacccaacagtgag | 2-11-4 | TTatacccaacagTGAG | 48_1 | 847 | -21 |
| 49 | tttatacccaacagtga | 3-11-3 | TTTatacccaacagTGA | 49_1 | 848 | -21 |
| 50 | cctttatacccaacag | 3-10-3 | CCTttatacccaaCAG | 50_1 | 851 | -23 |
| 51 | taacctttatacccaa | 4-8-4 | TAACctttatacCCAA | 51_1 | 854 | -22 |
| 52 | aataacctttataccca | 3-10-4 | AATaacctttataCCCA | 52_1 | 855 | -23 |
| 53 | gtaaataacctttata | 3-11-2 | GTAaataaccttaTA | 53_1 | 859 | -14 |
| 54 | actgtaaataaccttat | 4-10-4 | ACTGtaaataacctTTAT | 54_1 | 860 | -20 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 55 | atatatatgcaatgag | 3-11-2 | ATAtatatgcaatgAG | 55_1 | 903 | -14 |
| 56 | agatatatatgcaatg | 2-12-2 | AGatatatatgcaaTG | 56_1 | 905 | -12 |
| 57 | gagatatatatgcaat | 3-10-3 | GAGatatatatgcAAT | 57_1 | 906 | -15 |
| 58 | ccagagatatatatgc | 2-11-3 | CCagagatatataTGC | 58_1 | 909 | -19 |
| 59 | caatattccagagatat | 4-9-4 | CAATattccagagATAT | 59_1 | 915 | -20 |
| 60 | gcaatattccagagata | 4-10-3 | GCAAtattccagagATA | 60_1 | 916 | -22 |
| 61 | agcaatattccagagat | 3-11-3 | AGCaatattccagaGAT | 61_1 | 917 | -22 |
| 62 | cagcaatattccagag | 3-9-4 | CAGcaatattccAGAG | 62_1 | 919 | -22 |
| 63 | aatcagcaatattccag | 4-9-4 | AATCagcaatattCCAG | 63_1 | 921 | -23 |
| 64 | acaatcagcaatattcc | 4-9-4 | ACAAtcagcaataTTCC | 64_1 | 923 | -21 |
| 65 | actaagtagttacacttct | 2-14-3 | ACtaagtagttacactTCT | 65_1 | 957 | -20 |
| 66 | ctaagtagttacacttc | 4-11-2 | CTAAgtagttacactTC | 66_1 | 958 | -18 |
| 67 | gactaagtagttacactt | 3-12-3 | GACtaagtagttacaCTT | 67_1 | 959 | -20 |
| 68 | tgactaagtagttaca | 3-9-4 | TGActaagtagtTACA | 68_1 | 962 | -19 |
| 69 | ctttgactaagtagtta | 4-10-3 | CTTTgactaagtagTTA | 69_1 | 964 | -19 |
| 70 | ctctttgactaagtag | 3-10-3 | CTCtttgactaagTAG | 70_1 | 967 | -19 |
| 71 | gctctttgactaagta | 4-10-2 | GCTCtttgactaagTA | 71_1 | 968 | -21 |
| 72 | ccttaaatactgttgac | 2-11-4 | CCttaaatactgtTGAC | 72_1 | 1060 | -20 |
| 73 | cttaaatactgttgac | 2-12-2 | CTtaaatactgttgAC | 73_1 | 1060 | -13 |
| 74 | tccttaaatactgttg | 3-10-3 | TCCttaaatactgTTG | 74_1 | 1062 | -18 |
| 75 | tctccttaaatactgtt | 4-11-2 | TCTCcttaaatactgTT | 75_1 | 1063 | -19 |
| 76 | tatcatagttctcctt | 2-10-4 | TAtcatagttctCCTT | 76_1 | 1073 | -21 |
| 77 | agtatcatagttctcc | 3-10-3 | AGTatcatagttcTCC | 77_1 | 1075 | -22 |
| 78 | gagtatcatagttctc | 2-11-3 | GAgtatcatagttCTC | 78_1 | 1076 | -18 |
| 79 | agagtatcatagttct | 2-10-4 | AGagtatcatagTTCT | 79_1 | 1077 | -18 |
| 79 | agagtatcatagttct | 3-10-3 | AGAgtatcatagtTCT | 79_2 | 1077 | -19 |
| 80 | cagagtatcatagttc | 3-10-3 | CAGagtatcatagTTC | 80_1 | 1078 | -18 |
| 81 | ttcagagtatcatagt | 4-10-2 | TTCAgagtatcataGT | 81_1 | 1080 | -18 |
| 82 | cttcagagtatcatag | 3-9-4 | CTTcagagtatcATAG | 82_1 | 1081 | -19 |
| 83 | ttcttcagagtatcata | 4-11-2 | TTCTtcagagtatcaTA | 83_1 | 1082 | -19 |
| 84 | tttcttcagagtatcat | 3-10-4 | TTTcttcagagtaTCAT | 84_1 | 1083 | -20 |
| 85 | gagaaaggctaagttt | 4-9-3 | GAGAaaggctaagTTT | 85_1 | 1099 | -19 |
| 86 | gacactcttgtacatt | 2-10-4 | GAcactcttgtaCATT | 86_1 | 1213 | -19 |
| 87 | tgagacactcttgtaca | 2-13-2 | TGagacactcttgtaCA | 87_1 | 1215 | -18 |
| 88 | tgagacactcttgtac | 2-11-3 | TGagacactcttgTAC | 88_1 | 1216 | -18 |
| 89 | ctttattaaactccat | 2-10-4 | CTttattaaactCCAT | 89_1 | 1266 | -18 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 90 | accaaactttattaaa | 4-10-2 | ACCAaactttattaAA | 90_1 | 1272 | -14 |
| 91 | aaacctctactaagtg | 4-10-2 | AAACctctactaagTG | 91_1 | 1288 | -16 |
| 92 | agattaagacagttga | 2-11-3 | AGattaagacagtTGA | 92_1 | 1310 | -16 |
| 93 | aagtaggagcaagaggc | 2-12-3 | AAgtaggagcaagaGGC | 93_1 | 1475 | -22 |
| 94 | aaagtaggagcaagagg | 4-10-3 | AAAGtaggagcaagAGG | 94_1 | 1476 | -20 |
| 95 | gttaagcagccaggag | 2-12-2 | GTtaagcagccaggAG | 95_1 | 1806 | -20 |
| 96 | agggtaggatgggtag | 2-12-2 | AGggtaggatgggtAG | 96_1 | 1842 | -20 |
| 97 | aagggtaggatgggta | 3-11-2 | AAGggtaggatgggTA | 97_1 | 1843 | -20 |
| 98 | caagggtaggatgggt | 2-12-2 | CAagggtaggatggGT | 98_2 | 1844 | -20 |
| 98 | caagggtaggatgggt | 3-11-2 | CAAgggtaggatggGT | 98_1 | 1844 | -21 |
| 99 | ccaagggtaggatggg | 2-12-2 | CCaagggtaggatgGG | 99_1 | 1845 | -22 |
| 100 | tccaagggtaggatgg | 2-12-2 | TCcaagggtaggatGG | 100_1 | 1846 | -20 |
| 101 | cttccaagggtaggat | 4-10-2 | CTTCcaagggtaggAT | 101_1 | 1848 | -21 |
| 102 | atcttccaagggtagga | 3-12-2 | ATCttccaagggtagGA | 102_1 | 1849 | -22 |
| 103 | agaagtgatggctcatt | 2-11-4 | AGaagtgatggctCATT | 103_1 | 1936 | -21 |
| 104 | aagaagtgatggctcat | 3-10-4 | AAGaagtgatggcTCAT | 104_1 | 1937 | -21 |
| 105 | gaagaagtgatggctca | 3-11-3 | GAAgaagtgatggcTCA | 105_1 | 1938 | -21 |
| 106 | atgaaatgtaaactggg | 4-9-4 | ATGAaatgtaaacTGGG | 106_1 | 1955 | -21 |
| 107 | caatgaaatgtaaactgg | 4-10-4 | CAATgaaatgtaaaCTGG | 107_1 | 1956 | -20 |
| 108 | gcaatgaaatgtaaactg | 4-10-4 | GCAAtgaaatgtaaACTG | 108_1 | 1957 | -20 |
| 109 | agcaatgaaatgtaaact | 4-10-4 | AGCAatgaaatgtaAACT | 109_1 | 1958 | -20 |
| 110 | gagcaatgaaatgtaaac | 4-10-4 | GAGCaatgaaatgtAAAC | 110_1 | 1959 | -19 |
| 111 | tgaattcccatatccga | 2-12-3 | TGaattcccatatcCGA | 111_1 | 1992 | -22 |
| 112 | agaattatgaccatat | 2-11-3 | AGaattatgaccaTAT | 112_1 | 2010 | -15 |
| 113 | aggtaagaattatgacc | 3-10-4 | AGGtaagaattatGACC | 113_1 | 2014 | -21 |
| 114 | tcaggtaagaattatgac | 4-10-4 | TCAGgtaagaattaTGAC | 114_1 | 2015 | -22 |
| 115 | cttcaggtaagaattatg | 4-10-4 | CTTCaggtaagaatTATG | 115_1 | 2017 | -21 |
| 116 | tcttcaggtaagaatta | 4-9-4 | TCTTcaggtaagaATTA | 116_1 | 2019 | -20 |
| 117 | cttcttcaggtaagaat | 4-9-4 | CTTCttcaggtaaGAAT | 117_1 | 2021 | -21 |
| 118 | tcttcttcaggtaagaa | 4-10-3 | TCTTcttcaggtaaGAA | 118_1 | 2022 | -20 |
| 119 | tcttcttcaggtaaga | 3-10-3 | TCTtcttcaggtaAGA | 119_1 | 2023 | -20 |
| 120 | tggtctaagagaagaag | 3-10-4 | TGGtctaagagaaGAAG | 120_1 | 2046 | -20 |
| 121 | gttggtctaagagaag | 4-9-3 | GTTGgtctaagagAAG | 121_1 | 2049 | -19 |
| 123 | cagttggtctaagagaa | 2-11-4 | CAgttggtctaagAGAA | 123_1 | 2050 | -20 |
| 124 | gcagttggtctaagagaa | 3-13-2 | GCAgttggtctaagagAA | 124_1 | 2050 | -22 |
| 122 | agttggtctaagagaa | 3-9-4 | AGTtggtctaagAGAA | 122_1 | 2050 | -20 |
| 126 | gcagttggtctaagaga | 2-13-2 | GCagttggtctaagaGA | 126_1 | 2051 | -21 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 125 | cagttggtctaagaga | 4-10-2 | CAGTtggtctaagaGA | 125_1 | 2051 | −21 |
| 127 | gcagttggtctaagag | 2-11-3 | GCagttggtctaaGAG | 127_1 | 2052 | −21 |
| 128 | ctcatatcagggcagt | 2-10-4 | CTcatatcagggCAGT | 128_1 | 2063 | −24 |
| 129 | cacacatgttctttaac | 4-11-2 | CACAcatgttctttaAC | 129_1 | 2087 | −18 |
| 130 | taaatacacacatgttct | 3-11-4 | TAAatacacacatgTTCT | 130_1 | 2092 | −19 |
| 131 | gtaaatacacacatgttc | 4-11-3 | GTAAatacacacatgTTC | 131_1 | 2093 | −19 |
| 132 | tgtaaatacacacatgtt | 4-10-4 | TGTAaatacacacaTGTT | 132_1 | 2094 | −22 |
| 133 | gatcatgtaaatacacac | 4-10-4 | GATCatgtaaatacACAC | 133_1 | 2099 | −20 |
| 134 | agatcatgtaaatacaca | 4-10-4 | AGATcatgtaaataCACA | 134_1 | 2100 | −21 |
| 135 | caaagatcatgtaaatacac | 4-12-4 | CAAAgatcatgtaaatACAC | 135_1 | 2101 | −19 |
| 136 | acaaagatcatgtaaataca | 4-12-4 | ACAAagatcatgtaaaTACA | 136_1 | 2102 | −20 |
| 137 | gaatacaaagatcatgta | 4-10-4 | GAATacaaagatcaTGTA | 137_1 | 2108 | −20 |
| 138 | agaatacaaagatcatgt | 4-10-4 | AGAAtacaaagatcATGT | 138_1 | 2109 | −20 |
| 139 | cagaatacaaagatcatg | 4-10-4 | CAGAatacaaagatCATG | 139_1 | 2110 | −21 |
| 140 | gcagaatacaaagatca | 4-9-4 | GCAGaatacaaagATCA | 140_1 | 2112 | −22 |
| 141 | aggcagaatacaaagat | 4-11-2 | AGGCagaatacaaagAT | 141_1 | 2114 | −19 |
| 142 | aaggcagaatacaaaga | 4-10-3 | AAGGcagaatacaaAGA | 142_1 | 2115 | −19 |
| 143 | attagtgagggacgaa | 3-10-3 | ATTagtgagggacGAA | 143_1 | 2132 | −18 |
| 144 | cattagtgagggacga | 2-11-3 | CAttagtgagggaCGA | 144_1 | 2133 | −20 |
| 145 | gagggtgatggattag | 2-11-3 | GAgggtgatggatTAG | 145_1 | 2218 | −19 |
| 146 | ttaggagtaataaagg | 2-10-4 | TTaggagtaataAAGG | 146_1 | 2241 | −14 |
| 147 | ttaatgaatttggttg | 3-11-2 | TTAatgaatttggtTG | 147_1 | 2263 | −13 |
| 148 | ctttaatgaatttggt | 2-12-2 | CTttaatgaatttgGT | 148_1 | 2265 | −14 |
| 149 | catggattacaactaa | 4-10-2 | CATGgattacaactAA | 149_1 | 2322 | −16 |
| 150 | tcatggattacaacta | 2-11-3 | TCatggattacaaCTA | 150_1 | 2323 | −16 |
| 151 | gtcatggattacaact | 3-11-2 | GTCatggattacaaCT | 151_1 | 2324 | −18 |
| 152 | cattaaatctagtcat | 2-10-4 | CAttaaatctagTCAT | 152_1 | 2335 | −16 |
| 153 | gacattaaatctagtca | 4-10-3 | GACAttaaatctagTCA | 153_1 | 2336 | −19 |
| 154 | agggacattaaatcta | 4-10-2 | AGGGacattaaatcTA | 154_1 | 2340 | −18 |
| 155 | caaagcattataacca | 4-9-3 | CAAAgcattataaCCA | 155_1 | 2372 | −18 |
| 156 | acttactaggcagaag | 2-10-4 | ACttactaggcaGAAG | 156_1 | 2415 | −19 |
| 157 | cagagttaactgtaca | 4-10-2 | CAGAgttaactgtaCA | 157_1 | 2545 | −20 |
| 158 | ccagagttaactgtac | 4-10-2 | CCAGagttaactgtAC | 158_1 | 2546 | −20 |
| 159 | gccagagttaactgta | 2-12-2 | GCcagagttaactgTA | 159_1 | 2547 | −20 |
| 160 | tgggccagagttaact | 2-12-2 | TGggccagagttaaCT | 160_1 | 2550 | −21 |
| 161 | cagcatctatcagact | 2-12-2 | CAgcatctatcagaCT | 161_1 | 2576 | −19 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 162 | tgaaataacatgagtcat | 3-11-4 | TGAaataacatgagTCAT | 162_1 | 2711 | -19 |
| 163 | gtgaaataacatgagtc | 3-10-4 | GTGaaataacatgAGTC | 163_1 | 2713 | -19 |
| 164 | tctgtttatgtcactg | 4-10-2 | TCTGtttatgtcacTG | 164_1 | 2781 | -20 |
| 165 | gtctgtttatgtcact | 4-10-2 | GTCTgtttatgtcaCT | 165_1 | 2782 | -22 |
| 166 | tggtctgtttatgtca | 2-10-4 | TGgtctgtttatGTCA | 166_1 | 2784 | -21 |
| 167 | ttggtctgtttatgtc | 4-10-2 | TTGGtctgtttatgTC | 167_1 | 2785 | -20 |
| 168 | tcacccattgtttaaa | 2-12-2 | TCacccattgtttaAA | 168_1 | 2842 | -15 |
| 169 | ttcagcaaatattcgt | 2-10-4 | TTcagcaaatatTCGT | 169_1 | 2995 | -17 |
| 170 | gtgtgttcagcaaatat | 3-10-4 | GTGtgttcagcaaATAT | 170_1 | 2999 | -21 |
| 171 | tctattgttaggtatc | 3-10-3 | TCTattgttaggtATC | 171_1 | 3053 | -18 |
| 172 | attgcccatcttactg | 2-12-2 | ATtgcccatcttacTG | 172_1 | 3118 | -19 |
| 173 | tattgcccatcttact | 3-11-2 | TATtgcccatcttaCT | 173_1 | 3119 | -21 |
| 174 | aaatattgcccatctt | 2-11-3 | AAatattgcccatCTT | 174_1 | 3122 | -17 |
| 175 | ataaccttatcataca | 3-11-2 | ATAaccttatcataCA | 175_1 | 3174 | -16 |
| 176 | tataaccttatcatac | 2-11-3 | TAtaaccttatcaTAC | 176_1 | 3175 | -14 |
| 177 | ttataaccttatcata | 3-11-2 | TTAtaaccttatcaTA | 177_1 | 3176 | -14 |
| 178 | tttataaccttatcat | 3-10-3 | TTTataaccttatCAT | 178_1 | 3177 | -16 |
| 179 | actgctattgctatct | 2-11-3 | ACtgctattgctaTCT | 179_1 | 3375 | -19 |
| 180 | aggactgctattgcta | 2-11-3 | AGgactgctattgCTA | 180_1 | 3378 | -21 |
| 181 | gaggactgctattgct | 3-11-2 | GAGgactgctattgCT | 181_1 | 3379 | -22 |
| 182 | acgtagaataataaca | 2-12-2 | ACgtagaataataaCA | 182_1 | 3561 | -11 |
| 183 | ccaagtgatataatgg | 2-10-4 | CCaagtgatataATGG | 183_1 | 3613 | -19 |
| 184 | ttagcagaccaagtga | 2-10-4 | TTagcagaccaaGTGA | 184_1 | 3621 | -21 |
| 185 | gtttagcagaccaagt | 2-12-2 | GTttagcagaccaaGT | 185_1 | 3623 | -19 |
| 186 | tgacagtgattatatt | 2-12-2 | TGacagtgattataTT | 186_1 | 3856 | -13 |
| 187 | tgtccaagatattgac | 4-10-2 | TGTCcaagatattgAC | 187_1 | 3868 | -18 |
| 188 | gaatatcctagattgt | 3-10-3 | GAAtatcctagatTGT | 188_1 | 4066 | -18 |
| 189 | caaactgagaatatcc | 2-11-3 | CAaactgagaataTCC | 189_1 | 4074 | -16 |
| 190 | gcaaactgagaatatc | 3-11-2 | GCAaactgagaataTC | 190_1 | 4075 | -16 |
| 191 | tcctattacaatcgta | 3-11-2 | TCCtattacaatcgTA | 191_1 | 4214 | -19 |
| 192 | ttcctattacaatcgt | 4-10-2 | TTCCtattacaatcGT | 192_1 | 4215 | -19 |
| 193 | actaatgggaggattt | 2-12-2 | ACtaatgggaggatTT | 193_1 | 4256 | -15 |
| 194 | tagttcagagaataag | 2-12-2 | TAgttcagagaataAG | 194_1 | 4429 | -13 |
| 195 | taacatatagttcaga | 2-11-3 | TAacatatagttcAGA | 195_1 | 4436 | -15 |
| 196 | ataacatatagttcag | 3-11-2 | ATAacatatagttcAG | 196_1 | 4437 | -14 |
| 197 | cataacatatagttca | 2-12-2 | CAtaacatatagttCA | 197_1 | 4438 | -13 |
| 198 | tcataacatatagttc | 2-12-2 | TCataacatatagtTC | 198_1 | 4439 | -12 |

TABLE 5-continued list of oligonucleotide motif sequences (indicated by SEQ ID NO) targeting the human
PD-L1 transcript (SEQ ID NO: 1), designs of these, as well as specific antisense
oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 199 | tagctcctaacaatca | 4-10-2 | TAGCtcctaacaatCA | 199_1 | 4507 | −22 |
| 200 | ctccaatctttgtata | 4-10-2 | CTCCaatctttgtaTA | 200_1 | 4602 | −20 |
| 201 | tctccaatctttgtat | 4-10-2 | TCTCcaatctttgtAT | 201_1 | 4603 | −19 |
| 202 | tctatttcagccaatc | 2-12-2 | TCtatttcagccaaTC | 202_1 | 4708 | −17 |
| 203 | cggaagtcagagtgaa | 3-10-3 | CGGaagtcagagtGAA | 203_1 | 4782 | −19 |
| 204 | ttaagcatgaggaata | 4-10-2 | TTAAgcatgaggaaTA | 204_1 | 4798 | −16 |
| 205 | tgattgagcacctctt | 3-10-3 | TGAttgagcacctCTT | 205_1 | 4831 | −22 |
| 206 | gactaattatttcgtt | 3-11-2 | GACtaattatttcgTT | 206_1 | 4857 | −15 |
| 207 | tgactaattatttcgt | 3-10-3 | TGActaattatttCGT | 207_1 | 4858 | −17 |
| 208 | gtgactaattatttcg | 3-10-3 | GTGactaattattTCG | 208_1 | 4859 | −17 |
| 209 | ctgcttgaaatgtgac | 4-10-2 | CTGCttgaaatgtgAC | 209_1 | 4870 | −20 |
| 210 | cctgcttgaaatgtga | 2-11-3 | CCtgcttgaaatgTGA | 210_1 | 4871 | −21 |
| 211 | atcctgcttgaaatgt | 2-10-4 | ATcctgcttgaaATGT | 211_1 | 4873 | −20 |
| 212 | attataaatctattct | 3-10-3 | ATTataaatctatTCT | 212_1 | 5027 | −13 |
| 213 | gctaaatactttcatc | 2-11-3 | GCtaaatactttcATC | 213_1 | 5151 | −16 |
| 214 | cattgtaacatacaccta | 2-10-4 | CAttgtaacataCCTA | 214_1 | 5251 | −19 |
| 215 | gcattgtaacatacct | 2-12-2 | GCattgtaacatacCT | 215_1 | 5252 | −18 |
| 216 | taatattgcaccaaat | 2-12-2 | TAatattgcaccaaAT | 216_1 | 5295 | −13 |
| 217 | gataatattgcaccaa | 2-11-3 | GAtaatattgcacCAA | 217_1 | 5297 | −16 |
| 218 | agataatattgcacca | 2-12-2 | AGataatattgcacCA | 218_1 | 5298 | −16 |
| 219 | gccaagaagataatat | 2-10-4 | GCcaagaagataATAT | 219_1 | 5305 | −17 |
| 220 | cacagccacataaact | 4-10-2 | CACAgccacataaaCT | 220_1 | 5406 | −21 |
| 221 | ttgtaattgtggaaac | 2-12-2 | TTgtaattgtggaaAC | 221_1 | 5463 | −12 |
| 222 | tgacttgtaattgtgg | 2-11-3 | TGacttgtaattgTGG | 222_1 | 5467 | −18 |
| 223 | tctaactgaaatagtc | 2-12-2 | TCtaactgaaatagTC | 223_1 | 5503 | −13 |
| 224 | gtggttctaactgaaa | 3-11-2 | GTGgttctaactgaAA | 224_1 | 5508 | −16 |
| 225 | caatatgggacttggt | 2-12-2 | CAatatgggacttgGT | 225_1 | 5522 | −18 |
| 226 | atgacaatatgggact | 3-11-2 | ATGacaatatgggaCT | 226_1 | 5526 | −17 |
| 227 | tatgacaatatgggac | 4-10-2 | TATGacaatatgggAC | 227_1 | 5527 | −17 |
| 228 | atatgacaatatggga | 4-10-2 | ATATgacaatatggGA | 228_1 | 5528 | −17 |
| 229 | cttcacttaataatta | 2-11-3 | CTtcacttaataaTTA | 229_1 | 5552 | −13 |
| 230 | ctgcttcacttaataa | 4-10-2 | CTGCttcacttaatAA | 230_1 | 5555 | −18 |
| 231 | aagactgcttcactta | 2-11-3 | AAgactgcttcacTTA | 231_1 | 5559 | −17 |
| 232 | gaatgccctaattatg | 4-10-2 | GAATgccctaattaTG | 232_1 | 5589 | −19 |
| 233 | tggaatgccctaatta | 3-11-2 | TGGaatgccctaatTA | 233_1 | 5591 | −19 |
| 234 | gcaaatgccagtaggt | 3-11-2 | GCAaatgccagtagGT | 234_1 | 5642 | −23 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 235 | ctaatggaaggatttg | 3-11-2 | CTAatggaaggattTG | 235_1 | 5673 | -15 |
| 236 | aatatagaacctaatg | 2-12-2 | AAtatagaacctaaTG | 236_1 | 5683 | -10 |
| 237 | gaaagaatagaatgtt | 3-10-3 | GAAagaatagaatGTT | 237_1 | 5769 | -12 |
| 238 | atgggtaatagattat | 3-11-2 | ATGggtaatagattAT | 238_1 | 5893 | -15 |
| 239 | gaaagagcacagggtg | 2-12-2 | GAaagagcacagggTG | 239_1 | 6103 | -18 |
| 240 | ctacatagagggaatg | 4-10-2 | CTACatagagggaaTG | 240_1 | 6202 | -18 |
| 241 | gcttcctacatagagg | 2-10-4 | GCttcctacataGAGG | 241_1 | 6207 | -24 |
| 242 | tgcttcctacatagag | 4-10-2 | TGCTtcctacatagAG | 242_1 | 6208 | -22 |
| 243 | tgggcttgaaatatgt | 2-11-3 | TGggcttgaaataTGT | 243_1 | 6417 | -19 |
| 244 | cattatatttaagaac | 3-11-2 | CATtatatttaagaAC | 244_1 | 6457 | -11 |
| 245 | tcggttatgttatcat | 2-10-4 | TCggttatgttaTCAT | 245_1 | 6470 | -19 |
| 246 | cactttatctggtcgg | 2-10-4 | CActttatctggTCGG | 246_1 | 6482 | -22 |
| 247 | aaattggcacagcgtt | 3-10-3 | AAAttggcacagcGTT | 247_1 | 6505 | -18 |
| 248 | accgtgacagtaaatg | 4-9-3 | ACCGtgacagtaaATG | 248_1 | 6577 | -20 |
| 249 | tgggaaccgtgacagta | 2-13-2 | TGggaaccgtgacagTA | 249_1 | 6581 | -22 |
| 250 | ccacatataggtcctt | 2-11-3 | CCacatataggtcCTT | 250_1 | 6597 | -21 |
| 251 | catattgctaccatac | 2-11-3 | CAtattgctaccaTAC | 251_1 | 6617 | -18 |
| 252 | tcatattgctaccata | 3-10-3 | TCAtattgctaccATA | 252_1 | 6618 | -19 |
| 253 | caattgtcatattgct | 4-8-4 | CAATtgtcatatTGCT | 253_1 | 6624 | -21 |
| 254 | cattcaattgtcatattg | 3-12-3 | CATtcaattgtcataTTG | 254_1 | 6626 | -18 |
| 255 | tttctactgggaatttg | 4-9-4 | TTTCtactgggaaTTTG | 255_1 | 6644 | -20 |
| 256 | caattagtgcagccag | 3-10-3 | CAAttagtgcagcCAG | 256_1 | 6672 | -21 |
| 257 | gaataatgttcttatcc | 4-10-3 | GAATaatgttcttaTCC | 257_1 | 6704 | -20 |
| 258 | cacaaattgaataatgttct | 4-13-3 | CACAaattgaataatgtTCT | 258_1 | 6709 | -20 |
| 259 | catgcacaaattgaataat | 4-11-4 | CATGcacaaattgaaTAAT | 259_1 | 6714 | -20 |
| 260 | atcctgcaatttcacat | 3-11-3 | ATCctgcaatttcaCAT | 260_1 | 6832 | -22 |
| 261 | ccaccatagctgatca | 2-12-2 | CCaccatagctgatCA | 261_1 | 6868 | -22 |
| 262 | accaccatagctgatca | 2-12-3 | ACcaccatagctgaTCA | 262_1 | 6868 | -23 |
| 263 | caccaccatagctgatc | 2-13-2 | CAccaccatagctgaTC | 263_1 | 6869 | -21 |
| 264 | tagtcggcaccaccat | 2-12-2 | TAgtcggcaccaccAT | 264_1 | 6877 | -22 |
| 265 | cttgtagtcggcaccac | 1-14-2 | Cttgtagtcggcaccac | 265_1 | 6880 | -21 |
| 266 | cttgtagtcggcacca | 1-13-2 | CttgtagtcggcacCA | 266_1 | 6881 | -21 |
| 267 | cgcttgtagtcggcac | 2-12-2 | CGcttgtagtcggcAC | 267_1 | 6883 | -21 |
| 268 | tcaataaagatcaggc | 3-11-2 | TCAataaagatcagGC | 268_1 | 6942 | -17 |
| 269 | tggacttacaagaatg | 2-12-2 | TGgacttacaagaaTG | 269_1 | 6986 | -14 |
| 270 | atggacttacaagaat | 3-11-2 | ATGgacttacaagaAT | 270_1 | 6987 | -15 |
| 271 | gctcaagaaattggat | 4-10-2 | GCTCaagaaattggAT | 271_1 | 7073 | -19 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 272 | tactgtagaacatggc | 4-10-2 | TACTgtagaacatgGC | 272_1 | 7133 | -21 |
| 273 | gcaattcatttgatct | 4-9-3 | GCAAttcatttgaTCT | 273_1 | 7239 | -20 |
| 274 | tgaagggaggagggacac | 2-14-2 | TGaagggaggagggacAC | 274_1 | 7259 | -20 |
| 275 | agtggtgaagggaggag | 2-13-2 | AGtggtgaagggaggAG | 275_1 | 7265 | -21 |
| 276 | tagtggtgaagggaggag | 2-14-2 | TAgtggtgaagggaggAG | 276_1 | 7265 | -21 |
| 277 | atagtggtgaagggaggag | 1-16-2 | Atagtggtgaagggaggag | 277_1 | 7265 | -20 |
| 278 | tagtggtgaagggagga | 2-13-2 | TAgtggtgaagggagGA | 278_1 | 7266 | -21 |
| 279 | atagtggtgaagggagga | 2-14-2 | ATagtggtgaagggagGA | 279_1 | 7266 | -21 |
| 280 | tagtggtgaagggagg | 3-11-2 | TAGtggtgaagggaGG | 280_1 | 7267 | -21 |
| 281 | atagtggtgaagggagg | 3-12-2 | ATAgtggtgaagggaGG | 281_1 | 7267 | -22 |
| 282 | gatagtggtgaagggagg | 2-14-2 | GAtagtggtgaagggaGG | 282_1 | 7267 | -21 |
| 283 | atagtggtgaagggag | 4-10-2 | ATAGtggtgaagggAG | 283_1 | 7268 | -20 |
| 284 | gatagtggtgaagggag | 2-12-3 | GAtagtggtgaaggGAG | 284_1 | 7268 | -21 |
| 285 | gagatagtggtgaagg | 2-10-4 | GAgatagtggtgAAGG | 285_1 | 7271 | -20 |
| 286 | catgggagatagtggt | 4-10-2 | CATGggagatagtgGT | 286_1 | 7276 | -22 |
| 287 | acaaataatggttactct | 4-10-4 | ACAAataatggttaCTCT | 287_1 | 7302 | -20 |
| 288 | acacacaaataatggtta | 4-10-4 | ACACacaaataatgGTTA | 288_1 | 7306 | -20 |
| 289 | gagggacacacaaataat | 3-11-4 | GAGggacacacaaaTAAT | 289_1 | 7311 | -21 |
| 290 | atatagagaggctcaa | 4-8-4 | ATATagagaggcTCAA | 290_1 | 7390 | -21 |
| 291 | ttgatatagagaggct | 2-10-4 | TTgatatagagaGGCT | 291_1 | 7393 | -20 |
| 292 | gcatttgatatagaga | 4-9-3 | GCATttgatatagAGA | 292_1 | 7397 | -20 |
| 293 | tttgcatttgatatag | 2-11-3 | TTtgcatttgataTAG | 293_1 | 7400 | -15 |
| 294 | ctggaagaataggttc | 3-11-2 | CTGgaagaataggtTC | 294_1 | 7512 | -17 |
| 295 | actggaagaataggtt | 4-10-2 | ACTGgaagaataggTT | 295_1 | 7513 | -18 |
| 296 | tactggaagaataggt | 4-10-2 | TACTggaagaatagGT | 296_1 | 7514 | -18 |
| 297 | tggcttatcctgtact | 4-10-2 | TGGCttatcctgtaCT | 297_1 | 7526 | -25 |
| 298 | atggcttatcctgtac | 2-10-4 | ATggcttatcctGTAC | 298_1 | 7527 | -22 |
| 299 | tatggcttatcctgta | 4-10-2 | TATGgcttatcctgTA | 299_1 | 7528 | -22 |
| 300 | gtatggcttatcctgt | 3-10-3 | GTAtggcttatccTGT | 300_1 | 7529 | -23 |
| 301 | atgaatatatgcccagt | 2-11-4 | ATgaatatatgccCAGT | 301_1 | 7547 | -22 |
| 302 | gatgaatatatgccca | 2-10-4 | GAtgaatatatgCCCA | 302_1 | 7549 | -22 |
| 303 | caagatgaatatatgcc | 3-10-4 | CAAgatgaatataTGCC | 303_1 | 7551 | -21 |
| 304 | gacaacatcagtataga | 4-9-4 | GACAacatcagtaTAGA | 304_1 | 7572 | -22 |
| 305 | caagacaacatcagta | 4-8-4 | CAAGacaacatcAGTA | 305_1 | 7576 | -20 |
| 306 | cactcctagttccttt | 3-10-3 | CACtcctagttccTTT | 306_1 | 7601 | -22 |
| 307 | aacactcctagttcct | 3-10-3 | AACactcctagttCCT | 307_1 | 7603 | -22 |

TABLE 5-continued list of oligonucleotide motif sequences (indicated by SEQ ID NO) targeting the human
PD-L1 transcript (SEQ ID NO: 1), designs of these, as well as specific antisense
oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 308 | taacactcctagttcc | 2-11-3 | TAacactcctagtTCC | 308_1 | 7604 | −20 |
| 309 | ctaacactcctagttc | 2-12-2 | CTaacactcctagtTC | 309_1 | 7605 | −18 |
| 310 | tgataacataactgtg | 2-12-2 | TGataacataactgTG | 310_1 | 7637 | −13 |
| 311 | ctgataacataactgt | 2-10-4 | CTgataacataaCTGT | 311_1 | 7638 | −18 |
| 312 | tttgaactcaagtgac | 4-10-2 | TTTGaactcaagtgAC | 312_1 | 7654 | −16 |
| 313 | tcctttacttagctag | 4-9-3 | TCCTttacttagcTAG | 313_1 | 7684 | −23 |
| 314 | gagtttggattagctg | 2-11-3 | GAgtttggattagCTG | 314_1 | 7764 | −20 |
| 315 | tgggatatgacaggga | 2-11-3 | TGggatatgacagGGA | 315_1 | 7838 | −21 |
| 316 | tgtgggatatgacagg | 4-10-2 | TGTGggatatgacaGG | 316_1 | 7840 | −22 |
| 317 | atatggaagggatatc | 4-10-2 | ATATggaagggataTC | 317_1 | 7875 | −17 |
| 318 | acaggatatggaaggg | 3-10-3 | ACAggatatggaaGGG | 318_1 | 7880 | −21 |
| 319 | atttcaacaggatatgg | 4-9-4 | ATTTcaacaggatATGG | 319_1 | 7885 | −20 |
| 320 | gagtaatttcaacagg | 2-11-3 | GAgtaatttcaacAGG | 320_1 | 7891 | −17 |
| 321 | agggagtaatttcaaca | 4-9-4 | AGGGagtaatttcAACA | 321_1 | 7893 | −22 |
| 322 | attagggagtaattttca | 4-9-4 | ATTAgggagtaatTTCA | 322_1 | 7896 | −21 |
| 323 | cttactattagggagt | 2-10-4 | CTtactattaggGAGT | 323_1 | 7903 | −20 |
| 324 | cagcttactattaggg | 2-11-3 | CAgcttactattaGGG | 324_1 | 7906 | −20 |
| 326 | atttcagcttactattag | 3-11-4 | ATTtcagcttactaTTAG | 326_1 | 7908 | −20 |
| 325 | tcagcttactattagg | 3-10-3 | TCAgcttactattAGG | 325_1 | 7907 | −20 |
| 327 | ttcagcttactattag | 2-10-4 | TTcagcttactaTTAG | 327_1 | 7908 | −17 |
| 328 | cagatttcagcttact | 4-10-2 | CAGAtttcagcttaCT | 328_1 | 7913 | −21 |
| 329 | gactacaactagaggg | 3-11-2 | GACtacaactagagGG | 329_1 | 7930 | −19 |
| 330 | agactacaactagagg | 4-10-2 | AGACtacaactagaGG | 330_1 | 7931 | −19 |
| 331 | aagactacaactagag | 2-12-2 | AAgactacaactagAG | 331_1 | 7932 | −13 |
| 332 | atgatttaattctagtcaaa | 4-12-4 | ATGAtttaattctagtCAAA | 332_1 | 7982 | −20 |
| 333 | tttaattctagtcaaa | 3-10-3 | TTTaattctagtcAAA | 333_1 | 7982 | −12 |
| 334 | gatttaattctagtca | 4-8-4 | GATTtaattctaGTCA | 334_1 | 7984 | −20 |
| 771 | tgatttaattctagtca | 3-10-4 | TGAtttaattctaGTCA | 771_1 | 7984 | −20 |
| 335 | atgatttaattctagtca | 4-11-3 | ATGAtttaattctagTCA | 335_1 | 7984 | −20 |
| 336 | gatgatttaattctagtca | 4-13-2 | GATGatttaattctagtCA | 336_1 | 7984 | −20 |
| 337 | gatttaattctagtca | 2-10-4 | GAtttaattctaGTCA | 337_1 | 7984 | −18 |
| 338 | gatgatttaattctagtc | 4-11-3 | GATGatttaattctaGTC | 338_1 | 7985 | −20 |
| 339 | tgatttaattctagtc | 2-12-2 | TGatttaattctagTC | 339_1 | 7985 | −13 |
| 340 | gagatgatttaattcta | 4-9-4 | GAGAtgatttaatTCTA | 340_1 | 7988 | −20 |
| 341 | gagatgatttaattct | 3-10-3 | GAGatgatttaatTCT | 341_1 | 7989 | −16 |
| 342 | cagattgatggtagtt | 4-10-2 | CAGAttgatggtagTT | 342_1 | 8030 | −19 |
| 343 | ctcagattgatggtag | 2-10-4 | CTcagattgatgGTAG | 343_1 | 8032 | −20 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 344 | gttagccctcagattg | 3-10-3 | GTTagccctcagaTTG | 344_1 | 8039 | −23 |
| 345 | tgtattgttagccctc | 2-10-4 | TGtattgttagcCCTC | 345_1 | 8045 | −24 |
| 346 | acttgtattgttagcc | 2-10-4 | ACttgtattgttAGCC | 346_1 | 8048 | −22 |
| 347 | agccagtatcagggac | 3-11-2 | AGCcagtatcagggAC | 347_1 | 8191 | −23 |
| 348 | ttgacaatagtggcat | 2-10-4 | TTgacaatagtgGCAT | 348_1 | 8213 | −20 |
| 349 | acaagtggtatcttct | 3-10-3 | ACAagtggtatctTCT | 349_1 | 8228 | −19 |
| 350 | aatctactttacaagt | 4-10-2 | AATCtactttacaaGT | 350_1 | 8238 | −16 |
| 351 | cacagtagatgcctgata | 2-12-4 | CAcagtagatgcctGATA | 351_1 | 8351 | −24 |
| 352 | gaacacagtagatgcc | 2-11-3 | GAacacagtagatGCC | 352_1 | 8356 | −21 |
| 353 | cttggaacacagtagat | 4-11-2 | CTTGgaacacagtagAT | 353_1 | 8359 | −20 |
| 354 | atatcttggaacacag | 3-10-3 | ATAtcttggaacaCAG | 354_1 | 8364 | −18 |
| 355 | tctttaatatcttggaac | 3-11-4 | TCTttaatatcttgGAAC | 355_1 | 8368 | −19 |
| 356 | tgatttctttaatatcttg | 2-13-4 | TGatttctttaatatCTTG | 356_1 | 8372 | −19 |
| 357 | tgatgatttctttaatatc | 2-13-4 | TGatgatttctttaaTATC | 357_1 | 8375 | −18 |
| 358 | aggctaagtcatgatg | 3-11-2 | AGGctaagtcatgaTG | 358_1 | 8389 | −19 |
| 359 | ttgatgaggctaagtc | 4-10-2 | TTGAtgaggctaagTC | 359_1 | 8395 | −19 |
| 360 | ccaggattatactctt | 3-11-2 | CCAggattatactcTT | 360_1 | 8439 | −20 |
| 361 | gccaggattatactct | 2-10-4 | GCcaggattataCTCT | 361_1 | 8440 | −23 |
| 362 | ctgccaggattatact | 3-11-2 | CTGccaggattataCT | 362_1 | 8442 | −21 |
| 363 | cagaaacttatactttatg | 4-13-2 | CAGAaacttatactttaTG | 363_1 | 8473 | −19 |
| 364 | aagcagaaacttatact | 4-9-4 | AAGCagaaacttaTACT | 364_1 | 8478 | −20 |
| 365 | gaagcagaaacttatact | 3-11-4 | GAAgcagaaacttaTACT | 365_1 | 8478 | −20 |
| 366 | tggaagcagaaacttatact | 3-15-2 | TGGaagcagaaacttataCT | 366_1 | 8478 | −21 |
| 367 | tggaagcagaaacttatac | 3-13-3 | TGGaagcagaaacttaTAC | 367_1 | 8479 | −20 |
| 368 | aagcagaaacttatac | 2-11-3 | AAgcagaaacttaTAC | 368_1 | 8479 | −13 |
| 369 | tggaagcagaaacttata | 3-11-4 | TGGaagcagaaactTATA | 369_1 | 8480 | −21 |
| 370 | aagggatattatggag | 4-10-2 | AAGGgatattatggAG | 370_1 | 8587 | −18 |
| 371 | tgccggaagatttcct | 2-12-2 | TGccggaagatttcCT | 371_1 | 8641 | −21 |
| 372 | atggattgggagtaga | 4-10-2 | ATGGattgggagtaGA | 372_1 | 8772 | −21 |
| 373 | agatggattgggagta | 2-12-2 | AGatggattgggagTA | 373_1 | 8774 | −18 |
| 374 | aagatggattgggagt | 3-11-2 | AAGatggattgggaGT | 374_1 | 8775 | −18 |
| 375 | acaagatggattggga | 2-10-4 | ACaagatggattGGGA | 375_1 | 8777 | −20 |
| 375 | acaagatggattggga | 2-12-2 | ACaagatggattggGA | 375_2 | 8777 | −17 |
| 376 | agaaggttcagacttt | 3-9-4 | AGAaggttcagaCTTT | 376_1 | 8835 | −20 |
| 377 | gcagaaggttcagact | 2-11-3 | GCagaaggttcagACT | 377_1 | 8837 | −21 |
| 377 | gcagaaggttcagact | 3-11-2 | GCAgaaggttcagaCT | 377_2 | 8837 | −22 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 378 | tgcagaaggttcagac | 4-10-2 | TGCAgaaggttcagAC | 378_1 | 8838 | -22 |
| 379 | agtgcagaaggttcag | 2-11-3 | AGtgcagaaggttCAG | 379_1 | 8840 | -20 |
| 379 | agtgcagaaggttcag | 4-10-2 | AGTGcagaaggttcAG | 379_2 | 8840 | -21 |
| 380 | aagtgcagaaggttca | 4-10-2 | AAGTgcagaaggttCA | 380_1 | 8841 | -20 |
| 381 | taagtgcagaaggttc | 2-10-4 | TAagtgcagaagGTTC | 381_1 | 8842 | -19 |
| 382 | tctaagtgcagaaggt | 2-10-4 | TCtaagtgcagaAGGT | 382_1 | 8844 | -21 |
| 383 | ctcaggagttctacttc | 3-12-2 | CTCaggagttctactTC | 383_1 | 8948 | -20 |
| 384 | ctcaggagttctactt | 3-10-3 | CTCaggagttctaCTT | 384_1 | 8949 | -21 |
| 385 | atggaggtgactcaggag | 1-15-2 | Atggaggtgactcaggag | 385_1 | 8957 | -20 |
| 386 | atggaggtgactcagga | 2-13-2 | ATggaggtgactcagGA | 386_1 | 8958 | -21 |
| 387 | atggaggtgactcagg | 2-11-3 | ATggaggtgactcAGG | 387_1 | 8959 | -21 |
| 388 | tatggaggtgactcagg | 2-12-3 | TAtggaggtgactcAGG | 388_1 | 8959 | -21 |
| 389 | atatggaggtgactcagg | 2-14-2 | ATatggaggtgactcaGG | 389_1 | 8959 | -21 |
| 390 | tatggaggtgactcag | 4-10-2 | TATGgaggtgactcAG | 390_1 | 8960 | -21 |
| 391 | atatggaggtgactcag | 2-11-4 | ATatggaggtgacTCAG | 391_1 | 8960 | -22 |
| 392 | catatggaggtgactcag | 2-14-2 | CAtatggaggtgactcAG | 392_1 | 8960 | -20 |
| 393 | atatggaggtgactca | 3-10-3 | ATAtggaggtgacTCA | 393_1 | 8961 | -20 |
| 394 | catatggaggtgactca | 2-12-3 | CAtatggaggtgacTCA | 394_1 | 8961 | -21 |
| 395 | catatggaggtgactc | 2-10-4 | CAtatggaggtgACTC | 395_1 | 8962 | -20 |
| 396 | gcatatggaggtgactc | 2-13-2 | GCatatggaggtgacTC | 396_1 | 8962 | -21 |
| 397 | tgcatatggaggtgactc | 2-14-2 | TGcatatggaggtgacTC | 397_1 | 8962 | -21 |
| 398 | ttgcatatggaggtgactc | 1-16-2 | Ttgcatatggaggtgactc | 398_1 | 8962 | -20 |
| 399 | tttgcatatggaggtgactc | 1-17-2 | Tttgcatatggaggtgactc | 399_1 | 8962 | -21 |
| 400 | gcatatggaggtgact | 2-12-2 | GCatatggaggtgaCT | 400_1 | 8963 | -20 |
| 401 | tgcatatggaggtgact | 2-13-2 | TGcatatggaggtgaCT | 401_1 | 8963 | -20 |
| 402 | ttgcatatggaggtgact | 3-13-2 | TTGcatatggaggtgaCT | 402_1 | 8963 | -22 |
| 403 | tttgcatatggaggtgact | 1-16-2 | Tttgcatatggaggtgact | 403_1 | 8963 | -20 |
| 404 | tgcatatggaggtgac | 3-11-2 | TGCatatggaggtgAC | 404_1 | 8964 | -20 |
| 405 | ttgcatatggaggtgac | 3-11-3 | TTGcatatggaggtGAC | 405_1 | 8964 | -21 |
| 406 | tttgcatatggaggtgac | 4-12-2 | TTTGcatatggaggtgAC | 406_1 | 8964 | -21 |
| 407 | tttgcatatggaggtga | 4-11-2 | TTTGcatatggaggtGA | 407_1 | 8965 | -21 |
| 408 | tttgcatatggaggtg | 2-10-4 | TTtgcatatggaGGTG | 408_1 | 8966 | -21 |
| 409 | aagtgaagttcaacagc | 2-11-4 | AAgtgaagttcaaCAGC | 409_1 | 8997 | -20 |
| 410 | tgggaagtgaagttca | 2-10-4 | TGggaagtgaagTTCA | 410_1 | 9002 | -20 |
| 411 | atgggaagtgaagttc | 2-11-3 | ATgggaagtgaagTTC | 411_1 | 9003 | -17 |
| 412 | gatgggaagtgaagtt | 4-9-3 | GATGggaagtgaaGTT | 412_1 | 9004 | -21 |
| 413 | ctgtgatgggaagtgaa | 3-11-3 | CTGtgatgggaagtGAA | 413_1 | 9007 | -20 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 414 | attgagtgaatccaaa | 3-10-3 | ATTgagtgaatccAAA | 414_1 | 9119 | -14 |
| 415 | aattgagtgaatccaa | 2-10-4 | AAttgagtgaatCCAA | 415_1 | 9120 | -16 |
| 416 | gataattgagtgaatcc | 4-10-3 | GATAattgagtgaaTCC | 416_1 | 9122 | -20 |
| 417 | gtgataattgagtgaa | 3-10-3 | GTGataattgagtGAA | 417_1 | 9125 | -16 |
| 418 | aagaaaggtgcaataa | 3-10-3 | AAGaaaggtgcaaTAA | 418_1 | 9155 | -14 |
| 419 | caagaaaggtgcaata | 2-10-4 | CAagaaaggtgcAATA | 419_1 | 9156 | -15 |
| 420 | acaagaaaggtgcaat | 4-10-2 | ACAAgaaaggtgcaAT | 420_1 | 9157 | -16 |
| 421 | atttaaactcacaaac | 2-12-2 | ATttaaactcacaaAC | 421_1 | 9171 | -10 |
| 422 | ctgttaggttcagcga | 2-10-4 | CTgttaggttcaGCGA | 422_1 | 9235 | -24 |
| 423 | tctgaatgaacatttcg | 4-9-4 | TCTGaatgaacatTTCG | 423_1 | 9260 | -20 |
| 424 | ctcattgaaggttctg | 2-10-4 | CTcattgaaggtTCTG | 424_1 | 9281 | -20 |
| 425 | ctaatctcattgaagg | 3-11-2 | CTAatctcattgaaGG | 425_1 | 9286 | -17 |
| 426 | cctaatctcattgaag | 2-12-2 | CCtaatctcattgaAG | 426_1 | 9287 | -16 |
| 427 | actttgatctttcagc | 3-10-3 | ACTttgatctttcAGC | 427_1 | 9305 | -20 |
| 428 | actatgcaacactttg | 2-12-2 | ACtatgcaacactttG | 428_1 | 9315 | -15 |
| 429 | caaatagctttatcgg | 3-10-3 | CAAatagctttatCGG | 429_1 | 9335 | -17 |
| 430 | ccaaatagctttatcg | 2-10-4 | CCaaatagctttATCG | 430_1 | 9336 | -19 |
| 431 | tccaaatagctttatc | 4-10-2 | TCCAaatagctttaTC | 431_1 | 9337 | -18 |
| 432 | gatccaaatagcttta | 4-10-2 | GATCcaaatagcttTA | 432_1 | 9339 | -18 |
| 433 | atgatccaaatagctt | 2-10-4 | ATgatccaaataGCTT | 433_1 | 9341 | -19 |
| 434 | tatgatccaaatagct | 4-10-2 | TATGatccaaatagCT | 434_1 | 9342 | -18 |
| 435 | taaacagggctgggaat | 4-9-4 | TAAAcagggctggGAAT | 435_1 | 9408 | -22 |
| 436 | acttaaacagggctgg | 2-10-4 | ACttaaacagggCTGG | 436_1 | 9412 | -21 |
| 437 | acacttaaacagggct | 2-10-4 | ACacttaaacagGGCT | 437_1 | 9414 | -22 |
| 438 | gaacacttaaacaggg | 4-8-4 | GAACacttaaacAGGG | 438_1 | 9416 | -20 |
| 439 | agagaacacttaaacag | 4-9-4 | AGAGaacacttaaACAG | 439_1 | 9418 | -20 |
| 440 | ctacagagaacactta | 4-8-4 | CTACagagaacaCTTA | 440_1 | 9423 | -20 |
| 441 | atgctacagagaacact | 3-10-4 | ATGctacagagaaCACT | 441_1 | 9425 | -22 |
| 442 | ataaatgctacagagaaca | 4-11-4 | ATAAatgctacagagAACA | 442_1 | 9427 | -20 |
| 443 | agataaatgctacagaga | 2-12-4 | AGataaatgctacaGAGA | 443_1 | 9430 | -20 |
| 444 | tagagataaatgctaca | 4-9-4 | TAGAgataaatgcTACA | 444_1 | 9434 | -21 |
| 445 | tagatagagataaatgct | 4-11-3 | TAGAtagagataaatGCT | 445_1 | 9437 | -20 |
| 446 | caatatactagatagaga | 4-10-4 | CAATatactagataGAGA | 446_1 | 9445 | -21 |
| 447 | tacacaatatactagatag | 4-11-4 | TACAcaatatactagATAG | 447_1 | 9448 | -21 |
| 448 | ctacacaatatactag | 3-10-3 | CTAcacaatatacTAG | 448_1 | 9452 | -16 |
| 449 | gctacacaatatacta | 4-8-4 | GCTAcacaatatACTA | 449_1 | 9453 | -21 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 450 | atatgctacacaatatac | 4-10-4 | ATATgctacacaatATAC | 450_1 | 9455 | -20 |
| 451 | tgatatgctacacaat | 4-8-4 | TGATatgctacaCAAT | 451_1 | 9459 | -20 |
| 452 | atgatatgatatgctac | 4-9-4 | ATGAtatgatatgCTAC | 452_1 | 9464 | -21 |
| 453 | gaggagagagacaataaa | 4-10-4 | GAGGagagagacaaTAAA | 453_1 | 9495 | -20 |
| 454 | ctaggaggagagagaca | 3-11-3 | CTAggaggagagagACA | 454_1 | 9500 | -22 |
| 455 | tattctaggaggagaga | 4-10-3 | TATTctaggaggagAGA | 455_1 | 9504 | -21 |
| 456 | ttatattctaggaggag | 4-10-3 | TTATattctaggagGAG | 456_1 | 9507 | -21 |
| 457 | gtttatattctaggag | 3-9-4 | GTTtatattctaGGAG | 457_1 | 9510 | -20 |
| 458 | tggagtttatattctagg | 2-12-4 | TGgagtttatattcTAGG | 458_1 | 9512 | -22 |
| 459 | cgtaccaccactctgc | 2-11-3 | CGtaccaccactcTGC | 459_1 | 9590 | -25 |
| 460 | tgaggaaatcattcattc | 4-10-4 | TGAGgaaatcattcATTC | 460_1 | 9641 | -22 |
| 461 | tttgaggaaatcattcat | 4-10-4 | TTTGaggaaatcatTCAT | 461_1 | 9643 | -20 |
| 462 | aggctaatcctatttg | 4-10-2 | AGGCtaatcctattTG | 462_1 | 9657 | -22 |
| 463 | tttaggctaatcctat | 4-8-4 | TTTAggctaatcCTAT | 463_1 | 9660 | -22 |
| 464 | tgctccagtgtaccct | 3-11-2 | TGCtccagtgtaccCT | 464_1 | 9755 | -27 |
| 465 | tagtagtactcgatag | 2-10-4 | TAgtagtactcgATAG | 465_1 | 9813 | -18 |
| 466 | ctaattgtagtagtactc | 3-12-3 | CTAattgtagtagtaCTC | 466_1 | 9818 | -20 |
| 467 | tgctaattgtagtagt | 2-10-4 | TGctaattgtagTAGT | 467_1 | 9822 | -19 |
| 468 | agtgctaattgtagta | 4-10-2 | AGTGctaattgtagTA | 468_1 | 9824 | -19 |
| 469 | gcaagtgctaattgta | 4-10-2 | GCAAgtgctaattgTA | 469_1 | 9827 | -20 |
| 470 | gaggaaatgaactaattta | 4-13-2 | GAGGaaatgaactaattTA | 470_1 | 9881 | -18 |
| 471 | caggaggaaatgaacta | 4-11-2 | CAGGaggaaatgaacTA | 471_1 | 9886 | -19 |
| 472 | ccctagagtcatttcc | 2-11-3 | CCctagagtcattTCC | 472_1 | 9902 | -24 |
| 473 | atcttacatgatgaagc | 3-11-3 | ATCttacatgatgaAGC | 473_1 | 9925 | -20 |
| 475 | agacacactcagatttcag | 2-15-2 | AGacacactcagatttcAG | 475_1 | 9967 | -20 |
| 474 | gacacactcagatttcag | 3-13-2 | GACacactcagatttcAG | 474_1 | 9967 | -20 |
| 476 | aagacacactcagatttcag | 3-15-2 | AAGacacactcagatttcAG | 476_1 | 9967 | -21 |
| 477 | agacacactcagatttca | 2-13-3 | AGacacactcagattTCA | 477_1 | 9968 | -20 |
| 478 | aagacacactcagatttca | 3-13-3 | AAGacacactcagattTCA | 478_1 | 9968 | -21 |
| 479 | aaagacacactcagatttca | 2-14-4 | AAagacacactcagatTTCA | 479_1 | 9968 | -20 |
| 480 | gaaagacacactcagatttc | 3-14-3 | GAAagacacactcagatTTC | 480_1 | 9969 | -20 |
| 481 | aagacacactcagatttc | 4-11-3 | AAGAcacactcagatTTC | 481_1 | 9969 | -21 |
| 482 | aaagacacactcagatttc | 4-11-4 | AAAGacacactcagaTTTC | 482_1 | 9969 | -20 |
| 483 | tgaaagacacactcagattt | 4-14-2 | TGAAagacacactcagatTT | 483_1 | 9970 | -20 |
| 484 | tgaaagacacactcagatt | 2-13-4 | TGaaagacacactcaGATT | 484_1 | 9971 | -21 |
| 485 | tgaaagacacactcagat | 3-12-3 | TGAaagacacactcaGAT | 485_1 | 9972 | -20 |
| 486 | attgaaagacacactca | 4-10-3 | ATTGaaagacacacTCA | 486_1 | 9975 | -19 |

TABLE 5-continued list of oligonucleotide motif sequences (indicated by SEQ ID NO) targeting the human
PD-L1 transcript (SEQ ID NO: 1), designs of these, as well as specific antisense
oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 487 | tcattgaaagacacact | 2-11-4 | TCattgaaagacaCACT | 487_1 | 9977 | -18 |
| 488 | ttccatcattgaaaga | 3-9-4 | TTCcatcattgaAAGA | 488_1 | 9983 | -18 |
| 489 | ataataccacttatcat | 4-9-4 | ATAAtaccacttaTCAT | 489_1 | 10010 | -20 |
| 490 | ttacttaatttctttgga | 2-12-4 | TTacttaatttcttTGGA | 490_1 | 10055 | -20 |
| 491 | ttagaactagctttatca | 3-12-3 | TTAgaactagctttaTCA | 491_1 | 10101 | -20 |
| 492 | gaggtacaaatatagg | 3-10-3 | GAGgtacaaatatAGG | 492_1 | 10171 | -18 |
| 493 | cttatgatacaactta | 3-10-3 | CTTatgatacaacTTA | 493_1 | 10384 | -15 |
| 494 | tcttatgatacaactt | 2-11-3 | TCttatgatacaaCTT | 494_1 | 10385 | -15 |
| 495 | ttcttatgatacaact | 3-11-2 | TTCttatgatacaaCT | 495_1 | 10386 | -15 |
| 496 | cagtttcttatgatac | 2-11-3 | CAgtttcttatgaTAC | 496_1 | 10390 | -16 |
| 497 | gcagtttcttatgata | 3-11-2 | GCAgtttcttatgaTA | 497_1 | 10391 | -19 |
| 498 | tacaaatgtctattaggtt | 4-12-3 | TACAaatgtctattagGTT | 498_1 | 10457 | -21 |
| 499 | tgtacaaatgtctattag | 4-11-3 | TGTAcaaatgtctatTAG | 499_1 | 10460 | -20 |
| 500 | agcatcacaattagta | 3-11-2 | AGCatcacaattagTA | 500_1 | 10535 | -18 |
| 501 | ctaatgatagtgaagc | 3-11-2 | CTAatgatagtgaaGC | 501_1 | 10548 | -17 |
| 502 | agctaatgatagtgaa | 3-11-2 | AGCtaatgatagtgAA | 502_1 | 10550 | -16 |
| 503 | atgccttgacatatta | 4-10-2 | ATGCcttgacatatTA | 503_1 | 10565 | -20 |
| 504 | ctcaagattattgacac | 4-9-4 | CTCAagattattgACAC | 504_1 | 10623 | -20 |
| 505 | acctcaagattattga | 2-10-4 | ACctcaagattaTTGA | 505_2 | 10626 | -18 |
| 505 | acctcaagattattga | 3-9-4 | ACCtcaagattaTTGA | 505_1 | 10626 | -20 |
| 506 | aacctcaagattattg | 4-10-2 | AACCtcaagattatTG | 506_1 | 10627 | -17 |
| 507 | cacaaacctcaagattatt | 4-13-2 | CACAaacctcaagattaTT | 507_1 | 10628 | -20 |
| 508 | gtacttaattagacct | 3-9-4 | GTActtaattagACCT | 508_1 | 10667 | -21 |
| 509 | agtacttaattagacc | 4-9-3 | AGTActtaattagACC | 509_1 | 10668 | -20 |
| 510 | gtatgaggtggtaaac | 4-10-2 | GTATgaggtggtaaAC | 510_1 | 10688 | -18 |
| 511 | aggaaacagcagaagtg | 2-11-4 | AGgaaacagcagaAGTG | 511_1 | 10723 | -21 |
| 512 | gcacaacccagaggaa | 2-12-2 | GCacaacccagaggAA | 512_1 | 10735 | -20 |
| 513 | caagcacaacccagag | 3-11-2 | CAAgcacaacccagAG | 513_1 | 10738 | -20 |
| 514 | ttcaagcacaacccag | 3-10-3 | TTCaagcacaaccCAG | 514_1 | 10740 | -21 |
| 515 | aattcaagcacaaccc | 2-10-4 | AAttcaagcacaACCC | 515_1 | 10742 | -20 |
| 516 | taataattcaagcacaacc | 4-13-2 | TAATaattcaagcacaaCC | 516_1 | 10743 | -20 |
| 517 | actaataattcaagcac | 4-9-4 | ACTAataattcaaGCAC | 517_1 | 10747 | -20 |
| 518 | ataatactaataattcaagc | 4-12-4 | ATAAtactaataattcAAGC | 518_1 | 10749 | -19 |
| 519 | tagatttgtgaggtaa | 2-10-4 | TAgatttgtgagGTAA | 519_1 | 11055 | -18 |
| 520 | agccttaattctccat | 4-10-2 | AGCCttaattctccAT | 520_1 | 11091 | -24 |
| 521 | aatgatctagagcctta | 4-9-4 | AATGatctagagcCTTA | 521_1 | 11100 | -22 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 522 | ctaatgatctagagcc | 3-10-3 | CTAatgatctagaGCC | 522_1 | 11103 | -22 |
| 523 | actaatgatctagagc | 3-9-4 | ACTaatgatctaGAGC | 523_1 | 11104 | -21 |
| 524 | cattaacatgttcttatt | 3-11-4 | CATtaacatgttctTATT | 524_1 | 11165 | -19 |
| 525 | acaagtacattaacatgttc | 4-12-4 | ACAAgtacattaacatGTTC | 525_1 | 11170 | -22 |
| 526 | ttacaagtacattaacatg | 4-11-4 | TTACaagtacattaaCATG | 526_1 | 11173 | -20 |
| 527 | gctttattcatgtttat | 4-9-4 | GCTTtattcatgtTTAT | 527_1 | 11195 | -22 |
| 528 | gctttattcatgttta | 3-11-2 | GCTttattcatgttTA | 528_1 | 11196 | -18 |
| 529 | agagctttattcatgttt | 3-13-2 | AGAgctttattcatgtTT | 529_1 | 11197 | -20 |
| 530 | ataagagctttattcatg | 4-10-4 | ATAAgagctttattCATG | 530_1 | 11200 | -21 |
| 531 | cataagagctttattca | 4-9-4 | CATAagagctttaTTCA | 531_1 | 11202 | -21 |
| 532 | agcataagagctttat | 4-8-4 | AGCAtaagagctTTAT | 532_1 | 11205 | -22 |
| 533 | tagattgtttagtgca | 3-10-3 | TAGattgtttagtGCA | 533_1 | 11228 | -20 |
| 534 | gtagattgtttagtgc | 2-10-4 | GTagattgtttaGTGC | 534_1 | 11229 | -21 |
| 535 | gacaattctagtagatt | 4-9-4 | GACAattctagtaGATT | 535_1 | 11238 | -21 |
| 536 | ctgacaattctagtag | 3-9-4 | CTGacaattctaGTAG | 536_1 | 11241 | -20 |
| 537 | gctgacaattctagta | 4-10-2 | GCTGacaattctagTA | 537_1 | 11242 | -21 |
| 538 | aggattaagatacgta | 2-12-2 | AGgattaagatacgTA | 538_1 | 11262 | -15 |
| 539 | caggattaagatacgt | 2-11-3 | CAggattaagataCGT | 539_1 | 11263 | -17 |
| 540 | tcaggattaagatacg | 3-11-2 | TCAggattaagataCG | 540_1 | 11264 | -16 |
| 541 | ttcaggattaagatac | 2-10-4 | TTcaggattaagATAC | 541_1 | 11265 | -15 |
| 542 | aggaagaaagtttgattc | 4-10-4 | AGGAagaaagtttgATTC | 542_1 | 11308 | -21 |
| 543 | tcaaggaagaaagtttga | 4-10-4 | TCAAggaagaaagtTTGA | 543_1 | 11311 | -20 |
| 544 | ctcaaggaagaaagtttg | 4-10-4 | CTCAaggaagaaagTTTG | 544_1 | 11312 | -20 |
| 545 | tgctcaaggaagaaagt | 3-10-4 | TGCtcaaggaagaAAGT | 545_1 | 11315 | -21 |
| 546 | aattatgctcaaggaaga | 4-11-3 | AATTatgctcaaggaAGA | 546_1 | 11319 | -20 |
| 547 | taggataccacattatga | 4-12-2 | TAGGataccacattatGA | 547_1 | 11389 | -22 |
| 548 | cataatttattccattcctc | 2-15-3 | CAtaatttattccattcCTC | 548_1 | 11449 | -22 |
| 549 | tgcataatttattccat | 4-10-3 | TGCAtaatttattcCAT | 549_1 | 11454 | -22 |
| 550 | actgcataatttattcc | 4-10-3 | ACTGcataatttatTCC | 550_1 | 11456 | -21 |
| 551 | ctaaactgcataatttatt | 4-11-4 | CTAAactgcataattTATT | 551_1 | 11458 | -20 |
| 552 | ataactaaactgcata | 2-10-4 | ATaactaaactgCATA | 552_1 | 11465 | -16 |
| 553 | ttattaataactaaactgc | 3-12-4 | TTAttaataactaaaCTGC | 553_1 | 11468 | -19 |
| 554 | tagtacattattaataact | 4-13-2 | TAGTacattattaataaCT | 554_1 | 11475 | -18 |
| 555 | cataactaaggacgtt | 4-10-2 | CATAactaaggacgTT | 555_1 | 11493 | -17 |
| 556 | tcataactaaggacgt | 2-11-3 | TCataactaaggaCGT | 556_1 | 11494 | -16 |
| 557 | cgtcataactaaggac | 4-10-2 | CGTCataactaaggAC | 557_1 | 11496 | -17 |
| 558 | tcgtcataactaagga | 2-12-2 | TCgtcataactaagGA | 558_1 | 11497 | -16 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 559 | atcgtcataactaagg | 2-10-4 | ATcgtcataactAAGG | 559_1 | 11498 | -17 |
| 560 | gttagtatcttacatt | 2-11-3 | GTtagtatcttacATT | 560_1 | 11525 | -15 |
| 561 | ctctattgttagtatc | 3-10-3 | CTCtattgttagtATC | 561_1 | 11532 | -17 |
| 562 | agtatagagttactgt | 3-10-3 | AGTatagagttacTGT | 562_1 | 11567 | -19 |
| 563 | ttcctggtgatacttt | 4-10-2 | TTCCtggtgatactTT | 563_1 | 11644 | -21 |
| 564 | gttcctggtgatactt | 4-10-2 | GTTCctggtgatacTT | 564_1 | 11645 | -21 |
| 565 | tgttcctggtgatact | 2-12-2 | TGttcctggtgataCT | 565_1 | 11646 | -20 |
| 566 | ataaacatgaatctctcc | 2-12-4 | ATaaacatgaatctCTCC | 566_1 | 11801 | -20 |
| 567 | ctttataaacatgaatctc | 3-12-4 | CTTtataaacatgaaTCTC | 567_1 | 11804 | -19 |
| 568 | ctgtctttataaacatg | 3-10-4 | CTGtcctttataaaCATG | 568_1 | 11810 | -19 |
| 569 | ttgttataaatctgtctt | 2-12-4 | TTgttataaatctgTCTT | 569_1 | 11820 | -18 |
| 570 | ttaaatttattcttggata | 3-12-4 | TTAaatttattcttgGATA | 570_1 | 11849 | -19 |
| 571 | cttaaatttattcttgga | 2-12-4 | CTtaaatttattctTGGA | 571_1 | 11851 | -19 |
| 572 | cttcttaaatttattcttg | 4-13-2 | CTTCttaaatttattctTG | 572_1 | 11853 | -18 |
| 573 | tatgtttctcagtaaag | 4-9-4 | TATGtttctcagtAAAG | 573_1 | 11877 | -19 |
| 574 | gaattatctttaaacca | 3-10-4 | GAAttatctttaaACCA | 574_1 | 11947 | -18 |
| 575 | cccttaaatttctaca | 3-11-2 | CCCttaaatttctaCA | 575_1 | 11980 | -20 |
| 576 | acactgctcttgtacc | 4-10-2 | ACACtgctcttgtaCC | 576_1 | 11995 | -23 |
| 577 | tgacaacactgctctt | 3-10-3 | TGAcaacactgctCTT | 577_1 | 12000 | -21 |
| 578 | tacatttattgggctc | 4-10-2 | TACAtttattgggcTC | 578_1 | 12081 | -19 |
| 579 | gtacatttattgggct | 2-10-4 | GTacatttattgGGCT | 579_1 | 12082 | -23 |
| 580 | ttggtacatttattgg | 3-10-3 | TTGgtacatttatTGG | 580_1 | 12085 | -18 |
| 581 | catgttggtacattttat | 4-10-3 | CATGttggtacattTAT | 581_1 | 12088 | -21 |
| 582 | aatcatgttggtacat | 4-10-2 | AATCatgttggtacAT | 582_1 | 12092 | -16 |
| 583 | aaatcatgttggtaca | 2-12-2 | AAatcatgttggtaCA | 583_1 | 12093 | -14 |
| 584 | gacaagtttggattaa | 3-11-2 | GACaagtttggattAA | 584_1 | 12132 | -14 |
| 585 | aatgttcagatgcctc | 2-10-4 | AAtgttcagatgCCTC | 585_1 | 12197 | -21 |
| 586 | gcttaatgttcagatg | 2-12-2 | GCttaatgttcagaTG | 586_1 | 12201 | -17 |
| 587 | cgtacatagcttgatg | 4-10-2 | CGTAcatagcttgaTG | 587_1 | 12267 | -20 |
| 588 | gtgaggaattaggata | 3-11-2 | GTGaggaattaggaTA | 588_1 | 12753 | -17 |
| 589 | gtaacaatatggtttg | 3-11-2 | GTAacaatatggttTG | 589_1 | 12780 | -15 |
| 590 | gaaatattgtagacta | 2-11-3 | GAaatattgtagaCTA | 590_1 | 13151 | -14 |
| 591 | ttgaaatattgtagac | 3-11-2 | TTGaaatattgtagAC | 591_1 | 13153 | -12 |
| 592 | aagtctagtaatttgc | 2-10-4 | AAgtctagtaatTTGC | 592_1 | 13217 | -17 |
| 593 | gctcagtagattataa | 4-10-2 | GCTCagtagattatAA | 593_1 | 13259 | -17 |
| 594 | catacactgttgctaa | 3-10-3 | CATacactgttgcTAA | 594_1 | 13296 | -19 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 595 | atggtctcaaatcatt | 3-10-3 | ATGgtctcaaatcATT | 595_1 | 13314 | -17 |
| 596 | caatggtctcaaatca | 4-10-2 | CAATggtctcaaatCA | 596_1 | 13316 | -18 |
| 597 | ttcctattgattgact | 4-10-2 | TTCCtattgattgaCT | 597_1 | 13568 | -20 |
| 598 | tttctgttcacaacac | 4-10-2 | TTTCtgttcacaacAC | 598_1 | 13600 | -17 |
| 599 | aggaacccactaatct | 2-11-3 | AGgaacccactaaTCT | 599_1 | 13702 | -20 |
| 600 | taaatggcaggaaccc | 3-11-2 | TAAatggcaggaacCC | 600_1 | 13710 | -19 |
| 601 | gtaaatggcaggaacc | 4-10-2 | GTAAatggcaggaaCC | 601_1 | 13711 | -20 |
| 602 | ttgtaaatggcaggaa | 2-11-3 | TTgtaaatggcagGAA | 602_1 | 13713 | -16 |
| 603 | ttatgagttaggcatg | 2-10-4 | TTatgagttaggCATG | 603_1 | 13835 | -19 |
| 604 | ccaggtgaaactttaa | 3-11-2 | CCAggtgaaactttAA | 604_1 | 13935 | -17 |
| 605 | cccttagtcagctcct | 3-10-3 | CCCttagtcagctCCT | 605_1 | 13997 | -30 |
| 606 | acccttagtcagctcc | 2-10-4 | ACccttagtcagCTCC | 606_1 | 13998 | -27 |
| 607 | cacccttagtcagctc | 2-11-3 | CAcccttagtcagCTC | 607_1 | 13999 | -24 |
| 608 | tctcttactaggctcc | 3-10-3 | TCTcttactaggcTCC | 608_1 | 14091 | -24 |
| 609 | cctatctgtcatcatg | 2-11-3 | CCtatctgtcatcATG | 609_1 | 14178 | -20 |
| 610 | tcctatctgtcatcat | 3-11-2 | TCCtatctgtcatcAT | 610_1 | 14179 | -20 |
| 611 | gagaagtgtgagaagc | 3-11-2 | GAGaagtgtgagaaGC | 611_1 | 14808 | -19 |
| 612 | catccttgaagtttag | 4-10-2 | CATCcttgaagtttAG | 612_1 | 14908 | -19 |
| 613 | taataagatggctccc | 3-10-3 | TAAtaagatggctCCC | 613_1 | 15046 | -21 |
| 614 | caaggcataataagat | 3-11-2 | CAAggcataataagAT | 614_1 | 15053 | -14 |
| 615 | ccaaggcataataaga | 2-10-4 | CCaaggcataatAAGA | 615_1 | 15054 | -18 |
| 616 | tgatccaattctcacc | 2-12-2 | TGatccaattctcaCC | 616_1 | 15151 | -19 |
| 617 | atgatccaattctcac | 3-10-3 | ATGatccaattctCAC | 617_1 | 15152 | -19 |
| 618 | cgcttcatcttcaccc | 3-11-2 | CGCttcatcttcacCC | 618_1 | 15260 | -26 |
| 619 | tatgacactgcatctt | 2-10-4 | TAtgacactgcaTCTT | 619_1 | 15317 | -19 |
| 620 | gtatgacactgcatct | 3-10-3 | GTAtgacactgcaTCT | 620_1 | 15318 | -21 |
| 621 | tgtatgacactgcatc | 2-10-4 | TGtatgacactgCATC | 621_1 | 15319 | -20 |
| 622 | ttctcttctgtaagtc | 4-10-2 | TTCTcttctgtaagTC | 622_1 | 15363 | -19 |
| 623 | ttctacagaggaacta | 2-10-4 | TTctacagaggaACTA | 623_1 | 15467 | -17 |
| 624 | actacagttctacaga | 3-10-3 | ACTacagttctacAGA | 624_1 | 15474 | -19 |
| 625 | ttcccacaggtaaatg | 4-10-2 | TTCCcacaggtaaaTG | 625_1 | 15561 | -21 |
| 626 | attatttgaatatactcatt | 4-12-4 | ATTAtttgaatatactCATT | 626_1 | 15594 | -20 |
| 627 | tgggaggaaattatttg | 4-10-3 | TGGGaggaaattatTTG | 627_1 | 15606 | -20 |
| 628 | tgactcatcttaaatg | 4-10-2 | TGACtcatcttaaaTG | 628_1 | 15621 | -17 |
| 629 | ctgactcatcttaaat | 3-11-2 | CTGactcatcttaaAT | 629_1 | 15622 | -16 |
| 630 | tttactctgactcatc | 3-10-3 | TTTactctgactcATC | 630_1 | 15628 | -17 |
| 631 | tattggaggaattatt | 3-11-2 | TATtggaggaattaTT | 631_1 | 15642 | -14 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 632 | gtattggaggaattat | 3-11-2 | GTAttggaggaattAT | 632_1 | 15643 | -16 |
| 633 | tggtatacttctctaagtat | 2-15-3 | TGgtatacttctctaagTAT | 633_1 | 15655 | -22 |
| 634 | gatctcttggtatact | 4-10-2 | GATCtcttggtataCT | 634_1 | 15666 | -20 |
| 635 | cagacaactctatacc | 2-12-2 | CAgacaactctataCC | 635_1 | 15689 | -18 |
| 636 | aacatcagacaactcta | 4-9-4 | AACAtcagacaacTCTA | 636_1 | 15693 | -21 |
| 637 | taacatcagacaactc | 4-10-2 | TAACatcagacaacTC | 637_1 | 15695 | -16 |
| 638 | tttaacatcagacaactc | 4-10-4 | TTTAacatcagacaACTC | 638_1 | 15695 | -20 |
| 639 | atttaacatcagacaa | 2-12-2 | ATttaacatcagacAA | 639_1 | 15698 | -11 |
| 640 | cctatttaacatcagac | 2-11-4 | CCtatttaacatcAGAC | 640_1 | 15700 | -20 |
| 641 | tccctatttaacatca | 3-10-3 | TCCctatttaacaTCA | 641_1 | 15703 | -21 |
| 642 | tcaacgactattggaat | 4-9-4 | TCAAcgactattgGAAT | 642_1 | 15737 | -20 |
| 643 | cttatattctggctat | 4-9-3 | CTTAtattctggcTAT | 643_1 | 15850 | -20 |
| 644 | atccttatattctggc | 4-10-2 | ATCCttatattctgGC | 644_1 | 15853 | -23 |
| 645 | gatccttatattctgg | 2-10-4 | GAtccttatattCTGG | 645_1 | 15854 | -21 |
| 646 | tgatccttatattctg | 3-10-3 | TGAtccttatattCTG | 646_1 | 15855 | -19 |
| 647 | attgaaacttgatcct | 4-8-4 | ATTGaaacttgaTCCT | 647_1 | 15864 | -21 |
| 648 | actgtcattgaaactt | 2-10-4 | ACtgtcattgaaACTT | 648_1 | 15870 | -16 |
| 649 | tcttactgtcattgaa | 3-11-2 | TCTtactgtcattgAA | 649_1 | 15874 | -16 |
| 650 | aggatcttactgtcatt | 2-11-4 | AGgatcttactgtCATT | 650_1 | 15877 | -21 |
| 651 | gcaaatcaactccatc | 3-10-3 | GCAaatcaactccATC | 651_1 | 15896 | -20 |
| 652 | gtgcaaatcaactcca | 3-10-3 | GTGcaaatcaactCCA | 652_1 | 15898 | -22 |
| 653 | caattatttctttgtgc | 4-10-3 | CAATtatttctttgTGC | 653_1 | 15910 | -21 |
| 654 | tggcaacaattatttctt | 3-11-4 | TGGcaacaattattTCTT | 654_1 | 15915 | -21 |
| 655 | gctggcaacaattatt | 3-9-4 | GCTggcaacaatTATT | 655_1 | 15919 | -21 |
| 656 | atccatttctactgcc | 4-10-2 | ATCCatttctactgCC | 656_1 | 15973 | -24 |
| 657 | taatatctattgatttcta | 4-11-4 | TAATatctattgattTCTA | 657_1 | 15988 | -20 |
| 658 | tcaatagtgtagggca | 2-12-2 | TCaatagtgtagggCA | 658_1 | 16093 | -18 |
| 659 | ttcaatagtgtagggc | 3-11-2 | TTCaatagtgtaggGC | 659_1 | 16094 | -19 |
| 660 | aggttaattaattcaatag | 4-11-4 | AGGTtaattaattcaATAG | 660_1 | 16102 | -21 |
| 661 | catttgtaatccctag | 3-10-3 | CATttgtaatcccTAG | 661_2 | 16163 | -20 |
| 661 | catttgtaatccctag | 3-9-4 | CATttgtaatccCTAG | 661_1 | 16163 | -22 |
| 662 | acatttgtaatcccta | 3-10-3 | ACAtttgtaatccCTA | 662_1 | 16164 | -20 |
| 663 | aacatttgtaatccct | 2-10-4 | AAcatttgtaatCCCT | 663_2 | 16165 | -21 |
| 663 | aacatttgtaatccct | 3-9-4 | AACatttgtaatCCCT | 663_1 | 16165 | -22 |
| 664 | taaatttcaagttctg | 2-11-3 | TAaatttcaagttCTG | 664_1 | 16184 | -14 |
| 665 | gtttaaatttcaagttct | 3-11-4 | GTTtaaatttcaagTTCT | 665_1 | 16185 | -19 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 666 | ccaagtttaaatttcaag | 4-10-4 | CCAgtttaaatttCAAG | 666_1 | 16189 | -21 |
| 667 | acccaagtttaaatttc | 4-9-4 | ACCCaagtttaaaTTTC | 667_1 | 16192 | -22 |
| 668 | catacagtgacccaagttt | 2-14-3 | CAtacagtgacccaagTTT | 668_1 | 16199 | -23 |
| 669 | acatcccatacagtga | 2-11-3 | ACatcccatacagTGA | 669_1 | 16208 | -21 |
| 670 | agcacagctctacatc | 2-10-4 | AGcacagctctaCATC | 670_1 | 16219 | -22 |
| 671 | atatagcacagctcta | 3-9-4 | ATAtagcacagcTCTA | 671_1 | 16223 | -21 |
| 672 | tccatatagcacagct | 3-11-2 | TCCatatagcacagCT | 672_1 | 16226 | -22 |
| 673 | atttccatatagcaca | 3-9-4 | ATTtccatatagCACA | 673_1 | 16229 | -20 |
| 674 | tttatttccatatagca | 4-9-4 | TTTAtttccatatAGCA | 674_1 | 16231 | -22 |
| 675 | tttatttccatatagc | 3-10-3 | TTTatttccatatAGC | 675_1 | 16232 | -18 |
| 676 | aaggagaggagattatg | 4-9-4 | AAGGagaggagatTATG | 676_1 | 16409 | -21 |
| 677 | agttcttgtgttagct | 3-11-2 | AGTtcttgtgttagCT | 677_1 | 16456 | -21 |
| 678 | gagttcttgtgttagc | 2-12-2 | GAgttcttgtgttaGC | 678_1 | 16457 | -20 |
| 679 | attaattatccatccac | 3-10-4 | ATTaattatccatCCAC | 679_1 | 16590 | -21 |
| 680 | atcaattaattatccatc | 3-11-4 | ATCaattaattatcCATC | 680_1 | 16593 | -19 |
| 681 | agaatcaattaattatcc | 3-12-3 | AGAatcaattaattaTCC | 681_1 | 16596 | -18 |
| 682 | tgagataccgtgcatg | 2-12-2 | TGagataccgtgcaTG | 682_1 | 16656 | -18 |
| 683 | aatgagataccgtgca | 2-10-4 | AAtgagataccgTGCA | 683_1 | 16658 | -21 |
| 684 | ctgtggttaggctaat | 3-11-2 | CTGtggttaggctaAT | 684_1 | 16834 | -19 |
| 685 | aagagtaagggtctgtggtt | 1-17-2 | AagagtaagggtctgtggTT | 685_1 | 16842 | -21 |
| 686 | gatgggttaagagtaa | 4-9-3 | GATGggttaagagTAA | 686_1 | 16854 | -19 |
| 687 | agcagatgggttaaga | 3-11-2 | AGCagatgggttaaGA | 687_1 | 16858 | -20 |
| 688 | tgtaaacatttgtagc | 2-10-4 | TGtaaacatttgTAGC | 688_1 | 16886 | -19 |
| 689 | cctgcttataaatgta | 3-11-2 | CCTgcttataaatgTA | 689_1 | 16898 | -19 |
| 690 | tgccctgcttataaat | 4-10-2 | TGCCctgcttataaAT | 690_1 | 16901 | -23 |
| 691 | tcttcttagttcaata | 2-12-2 | TCttcttagttcaaTA | 691_1 | 16935 | -15 |
| 692 | tggtttctaactacat | 2-10-4 | TGgtttctaactACAT | 692_1 | 16980 | -18 |
| 693 | agtttggtttctaacta | 2-12-3 | AGtttggtttctaaCTA | 693_1 | 16983 | -19 |
| 694 | gaatgaaacttgcctg | 3-10-3 | GAAtgaaacttgcCTG | 694_1 | 17047 | -18 |
| 695 | attatccttacatgat | 3-10-3 | ATTatccttacatGAT | 695_1 | 17173 | -17 |
| 696 | gtacccaattatcctt | 2-11-3 | GTacccaattatcCTT | 696_1 | 17180 | -21 |
| 697 | tgtacccaattatcct | 3-10-3 | TGTacccaattatCCT | 697_1 | 17181 | -24 |
| 698 | ttgtacccaattatcc | 2-11-3 | TTgtacccaattaTCC | 698_1 | 17182 | -20 |
| 699 | tttgtacccaattatc | 3-11-2 | TTTgtacccaattaTC | 699_1 | 17183 | -17 |
| 700 | agcagcaggttatatt | 4-10-2 | AGCAgcaggttataTT | 700_1 | 17197 | -22 |
| 701 | tgggaagtggtctggg | 3-10-3 | TGGgaagtggtctGGG | 701_1 | 17292 | -25 |
| 702 | ctggagagtgataata | 3-11-2 | CTGgagagtgataaTA | 702_1 | 17322 | -17 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 703 | aatgctggattacgtc | 4-10-2 | AATGctggattacgTC | 703_1 | 17354 | -19 |
| 704 | caatgctggattacgt | 2-11-3 | CAatgctggattaCGT | 704_1 | 17355 | -19 |
| 705 | ttgttcagaagtatcc | 2-10-4 | TTgttcagaagtATCC | 705_1 | 17625 | -19 |
| 706 | gatgatttgcttggag | 2-10-4 | GAtgatttgcttGGAG | 706_1 | 17646 | -21 |
| 707 | gaaatcattcacaacc | 3-10-3 | GAAatcattcacaACC | 707_1 | 17860 | -17 |
| 708 | ttgtaacatctactac | 3-10-3 | TTGtaacatctacTAC | 708_1 | 17891 | -16 |
| 709 | cattaagcagcaagtt | 3-11-2 | CATtaagcagcaagTT | 709_1 | 17923 | -17 |
| 710 | ttactagatgtgagca | 3-11-2 | TTActagatgtgagCA | 710_1 | 17942 | -18 |
| 711 | tttactagatgtgagc | 2-11-3 | TTtactagatgtgAGC | 711_1 | 17943 | -18 |
| 712 | gaccaagcaccttaca | 3-11-2 | GACcaagcaccttaCA | 712_1 | 17971 | -22 |
| 713 | agaccaagcaccttac | 3-10-3 | AGAccaagcacctTAC | 713_1 | 17972 | -22 |
| 714 | atgggttaaataaagg | 2-10-4 | ATggggttaaataAAGG | 714_1 | 18052 | -15 |
| 715 | tcaaccagagtattaa | 2-12-2 | TCaaccagagtattAA | 715_1 | 18067 | -13 |
| 716 | gtcaaccagagtatta | 3-11-2 | GTCaaccagagtatTA | 716_1 | 18068 | -18 |
| 717 | attgtaaagctgatat | 2-11-3 | ATtgtaaagctgaTAT | 717_1 | 18135 | -14 |
| 718 | cacataattgtaaagc | 2-10-4 | CAcataattgtaAAGC | 718_1 | 18141 | -16 |
| 719 | gaggtctgctatttac | 2-11-3 | GAggtctgctattTAC | 719_1 | 18274 | -19 |
| 720 | tgtagattcaatgcct | 2-11-3 | TGtagattcaatgCCT | 720_1 | 18404 | -20 |
| 721 | cctcattatactatga | 2-11-3 | CCtcattatactaTGA | 721_1 | 18456 | -19 |
| 722 | ccttatgctatgacac | 2-12-2 | CCttatgctatgacAC | 722_1 | 18509 | -18 |
| 723 | tccttatgctatgaca | 4-10-2 | TCCTtatgctatgaCA | 723_1 | 18510 | -22 |
| 724 | aagatgtttaagtata | 3-10-3 | AAGatgtttaagtATA | 724_1 | 18598 | -13 |
| 725 | ctgattattaagatgt | 2-10-4 | CTgattattaagATGT | 725_1 | 18607 | -17 |
| 726 | tggaaaggtatgaatt | 2-12-2 | TGgaaaggtatgaaTT | 726_1 | 18808 | -13 |
| 727 | acttgaatggcttgga | 2-12-2 | ACttgaatggcttgGA | 727_1 | 18880 | -18 |
| 728 | aacttgaatggcttgg | 3-10-3 | AACttgaatggctTGG | 728_1 | 18881 | -19 |
| 729 | caatgtgttactattt | 4-10-2 | CAATgtgttactatTT | 729_1 | 19004 | -16 |
| 730 | acaatgtgttactatt | 3-10-3 | ACAatgtgttactATT | 730_1 | 19005 | -15 |
| 731 | catctgctatataaga | 4-10-2 | CATCtgctatataaGA | 731_1 | 19063 | -18 |
| 732 | cctagagcaaatactt | 4-10-2 | CCTAgagcaaataTT | 732_1 | 19223 | -20 |
| 733 | cagagttaataataag | 3-10-3 | CAGagttaataatAAG | 733_1 | 19327 | -13 |
| 734 | gttcaagcacaacgaa | 4-10-2 | GTTCaagcacaacgAA | 734_1 | 19493 | -18 |
| 735 | agggttcaagcacaac | 2-11-3 | AGggttcaagcacAAC | 735_1 | 19496 | -18 |

TABLE 5-continued list of oligonucleotide motif sequences (indicated by SEQ ID NO) targeting the human PD-L1 transcript (SEQ ID NO: 1), designs of these, as well as specific antisense oligonucleotide compounds (indicated by CMP ID NO) designed based on the motif sequence.

| SEQ ID NO | Motif sequence | Design | Oligonucleotide Compound | CMP ID NO | Start ID NO: 1 | dG |
|---|---|---|---|---|---|---|
| 736 | tgttggagacactgtt | 2-12-2 | TGttggagacactgTT | 736_1 | 19677 | −17 |
| 737 | aaggaggagttaggac | 3-11-2 | AAGgaggagttaggAC | 737_1 | 19821 | −18 |
| 738 | ctatgccatttacgat | 4-10-2 | CTATgccatttacgAT | 738_1 | 19884 | −21 |
| 739 | tcaaatgcagaattag | 2-12-2 | TCaaatgcagaattAG | 739_1 | 19913 | −12 |
| 740 | agtgacaatcaaatgc | 2-10-4 | AGtgacaatcaaATGC | 740_1 | 19921 | −18 |
| 741 | aagtgacaatcaaatg | 2-11-3 | AAgtgacaatcaaATG | 741_1 | 19922 | −12 |
| 742 | gtgtaccaagtaacaa | 3-11-2 | GTGtaccaagtaacAA | 742_1 | 19978 | −16 |
| 743 | tgggatgttaaactga | 3-10-3 | TGGgatgttaaacTGA | 743_1 | 20037 | −20 |

Motif sequences represent the contiguous sequence of nucleobases present in the oligonucleotide.

Designs refer to the gapmer design, F-G-F', where each number represents the number of consecutive modified nucleosides, e.g. 2' modified nucleosides (first number=5' flank), followed by the number of DNA nucleosides (second number=gap region), followed by the number of modified nucleosides, e.g. 2' modified nucleosides (third number=3' flank), optionally preceded by or followed by further repeated regions of DNA and LNA, which are not necessarily part of the contiguous sequence that is complementary to the target nucleic acid.

Oligonucleotide compounds represent specific designs of a motif sequence. Capital letters represent beta-D-oxy LNA nucleosides, lowercase letters represent DNA nucleosides, all LNA C are 5-methyl cytosine, all internucleoside linkages are phosphorothioate internucleoside linkages.

TABLE 6

Oligonucleotides targeting mouse PD-L1 transcript (SEQ ID NO: 4) designs of these, as well as specific oligonucleotide compounds (indicated by CMP ID NO) designed based on the motif sequence.

| SEQ ID NO | Motif sequence | Design | Oligonucleotide Compound | CMP ID NO | Start on SEQ ID NO: 4 | dG |
|---|---|---|---|---|---|---|
| 744 | agtttacattttctgc | 3-10-3 | AGTttacattttcTGC | 744_1 | 4189 | −20 |
| 745 | tatgtgaagaggagag | 3-10-3 | TATgtgaagaggaGAG | 745_1 | 7797 | −19 |
| 746 | cacctttaaaacccca | 3-10-3 | CACctttaaaaccCCA | 746_1 | 9221 | −23 |
| 747 | tcctttataatcacac | 3-10-3 | TCCtttataatcaCAC | 747_1 | 10386 | −19 |
| 748 | acggtattttcacagg | 3-10-3 | ACGgtattttcacAGG | 748_1 | 12389 | −21 |
| 749 | gacactacaatgagga | 3-10-3 | GACactacaatgaGGA | 749_1 | 15088 | −20 |
| 750 | tggttttaggactgt | 3-10-3 | TGGttttaggacTGT | 750_1 | 16410 | −21 |
| 751 | cgacaaattctatcct | 3-10-3 | CGAcaaattctatCCT | 751_1 | 18688 | −20 |
| 752 | tgatatacaatgctac | 3-10-3 | TGAtatacaatgcTAC | 752_1 | 18735 | −16 |
| 753 | tcgttgggtaaattta | 3-10-3 | TCGttgggtaaatTTA | 753_1 | 19495 | −17 |
| 754 | tgctttataaatggtg | 3-10-3 | TGCtttataaatgGTG | 754_1 | 19880 | −19 |

Motif sequences represent the contiguous sequence of nucleobases present in the oligonucleotide.

Designs refer to the gapmer design, F-G-F', where each number represents the number of consecutive modified nucleosides, e.g. 2' modified nucleosides (first number=5' flank), followed by the number of DNA nucleosides (second number=gap region), followed by the number of modified nucleosides, e.g. 2' modified nucleosides (third number=3' flank), optionally preceded by or followed by further repeated regions of DNA and LNA, which are not necessarily part of the contiguous sequence that is complementary to the target nucleic acid.

Oligonucleotide compounds represent specific designs of a motif sequence. Capital letters represent beta-D-oxy LNA nucleosides, lowercase letters represent DNA nucleosides, all LNA C are 5-methyl cytosine, all internucleoside linkages are phosphorothioate internucleoside linkages.

TABLE 7

Oligonucleotide motif sequences and antisense compounds with 5' ca biocleavable linker.

| SEQ ID NO | motif sequence | oligonucleotide compound with ca linker | CMP ID NO |
|---|---|---|---|
| 755 | caagtttacatttctgc | c$_o$a$_o$AGTttacattttcTGC | 755_1 |
| 756 | catatgtgaagaggagag | c$_o$a$_o$TATgtgaagaggaGAG | 756_1 |
| 757 | caccttttaaaacccca | c$_o$a$_o$CACctttaaaaccCCA | 757_1 |
| 758 | catcctttataatcacac | c$_o$a$_o$TCCtttataatcaCAC | 758_1 |
| 759 | caacggtattttcacagg | c$_o$a$_o$ACGgtattttcacAGG | 759_1 |
| 760 | cagacactacaatgagga | c$_o$a$_o$GACactacaatgaGGA | 760_1 |
| 761 | catggtttttaggactgt | c$_o$a$_o$TGGtttttaggacTGT | 761_1 |
| 762 | cacgacaaattctatcct | c$_o$a$_o$CGAcaaattctatCCT | 762_1 |
| 763 | catgatatacaatgctac | c$_o$a$_o$TGAtatacaatgcTAC | 763_1 |
| 764 | catcgttgggtaaattta | c$_o$a$_o$TCGttgggtaaatTTA | 764_1 |
| 765 | catgctttataaatggtg | c$_o$a$_o$TGCtttataaatgGTG | 765_1 |
| 766 | caacaaataatggttactct | c$_o$a$_o$ACAAataatggttaCTCT | 766_1 |
| 767 | cacagattgatggtagtt | c$_o$a$_o$CAGAttgatggtagTT | 767_1 |
| 768 | caccctatttaacatcagac | c$_o$a$_o$CCtatttaacatcAGAC | 768_1 |
| 769 | cactaattgtagtagtactc | c$_o$a$_o$CTAattgtagtagtaCTC | 769_1 |
| 770 | caataaacatgaatctctcc | c$_o$a$_o$ATaaacatgaatctCTCC | 770_1 |

Capital letters represent beta-D-oxy LNA nucleosides, lowercase letters represent DNA nucleosides, all LNA C are 5-methyl cytosine, subscript o represent a phosphodiester internucleoside linkage and unless otherwise indicated other internucleoside linkages are phosphorothioate internucleoside linkages.

TABLE 8

GalNAc conjugated antisense oligonucleotide compounds.

| antisense oligonucleotide conjugate | CMP ID NO | SEQ ID NO |
|---|---|---|
| GN2-C6$_o$c$_o$a$_o$AGTttacattttcTGC | 755_2 | 744 |
| GN2-C6$_o$c$_o$a$_o$TATgtgaagaggaGAG | 756_2 | 745 |
| GN2-C6$_o$c$_o$a$_o$CACctttaaaaccCCA | 757_2 | 746 |
| GN2-C6$_o$c$_o$a$_o$TCCtttataatcaCAC | 758_2 | 747 |
| GN2-C6$_o$c$_o$a$_o$ACGgtattttcacAGG | 759_2 | 748 |
| GN2-C6$_o$c$_o$a$_o$GACactacaatgaGGA | 760_2 | 749 |
| GN2-C6$_o$c$_o$a$_o$TGGtttttaggacTGT | 761_2 | 750 |
| GN2-C6$_o$c$_o$a$_o$CGAcaaattctatCCT | 762_2 | 751 |
| GN2-C6$_o$c$_o$a$_o$TGAtatacaatgcTAC | 763_2 | 752 |
| GN2-C6$_o$c$_o$a$_o$TCGttgggtaaatTTA | 764_2 | 753 |
| GN2-C6$_o$c$_o$a$_o$TGCtttataaatgGTG | 765_2 | 754 |
| GN2-C6$_o$c$_o$a$_o$ACAAataatggttaCTCT | 766_2 | 287 |
| GN2-C6$_o$c$_o$a$_o$CAGAttgatggtagTT | 767_2 | 342 |
| GN2-C6$_o$c$_o$a$_o$CCtatttaacatcAGAC | 768_2 | 640 |

TABLE 8-continued

GalNAc conjugated antisense oligonucleotide compounds.

| antisense oligonucleotide conjugate | CMP ID NO | SEQ ID NO |
|---|---|---|
| GN2-C6$_o$c$_o$a$_o$CTAattgtagtagtaCTC | 769_2 | 466 |
| GN2-C6$_o$c$_o$a$_o$ATaaacatgaatctCTCC | 770_2 | 566 |

GN2 represents the trivalent GalNAc cluster shown in FIG. 3, C6 represents an amino alkyl group with 6 carbons, capital letters represent beta-D-oxy LNA nucleosides, lowercase letters represent DNA nucleosides, all LNA C are 5-methyl cytosine, subscript o represent a phosphodiester nucleoside linkage and unless otherwise indicated internucleoside linkages are phosphorothioate internucleoside linkages. Chemical drawings representing some of the molecules are shown in FIGS. 4 to 8.

AAV/HBV Mouse Models

Pasteur Model:

HLA-A2.1-/HLA-DR1-transgenic H-2 class I-/class II-knockout (here referred to as HLA-A2/DR1) mice were created and bred at the Institut Pasteur. These mice represent an in vivo experimental model for human immune function studies without any interference with mouse MHC response (Pajot et al 2004 Eur J Immunol. 34(11):3060-9.

Adeno-associated virus (AAV) vector, AAV serotype 2/8 carrying a replication competent HBV DNA genome was used in these studies. The AAV-HBV vector (batch GVPN #6163) was diluted in sterile Phosphate buffered Saline (PBS) to reach a titer of $5\times10^{11}$ vg/mL. Mice were injected intravenously (i.v.) with 100 µL of this diluted solution (dose/mouse: $5\times10^{10}$ vg) in a tail vein. Complete viral particles containing HBV DNA were detected in the blood of HBV-carrier mice. HBcAg was detected for up to one year in the liver together with HBV circulating proteins HBeAg and HBsAg in the blood. In all AAV2/8-HBV-transduced mice, HBsAg, HBeAg, and HBV DNA persisted in serum for at least one year (Dion et al 2013 *J Virol* 87:5554-5563).

Shanghai Model:

In this model, mice infected with a recombinant adeno-associated virus (AAV) carrying the HBV genome (AAV/HBV) maintains stable viremia and antigenimia for more than 30 weeks (Dan Yang, et al. 2014 Cellular & Molecular Immunology 11, 71-78).

Male C57BL/6 mice (4-6 weeks old), specific pathogen free, were purchased from SLAC (Shanghai Laboratory Animal Center of Chinese Academy of Sciences) and housed in an animal care facility in individually ventilated cages. Guidelines were followed for the care and use of animals as indicated by WuXi IACUC (Institutional Animal Care and Use Committee, WUXI IACUC protocol number R20131126-Mouse). Mice were allowed to acclimate to the new environment for 3 days and are grouped according to the experimental design.

Recombinant AAV-HBV was diluted in PBS, 200 µL per injection. This recombinant virus carries 1.3 copies of the HBV genome (genotype D, serotype ayw).

On day 0, all mice were injected through tail vein with 200 µL AAV-HBV. On days 6, 13 and 20 after AAV injection, all mice in were submandibularly bled (0.1 ml blood/mouse) for serum collection. On day 22 post injection, mice with stable viremia were ready for oligonucleotide treatment. The oligonucleotides can be unconjugated or GalNAc conjugated.

DNA Vaccine

Plasmid DNA were endotoxin-free and manufactured by Plasmid-Factory (Germany). pCMV-S2.S ayw encodes the preS2 and S domains of the HBsAg (genotype D), and its expression is controlled by the cytomegalovirus immediate early gene promoter (Michel et al 1995 Proc Natl Acad Sci USA 92:5307-5311). pCMV-HBc encodes the HBV capsid carrying the hepatitis core (HBc) Ag (Dion et al 2013 J Virol 87:5554-5563).

Treatment with DNA vaccine was conducted as described here. Five days prior to vaccination cardiotoxine (CaTx, Latoxan refL81-02, 50 µl/muscle) was injected into the muscle of the mice. CaTx depolarizees the muscular fibers to induce cell degeneration, 5 days post injection, new muscular fibers will appear and will receive the DNA vaccine for a better efficacy for transfection. The pCMV-S2.S ayw and pCMVCore at 1 mg/ml each were mixed in equal amount and each mouse received a total of 100 µg by bilateral intramuscular injection into cardiotoxin-treated tibialis anterior muscles as previously described in Michel et al 1995 Proc Natl Acad Sci USA 92:5307-5311, under anesthesia (100 µL of 12.5 mg/mL ketamine, 1.25 mg/mL xylazine).

Anti-PD-L1 Antibody

This is a mouse anti mouse PD-L1 IgG1 antibody clone 6E11 internally produced at Genetech. It is a surrogate antibody that cross blocks Atezolizumab and has similar in vitro blocking activity Atezolizumab produced internally at Roche. The antibody was administered by intraperitoneal (i.p.) injection at a dose of 12.5 µg/g.

Oligonucleotide Synthesis

Oligonucleotide synthesis is generally known in the art. Below is a protocol which may be applied. The oligonucleotides of the present invention may have been produced by slightly varying methods in terms of apparatus, support and concentrations used.

Oligonucleotides are synthesized on uridine universal supports using the phosphoramidite approach on an Oligomaker 48 at 1 µmol scale. At the end of the synthesis, the oligonucleotides are cleaved from the solid support using aqueous ammonia for 5-16 hours at 60° C. The oligonucleotides are purified by reverse phase HPLC (RP-HPLC) or by solid phase extractions and characterized by UPLC, and the molecular mass is further confirmed by ESI-MS.

Elongation of the Oligonucleotide:

The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), or LNA-T) is performed by using a solution of 0.1 M of the 5'-O-DMT-protected amidite in acetonitrile and DCI (4,5-dicyanoimidazole) in acetonitrile (0.25 M) as activator. For the final cycle a phosphoramidite with desired modifications can be used, e.g. a C6 linker for attaching a conjugate group or a conjugate group as such. Thiolation for introduction of phosphorthioate linkages is carried out by using xanthane hydride (0.01 M in acetonitrile/pyridine 9:1). Phosphordiester linkages can be introduced using 0.02 M iodine in THF/Pyridine/water 7:2:1. The rest of the reagents are the ones typically used for oligonucleotide synthesis.

For post solid phase synthesis conjugation a commercially available C6 amino linker phosphoramidite can be used in the last cycle of the solid phase synthesis and after deprotection and cleavage from the solid support the aminolinked deprotected oligonucleotide is isolated. The conjugates are introduced via activation of the functional group using standard synthesis methods.

Alternatively, the conjugate moiety can be added to the oligonucleotide while still on the solid support by using a GalNAc- or GalNAc-cluster phosphoramidite as described in PCT/EP2015/073331 or in EP appl. NO. 15194811.4.

Purification by RP-HPLC:

The crude compounds are purified by preparative RP-HPLC on a Phenomenex Jupiter C18 10μ 150×10 mm column. 0.1 M ammonium acetate pH 8 and acetonitrile is used as buffers at a flow rate of 5 mL/min. The collected fractions are lyophilized to give the purified compound typically as a white solid.

Abbreviations

DCI: 4,5-Dicyanoimidazole
DCM: Dichloromethane
DMF: Dimethylformamide
DMT: 4,4'-Dimethoxytrityl
THF: Tetrahydrofurane
Bz: Benzoyl
Ibu: Isobutyryl
RP-HPLC: Reverse phase high performance liquid chromatography $T_m$ Assay Oligonucleotide and RNA target (phosphate linked, PO) duplexes are diluted to 3 mM in 500 ml RNase-free water and mixed with 500 ml 2×$T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 20° C. to 95° C. and then down to 25° C., recording absorption at 260 nm. First derivative and the local maximums of both the melting and annealing are used to assess the duplex $T_m$.

Tissue Specific In Vitro Linker Cleavage Assay

FAM-labeled oligonucleotides with the biocleavable linker to be tested (e.g. a DNA phosphodiester linker (PO linker)) are subjected to in vitro cleavage using homogenates of the relevant tissues (e.g. liver or kidney) and Serum.

The tissue and serum samples are collected from a suitable animal (e.g. mice, monkey, pig or rat) and homogenized in a homogenisation buffer (0.5% Igepal CA-630, 25 mM Tris pH 8.0, 100 mM NaCl, pH 8.0 (adjusted with 1 N NaOH). The tissue homogenates and Serum are spiked with oligonucleotide to concentrations of 200 μg/g tissue. The samples are incubated for 24 hours at 37° C. and thereafter the samples are extracted with phenol-chloroform. The solutions are subjected to AIE HPLC analyses on a Dionex Ultimate 3000 using an Dionex DNApac p-100 column and a gradient ranging from 10 mM-1 M sodium perchlorate at pH 7.5. The content of cleaved and non-cleaved oligonucleotide are determined against a standard using both a fluorescence detector at 615 nm and a uv detector at 260 nm.

S1 Nuclease Cleavage Assay

FAM-labelled oligonucleotides with S1 nuclease susceptible linkers (e.g. a DNA phosphodiester linker (PO linker)) are subjected to in vitro cleavage in S1 nuclease extract or Serum.

100 μM of the oligonucleotides are subjected to in vitro cleavage by S1 nuclease in nuclease buffer (60 U pr. 100 μL) for 20 and 120 minutes. The enzymatic activity is stopped by adding EDTA to the buffer solution. The solutions are subjected to AIE HPLC analyses on a Dionex Ultimate 3000 using an Dionex DNApac p-100 column and a gradient ranging from 10 mM-1 M sodium perchlorate at pH 7.5. The content of cleaved and non-cleaved oligonucleotide is determined against a standard using both a fluorescence detector at 615 nm and a uv detector at 260 nm.

Preparation of Liver Mononuclear Cells

Liver cells from AAV/HBV mice were prepared as described below and according to a method described by Tupin et al 2006 Methods Enzymol 417:185-201 with minor modifications. After mouse euthanasia, the liver was perfused with 10 ml of sterile PBS via hepatic portal vein using syringe with G25 needle. When organ is pale, the organ was harvested in Hank's Balanced Salt Solution (HBSS) (GIBCO® HBSS, 24020)+5% decomplemented fetal calf serum (FCS). The harvested liver was gently pressed through 100 μm cell-strainer (BD Falcon, 352360) and cells were suspended in 30 ml of HBSS+5% FCS. Cell suspension was centrifuged at 50 g for 5 min. Supernatants were then centrifuged at 289 g for 10 min at 4° C. After centrifugation, supernatants were discarded and pellets were re-suspended in 15 mL at room temperature in a 35% isotonic Percoll solution (GE Healthcare Percoll #17-0891-01 diluted into RPMI 1640 (GIBCO, 31870)) and transferred to a 15 ml tube. Cells were further centrifuged at 1360 g for 25 min at room temperature. The supernatant was discarded by aspiration and the pellet containing mononuclear cells was washed twice with HBSS+5% FCS.

Cells were cultured in complete medium (α-minimal essential medium (Gibco, 22571) supplemented with 10% FCS (Hyclone, #SH30066, lot APG21570), 100 U/mL penicillin+100 μg/mL streptomycin+0.3 mg/mL L-glutamine (Gibco, 10378), 1× non-essential amino acids (Gibco, 11140), 10 mM Hepes (Gibco, 15630), 1 mM sodium pyruvate (Gibco, 11360) and 50 μM β-mercaptoethanol (LKB, 1830)).

Surface Labeling of Cells

Cells were seeded in U-bottom 96-well plates and washed with PBS FACS (PBS containing 1% bovine serum albumin and 0.01% sodium azide). Cells were incubated with 5 μL of PBS FACS containing a rat anti-mouse CD16/CD32 antibody and a viability marker LD fixable yellow, Thermofisher, L34959 for 10 min in the dark at 4° C. Then, cells were stained for 20 min in the dark at 4° C. with 25 μL of PBS FACS containing monoclonal antibodies (Mab) against NK P46 BV421 (Rat Mab anti mouse NK P46, Biolegend, 137612) and F4/80 (rat Mab anti-mouse F4/80 FITC, BD Biolegend, 123108) and two supplemental surface markers: PD1 (rat Mab anti-mouse PD1 PE, BD Biosciences, 551892) and PDL1 (rat Mab anti-mouse PDL1 BV711, Biolegend, 124319) were also added.

Intracelluar Cytokine Staining (ICS) Assay

ICS assays were performed on both splenocytes and liver mononuclear cells. Cells were seeded in Ubottom 96-well plates. Plates with cells were incubated overnight at 37° C. either in complete medium alone as negative control or with the peptides described in Table 9 at a concentration of 2 µg/ml. Brefeldin A at 2 µg/mL (Sigma, B6542) was added after one hour of incubation.

After the overnight culture, cells were washed with PBS FACS and incubated with 5 µL of PBS FACS containing rat anti-mouse CD16/CD32 antibody and a viability marker LD fixable yellow, Thermofisher, L34959 for 10 min in the dark at 4° C. Then, cells were stained for 20 min in the dark at 4° C. with 25 µL of PBS FACS containing Mab. The mix was composed of monoclonal antibodies against CD3 (hamster Mab anti-mouse CD3-PerCP, BD Biosciences, 553067), CD8 (rat Mab anti-mouse CD8-APC-H7, BD Biosciences, 560182), CD4 (rat Mab anti-mouse CD4-PE-Cy7, BD Bio-sciences, 552775), and NK cells (Rat Mab anti mouse NK P46 BV421, Biolegend, 137612). Cells were fixed after several washes and permeabilized for 20 min in the dark at room temperature with Cytofix/Cytoperm, washed with Perm/Wash solution (BD Biosciences, 554714) at 4° C.

Intracellular cytokine staining with antibodies against IFNγ (rat Mab anti-mouse IFNγ-APC, clone XMG1.2, BD Biosciences, 554413) and tumor necrosis factor alpha (TNFα) (rat Mab anti-mouse TNFα-FITC, clone MP6-XT22; 1/250 (BD Biosciences 554418) was performed for 30 min in the dark at 4° C. Before analysis by flow cytometry using the MACSQuant Analyzer, cells were washed with Perm/Wash and re-suspended in PBS FACS containing 1% Formaldehyde.

Live CD3+CD8+CD4− and cells CD3+CD8−CD4+ were gated and presented on dot-plot. Two regions were defined to gate for positive cells for each cytokine. Numbers of events found in these gates were divided by total number of events in parental population to yield percentages of responding T cells. For each mouse, the percentage obtained in medium alone was considered as background and subtracted from the percentage obtained with peptide stimulations.

Threshold of positivity was defined according to experiment background i.e. the mean percentage of stained cells obtained for each group in medium alone condition plus two standard deviations. Only percentage of cytokine represented at least 5 events were considered as positive.

TABLE 9

HLA-A2/DR1 restricted epitopes contained in the HBV Core protein and the Envelope domains of the HBsAg (S2 + S).

| Protein | Start Position | End Position | Sequence | HLA restriction | References |
|---|---|---|---|---|---|
| Core | 18 | 27 | FLPSDFFPSV (SEQ ID NO: 773) | A2 | Bertoletti et al Gastroenterology 1997; 112:193-199 |
|  | 111 | 125 | GRETVLEYLVSFGVW (SEQ ID NO: 774) | DR1 | (Bertoletti et al Gastroenterology 1997; 112:193-199 |
| Envelope (S2 + S) | 114 | 128 | TTFHQTLQDPRVRGL (SEQ ID NO: 775) | DR1 | Pajot et al Microbes Infect 2006; 8:2783-2790. |
|  | 179 | 194 | QAGFFLLTRILTIPQS (SEQ ID NO: 776) | A2 + DR1 | Pajot et al Microbes Infect 2006; 8:2783-2790. |
|  | 183 | 191 | FLLTRILTI (SEQ ID NO: 777) | A2 | Sette et al J Immunol 1994; 153:5586-5592. |
|  | 200 | 214 | TSLNFLGGTTVCLGQ (SEQ ID NO: 778) | A2 + DR1 | Pajot et al Microbes Infect 2006; 8:2783-2790. |
|  | 204 | 212 | FLGGTTVCL (SEQ ID NO: 779) | A2 | Rehermann et al J Exp Med 1995; 181: 1047-1058. |
|  | 335 | 343 | WLSLLVPFV (SEQ ID NO: 780) | A2 | Nayersina et alJ Immunol 1993; 150: 4659-4671. |
|  | 337 | 357 | SLLVPFVQWFVGLSPTVWLSV (SEQ ID NO: 781) | A2 + DR1 | Loirat et al J Immunol 2000; 165: 4748-4755 |
|  | 348 | 357 | GLSPTVWLSV (SEQ ID NO: 782) | A2 | Loirat et al J Immunol 2000; 165: 4748-4755 |
|  | 370 | 379 | SILSPFLPLL (SEQ ID NO: 783) | A2 | Mizukoshi et al J Immunol 2004; 173: 5863-5871. |

Example 1 Testing In Vitro Efficacy

A gene walk was performed across the human PD-L1 transcript primarily using 16 to 20mer gapmers. Efficacy testing was performed in an in vitro experiment in the human leukemia monocytic cell line THP1 and in the human non-Hodgkin's K lymphoma cell line (KARPAS-299).

Cell Lines

THP1 and Karpas-299 cell line were originally purchased from European Collection of Authenticated Cell Cultures (ECACC) and maintained as recommended by the supplier in a humidified incubator at 37° C. with 5% $CO_2$.

Oligonucleotide Efficacy

THP-1 cells (3.104 in RPMI-GLutamax, 10% FBS, 1% Pen-Strep (Thermo Fisher Scientific) were added to the oligonucleotides (4-5 ul) into 96-well round bottom plates and cultured for 6 days in a final volume of 100 μl/well. Oligonucleotides were screened at one single concentration (20 μM) and in dose-range concentrations from 25 μM to 0.004 μM (1:3 dilution in water). Total mRNA was extracted using the MagNA Pure 96 Cellular RNA Large Volume Kit on the MagNA Pure 96 System (Roche Diagnostics) according to the manufacturer's instructions. For gene expression analysis, RT-qPCR was performed using the TaqMan RNA-to-ct 1-Step kit (Thermo Fisher Scientific) on the QuantStudio machine (Applied Biosystems) with pre-designed Taqman primers targeting human PDL1 and ACTB used as endogenous control (Thermo Fisher Scientific). The relative PD-L1 mRNA expression level was calculated using 2(−Delta Delta C(T)) method and the percentage of inhibition as the % compared to the control sample (non-treated cells).

Karpas-299 cells were cultured in RPMI 1640, 2 mM Glutamine and 20% FBS (Sigma). The cells were plated at 10000 cell/well in 96 wells plates incubated for 24 hours before addition of oligonucleotides dissolved in PBS. Final concentration of oligonucleotides was in a single dose of 5 μM, in a final culture volume was 100 μl/well or added in a dose response ranging from 50 μM, 15.8 μM, 5.0 μM, 1.58 μM, 0.5 μM, 0.158 μM, 0.05 μM, to 0.0158 μM in 100 μL culture volume. The cells were harvested 3 days after addition of oligonucleotide compounds and RNA was extracted using the PureLink Pro 96 RNA Purification kit (Ambion), according to the manufacturer's instructions. cDNA was synthesized using M-MLT Reverse Transcriptase, random decamers RETROscript, RNase inhibitor (Ambion) and 100 mM dNTP set (Invitrogen, PCR Grade) according to the manufacturer's instruction. For gene expressions analysis, qPCR was performed using TaqMan Fast Advanced Master Mix (2×) (Ambion) in a duplex set up with TaqMan primer assays for the PD-L1 (Applied Biosystems; Hs01125299_m1) and TBP (Applied Biosystems; 4325803). The relative PD-L1 mRNA expression level is shown in table 10 as % of control sample (PBS-treated cells).

TABLE 10 in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 μM CMP | | THP1 cells 20 μM CMP | | Compound (CMP) | Start on SEQ ID NO 1 | SEQ ID NO |
| | % mRNA of control | sd | % mRNA of control | sd | | | |
| --- | --- | --- | --- | --- | --- | --- | --- |
| 4_1 | 50 | 1 | 32 | 11 | TAattggctctacTGC | 236 | 5 |
| 5_1 | 25 | 5 | 9 | 6 | TCGCataagaatgaCT | 371 | 6 |
| 6_1 | 29 | 2 | 15 | 5 | TGaacacacagtcgCA | 382 | 7 |
| 7_1 | 27 | 7 | 3 | 1 | CTGaacacacagtCGC | 383 | 8 |
| 8_1 | 23 | 4 | 11 | 3 | TCTgaacacacagtCG | 384 | 9 |
| 9_1 | 32 | 3 | 19 | 6 | TTCtgaacacacagTC | 385 | 10 |
| 10_1 | 57 | 5 | 39 | 16 | ACaagtcatgttaCTA | 463 | 11 |
| 11_1 | 75 | 5 | 37 | 12 | ACacaagtcatgttAC | 465 | 12 |
| 12_1 | 22 | 2 | 10 | 3 | CTtacttagatgcTGC | 495 | 13 |
| 13_1 | 33 | 4 | 23 | 11 | ACttacttagatgCTG | 496 | 14 |
| 14_1 | 33 | 7 | 21 | 6 | GACttacttagatgCT | 497 | 15 |
| 15_1 | 41 | 6 | 18 | 10 | AGacttacttagaTGC | 498 | 16 |
| 16_1 | 96 | 14 | 40 | 7 | GCAggaagagactTAC | 506 | 17 |
| 17_1 | 22 | 2 | 9 | 3 | AATAaattccgttCAGG | 541 | 18 |
| 18_1 | 34 | 6 | 21 | 9 | GCAAataaattcCGTT | 545 | 19 |
| 18_2 | 51 | 4 | 27 | 11 | GCAaataaattccGTT | 545 | 19 |
| 19_1 | 38 | 5 | 23 | 7 | AGCAaataaattcCGT | 546 | 20 |
| 20_1 | 73 | 8 | 56 | 15 | CAGAgcaaataaatTCC | 548 | 21 |
| 21_1 | 83 | 8 | 65 | 10 | TGGAcagagcaaataAAT | 551 | 22 |
| 22_1 | 86 | 6 | 80 | 8 | ATGGacagagcaAATA | 554 | 23 |
| 23_1 | 44 | 4 | 30 | 2 | CAgaatggacagaGCA | 558 | 24 |
| 24_1 | 63 | 10 | 40 | 11 | TTCtcagaatggacAG | 562 | 25 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
|---|---|---|---|---|---|---|---|
| | % mRNA of control | sd | % mRNA of control | sd | | | |
| 25_1 | 31 | 1 | 39 | 5 | CTGAactttgacATAG | 663 | 26 |
| 26_1 | 60 | 4 | 56 | 19 | AAgacaaacccagacTGA | 675 | 27 |
| 27_1 | 36 | 4 | 34 | 10 | TATAagacaaacccAGAC | 678 | 28 |
| 28_1 | 40 | 4 | 28 | 13 | TTATaagacaaaccCAGA | 679 | 29 |
| 29_1 | 30 | 2 | 18 | 6 | TGTTataagacaaaCCC | 682 | 30 |
| 30_1 | 77 | 3 | 67 | 10 | TAGAacaatggtaCTTT | 708 | 31 |
| 31_1 | 81 | 17 | 20 | 14 | GTAGaacaatggtaCT | 710 | 32 |
| 32_1 | 29 | 5 | 14 | 8 | AGGtagaacaatgGTA | 712 | 33 |
| 33_1 | 32 | 1 | 43 | 20 | AAGAggtagaacaATGG | 714 | 34 |
| 34_1 | 70 | 4 | 35 | 13 | GCatccacagtaaaTT | 749 | 35 |
| 35_1 | 83 | 2 | 66 | 21 | GAaggttatttaaTTC | 773 | 36 |
| 36_1 | 18 | 2 | 15 | 5 | CTAAtcgaatgcaGCA | 805 | 37 |
| 37_1 | 64 | 7 | 35 | 10 | TACccaatctaatCGA | 813 | 38 |
| 38_1 | 69 | 1 | 49 | 13 | TAGttacccaatcTAA | 817 | 39 |
| 39_1 | 49 | 5 | 26 | 9 | CATttagttacccAAT | 821 | 40 |
| 40_1 | 23 | 7 | 8 | 2 | TCAtttagttaccCAA | 822 | 41 |
| 41_1 | 24 | 6 | 12 | 3 | TTcatttagttaCCCA | 823 | 42 |
| 42_1 | 51 | 7 | 40 | 5 | GAATtaatttcattTAGT | 829 | 43 |
| 43_1 | 71 | 9 | 45 | 3 | CAGTgaggaattaATTT | 837 | 44 |
| 44_1 | 60 | 5 | 45 | 17 | CCAAcagtgaggAATT | 842 | 45 |
| 45_1 | 63 | 1 | 37 | 15 | CCCaacagtgaggAAT | 843 | 46 |
| 46_1 | 31 | 3 | 29 | 12 | TAtacccaacagtgAGG | 846 | 47 |
| 47_1 | 44 | 3 | 27 | 0 | TTatacccaacagTGAG | 847 | 48 |
| 48_1 | 38 | 3 | 26 | 6 | TTTatacccaacagTGA | 848 | 49 |
| 49_1 | 20 | 4 | 7 | 1 | CCTttatacccaaCAG | 851 | 50 |
| 50_1 | 22 | 3 | 6 | 2 | TAACctttatacCCAA | 854 | 51 |
| 51_1 | 28 | 1 | 29 | 16 | AATaaccttttataCCCA | 855 | 52 |
| 52_1 | 80 | 11 | 48 | 10 | GTAaataacctttaTA | 859 | 53 |
| 53_1 | 54 | 4 | 37 | 14 | ACTGtaaataaccaTAT | 860 | 54 |
| 54_1 | 81 | 4 | 53 | 15 | ATAtatatgcaatgAG | 903 | 55 |
| 55_1 | 86 | 12 | 70 | 15 | AGatatatatgcaaTG | 905 | 56 |
| 56_1 | 56 | 8 | 27 | 7 | GAGatatatatgcAAT | 906 | 57 |
| 57_1 | 28 | 7 | 13 | 5 | CCagagatatataTGC | 909 | 58 |
| 58_1 | 88 | 13 | 69 | 23 | CAAtattccagagATAT | 915 | 59 |
| 59_1 | 29 | 3 | 14 | 6 | GCAatattccagagATA | 916 | 60 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
| --- | --- | --- | --- | --- | --- | --- | --- |
| | % mRNA of control | sd | % mRNA of control | sd | | | |
| 60_1 | 25 | 3 | 14 | 3 | AGCaatattccagaGAT | 917 | 61 |
| 61_1 | 29 | 4 | 17 | 2 | CAGcaatattccAGAG | 919 | 62 |
| 62_1 | 27 | 3 | 14 | 3 | AATCagcaatattCCAG | 921 | 63 |
| 63_1 | 23 | 6 | 12 | 6 | ACAAtcagcaataTTCC | 923 | 64 |
| 64_1 | 53 | 9 | 43 | 15 | ACtaagtagttacactTCT | 957 | 65 |
| 65_1 | 32 | 5 | 14 | 6 | CTAAgtagttacactTC | 958 | 66 |
| 66_1 | 35 | 4 | 31 | 6 | GACtaagtagttacaCTT | 959 | 67 |
| 67_1 | 64 | 10 | 55 | 14 | TGActaagtagtTACA | 962 | 68 |
| 68_1 | 62 | 11 | 57 | 16 | CTTTgactaagtagTTA | 964 | 69 |
| 69_1 | 42 | 9 | 59 | 13 | CTCtttgactaagTAG | 967 | 70 |
| 70_1 | 81 | 6 | 56 | 12 | GCTCtttgactaagTA | 968 | 71 |
| 71_1 | 27 | 3 | 39 | 9 | CCttaaatactgtTGAC | 1060 | 72 |
| 72_1 | 75 | 5 | 36 | 7 | CTtaaatactgttgAC | 1060 | 73 |
| 73_1 | 35 | 6 | 43 | 13 | TCCttaaatactgTTG | 1062 | 74 |
| 74_1 | 57 | 4 | 79 | 25 | TCTCcttaaatactgTT | 1063 | 75 |
| 75_1 | 53 | 6 | 28 | 6 | TAtcatagttctCCTT | 1073 | 76 |
| 76_1 | 26 | 4 | 9 | 2 | AGTatcatagttcTCC | 1075 | 77 |
| 77_1 | 74 | 5 | 39 | 12 | GAgtatcatagttCTC | 1076 | 78 |
| 78_1 | 49 | 5 | 35 | 6 | AGagtatcatagTTCT | 1077 | 79 |
| 78_2 | 74 | 6 | 36 | 8 | AGAgtatcatagtTCT | 1077 | 79 |
| 79_1 | 19 | 2 | 19 | 13 | CAGagtatcatagTTC | 1078 | 80 |
| 80_1 | 23 | 2 | 26 | 2 | TTCAgagtatcataGT | 1080 | 81 |
| 81_1 | 35 | 3 | 36 | 11 | CTTcagagtatcATAG | 1081 | 82 |
| 82_1 | 24 | 6 | 20 | 7 | TTCTtcagagtatcaTA | 1082 | 83 |
| 83_1 | 20 | 2 | 16 | 2 | TTTcttcagagtaTCAT | 1083 | 84 |
| 84_1 | 33 | 4 | 37 | 10 | GAGAaaggctaagTTT | 1099 | 85 |
| 85_1 | 42 | 2 | 35 | 18 | GAcactcttgtaCATT | 1213 | 86 |
| 86_1 | 50 | 4 | 54 | 8 | TGagacactcttgtaCA | 1215 | 87 |
| 87_1 | 50 | 8 | 28 | 8 | TGagacactcttgTAC | 1216 | 88 |
| 88_1 | 61 | 4 | 33 | 6 | CTttattaaactCCAT | 1266 | 89 |
| 89_1 | 71 | 8 | 43 | 12 | ACCAaactttattaAA | 1272 | 90 |
| 90_1 | 62 | 5 | 42 | 9 | AAACctctactaagTG | 1288 | 91 |
| 91_1 | 22 | 3 | 12 | 5 | AGattaagacagtTGA | 1310 | 92 |
| 92_1 | 46 | 3 | ND | ND | AAgtaggagcaagaGGC | 1475 | 93 |
| 93_1 | 42 | 4 | 60 | 24 | AAAGtaggagcaagAGG | 1476 | 94 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
| --- | --- | --- | --- | --- | --- | --- | --- |
| | % mRNA of control | sd | % mRNA of control | sd | | | |
| 94_1 | 86 | 15 | 46 | 10 | GTtaagcagccaggAG | 1806 | 95 |
| 95_1 | 66 | 6 | 82 | 27 | AGggtaggatgggtAG | 1842 | 96 |
| 96_1 | 83 | 19 | 62 | 36 | AAGggtaggatgggTA | 1843 | 97 |
| 97_1 | 60 | 9 | 69 | 5 | CAAgggtaggatggGT | 1844 | 98 |
| 97_2 | 76 | 13 | 34 | 7 | CAagggtaggatggGT | 1844 | 98 |
| 98_1 | 65 | 8 | 76 | 28 | CCaagggtaggatgGG | 1845 | 99 |
| 99_1 | 61 | 2 | 75 | 17 | TCcaagggtaggatGG | 1846 | 100 |
| 100_1 | 83 | 4 | 82 | 13 | CTTCcaagggtaggAT | 1848 | 101 |
| 101_1 | 45 | 3 | 52 | 14 | ATCttccaagggtagGA | 1849 | 102 |
| 102_1 | 29 | 2 | 17 | 7 | AGaagtgatggctCATT | 1936 | 103 |
| 103_1 | 26 | 3 | 22 | 1 | AAGaagtgatggcTCAT | 1937 | 104 |
| 104_1 | 34 | 6 | 22 | 2 | GAAgaagtgatggcTCA | 1938 | 105 |
| 105_1 | 41 | 5 | 21 | 5 | ATGAaatgtaaacTGGG | 1955 | 106 |
| 106_1 | 40 | 8 | 29 | 6 | CAATgaaatgtaaaCTGG | 1956 | 107 |
| 107_1 | 24 | 3 | 16 | 4 | GCAAtgaaatgtaaACTG | 1957 | 108 |
| 108_1 | 30 | 4 | 20 | 6 | AGCAatgaaatgtaAACT | 1958 | 109 |
| 109_1 | 44 | 4 | 34 | 14 | GAGCaatgaaatgtAAAC | 1959 | 110 |
| 110_1 | 18 | 1 | 13 | 3 | TGaattcccatatcCGA | 1992 | 111 |
| 111_1 | 69 | 8 | 35 | 8 | AGaattatgaccaTAT | 2010 | 112 |
| 112_1 | 77 | 7 | 38 | 10 | AGGtaagaattatGACC | 2014 | 112 |
| 113_1 | 97 | 10 | 56 | 13 | TCAGgtaagaattaTGAC | 2015 | 114 |
| 114_1 | 69 | 8 | 54 | 21 | CTTCaggtaagaatTATG | 2017 | 115 |
| 115_1 | 91 | 7 | 115 | 42 | TCTTcaggtaagaATTA | 2019 | 116 |
| 116_1 | 88 | 6 | 104 | 36 | CTTCttcaggtaaGAAT | 2021 | 117 |
| 117_1 | 85 | 6 | 118 | 17 | TCTTcttcaggtaaGAA | 2022 | 118 |
| 118_1 | 105 | 14 | 102 | 9 | TCTtcttcaggtaAGA | 2023 | 119 |
| 119_1 | 37 | 2 | 76 | 18 | TGGtctaagagaaGAAG | 2046 | 120 |
| 120_1 | 46 | 6 | 81 | 11 | GTTGgtctaagagAAG | 2049 | 121 |
| 121_1 | 74 | 11 | 64 | 4 | AGTtggtctaagAGAA | 2050 | 122 |
| 122_1 | 74 | 9 | 55 | 21 | CAgttggtctaagAGAA | 2050 | 123 |
| 123_1 | 65 | 9 | 95 | 21 | GCAgttggtctaagagAA | 2050 | 124 |
| 124_1 | 63 | 7 | ND | ND | CAGTtggtctaagaGA | 2051 | 125 |
| 125_1 | 65 | 6 | ND | ND | GCagttggtctaagaGA | 2051 | 126 |
| 126_1 | 67 | 14 | 104 | 34 | GCagttggtctaaGAG | 2052 | 127 |
| 127_1 | 22 | 6 | 10 | 3 | CTcatatcagggCAGT | 2063 | 128 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
| --- | --- | --- | --- | --- | --- | --- | --- |
| | % mRNA of control | sd | % mRNA of control | sd | | | |
| 128_1 | 50 | 4 | 46 | 9 | CACAcatgttctttaAC | 2087 | 129 |
| 129_1 | 22 | 4 | 12 | 12 | TAAatacacacatgTTCT | 2092 | 130 |
| 130_1 | 24 | 2 | 43 | 28 | GTAAatacacacatgTTC | 2093 | 131 |
| 131_1 | 33 | 3 | 20 | 12 | TGTAaatacacacaTGTT | 2094 | 132 |
| 132_1 | 73 | 17 | 57 | 21 | GATCatgtaaatacACAC | 2099 | 133 |
| 133_1 | 47 | 5 | 28 | 14 | AGATcatgtaaataCACA | 2100 | 134 |
| 134_1 | 35 | 6 | 26 | 11 | CAAgatcatgtaaatACAC | 2101 | 135 |
| 135_1 | 30 | 2 | 14 | 3 | ACAAgatcatgtaaaTACA | 2102 | 136 |
| 136_1 | 52 | 6 | 24 | 18 | GAATacaaagatcaTGTA | 2108 | 137 |
| 137_1 | 33 | 5 | 20 | 6 | AGAAtacaaagatcATGT | 2109 | 138 |
| 138_1 | 37 | 1 | 22 | 15 | CAGAatacaaagatCATG | 2110 | 139 |
| 139_1 | 85 | 6 | 53 | 8 | GCAGaatacaaagATCA | 2112 | 140 |
| 140_1 | 79 | 4 | 40 | 6 | AGGCagaatacaaagAT | 2114 | 141 |
| 141_1 | 56 | 2 | 53 | 20 | AAGGcagaatacaaAGA | 2115 | 142 |
| 142_1 | 28 | 5 | 20 | 5 | ATTagtgagggacGAA | 2132 | 143 |
| 143_1 | 26 | 2 | 22 | 10 | CAttagtgagggaCGA | 2133 | 144 |
| 144_1 | 29 | 6 | 16 | 4 | GAgggtgatggatTAG | 2218 | 145 |
| 145_1 | 45 | 6 | 22 | 5 | TTaggagtaataAAGG | 2241 | 146 |
| 146_1 | 65 | 7 | 44 | 9 | TTAatgaatttggtTG | 2263 | 147 |
| 147_1 | 84 | 8 | 43 | 10 | CTttaatgaatttgGT | 2265 | 148 |
| 148_1 | 32 | 0 | 15 | 3 | CATGgattacaactAA | 2322 | 149 |
| 149_1 | 33 | 2 | 20 | 4 | TCatggattacaaCTA | 2323 | 150 |
| 150_1 | 29 | 1 | 11 | 3 | GTCatggattacaaCT | 2324 | 151 |
| 151_1 | 64 | 2 | 40 | 9 | CAttaaatctagTCAT | 2335 | 152 |
| 152_1 | 97 | 8 | 63 | 22 | GACAttaaatctagTCA | 2336 | 153 |
| 153_1 | 92 | 7 | ND | ND | AGGGacattaaatcTA | 2340 | 154 |
| 154_1 | 35 | 4 | 25 | 15 | CAAAgcattataaCCA | 2372 | 155 |
| 155_1 | 34 | 3 | 24 | 6 | ACttactaggcaGAAG | 2415 | 156 |
| 156_1 | 102 | 6 | 113 | 18 | CAGAgttaactgtaCA | 2545 | 157 |
| 157_1 | 102 | 10 | 103 | 15 | CCAGagttaactgtAC | 2546 | 158 |
| 158_1 | 88 | 7 | 95 | 18 | GCcagagttaactgTA | 2547 | 159 |
| 159_1 | 78 | 10 | ND | ND | TGggccagagttaaCT | 2550 | 160 |
| 160_1 | 59 | 5 | 26 | 5 | CAgcatctatcagaCT | 2576 | 161 |
| 161_1 | 78 | 8 | 42 | 10 | TGAaataacatgagTCAT | 2711 | 162 |
| 162_1 | 31 | 6 | ND | ND | GTGaaataacatgAGTC | 2713 | 163 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
| --- | --- | --- | --- | --- | --- | --- | --- |
| | % mRNA of control | sd | % mRNA of control | sd | | | |
| 163_1 | 18 | 2 | 11 | 3 | TCTGtttatgtcacTG | 2781 | 164 |
| 164_1 | 56 | 5 | 29 | 9 | GTCTgtttatgtcaCT | 2782 | 165 |
| 165_1 | 37 | 8 | 12 | 5 | TGgtctgtttatGTCA | 2784 | 166 |
| 166_1 | 39 | 1 | 19 | 3 | TTGGtctgtttatgTC | 2785 | 167 |
| 167_1 | 41 | 3 | 35 | 14 | TCacccattgtttaAA | 2842 | 168 |
| 168_1 | 18 | 3 | 14 | 4 | TTcagcaaatatTCGT | 2995 | 169 |
| 169_1 | 36 | 8 | 13 | 2 | GTGtgttcagcaaATAT | 2999 | 170 |
| 170_1 | 18 | 2 | 11 | 4 | TCTattgttaggtATC | 3053 | 171 |
| 171_1 | 67 | 4 | 26 | 12 | ATtgcccatcttacTG | 3118 | 172 |
| 172_1 | 71 | 2 | 33 | 9 | TATtgcccatcttaCT | 3119 | 173 |
| 173_1 | 47 | 4 | 20 | 5 | AAatattgcccatCTT | 3122 | 174 |
| 174_1 | 74 | 4 | 34 | 7 | ATAaccttatcataCA | 3174 | 175 |
| 175_1 | 98 | 19 | 44 | 12 | TAtaaccttatcaTAC | 3175 | 176 |
| 176_1 | 100 | 10 | 64 | 11 | TTAtaaccttatcaTA | 3176 | 177 |
| 177_1 | 72 | 38 | 28 | 5 | TTTataaccttatCAT | 3177 | 178 |
| 178_1 | 47 | 6 | 34 | 6 | ACtgctattgctaTCT | 3375 | 179 |
| 179_1 | 41 | 3 | 23 | 6 | AGgactgctattgCTA | 3378 | 180 |
| 180_1 | 32 | 6 | 27 | 7 | GAGgactgctattgCT | 3379 | 181 |
| 181_1 | 83 | 1 | 46 | 20 | ACgtagaataataaCA | 3561 | 182 |
| 182_1 | 94 | 4 | 52 | 9 | CCaagtgatataATGG | 3613 | 183 |
| 183_1 | 49 | 2 | 16 | 3 | TTagcagaccaaGTGA | 3621 | 184 |
| 184_1 | 96 | 3 | 26 | 5 | GTttagcagaccaaGT | 3623 | 185 |
| 185_1 | 78 | 3 | 46 | 10 | TGacagtgattataTT | 3856 | 186 |
| 186_1 | 88 | 5 | 45 | 21 | TGTCcaagatattgAC | 3868 | 187 |
| 187_1 | 46 | 6 | 23 | 6 | GAAtatcctagatTGT | 4066 | 188 |
| 188_1 | 79 | 3 | 45 | 14 | CAaactgagaataTCC | 4074 | 189 |
| 189_1 | 63 | 5 | 27 | 8 | GCAaactgagaataTC | 4075 | 190 |
| 190_1 | 77 | 9 | 37 | 11 | TCCtattacaatcgTA | 4214 | 191 |
| 191_1 | 74 | 10 | 36 | 9 | TTCCtattacaatcGT | 4215 | 192 |
| 192_1 | 91 | 8 | 51 | 28 | ACtaatgggaggatTT | 4256 | 193 |
| 193_1 | 95 | 14 | 67 | 24 | TAgttcagagaataAG | 4429 | 194 |
| 194_1 | 86 | 5 | 47 | 16 | TAacatatagttcAGA | 4436 | 195 |
| 195_1 | 87 | 4 | 81 | 20 | ATAacatatagttcAG | 4437 | 196 |
| 196_1 | 101 | 6 | 67 | 20 | CAtaacatatagttCA | 4438 | 197 |
| 197_1 | 91 | 6 | 60 | 13 | TCataacatatagtTC | 4439 | 198 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
|---|---|---|---|---|---|---|---|
| | % mRNA of control | sd | % mRNA of control | sd | | | |
| 198_1 | 61 | 3 | 31 | 10 | TAGCtcctaacaatCA | 4507 | 199 |
| 199_1 | 79 | 12 | 49 | 11 | CTCCaatctttgtaTA | 4602 | 200 |
| 200_1 | 74 | 2 | 58 | 13 | TCTCcaatctttgtAT | 4603 | 201 |
| 201_1 | 53 | 3 | 33 | 10 | TCtatttcagccaaTC | 4708 | 202 |
| 202_1 | 25 | 4 | 30 | 9 | CGGaagtcagagtGAA | 4782 | 203 |
| 203_1 | 32 | 5 | 21 | 7 | TTAAgcatgaggaaTA | 4798 | 204 |
| 204_1 | 34 | 10 | 26 | 11 | TGAttgagcacctCTT | 4831 | 205 |
| 205_1 | 81 | 12 | 62 | 12 | GACtaattatttcgTT | 4857 | 206 |
| 206_1 | 57 | 7 | 37 | 7 | TGActaattatttCGT | 4858 | 207 |
| 207_1 | 26 | 5 | 21 | 6 | GTGactaattattTCG | 4859 | 208 |
| 208_1 | 48 | 3 | 33 | 13 | CTGCttgaaatgtgAC | 4870 | 209 |
| 209_1 | 32 | 1 | 34 | 13 | CCtgcttgaaatgTGA | 4871 | 210 |
| 210_1 | 60 | 5 | 50 | 19 | ATcctgcttgaaATGT | 4873 | 211 |
| 211_1 | 111 | 8 | 110 | 26 | ATTataaatctatTCT | 5027 | 212 |
| 212_1 | 107 | 1 | 67 | 12 | GCtaaatactttcATC | 5151 | 213 |
| 213_1 | 26 | 3 | 19 | 6 | CAttgtaacataCCTA | 5251 | 214 |
| 214_1 | 33 | 2 | 20 | 4 | GCattgtaacatacCT | 5252 | 215 |
| 215_1 | 89 | 8 | 53 | 16 | TAatattgcaccaaAT | 5295 | 216 |
| 216_1 | 25 | 2 | 29 | 9 | GAtaatattgcacCAA | 5297 | 217 |
| 217_1 | 27 | 1 | 27 | 6 | AGataatattgcacCA | 5298 | 218 |
| 218_1 | 79 | 6 | 45 | 11 | GCcaagaagataATAT | 5305 | 219 |
| 219_1 | 159 | 16 | 68 | 14 | CACAgccacataaaCT | 5406 | 220 |
| 220_1 | 90 | 2 | 72 | 12 | TTgtaattgtggaaAC | 5463 | 221 |
| 221_1 | 10 | 2 | 11 | 5 | TGacttgtaattgTGG | 5467 | 222 |
| 222_1 | 82 | 1 | 67 | 18 | TCtaactgaaatagTC | 5503 | 223 |
| 223_1 | 30 | 1 | 32 | 9 | GTGgttctaactgaAA | 5508 | 224 |
| 224_1 | 53 | 7 | 53 | 15 | CAatatgggacttGT | 5522 | 225 |
| 225_1 | 44 | 1 | 33 | 10 | ATGacaatatgggaCT | 5526 | 226 |
| 226_1 | 49 | 1 | 41 | 14 | TATGacaatatgggAC | 5527 | 227 |
| 227_1 | 77 | 1 | 54 | 15 | ATATgacaatatggGA | 5528 | 228 |
| 228_1 | 100 | 3 | 98 | 29 | CTtcacttaataaTTA | 5552 | 229 |
| 229_1 | 90 | 12 | 80 | 19 | CTGCttcacttaatAA | 5555 | 230 |
| 230_1 | 91 | 0 | 79 | 23 | AAgactgcttcacTTA | 5559 | 231 |
| 231_1 | 49 | 8 | 77 | 34 | GAATgccctaattaTG | 5589 | 232 |
| 232_1 | 17 | 7 | 88 | 33 | TGGaatgccctaatTA | 5591 | 233 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
| --- | --- | --- | --- | --- | --- | --- | --- |
| | % mRNA of control | sd | % mRNA of control | sd | | | |
| 233_1 | 40 | 5 | 35 | 10 | GCAaatgccagtagGT | 5642 | 234 |
| 234_1 | 81 | 6 | 72 | 25 | CTAatggaaggattTG | 5673 | 235 |
| 235_1 | 97 | 17 | 87 | 25 | AAtatagaacctaaTG | 5683 | 236 |
| 236_1 | 98 | 4 | 83 | 21 | GAAagaatagaatGTT | 5769 | 237 |
| 237_1 | 93 | 2 | 102 | 26 | ATGggtaatatagattAT | 5893 | 238 |
| 238_1 | 110 | 24 | 44 | 14 | GAaagagcacagggTG | 6103 | 239 |
| 239_1 | 66 | 5 | 36 | 10 | CTACatagagggaaTG | 6202 | 240 |
| 240_1 | 70 | 4 | 34 | 8 | GCttcctacataGAGG | 6207 | 241 |
| 241_1 | 64 | NA | 33 | 6 | TGCTtcctacatagAG | 6208 | 242 |
| 242_1 | 30 | NA | 19 | 7 | TGggcttgaaataTGT | 6417 | 243 |
| 243_1 | 88 | 6 | 69 | 15 | CATtatatttaagaAC | 6457 | 244 |
| 244_1 | 8 | 2 | 5 | 2 | TCggttatgttaTCAT | 6470 | 245 |
| 245_1 | 18 | 9 | 12 | 4 | CActttatctggTCGG | 6482 | 246 |
| 246_1 | 37 | 2 | 19 | 5 | AAAttggcacagcGTT | 6505 | 247 |
| 247_1 | 46 | 12 | 29 | 8 | ACCGtgacagtaaATG | 6577 | 248 |
| 248_1 | 31 | 2 | 25 | 2 | TGggaaccgtgacagTA | 6581 | 249 |
| 249_1 | 17 | 2 | 23 | 9 | CCacatataggtcCTT | 6597 | 250 |
| 250_1 | 15 | 6 | 23 | 7 | CAtattgctaccaTAC | 6617 | 251 |
| 251_1 | 4 | 2 | 9 | 2 | TCAtattgctaccATA | 6618 | 252 |
| 252_1 | 65 | 12 | 85 | 14 | CAATtgtcatatTGCT | 6624 | 253 |
| 253_1 | 20 | 2 | 51 | 7 | CATtcaattgtcataTTG | 6626 | 254 |
| 254_1 | 48 | 8 | 91 | 41 | TTTCtactgggaaTTTG | 6644 | 255 |
| 255_1 | 11 | 5 | 23 | 8 | CAAttagtgcagcCAG | 6672 | 256 |
| 256_1 | 43 | 7 | 62 | 13 | GAATaatgttcttaTCC | 6704 | 257 |
| 257_1 | 28 | 2 | 36 | 19 | CACAaattgaataatgtTCT | 6709 | 258 |
| 258_1 | 64 | 4 | 78 | 22 | CATGcacaaattgaaTAAT | 6714 | 259 |
| 259_1 | 53 | 8 | 104 | 73 | ATCctgcaatttcaCAT | 6832 | 260 |
| 260_1 | 54 | 5 | 59 | 14 | CCaccatagctgatCA | 6868 | 261 |
| 261_1 | 42 | 8 | 52 | 22 | ACcaccatagctgaTCA | 6868 | 262 |
| 262_1 | 68 | 5 | 118 | 66 | CAccaccatagctgaTC | 6869 | 263 |
| 263_1 | 40 | 2 | 73 | 20 | TAgtcggcaccaccAT | 6877 | 264 |
| 264_1 | 64 | 6 | 72 | 35 | Cttgtagtcggcacc AC | 6880 | 265 |
| 265_1 | 56 | 4 | 82 | 35 | Cttgtagtcggcac CA | 6881 | 266 |
| 266_1 | 41 | 5 | 46 | 21 | CGcttgtagtcggcAC | 6883 | 267 |
| 267_1 | 51 | 4 | 33 | 14 | TCAataaagatcagGC | 6942 | 268 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
|---|---|---|---|---|---|---|---|
| | % mRNA of control | sd | % mRNA of control | sd | | | |
| 268_1 | 61 | 2 | 49 | 10 | TGgacttacaagaaTG | 6986 | 269 |
| 269_1 | 45 | 7 | 40 | 9 | ATGgacttacaagaAT | 6987 | 270 |
| 270_1 | 51 | 12 | 36 | 12 | GCTCaagaaattggAT | 7073 | 271 |
| 271_1 | 17 | 0 | 14 | 5 | TACTgtagaacatgGC | 7133 | 272 |
| 272_1 | 15 | 3 | 11 | 3 | GCAAttcatttgaTCT | 7239 | 273 |
| 273_1 | 64 | 11 | ND | ND | TGaagggaggagggacAC | 7259 | 274 |
| 274_1 | 52 | 6 | 50 | 28 | AGtggtgaagggaggAG | 7265 | 275 |
| 275_1 | 79 | 7 | ND | ND | TAgtggtgaagggaggAG | 7265 | 276 |
| 276_1 | 81 | 6 | ND | ND | Atagtggtgaagggagg AG | 7265 | 277 |
| 277_1 | 70 | 9 | ND | ND | TAgtggtgaagggagGA | 7266 | 278 |
| 278_1 | 84 | 9 | ND | ND | ATagtggtgaagggagGA | 7266 | 279 |
| 279_1 | 40 | 6 | 64 | 53 | TAGtggtgaagggaGG | 7267 | 280 |
| 280_1 | 42 | 10 | ND | ND | ATagtggtgaagggaGG | 7267 | 281 |
| 281_1 | 63 | 7 | ND | ND | GAtagtggtgaagggaGG | 7267 | 282 |
| 282_1 | 27 | 7 | 38 | 11 | ATAGtggtgaagggAG | 7268 | 283 |
| 283_1 | 60 | 22 | ND | ND | GAtagtggtgaaggGAG | 7268 | 284 |
| 284_1 | 23 | 3 | 97 | 54 | GAgatagtggtgAAGG | 7271 | 285 |
| 285_1 | 51 | 6 | 72 | 19 | CATGggagatagtgGT | 7276 | 286 |
| 286_1 | 7 | 1 | 21 | 9 | ACAAataatggttaCTCT | 7302 | 287 |
| 287_1 | 66 | 8 | 48 | 20 | ACACacaaataatgGTTA | 7306 | 288 |
| 288_1 | 67 | 6 | 58 | 20 | GAGggacacacaaaTAAT | 7311 | 289 |
| 289_1 | 46 | 2 | 50 | 21 | ATATagagaggcTCAA | 7390 | 290 |
| 290_1 | 22 | 6 | ND | ND | TTgatatagagaGGCT | 7393 | 291 |
| 291_1 | 11 | 2 | 17 | 3 | GCATttgatatagAGA | 7397 | 292 |
| 292_1 | 70 | 18 | 44 | 8 | TTtgcatttgataTAG | 7400 | 293 |
| 293_1 | 30 | 1 | 30 | 9 | CTGgaagaataggtTC | 7512 | 294 |
| 294_1 | 53 | 5 | 42 | 10 | ACTGgaagaataggTT | 7513 | 295 |
| 295_1 | 56 | 2 | 41 | 15 | TACTggaagaatagGT | 7514 | 296 |
| 296_1 | 80 | 8 | 53 | 13 | TGGCttatcctgtaCT | 7526 | 297 |
| 297_1 | 73 | 6 | 52 | 14 | ATggcttatcctGTAC | 7527 | 298 |
| 298_1 | 75 | 7 | 89 | 25 | TATGgcttatcctgTA | 7528 | 299 |
| 299_1 | 52 | 5 | 50 | 11 | GTAtggcttatccTGT | 7529 | 300 |
| 300_1 | 27 | 3 | 31 | 6 | ATgaatatatgccCAGT | 7547 | 301 |
| 301_1 | 41 | 8 | 33 | 9 | GAtgaatatatgCCCA | 7549 | 302 |
| 302_1 | 8 | 2 | ND | ND | CAAgatgaatataTGCC | 7551 | 303 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
| --- | --- | --- | --- | --- | --- | --- | --- |
|  | % mRNA of control | sd | % mRNA of control | sd |  |  |  |
| 303_1 | 32 | 5 | 37 | 14 | GACAacatcagtaTAGA | 7572 | 304 |
| 304_1 | 28 | 5 | 30 | 23 | CAAGacaacatcAGTA | 7576 | 305 |
| 305_1 | 47 | 5 | 41 | 9 | CACtcctagttccTTT | 7601 | 306 |
| 306_1 | 39 | 6 | 33 | 7 | AACactcctagttCCT | 7603 | 307 |
| 307_1 | 68 | 3 | 42 | 14 | TAacactcctagtTCC | 7604 | 308 |
| 308_1 | 115 | 5 | 69 | 22 | CTaacactcctagtTC | 7605 | 309 |
| 309_1 | 97 | 16 | 57 | 14 | TGataacataactgTG | 7637 | 310 |
| 310_1 | 36 | 1 | 23 | 10 | CTgataacataaCTGT | 7638 | 311 |
| 311_1 | 38 | 5 | 24 | 5 | TTTGaactcaagtgAC | 7654 | 312 |
| 312_1 | 42 | 3 | 39 | 5 | TCCTttacttagcTAG | 7684 | 313 |
| 313_1 | 15 | 2 | 14 | 3 | GAgtttggattagCTG | 7764 | 314 |
| 314_1 | 49 | 28 | ND | ND | TGggatatgacagGGA | 7838 | 315 |
| 315_1 | 34 | 6 | ND | ND | TGTGggatatgacaGG | 7840 | 316 |
| 316_1 | 47 | 3 | 37 | 8 | ATATggaagggataTC | 7875 | 317 |
| 317_1 | 11 | 3 | ND | ND | ACAggatatggaaGGG | 7880 | 318 |
| 318_1 | 48 | 4 | ND | ND | ATTTcaacaggatATGG | 7885 | 319 |
| 319_1 | 18 | 2 | 16 | 4 | GAgtaatttcaacAGG | 7891 | 320 |
| 320_1 | 74 | 6 | 44 | 5 | AGGGagtaatttcAACA | 7893 | 321 |
| 321_1 | 38 | 5 | 56 | 28 | ATTAgggagtaatTTCA | 7896 | 322 |
| 322_1 | 66 | 9 | 32 | 11 | CTtactattaggGAGT | 7903 | 323 |
| 323_1 | 13 | 1 | 15 | 5 | CAgcttactattaGGG | 7906 | 324 |
| 324_1 | 26 | 4 | 20 | 9 | TCAgcttactattAGG | 7907 | 325 |
| 325_1 | 43 | 4 | 17 | 2 | ATTtcagcttactaTTAG | 7908 | 326 |
| 326_1 | 54 | 5 | 57 | 16 | TTcagcttactaTTAG | 7908 | 327 |
| 327_1 | 28 | 3 | 8 | 2 | CAGAtttcagcttaCT | 7913 | 328 |
| 328_1 | 43 | 4 | 37 | 16 | GACtacaactagagGG | 7930 | 329 |
| 329_1 | 45 | 12 | 36 | 10 | AGACtacaactagaGG | 7931 | 330 |
| 330_1 | 99 | 8 | 94 | 32 | AAgactacaactagAG | 7932 | 331 |
| 331_1 | 59 | 4 | 52 | 19 | ATGAtttaattctagtCAAA | 7982 | 332 |
| 332_1 | 100 | 2 | 84 | 23 | TTTaattctagtcAAA | 7982 | 333 |
| 333_1 | 91 | 9 | 60 | 19 | GATTtaattctaGTCA | 7984 | 334 |
| 771_1 | 74 | 6 | 50 | 5 | TGAtttaattctaGTCA | 7984 | 771 |
| 334_1 | 73 | 5 | 54 | 12 | ATGAtttaattctagTCA | 7984 | 335 |
| 335_1 | 15 | 1 | 26 | 3 | GATGatttaattctagtCA | 7984 | 336 |
| 336_1 | 71 | 22 | 49 | 16 | GAtttaattctaGTCA | 7984 | 337 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
| --- | --- | --- | --- | --- | --- | --- | --- |
| | % mRNA of control | sd | % mRNA of control | sd | | | |
| 337_1 | 43 | 5 | 30 | 11 | GATGatttaattctaGTC | 7985 | 338 |
| 338_1 | 98 | 5 | 90 | 27 | TGatttaattctagTC | 7985 | 339 |
| 339_1 | 87 | 21 | 86 | 2 | GAGAtgatttaatTCTA | 7988 | 340 |
| 340_1 | 92 | 5 | 85 | 27 | GAGatgatttaatTCT | 7989 | 341 |
| 341_1 | 7 | 1 | 7 | 1 | CAGAttgatggtagTT | 8030 | 342 |
| 342_1 | 7 | 2 | 24 | 11 | CTcagattgatgGTAG | 8032 | 343 |
| 343_1 | 3 | 1 | 14 | 9 | GTTagccctcagaTTG | 8039 | 344 |
| 344_1 | 14 | 5 | 20 | 7 | TGtattgttagcCCTC | 8045 | 345 |
| 345_1 | 10 | 2 | 11 | 5 | ACttgtattgttAGCC | 8048 | 346 |
| 346_1 | 52 | 4 | 52 | 17 | AGCcagtatcagggAC | 8191 | 347 |
| 347_1 | 33 | 3 | 18 | 8 | TTgacaatagtgGCAT | 8213 | 348 |
| 348_1 | 7 | 2 | 13 | 5 | ACAagtggtatctTCT | 8228 | 349 |
| 349_1 | 63 | 8 | 44 | 15 | AATCtactttacaaGT | 8238 | 350 |
| 350_1 | 36 | 2 | ND | ND | CAcagtagatgcctGATA | 8351 | 351 |
| 351_1 | 24 | 2 | 30 | 9 | GAacacagtagatGCC | 8356 | 352 |
| 352_1 | 23 | 4 | 103 | 14 | CTTGgaacacagtagAT | 8359 | 353 |
| 353_1 | 20 | 2 | 45 | 2 | ATAtcttggaacaCAG | 8364 | 354 |
| 354_1 | 25 | 3 | 24 | 6 | TCTttaatatcttgGAAC | 8368 | 355 |
| 355_1 | 39 | 2 | 41 | 10 | TGatttctttaatatCTTG | 8372 | 356 |
| 356_1 | 54 | 5 | 88 | 43 | TGatgatttctttaaTATC | 8375 | 357 |
| 357_1 | 31 | 4 | 45 | 27 | AGGctaagtcatgaTG | 8389 | 358 |
| 358_1 | 18 | 3 | 43 | 20 | TTGAtgaggctaagTC | 8395 | 359 |
| 359_1 | 6 | 2 | 11 | 2 | CCAggattatactcTT | 8439 | 360 |
| 360_1 | 43 | 5 | 40 | 14 | GCcaggattataCTCT | 8440 | 361 |
| 361_1 | 56 | 8 | 73 | 13 | CTGccaggattataCT | 8442 | 362 |
| 362_1 | 23 | 1 | 33 | 7 | CAGAaacttatactttaTG | 8473 | 363 |
| 363_1 | 49 | 8 | 45 | 14 | AAGCagaaacttaTACT | 8478 | 364 |
| 364_1 | 39 | 6 | 37 | 4 | GAAgcagaaacttaTACT | 8478 | 365 |
| 365_1 | 26 | 4 | 45 | 13 | TGGaagcagaaacttataCT | 8478 | 366 |
| 366_1 | 21 | 4 | 44 | 5 | TGGaagcagaaacttaTAC | 8479 | 367 |
| 367_1 | 97 | 4 | 70 | 22 | AAgcagaaacttaTAC | 8479 | 368 |
| 368_1 | 34 | 3 | 32 | 11 | TGGaagcagaaactTATA | 8480 | 369 |
| 369_1 | 71 | 7 | 46 | 19 | AAGGgatattatggAG | 8587 | 370 |
| 370_1 | Si | 9 | 79 | 38 | TGccggaagatttcCT | 8641 | 371 |
| 371_1 | 45 | 6 | 52 | 25 | ATGGattgggagtaGA | 8772 | 372 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
| --- | --- | --- | --- | --- | --- | --- | --- |
| | % mRNA of control | sd | % mRNA of control | sd | | | |
| 372_1 | 27 | 7 | 30 | 8 | AGatggattgggagTA | 8774 | 373 |
| 373_1 | 13 | 3 | 28 | 6 | AAGatggattgggaGT | 8775 | 374 |
| 374_1 | 42 | 10 | 44 | 11 | ACaagatggattGGGA | 8777 | 375 |
| 374_2 | 41 | 3 | 45 | 14 | ACaagatggattggGA | 8777 | 375 |
| 375_1 | 83 | 9 | 88 | 32 | AGAaggttcagaCTTT | 8835 | 376 |
| 376_1 | 40 | 5 | 33 | 3 | GCAgaaggttcagaCT | 8837 | 377 |
| 376_2 | 28 | 5 | 20 | 4 | GCagaaggttcagACT | 8837 | 377 |
| 377_1 | 70 | 2 | 43 | 8 | TGCAgaaggttcagAC | 8838 | 378 |
| 378_1 | 23 | 3 | 55 | 17 | AGtgcagaaggttCAG | 8840 | 379 |
| 378_2 | Si | 6 | 41 | 8 | AGTGcagaaggttcAG | 8840 | 379 |
| 379_1 | 34 | 6 | 35 | 7 | AAGTgcagaaggttCA | 8841 | 380 |
| 380_1 | 44 | 11 | 24 | 6 | TAagtgcagaagGTTC | 8842 | 381 |
| 381_1 | 37 | 5 | 45 | 9 | TCtaagtgcagaAGGT | 8844 | 382 |
| 382_1 | 75 | 5 | 147 | 26 | CTCaggagttctactTC | 8948 | 383 |
| 383_1 | 90 | 10 | 141 | 55 | CTCaggagttctaCTT | 8949 | 384 |
| 384_1 | 73 | 8 | 234 | 116 | AtggaggtgactcaggAG | 8957 | 385 |
| 385_1 | 33 | 4 | 42 | 7 | ATggaggtgactcagGA | 8958 | 386 |
| 386_1 | 24 | 3 | 29 | 14 | ATggaggtgactcAGG | 8959 | 387 |
| 387_1 | 37 | 2 | 65 | 15 | TAtggaggtgactcAGG | 8959 | 388 |
| 388_1 | 50 | 10 | 81 | 19 | ATatggaggtgactcaGG | 8959 | 389 |
| 389_1 | 42 | 5 | 61 | 10 | TATGgaggtgactcAG | 8960 | 390 |
| 390_1 | 36 | 2 | 76 | 50 | ATatggaggtgacTCAG | 8960 | 391 |
| 391_1 | 52 | 6 | 64 | 6 | CAtatggaggtgactcAG | 8960 | 392 |
| 392_1 | 63 | 5 | 57 | 6 | ATAtggaggtgacTCA | 8961 | 393 |
| 393_1 | 53 | 7 | 64 | 12 | CAtatggaggtgacTCA | 8961 | 394 |
| 394_1 | Si | 5 | 56 | 24 | CAtatggaggtgACTC | 8962 | 395 |
| 395_1 | 23 | 3 | 41 | 34 | GCatatggaggtgacTC | 8962 | 396 |
| 396_1 | 34 | 3 | 54 | 10 | TGcatatggaggtgacTC | 8962 | 397 |
| 397_1 | 54 | 5 | 71 | 24 | Ttgcatatggaggtgactc | 8962 | 398 |
| 398_1 | 61 | 11 | 59 | 13 | Tttgcatatggaggtgactc | 8962 | 399 |
| 399_1 | 25 | 2 | 30 | 6 | GCatatggaggtgaCT | 8963 | 400 |
| 400_1 | 34 | 4 | 25 | 9 | TGcatatggaggtgaCT | 8963 | 401 |
| 401_1 | 25 | 4 | 31 | 20 | TTGcatatggaggtgaCT | 8963 | 402 |
| 402_1 | Si | 6 | 37 | 11 | Tttgcatatggaggtgact | 8963 | 403 |
| 403_1 | 26 | 1 | 33 | 5 | TGCatatggaggtgAC | 8964 | 404 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
|---|---|---|---|---|---|---|---|
| | % mRNA of control | sd | % mRNA of control | sd | | | |
| 404_1 | 25 | 2 | 69 | 19 | TTGcatatggaggtGAC | 8964 | 405 |
| 405_1 | 26 | 4 | 24 | 4 | TTTGcatatggaggtgAC | 8964 | 406 |
| 406_1 | 19 | 3 | 20 | 7 | TTTGcatatggaggtGA | 8965 | 407 |
| 407_1 | 16 | 5 | 46 | 16 | TTtgcatatggaGGTG | 8966 | 408 |
| 408_1 | 9 | 2 | 9 | 6 | AAgtgaagttcaaCAGC | 8997 | 409 |
| 409_1 | 26 | 8 | 109 | 52 | TGggaagtgaagTTCA | 9002 | 410 |
| 410_1 | 31 | 5 | 24 | 5 | ATgggaagtgaagTTC | 9003 | 411 |
| 411_1 | 49 | 9 | 19 | 10 | GATGggaagtgaaGTT | 9004 | 412 |
| 412_1 | 28 | 10 | 17 | 9 | CTGtgatgggaagtGAA | 9007 | 413 |
| 413_1 | 54 | 4 | 34 | 8 | ATTgagtgaatccAAA | 9119 | 414 |
| 414_1 | 11 | 1 | 14 | 2 | AAttgagtgaatCCAA | 9120 | 415 |
| 415_1 | 58 | 6 | 14 | 2 | GATAattgagtgaaTCC | 9122 | 416 |
| 416_1 | 5 | 1 | 16 | 3 | GTGataattgagtGAA | 9125 | 417 |
| 417_1 | 73 | 5 | 61 | 14 | AAGaaaggtgcaaTAA | 9155 | 418 |
| 418_1 | 86 | 6 | 64 | 13 | CAagaaaggtgcAATA | 9156 | 419 |
| 419_1 | 75 | 19 | 64 | 14 | ACAAgaaaggtgcaAT | 9157 | 420 |
| 420_1 | 75 | 8 | 50 | 13 | ATttaaactcacaaAC | 9171 | 421 |
| 421_1 | 21 | 8 | 23 | 6 | CTgttaggttcaGCGA | 9235 | 422 |
| 422_1 | 54 | 10 | 30 | 5 | TCTGaatgaacatTTCG | 9260 | 423 |
| 423_1 | 11 | 4 | 15 | 5 | CTcattgaaggtTCTG | 9281 | 424 |
| 424_1 | 87 | 3 | 52 | 8 | CTAatctcattgaaGG | 9286 | 425 |
| 425_1 | 95 | 1 | 85 | 13 | CCtaatctcattgaAG | 9287 | 426 |
| 426_1 | 31 | 7 | 22 | 7 | ACTttgatctttcAGC | 9305 | 427 |
| 427_1 | 64 | 7 | 49 | 16 | ACtatgcaacacttTG | 9315 | 428 |
| 428_1 | 18 | 6 | 21 | 3 | CAAatagctttatCGG | 9335 | 429 |
| 429_1 | 19 | 6 | 17 | 4 | CCaaatagctttATCG | 9336 | 430 |
| 430_1 | 35 | 4 | 27 | 8 | TCCAaatagctttaTC | 9337 | 431 |
| 431_1 | 75 | 8 | 43 | 7 | GATCcaaatagcttTA | 9339 | 432 |
| 432_1 | 67 | 11 | 32 | 8 | ATgatccaaataGCTT | 9341 | 433 |
| 433_1 | 53 | 5 | 43 | 6 | TATGatccaaatagCT | 9342 | 434 |
| 434_1 | 97 | 9 | 66 | 29 | TAAAcagggctggGAAT | 9408 | 435 |
| 435_1 | 58 | 12 | 44 | 17 | ACttaaacagggCTGG | 9412 | 436 |
| 436_1 | 58 | 10 | 30 | 12 | ACacttaaacagGGCT | 9414 | 437 |
| 437_1 | 87 | 38 | 41 | 3 | GAAcacttaaacAGGG | 9416 | 438 |
| 438_1 | 70 | 4 | 59 | 33 | AGAGaacacttaaACAG | 9418 | 439 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
| --- | --- | --- | --- | --- | --- | --- | --- |
| | % mRNA of control | sd | % mRNA of control | sd | | | |
| 439_1 | 83 | 17 | 28 | 9 | CTACagagaacaCTTA | 9423 | 440 |
| 440_1 | 49 | 12 | 27 | 4 | ATGctacagagaaCACT | 9425 | 441 |
| 441_1 | 53 | 10 | 24 | 13 | ATAAatgctacagagAACA | 9427 | 442 |
| 442_1 | 23 | 6 | 20 | 10 | AGataaatgctacaGAGA | 9430 | 443 |
| 443_1 | 48 | 6 | 27 | 7 | TAGAgataaatgcTACA | 9434 | 444 |
| 444_1 | 51 | 3 | 32 | 8 | TAGAtagagataaatGCT | 9437 | 445 |
| 445_1 | 38 | 5 | ND | ND | CAATatactagataGAGA | 9445 | 446 |
| 446_1 | 52 | 3 | 31 | 1 | TACAcaatatactagATAG | 9448 | 447 |
| 447_1 | 65 | 6 | 48 | 11 | CTAcacaatatacTAG | 9452 | 448 |
| 448_1 | 67 | 9 | 29 | 2 | GCTAcacaatatACTA | 9453 | 449 |
| 449_1 | 103 | 17 | 65 | 15 | ATATgctacacaatATAC | 9455 | 450 |
| 450_1 | 71 | 13 | 129 | 22 | TGATatgctacaCAAT | 9459 | 451 |
| 451_1 | 19 | 4 | 9 | 1 | ATGAatgatatgCTAC | 9464 | 452 |
| 452_1 | 75 | 10 | 45 | 21 | GAGGagagagacaaTAAA | 9495 | 453 |
| 453_1 | 68 | 6 | 43 | 10 | CTAggaggagagagACA | 9500 | 454 |
| 454_1 | 72 | 7 | 79 | 25 | TATTctaggaggagAGA | 9504 | 455 |
| 455_1 | 31 | 3 | 29 | 9 | TTATattctaggagGAG | 9507 | 456 |
| 456_1 | 38 | 5 | 62 | 17 | GTTtatattctaGGAG | 9510 | 457 |
| 457_1 | 15 | 6 | 15 | 8 | TGgagtttatattcTAGG | 9512 | 458 |
| 458_1 | 34 | 3 | 21 | 3 | CGtaccaccactcTGC | 9590 | 459 |
| 459_1 | 41 | 5 | 55 | 22 | TGAGgaaatcattcATTC | 9641 | 460 |
| 460_1 | 81 | 8 | 47 | 22 | TTTGaggaaatcatTCAT | 9643 | 461 |
| 461_1 | 76 | 8 | 39 | 5 | AGGCtaatcctattTG | 9657 | 462 |
| 462_1 | 93 | 12 | 216 | 12 | TTTAggctaatcCTAT | 9660 | 463 |
| 463_1 | 15 | 6 | 30 | 9 | TGCtccagtgtaccCT | 9755 | 464 |
| 464_1 | 27 | 3 | 25 | 6 | TAgtagtactcgATAG | 9813 | 465 |
| 465_1 | 9 | 2 | 7 | 3 | CTAattgtagtagtaCTC | 9818 | 466 |
| 466_1 | 52 | 3 | 32 | 6 | TGctaattgtagTAGT | 9822 | 467 |
| 467_1 | 68 | 11 | 36 | 16 | AGTGctaattgtagTA | 9824 | 468 |
| 468_1 | 35 | 6 | 32 | 3 | GCAagtgctaattgTA | 9827 | 469 |
| 469_1 | 91 | 9 | ND | ND | GAGGaaatgaactaattTA | 9881 | 470 |
| 470_1 | 92 | 5 | ND | ND | CAGGaggaaatgaacTA | 9886 | 471 |
| 471_1 | 67 | 5 | 42 | 6 | CCctagagtcattTCC | 9902 | 472 |
| 472_1 | 35 | 5 | 20 | 8 | ATCttacatgatgaAGC | 9925 | 473 |
| 473_1 | 13 | 1 | 20 | 5 | GACacactcagatttcAG | 9967 | 474 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
|---|---|---|---|---|---|---|---|
| | % mRNA of control | sd | % mRNA of control | sd | | | |
| 474_1 | 24 | 4 | 20 | 2 | AGacacactcagatttcAG | 9967 | 475 |
| 475_1 | 25 | 4 | 24 | 7 | AAGacacactcagatttcAG | 9967 | 476 |
| 476_1 | 26 | 6 | 19 | 4 | AGacacactcagattTCA | 9968 | 477 |
| 477_1 | 28 | 4 | 32 | 13 | AAGacacactcagattTCA | 9968 | 478 |
| 478_1 | 31 | 8 | 37 | 6 | AAagacacactcagatTTCA | 9968 | 479 |
| 479_1 | 63 | 7 | 51 | 26 | GAAagacacactcagatTTC | 9969 | 480 |
| 480_1 | 37 | 10 | ND | ND | AAGAcacactcagatTTC | 9969 | 481 |
| 481_1 | 41 | 4 | ND | ND | AAAGacacactcagaTTTC | 9969 | 482 |
| 482_1 | 19 | 5 | 48 | 14 | TGAAagacacactcagatTT | 9970 | 483 |
| 483_1 | 60 | 8 | 68 | 10 | TGaaagacacactcaGATT | 9971 | 484 |
| 484_1 | 42 | 8 | 63 | 22 | TGAaagacacactcaGAT | 9972 | 485 |
| 485_1 | 48 | 9 | 41 | 20 | ATTGaaagacacacTCA | 9975 | 486 |
| 486_1 | 27 | 6 | 27 | 12 | TCattgaaagacaCACT | 9977 | 487 |
| 487_1 | 88 | 13 | 121 | 33 | TTCcatcattgaAAGA | 9983 | 488 |
| 488_1 | 80 | 12 | ND | ND | ATAAtaccacttaTCAT | 10010 | 489 |
| 489_1 | 13 | 4 | 27 | 15 | TTacttaatttcttTGGA | 10055 | 490 |
| 490_1 | 32 | 5 | 60 | 24 | TTAgaactagctttaTCA | 10101 | 491 |
| 491_1 | 58 | 10 | 55 | 17 | GAGgtacaaatatAGG | 10171 | 492 |
| 492_1 | 4 | 1 | 12 | 3 | CTTatgatacaacTTA | 10384 | 493 |
| 493_1 | 37 | 6 | 35 | 5 | TCttatgatacaaCTT | 10385 | 494 |
| 494_1 | 30 | 0 | 27 | 6 | TTCttatgatacaaCT | 10386 | 495 |
| 495_1 | 27 | 8 | 18 | 3 | CAgtttcttatgaTAC | 10390 | 496 |
| 496_1 | 25 | 10 | 25 | 6 | GCAgtttcttatgaTA | 10391 | 497 |
| 497_1 | 77 | 6 | 72 | 29 | TACAaatgtctattagGTT | 10457 | 498 |
| 498_1 | 66 | 5 | 69 | 17 | TGTAcaaatgtctatTAG | 10460 | 499 |
| 499_1 | 27 | 10 | 20 | 4 | AGCatcacaattagTA | 10535 | 500 |
| 500_1 | 31 | 10 | 25 | 5 | CTAatgatagtgaaGC | 10548 | 501 |
| 501_1 | 21 | 7 | 30 | 8 | AGCtaatgatagtgAA | 10550 | 502 |
| 502_1 | 35 | 5 | 39 | 8 | ATGCcttgacatatTA | 10565 | 503 |
| 503_1 | 64 | 11 | 79 | 26 | CTCAagattattgACAC | 10623 | 504 |
| 504_2 | 25 | 4 | 83 | 32 | ACctcaagattaTTGA | 10626 | 505 |
| 504_1 | 94 | 7 | 22 | 6 | ACCtcaagattaTTGA | 10626 | 505 |
| 505_1 | 31 | 6 | 34 | 10 | AACCtcaagattatTG | 10627 | 506 |
| 506_1 | 55 | 6 | 62 | 17 | CACAaacctcaagattaTT | 10628 | 507 |
| 507_1 | 66 | 12 | 40 | 4 | GTActtaattagACCT | 10667 | 508 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
|---|---|---|---|---|---|---|---|
| | % mRNA of control | sd | % mRNA of control | sd | | | |
| 508_1 | 78 | 5 | 80 | 10 | AGTActtaattagACC | 10668 | 509 |
| 509_1 | 36 | 5 | 42 | 15 | GTATgaggtggtaaAC | 10688 | 510 |
| 510_1 | 40 | 4 | 48 | 22 | AGgaaacagcagaAGTG | 10723 | 511 |
| 511_1 | 27 | 7 | 13 | 6 | GCacaacccagaggAA | 10735 | 512 |
| 512_1 | 54 | 5 | ND | ND | CAAgcacaacccagAG | 10738 | 513 |
| 513_1 | 35 | 7 | ND | ND | TTCaagcacaaccCAG | 10740 | 514 |
| 514_1 | 49 | 6 | 52 | 15 | AAttcaagcacaACCC | 10742 | 515 |
| 515_1 | 72 | 4 | 106 | 49 | TAATaattcaagcacaaCC | 10743 | 516 |
| 516_1 | 43 | 4 | 57 | 21 | ACTAataattcaaGCAC | 10747 | 517 |
| 517_1 | 37 | 3 | 60 | 12 | ATAAtactaataattcAAGC | 10749 | 518 |
| 518_1 | 9 | 3 | 6 | 1 | TAgatttgtgagGTAA | 11055 | 519 |
| 519_1 | 59 | 10 | 31 | 5 | AGCCttaattctccAT | 11091 | 520 |
| 520_1 | 41 | 4 | 34 | 9 | AATGatctagagcCTTA | 11100 | 521 |
| 521_1 | 34 | 6 | 34 | 7 | CTAatgatctagaGCC | 11103 | 522 |
| 522_1 | 52 | 6 | 52 | 17 | ACTaatgatctaGAGC | 11104 | 523 |
| 523_1 | 60 | 4 | 54 | 10 | CATtaacatgttctTATT | 11165 | 524 |
| 524_1 | 57 | 4 | 55 | 8 | ACAAgtacattaacatGTTC | 11170 | 525 |
| 525_1 | 53 | 6 | 44 | 5 | TTACaagtacattaaCATG | 11173 | 526 |
| 526_1 | 54 | 11 | 49 | 17 | GCTTtattcatgtTTAT | 11195 | 527 |
| 527_1 | 34 | 7 | 17 | 5 | GCTttattcatgttTA | 11196 | 528 |
| 528_1 | 11 | 2 | 21 | 4 | AGAgctttattcatgtTT | 11197 | 529 |
| 529_1 | 22 | 4 | 33 | 7 | ATAAgagctttattCATG | 11200 | 530 |
| 530_1 | 30 | 5 | 32 | 15 | CATAagagctttaTTCA | 11202 | 531 |
| 531_1 | 77 | 8 | 24 | 4 | AGCAtaagagctTTAT | 11205 | 532 |
| 532_1 | 8 | 3 | 15 | 6 | TAGattgtttagtGCA | 11228 | 533 |
| 533_1 | 4 | 2 | 10 | 2 | GTagattgtttaGTGC | 11229 | 534 |
| 534_1 | 41 | 6 | 33 | 11 | GACAattctagtaGATT | 11238 | 535 |
| 535_1 | 50 | 1 | 37 | 7 | CTGacaattctaGTAG | 11241 | 536 |
| 536_1 | 49 | 7 | 36 | 6 | GCTGacaattctagTA | 11242 | 537 |
| 537_1 | 59 | 2 | 42 | 11 | AGgattaagatacgTA | 11262 | 538 |
| 538_1 | 28 | 11 | 28 | 4 | CAggattaagataCGT | 11263 | 539 |
| 539_1 | 96 | 5 | 20 | 6 | TCAggattaagataCG | 11264 | 540 |
| 540_1 | 70 | 11 | 59 | 11 | TTcaggattaagATAC | 11265 | 541 |
| 541_1 | 53 | 5 | 28 | 4 | AGGAagaaagtttgATTC | 11308 | 542 |
| 542_1 | 92 | 13 | 59 | 12 | TCAAggaagaaagtTTGA | 11311 | 543 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
| | % mRNA of control | sd | % mRNA of control | sd | | | |
| --- | --- | --- | --- | --- | --- | --- | --- |
| 543_1 | 44 | 3 | 67 | 7 | CTCAaggaagaaagTTTG | 11312 | 544 |
| 544_1 | 43 | 4 | 32 | 4 | TGCtcaaggaagaAAGT | 11315 | 545 |
| 545_1 | 41 | 7 | 44 | 20 | AATTatgctcaaggaAGA | 11319 | 546 |
| 546_1 | 11 | 4 | 26 | 8 | TAGGataccacattatGA | 11389 | 547 |
| 547_1 | 25 | 4 | 26 | 12 | CAtaatttattccattcCTC | 11449 | 548 |
| 548_1 | 64 | 6 | ND | ND | TGCAtaatttattcCAT | 11454 | 549 |
| 549_1 | 48 | 17 | 49 | 7 | ACTGcataatttatTCC | 11456 | 550 |
| 550_1 | 91 | 10 | 92 | 15 | CTAAactgcataattTATT | 11458 | 551 |
| 551_1 | 85 | 8 | 38 | 9 | ATaactaaactgCATA | 11465 | 552 |
| 552_1 | 86 | 4 | ND | ND | TTAttaataactaaaCTGC | 11468 | 553 |
| 553_1 | 91 | 13 | 92 | 21 | TAGTacattattaataaCT | 11475 | 554 |
| 554_1 | 50 | 4 | 37 | 7 | CATAactaaggacgTT | 11493 | 555 |
| 555_1 | 41 | 5 | 30 | 7 | TCataactaaggaCGT | 11494 | 556 |
| 556_1 | 80 | 7 | 55 | 13 | CGTCataactaaggAC | 11496 | 557 |
| 557_1 | 86 | 3 | 59 | 11 | TCgtcataactaagGA | 11497 | 558 |
| 558_1 | 81 | 9 | 33 | 12 | ATcgtcataactAAGG | 11498 | 559 |
| 559_1 | 91 | 6 | 65 | 26 | GTtagtatcttacATT | 11525 | 560 |
| 560_1 | 30 | 3 | 41 | 8 | CTCtattgttagtATC | 11532 | 561 |
| 561_1 | 59 | 8 | 18 | 6 | AGTatagagttacTGT | 11567 | 562 |
| 562_1 | 65 | 11 | 41 | 11 | TTCCtggtgatactTT | 11644 | 563 |
| 563_1 | 57 | 13 | 45 | 13 | GTTCctggtgatacTT | 11645 | 564 |
| 564_1 | 57 | 15 | 30 | 7 | TGttcctggtgataCT | 11646 | 565 |
| 565_1 | 17 | 4 | 35 | 4 | ATaaacatgaatctCTCC | 11801 | 566 |
| 566_1 | 16 | 3 | 30 | 4 | CTTtataaacatgaaTCTC | 11804 | 567 |
| 567_1 | 60 | 5 | 45 | 11 | CTGtctttataaaCATG | 11810 | 568 |
| 568_1 | 20 | 2 | 19 | 5 | TTgttataaatctgTCTT | 11820 | 569 |
| 569_1 | 68 | 9 | 44 | 4 | TTAaatttattcttgGATA | 11849 | 570 |
| 570_1 | 76 | 8 | 48 | 12 | CTtaaatttattctTGGA | 11851 | 571 |
| 571_1 | 62 | 5 | 66 | 5 | CTTCttaaatttattctTG | 11853 | 572 |
| 572_1 | 28 | 4 | 44 | 10 | TATGtttctcagtAAAG | 11877 | 573 |
| 573_1 | 29 | 6 | 36 | 11 | GAAttatctttaaACCA | 11947 | 574 |
| 574_1 | 74 | 6 | 34 | 7 | CCCttaaatttctaCA | 11980 | 575 |
| 575_1 | 37 | 8 | 30 | 9 | ACACtgctcttgtaCC | 11995 | 576 |
| 576_1 | 45 | 14 | 27 | 6 | TGAcaacactgctCTT | 12000 | 577 |
| 577_1 | 2 | 1 | 12 | 5 | TACAtttattgggcTC | 12081 | 578 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
| --- | --- | --- | --- | --- | --- | --- | --- |
| | % mRNA of control | sd | % mRNA of control | sd | | | |
| 578_1 | 65 | 14 | 39 | 9 | GTacatttattgGGCT | 12082 | 579 |
| 579_1 | 34 | 4 | 53 | 12 | TTGgtacatttatTGG | 12085 | 580 |
| 580_1 | 41 | 7 | 35 | 6 | CATGttggtacattTAT | 12088 | 581 |
| 581_1 | 11 | 4 | 12 | 5 | AATCatgttggtacAT | 12092 | 582 |
| 582_1 | 96 | 16 | 48 | 9 | AAatcatgttggtaCA | 12093 | 583 |
| 583_1 | 71 | 15 | 42 | 13 | GACaagtttggattAA | 12132 | 584 |
| 584_1 | 46 | 34 | 39 | 6 | AAtgttcagatgCCTC | 12197 | 585 |
| 585_1 | 37 | 26 | 28 | 12 | GCttaatgttcagaTG | 12201 | 586 |
| 586_1 | 75 | 8 | 43 | 12 | CGTAcatagcttgaTG | 12267 | 587 |
| 587_1 | 41 | 10 | 28 | 5 | GTGaggaattaggaTA | 12753 | 588 |
| 588_1 | 41 | 5 | 27 | 9 | GTAacaatatggtttTG | 12780 | 589 |
| 589_1 | 67 | 10 | 37 | 7 | GAaatattgtagaCTA | 13151 | 590 |
| 590_1 | 97 | 10 | 80 | 12 | TTGaaatattgtagAC | 13153 | 591 |
| 591_1 | 64 | 10 | 47 | 9 | AAgtctagtaatTTGC | 13217 | 592 |
| 592_1 | 84 | 7 | 60 | 9 | GCTCagtagattatAA | 13259 | 593 |
| 593_1 | 42 | 8 | 32 | 9 | CATacactgttgcTAA | 13296 | 594 |
| 594_1 | 101 | 6 | 79 | 17 | ATGgtctcaaatcATT | 13314 | 595 |
| 595_1 | 53 | 14 | 46 | 7 | CAATggtctcaaatCA | 13316 | 596 |
| 596_1 | 47 | 6 | 36 | 6 | TTCCtattgattgaCT | 13568 | 597 |
| 597_1 | 97 | 12 | 41 | 6 | TTTCtgttcacaacAC | 13600 | 598 |
| 598_1 | 85 | 1 | 49 | 11 | AGgaacccactaaTCT | 13702 | 599 |
| 599_1 | 56 | 3 | 34 | 7 | TAAatggcaggaacCC | 13710 | 600 |
| 600_1 | 15 | 4 | 24 | 8 | GTAAatggcaggaaCC | 13711 | 601 |
| 601_1 | 40 | 6 | 26 | 8 | TTgtaaatggcagGAA | 13713 | 602 |
| 602_1 | 59 | 12 | 26 | 6 | TTatgagttaggCATG | 13835 | 603 |
| 603_1 | 62 | 2 | 42 | 10 | CCAggtgaaactttAA | 13935 | 604 |
| 604_1 | 77 | 9 | 55 | 18 | CCCttagtcagctCCT | 13997 | 605 |
| 605_1 | 82 | 13 | 42 | 11 | ACccttagtcagCTCC | 13998 | 606 |
| 606_1 | 74 | 1 | 39 | 10 | CAcccttagtcagCTC | 13999 | 607 |
| 607_1 | 76 | 9 | 30 | 8 | TCTcttactaggcTCC | 14091 | 608 |
| 608_1 | 82 | 5 | 50 | 13 | CCtatctgtcatcATG | 14178 | 609 |
| 609_1 | 82 | 1 | 48 | 12 | TCCtatctgtcatcAT | 14179 | 610 |
| 610_1 | 41 | 6 | 50 | 13 | GAGaagtgtgagaaGC | 14808 | 611 |
| 611_1 | 70 | 5 | 84 | 19 | CATCcttgaagtttAG | 14908 | 612 |
| 612_1 | 64 | 14 | 61 | 16 | TAAtaagatggctCCC | 15046 | 613 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP % mRNA of control | sd | THP1 cells 20 µM CMP % mRNA of control | sd | Compound (CMP) | Start on SEQ ID NO 1 | SEQ ID NO |
|---|---|---|---|---|---|---|---|
| 613_1 | 85 | 2 | 51 | 14 | CAAggcataataagAT | 15053 | 614 |
| 614_1 | 47 | 1 | 35 | 10 | CCaaggcataatAAGA | 15054 | 615 |
| 615_1 | 74 | 8 | 53 | 11 | TGatccaattctcaCC | 15151 | 616 |
| 616_1 | 63 | 4 | 41 | 11 | ATGatccaattctCAC | 15152 | 617 |
| 617_1 | 46 | 7 | 42 | 9 | CGCttcatcttcacCC | 15260 | 618 |
| 618_1 | 104 | 4 | 15 | 4 | TAtgacactgcaTCTT | 15317 | 619 |
| 619_1 | 8 | 3 | 8 | 5 | GTAtgacactgcaTCT | 15318 | 620 |
| 620_1 | 21 | 3 | 27 | 10 | TGtatgacactgCATC | 15319 | 621 |
| 621_1 | 37 | 7 | 38 | 11 | TTCTcttctgtaagTC | 15363 | 622 |
| 622_1 | 49 | 7 | 36 | 11 | TTctacagaggaACTA | 15467 | 623 |
| 623_1 | 47 | 1 | 32 | 10 | ACTacagttctacAGA | 15474 | 624 |
| 624_1 | 78 | 8 | 69 | 6 | TTCCcacaggtaaaTG | 15561 | 625 |
| 625_1 | 70 | 7 | ND | ND | ATTAtttgaatatactCATT | 15594 | 626 |
| 626_1 | 73 | 7 | 49 | 25 | TGGGaggaaattatTTG | 15606 | 627 |
| 627_1 | 80 | 5 | 64 | 11 | TGACtcatcttaaaTG | 15621 | 628 |
| 628_1 | 71 | 6 | 66 | 19 | CTGactcatcttaaAT | 15622 | 629 |
| 629_1 | 31 | 6 | 41 | 6 | TTTactctgactcATC | 15628 | 630 |
| 630_1 | 88 | 2 | 68 | 18 | TATtggaggaattaTT | 15642 | 631 |
| 631_1 | 53 | 2 | 27 | 6 | GTAttggaggaattAT | 15643 | 632 |
| 632_1 | 23 | 3 | 39 | 7 | TGgtatacttctctaagTAT | 15655 | 633 |
| 633_1 | 42 | 9 | 33 | 3 | GATCtcttggtataCT | 15666 | 634 |
| 634_1 | 38 | 1 | 30 | 16 | CAgacaactctataCC | 15689 | 635 |
| 635_1 | 10 | 2 | 19 | 3 | AACAtcagacaacTCTA | 15693 | 636 |
| 636_1 | 13 | 1 | 11 | 3 | TAACatcagacaacTC | 15695 | 637 |
| 637_1 | 14 | 2 | 27 | 2 | TTTAacatcagacaACTC | 15695 | 638 |
| 638_1 | 101 | 14 | 81 | 16 | ATttaacatcagacAA | 15698 | 639 |
| 639_1 | 14 | 1 | 17 | 1 | CCtatttaacatcAGAC | 15700 | 640 |
| 640_1 | 65 | 2 | ND | ND | TCCctatttaacaTCA | 15703 | 641 |
| 641_1 | 41 | 6 | 42 | 12 | TCAAcgactattgGAAT | 15737 | 642 |
| 642_1 | 37 | 2 | 29 | 5 | CTTAtattctggcTAT | 15850 | 643 |
| 643_1 | 31 | 7 | 35 | 4 | ATCCttatattctgGC | 15853 | 644 |
| 644_1 | 13 | 3 | 8 | 1 | GAtccttatattCTGG | 15854 | 645 |
| 645_1 | 25 | 5 | 20 | 4 | TGAtccttatattCTG | 15855 | 646 |
| 646_1 | 33 | 6 | 54 | 10 | ATTGaaacttgaTCCT | 15864 | 647 |
| 647_1 | 43 | 3 | 27 | 6 | ACtgtcattgaaACTT | 15870 | 648 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
| --- | --- | --- | --- | --- | --- | --- | --- |
| | % mRNA of control | sd | % mRNA of control | sd | | | |
| 648_1 | 54 | 7 | 32 | 12 | TCTtactgtcattgAA | 15874 | 649 |
| 649_1 | 12 | 1 | 25 | 2 | AGgatcttactgtCATT | 15877 | 650 |
| 650_1 | 13 | 4 | 11 | 3 | GCAaatcaactccATC | 15896 | 651 |
| 651_1 | 10 | 5 | 16 | 3 | GTGcaaatcaactCCA | 15898 | 652 |
| 652_1 | 7 | 0 | 36 | 18 | CAATtatttctttgTGC | 15910 | 653 |
| 653_1 | 21 | 3 | 31 | 7 | TGGcaacaattattTCTT | 15915 | 654 |
| 654_1 | 75 | 9 | 73 | 24 | GCTggcaacaatTATT | 15919 | 655 |
| 655_1 | 21 | 6 | 39 | 6 | ATCCatttctactgCC | 15973 | 656 |
| 656_1 | 25 | 3 | 38 | 8 | TAATatctattgattTCTA | 15988 | 657 |
| 657_1 | 14 | 2 | 11 | 5 | TCaatagtgtagggCA | 16093 | 658 |
| 658_1 | 11 | 4 | 10 | 3 | TTCaatagtgtaggGC | 16094 | 659 |
| 659_1 | 18 | 1 | 32 | 12 | AGGTtaattaattcaATAG | 16102 | 660 |
| 660_1 | 33 | 7 | 25 | 10 | CATttgtaatccCTAG | 16163 | 661 |
| 660_2 | 64 | 14 | 31 | 8 | CATttgtaatcccTAG | 16163 | 661 |
| 661_1 | 48 | 6 | 34 | 6 | ACAtttgtaatccCTA | 16164 | 662 |
| 662_2 | 29 | 6 | 23 | 5 | AAcatttgtaatCCCT | 16165 | 663 |
| 662_1 | 30 | 6 | 18 | 6 | AACatttgtaatCCCT | 16165 | 663 |
| 663_1 | 49 | 1 | 26 | 6 | TAaatttcaagttCTG | 16184 | 664 |
| 664_1 | 17 | 3 | 30 | 10 | GTTtaaatttcaagTTCT | 16185 | 665 |
| 665_1 | 22 | 7 | 40 | 9 | CCAagtttaaatttCAAG | 16189 | 666 |
| 666_1 | 89 | 11 | ND | ND | ACCCaagtttaaaTTTC | 16192 | 667 |
| 667_1 | 60 | 16 | 87 | 8 | CAtacagtgacccaagTTT | 16199 | 668 |
| 668_1 | 65 | 9 | 50 | 12 | ACatcccatacagTGA | 16208 | 669 |
| 669_1 | 83 | 8 | 103 | 4 | AGcacagctctaCATC | 16219 | 670 |
| 670_1 | 80 | 9 | 150 | 36 | ATAtagcacagcTCTA | 16223 | 671 |
| 671_1 | 57 | 14 | ND | ND | TCCatatagcacagCT | 16226 | 672 |
| 672_1 | 53 | 10 | 106 | 8 | ATTccatatagCACA | 16229 | 673 |
| 673_1 | 78 | 3 | 96 | 14 | TTTAtttccatatAGCA | 16231 | 674 |
| 674_1 | 77 | 9 | 31 | 7 | TTTatttccatatAGC | 16232 | 675 |
| 675_1 | 32 | 6 | ND | ND | AAGGagaggagatTATG | 16409 | 676 |
| 676_1 | 32 | 5 | 24 | 6 | AGTtcttgtgttagCT | 16456 | 677 |
| 677_1 | 19 | 4 | 17 | 4 | GAgttcttgtgttaGC | 16457 | 678 |
| 678_1 | 14 | 3 | 25 | 3 | ATTaattatccatCCAC | 16590 | 679 |
| 679_1 | 11 | 2 | 20 | 6 | ATCaattaattatcCATC | 16593 | 680 |
| 680_1 | 31 | 5 | 40 | 11 | AGAatcaattaattaTCC | 16596 | 681 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
|---|---|---|---|---|---|---|---|
| | % mRNA of control | sd | % mRNA of control | sd | | | |
| 681_1 | 8 | 3 | 30 | 10 | TGagataccgtgcaTG | 16656 | 682 |
| 682_1 | 11 | 3 | ND | ND | AAtgagataccgTGCA | 16658 | 683 |
| 683_1 | 15 | 3 | 33 | 10 | CTGtggttaggctaAT | 16834 | 684 |
| 684_1 | 45 | 7 | 38 | 7 | AagagtaagggtctgtggTT | 16842 | 685 |
| 685_1 | 24 | 5 | ND | ND | GATGggttaagagTAA | 16854 | 686 |
| 686_1 | 11 | 2 | ND | ND | AGCagatgggttaaGA | 16858 | 687 |
| 687_1 | ND | ND | 51 | 7 | TGtaaacatttgTAGC | 16886 | 688 |
| 688_1 | 83 | 1 | 54 | 11 | CCTgcttataaatgTA | 16898 | 689 |
| 689_1 | 103 | 4 | 73 | 14 | TGCCctgcttataaAT | 16901 | 690 |
| 690_1 | 104 | 2 | 64 | 22 | TCttcttagttcaaTA | 16935 | 691 |
| 691_1 | ND | ND | 60 | 9 | TGgtttctaactACAT | 16980 | 692 |
| 692_1 | ND | ND | 94 | 22 | AGtttggtttctaaCTA | 16983 | 693 |
| 693_1 | 8 | 2 | 17 | 5 | GAAtgaaacttgcCTG | 17047 | 694 |
| 694_1 | 98 | 6 | 51 | 9 | ATTatccttacatGAT | 17173 | 695 |
| 695_1 | 48 | 4 | 18 | 4 | GTacccaattatcCTT | 17180 | 696 |
| 696_1 | 94 | 2 | 48 | 9 | TGTacccaattatCCT | 17181 | 697 |
| 697_1 | 31 | 5 | 42 | 13 | TTgtacccaattaTCC | 17182 | 698 |
| 698_1 | 41 | 4 | 39 | 6 | TTTgtacccaattaTC | 17183 | 699 |
| 699_1 | 63 | 0 | 28 | 12 | AGCAgcaggttataTT | 17197 | 700 |
| 700_1 | 99 | 6 | 43 | 12 | TGGgaagtggtctGGG | 17292 | 701 |
| 701_1 | 103 | 2 | 28 | 5 | CTGgagagtgataaTA | 17322 | 702 |
| 702_1 | 52 | 6 | 27 | 9 | AATGctggattacgTC | 17354 | 703 |
| 703_1 | 67 | 3 | 37 | 7 | CAatgctggattaCGT | 17355 | 704 |
| 704_1 | 36 | 10 | 80 | 12 | TTgttcagaagtATCC | 17625 | 705 |
| 705_1 | 19 | 9 | 47 | 9 | GAtgatttgcttGGAG | 17646 | 706 |
| 706_1 | 44 | NA | 60 | 9 | GAAatcattcacaACC | 17860 | 707 |
| 707_1 | 46 | 9 | 32 | 9 | TTGtaacatctacTAC | 17891 | 708 |
| 708_1 | 56 | 0 | 79 | 17 | CATtaagcagcaagTT | 17923 | 709 |
| 709_1 | 30 | 9 | 46 | 7 | TTActagatgtgagCA | 17942 | 710 |
| 710_1 | 29 | 4 | 36 | 6 | TTtactagatgtgAGC | 17943 | 711 |
| 711_1 | 41 | 13 | 41 | 6 | GACcaagcaccttaCA | 17971 | 712 |
| 712_1 | 36 | 19 | 49 | 11 | AGAccaagcacctTAC | 17972 | 713 |

TABLE 10-continued in vitro efficacy of anti-PD-L1 compounds in THP1 and KARPAS-299 cell lines (Average from n = 3 experiments). PD-L1 mRNA levels are normalized to TBP in KARPAS-299 cells or ACTB in THP1 cells and shown as % of control (PBS treated cells).

| CMP ID NO | KARPAS-299 cells 5 µM CMP | | THP1 cells 20 µM CMP | | Compound (CMP) | Start on SEQ ID NO 1 | SEQ ID NO |
| | % mRNA of control | sd | % mRNA of control | sd | | | |
|---|---|---|---|---|---|---|---|
| 713_1 | 30 | 6 | 34 | 7 | ATgggttaaataAAGG | 18052 | 714 |
| 714_1 | 70 | 2 | 24 | 8 | TCaaccagagtattAA | 18067 | 715 |
| 715_1 | 11 | 4 | 26 | 8 | GTCaaccagagtatTA | 18068 | 716 |
| 716_1 | 126 | 56 | 26 | 6 | ATtgtaaagctgaTAT | 18135 | 717 |
| 717_1 | 73 | 1 | 42 | 10 | CAcataattgtaAAGC | 18141 | 718 |
| 718_1 | 23 | 9 | 55 | 18 | GAggtctgctattTAC | 18274 | 719 |
| 719_1 | 50 | 1 | 42 | 11 | TGtagattcaatgCCT | 18404 | 720 |
| 720_1 | 79 | 3 | 39 | 10 | CCtcattatactaTGA | 18456 | 721 |
| 721_1 | 27 | 6 | 30 | 8 | CCttatgctatgacAC | 18509 | 722 |
| 722_1 | 26 | 7 | 50 | 13 | TCCTtatgctatgaCA | 18510 | 723 |
| 723_1 | 59 | 1 | 48 | 12 | AAGatgtttaagtATA | 18598 | 724 |
| 724_1 | 54 | 2 | 50 | 13 | CTgattattaagATGT | 18607 | 725 |
| 725_1 | 92 | 10 | 84 | 19 | TGgaaaggtatgaaTT | 18808 | 726 |
| 726_1 | 24 | 8 | 61 | 16 | ACttgaatggcttgGA | 18880 | 727 |
| 727_1 | 8 | 4 | 51 | 14 | AACttgaatggctTGG | 18881 | 728 |
| 728_1 | 35 | 4 | 35 | 10 | CAATgtgttactatTT | 19004 | 729 |
| 729_1 | 36 | 9 | 53 | 11 | ACAatgtgttactATT | 19005 | 730 |
| 730_1 | 70 | 2 | 41 | 11 | CATCtgctatataaGA | 19063 | 731 |
| 731_1 | 38 | NA | 42 | 9 | CCTAgagcaaatacTT | 19223 | 732 |
| 732_1 | 102 | 15 | 15 | 4 | CAGagttaataatAAG | 19327 | 733 |
| 733_1 | 37 | 10 | 8 | 5 | GTTCaagcacaacgAA | 19493 | 734 |
| 734_1 | 13 | 1 | 38 | 11 | AGggttcaagcacAAC | 19496 | 735 |
| 735_1 | 49 | NA | 36 | 11 | TGttggagacactgTT | 19677 | 736 |
| 736_1 | 48 | NA | 32 | 10 | AAGgaggagttaggAC | 19821 | 737 |
| 737_1 | 36 | NA | 64 | 11 | CTATgccatttacgAT | 19884 | 738 |
| 738_1 | 105 | 19 | 66 | 19 | TCaaatgcagaattAG | 19913 | 739 |
| 739_1 | 44 | NA | 41 | 6 | AGtgacaatcaaATGC | 19921 | 740 |
| 740_1 | 107 | NA | 68 | 18 | AAgtgacaatcaaATG | 19922 | 741 |
| 741_1 | 102 | 4 | 27 | 6 | GTGtaccaagtaacAA | 19978 | 742 |
| 742_1 | 110 | 10 | 30 | 16 | TGGgatgttaaacTGA | 20037 | 743 |

Example 2—Testing In Vitro Efficacy in a Dose Response Curve

A selection of oligonucleotides from Table 10 were tested in KARPAS-299 cells using half-log serial dilutions in in PBS (50 µM, 15.8 µM, 5.0 µM, 1.58 µM, 0.5 µM, 0.158 µM, 0.05 µM, to 0.0158 µM oligonucleotide) in the in vitro efficacy assay described in Example 1. IC 50 and max inhibition (% residual PD-L1 expression) was assessed for the oligonucleotides.

EC50 calculations were performed in GraphPad Prism6. The I050 and maximum PD-L1 knock down level is shown in table 11 as % of control (PBS) treated cells.

TABLE 11

Max inhibition as % of saline and EC50 in KARPAS-299 cell line.

| CMP ID NO | Max Inhibition (% residual PD-L1 expression; % of saline-treated) | | EC50 (µM) | | Compound CMP | Start on SEQ ID NO: 1 | SEQ ID NO |
|---|---|---|---|---|---|---|---|
| | Avg | SD | Avg | SD | | | |
| 6_1 | 11 | 3.3 | 0.69 | 0.11 | TCGCataagaatgaCT | 371 | 6 |
| 8_1 | 29 | 1.7 | 0.06 | 0.01 | CTGaacacacagtCGC | 383 | 8 |
| 9_1 | 19 | 1.7 | 0.23 | 0.02 | TCTgaacacacagtCG | 384 | 9 |
| 13_1 | 14 | 4.7 | 0.45 | 0.12 | CTtacttagatgcTGC | 495 | 13 |
| 41_1 | 10 | 1.8 | 0.19 | 0.02 | TCAtttagttaccCAA | 822 | 41 |
| 42_1 | 17 | 1.3 | 0.19 | 0.02 | TTcatttagttaCCCA | 823 | 42 |
| 58_1 | 23 | 1.5 | 0.17 | 0.01 | CCagagatatataTGC | 909 | 58 |
| 77_1 | 24 | 2.4 | 0.16 | 0.02 | AGTatcatagttcTCC | 1075 | 77 |
| 92_1 | 12 | 2.4 | 0.25 | 0.03 | AGattaagacagtTGA | 1310 | 92 |
| 111_1 | 3 | 2.0 | 0.27 | 0.03 | TGaattcccatatcCGA | 1992 | 111 |
| 128_1 | 11 | 1.8 | 0.25 | 0.03 | CTcatatcagggCAGT | 2063 | 128 |
| 151_1 | 16 | 2.7 | 0.28 | 0.05 | GTCatggattacaaCT | 2324 | 151 |
| 164_1 | 19 | 1.6 | 0.15 | 0.01 | TCTGtttatgtcacTG | 2781 | 164 |
| 166_1 | 36 | 1.7 | 0.11 | 0.02 | TGgtctgtttatGTCA | 2784 | 166 |
| 169_1 | 10 | 1.6 | 0.22 | 0.02 | TTcagcaaatatTCGT | 2995 | 169 |
| 171_1 | 12 | 2.0 | 0.21 | 0.02 | TCTattgttaggtATC | 3053 | 171 |
| 222_1 | 1 | 2.0 | 0.21 | 0.02 | TGacttgtaattgTGG | 5467 | 222 |
| 233_1 | 1 | 4.3 | 0.89 | 0.17 | TGGaatgccctaatTA | 5591 | 233 |
| 245_1 | 4 | 2.0 | 0.17 | 0.02 | TCggttatgttaTCAT | 6470 | 245 |
| 246_1 | 7 | 2.1 | 0.25 | 0.03 | CActttatctggTCGG | 6482 | 246 |
| 250_1 | 0 | 2.5 | 0.23 | 0.03 | CCacatataggtcCTT | 6597 | 250 |
| 251_1 | 0 | 2.8 | 0.75 | 0.10 | CAtattgctaccaTAC | 6617 | 251 |
| 252_1 | 3 | 2.2 | 0.19 | 0.02 | TCAtattgctaccATA | 6618 | 252 |
| 256_1 | 5 | 2.2 | 0.32 | 0.03 | CAAttagtgcagcCAG | 6672 | 256 |
| 272_1 | 1 | 3.2 | 0.69 | 0.10 | TACTgtagaacatgGC | 7133 | 272 |
| 273_1 | 3 | 2.8 | 0.28 | 0.04 | GCAAttcatttgaTCT | 7239 | 273 |
| 287_1 | 1 | 1.4 | 0.13 | 0.01 | ACAAataatggttaCTCT | 7302 | 287 |
| 292_1 | 2 | 2.1 | 0.21 | 0.02 | GCATttgatatagAGA | 7397 | 292 |
| 303_1 | 0 | 1.2 | 0.21 | 0.01 | CAAgatgaatataTGCC | 7551 | 303 |
| 314_1 | 3 | 2.1 | 0.39 | 0.04 | GAgtttggattagCTG | 7764 | 314 |
| 318_1 | 3 | 1.4 | 0.14 | 0.01 | ACAggatatggaaGGG | 7880 | 318 |
| 320_1 | 2 | 2.4 | 0.22 | 0.03 | GAgtaatttcaacAGG | 7891 | 320 |
| 324_1 | 0 | 2.4 | 0.44 | 0.05 | CAgcttactattaGGG | 7906 | 324 |
| 336_1 | 0 | 2.5 | 0.21 | 0.03 | GATGatttaattctagtCA | 7984 | 336 |
| 342_1 | 1 | 2.2 | 0.12 | 0.01 | CAGAttgatggtagTT | 8030 | 342 |
| 343_1 | 4 | 1.8 | 0.11 | 0.01 | CTcagattgatgGTAG | 8032 | 343 |

TABLE 11-continued

Max inhibition as % of saline and EC50 in KARPAS-299 cell line.

| CMP ID NO | Max Inhibition (% residual PD-L1 expression; % of saline-treated) | | EC50 (µM) | | Compound CMP | Start on SEQ ID NO: 1 | SEQ ID NO |
|---|---|---|---|---|---|---|---|
| | Avg | SD | Avg | SD | | | |
| 344_1 | 0 | 0.9 | 0.12 | 0.01 | GTTagccctcagaTTG | 8039 | 344 |
| 345_1 | 0 | 2.3 | 0.36 | 0.04 | TGtattgttagcCCTC | 8045 | 345 |
| 346_1 | 1 | 2.1 | 0.22 | 0.02 | ACttgtattgttAGCC | 8048 | 346 |
| 349_1 | 4 | 2.9 | 0.21 | 0.03 | ACAagtggtatcTCT | 8228 | 349 |
| 359_1 | 6 | 2.9 | 0.39 | 0.05 | TTGAtgaggctaagTC | 8395 | 359 |
| 360_1 | 0 | 1.7 | 0.18 | 0.02 | CCAggattatactcTT | 8439 | 360 |
| 374_1 | 5 | 1.7 | 0.33 | 0.03 | AAGatggattgggaGT | 8775 | 374 |
| 408_1 | 3 | 1.8 | 0.21 | 0.02 | TTtgcatatggaGGTG | 8966 | 408 |
| 409_1 | 0 | 1.8 | 0.21 | 0.02 | AAgtgaagttcaaCAGC | 8997 | 409 |
| 415_1 | 0 | 1.4 | 0.23 | 0.02 | AAttgagtgaatCCAA | 9120 | 415 |
| 417_1 | 7 | 0.9 | 0.15 | 0.01 | GTGataattgagtGAA | 9125 | 417 |
| 424_1 | 6 | 3.2 | 0.19 | 0.03 | CTcattgaaggtTCTG | 9281 | 424 |
| 429_1 | 5 | 2.5 | 0.48 | 0.05 | CAAatagctttatCGG | 9335 | 429 |
| 430_1 | 1 | 2.7 | 0.68 | 0.09 | CCaaatagctttATCG | 9336 | 430 |
| 458_1 | 0 | 4.1 | 0.35 | 0.07 | TGgagtttatattcTAGG | 9512 | 458 |
| 464_1 | 0 | 4.1 | 0.56 | 0.10 | TGCtccagtgtaccCT | 9755 | 464 |
| 466_1 | 1 | 2.1 | 0.21 | 0.02 | CTAattgtagtagtaCTC | 9818 | 466 |
| 474_1 | 0 | 2.4 | 0.27 | 0.03 | GACacactcagatttcAG | 9967 | 474 |
| 490_1 | 0 | 1.9 | 0.29 | 0.03 | TTacttaatttcttTGGA | 10055 | 490 |
| 493_1 | 3 | 1.8 | 0.20 | 0.02 | CTTatgatacaacTTA | 10384 | 493 |
| 512_1 | 0 | 3.3 | 0.63 | 0.10 | GCacaacccagaggAA | 10735 | 512 |
| 519_1 | 5 | 1.5 | 0.15 | 0.01 | TAgatttgtgagGTAA | 11055 | 519 |
| 529_1 | 0 | 2.7 | 0.24 | 0.03 | AGAgctttattcatgtTT | 11197 | 529 |
| 533_1 | 6 | 1.5 | 0.14 | 0.01 | TAGattgtttagtGCA | 11228 | 533 |
| 534_1 | 5 | 0.9 | 0.06 | 0.00 | GTagattgtttaGTGC | 11229 | 534 |
| 547_1 | 1 | 1.6 | 0.26 | 0.02 | TAGGataccacattatGA | 11389 | 547 |
| 566_1 | 0 | 3.0 | 0.40 | 0.06 | ATaaacatgaatctCTCC | 11801 | 566 |
| 567_1 | 2 | 2.5 | 0.34 | 0.04 | CTTtataaacatgaaTCTC | 11804 | 567 |
| 578_1 | 2 | 1.3 | 0.09 | 0.01 | TACAtttattgggcTC | 12081 | 578 |
| 582_1 | 1 | 1.6 | 0.20 | 0.02 | AATCatgttggtacAT | 12092 | 582 |
| 601_1 | 1 | 2.1 | 0.47 | 0.05 | GTAAatggcaggaaCC | 13711 | 601 |
| 619_1 | 4 | 3.4 | 0.44 | 0.08 | TAtgacactgcaTCTT | 15317 | 619 |

TABLE 11-continued

Max inhibition as % of saline and EC50 in KARPAS-299 cell line.

| CMP ID NO | Max Inhibition (% residual PD-L1 expression; % of saline-treated) | | EC50 (µM) | | Compound CMP | Start on SEQ ID NO: 1 | SEQ ID NO |
|---|---|---|---|---|---|---|---|
| | Avg | SD | Avg | SD | | | |
| 620_1 | 1 | 1.2 | 0.12 | 0.01 | GTAtgacactgcaTCT | 15318 | 620 |
| 636_1 | 0 | 1.3 | 0.19 | 0.01 | AACAtcagacaacTCTA | 15693 | 636 |
| 638_1 | 0 | 2.2 | 0.36 | 0.04 | TAACatcagacaacTC | 15695 | 638 |
| 637_1 | 0 | 2.1 | 0.21 | 0.02 | TTTAacatcagacaACTC | 15695 | 637 |
| 640_1 | 2 | 3.3 | 0.42 | 0.06 | CCtatttaacatcAGAC | 15700 | 640 |
| 645_1 | 1 | 2.9 | 0.34 | 0.04 | GAtccttatattCTGG | 15854 | 645 |
| 650_1 | 0 | 2.4 | 0.24 | 0.03 | AGgatcttactgtCATT | 15877 | 650 |
| 651_1 | 4 | 3.4 | 0.33 | 0.05 | GCAaatcaactccATC | 15896 | 651 |
| 652_1 | 0 | 1.3 | 0.16 | 0.01 | GTGcaaatcaactCCA | 15898 | 652 |
| 653_1 | 4 | 2.0 | 0.09 | 0.01 | CAATtatttctttgTGC | 15910 | 653 |
| 658_1 | 3 | 1.6 | 0.32 | 0.02 | TCaatagtgtagggCA | 16093 | 658 |
| 659_1 | 5 | 1.4 | 0.20 | 0.01 | TTCaatagtgtaggGC | 16094 | 659 |
| 660_1 | 4 | 2.1 | 0.22 | 0.02 | AGGTtaattaattcaATAG | 16102 | 660 |
| 665_1 | 3 | 1.8 | 0.18 | 0.02 | GTTtaaatttcaagTTCT | 16185 | 665 |
| 678_1 | 3 | 2.1 | 0.43 | 0.04 | GAgttcttgtgttaGC | 16457 | 678 |
| 679_1 | 0 | 3.5 | 0.31 | 0.05 | ATTaattatccatCCAC | 16590 | 679 |
| 680_1 | 4 | 1.6 | 0.12 | 0.01 | ATCaattaattatcCATC | 16593 | 680 |
| 682_1 | 3 | 2.4 | 0.27 | 0.03 | TGagataccgtgcaTG | 16656 | 682 |
| 683_1 | 0 | 3.2 | 0.16 | 0.03 | AAtgagataccgTGCA | 16658 | 683 |
| 684_1 | 2 | 2.3 | 0.25 | 0.03 | CTGtggttaggctaAT | 16834 | 684 |
| 687_1 | 5 | 1.3 | 0.13 | 0.01 | AGCagatgggttaaGA | 16858 | 687 |
| 694_1 | 0 | 1.7 | 0.16 | 0.02 | GAAtgaaacttgcCTG | 17047 | 694 |
| 706_1 | 15 | 3.6 | 0.27 | 0.06 | GAtgatttgcttGGAG | 17646 | 706 |
| 716_1 | 10 | 2.1 | 0.15 | 0.02 | GTCaaccagagtatTA | 18068 | 716 |
| 728_1 | 5 | 1.2 | 0.09 | 0.01 | AACttgaatggctTGG | 18881 | 728 |
| 733_1 | 0 | 12.7 | 8.01 | 3.62 | CAGagttaataatAAG | 19327 | 733 |
| 734_1 | 0 | 14.6 | 3.49 | 2.39 | GTTCaagcacaacgAA | 19493 | 734 |
| 735_1 | 0 | 2.5 | 0.30 | 0.04 | AGggttcaagcacAAC | 19496 | 735 |

A selection of oligonucleotides from Table 6 were tested in THP-1 cells using 1:3 serial in water from 25 µM to 0.004 µM in the in vitro efficacy assay described in Example 1. IC 50 and max inhibition (Percent residual PD-L1 expression) was assessed for the oligonucleotides.

EC50 calculations were performed in GraphPad Prism6. The I050 and maximum PD-L1 knock down level is shown in table 12 as % of control (PBS) treated cells.

TABLE 12

Max inhibition as % of saline and EC50 in THP1 cell line.

| CMP ID NO | Max Inhibition (% residual PD-L1 expression; % of saline) | | EC50 (µM) | | Compound CMP | Start on SEQ ID NO: 1 | SEQ ID NO |
|---|---|---|---|---|---|---|---|
| | Avg | SD | Avg | SD | | | |
| 6_1 | 12 | 11.5 | 0.73 | 0.38 | TCGCataagaatgaCT | 371 | 6 |
| 8_1 | 6 | 5.6 | 0.11 | 0.04 | CTGaacacacagtCGC | 383 | 8 |
| 9_1 | 1 | 14.3 | 0.36 | 0.27 | TCTgaacacacagtCG | 384 | 9 |
| 13_1 | 2 | 12.4 | 0.49 | 0.31 | CTtacttagatgcTGC | 495 | 13 |
| 41_1 | 14 | 14.6 | 0.38 | 0.27 | TCAtttagttaccCAA | 822 | 41 |
| 42_1 | 21 | 10.4 | 0.22 | 0.10 | TTcatttagttaCCCA | 823 | 42 |
| 58_1 | 6 | 19.8 | 0.97 | 0.81 | CCagagatatataTGC | 909 | 58 |
| 77_1 | 5 | 4.8 | 0.14 | 0.04 | AGTatcatagttcTCC | 1075 | 77 |
| 92_1 | 0 | 12.9 | 0.57 | 0.39 | AGattaagacagtTGA | 1310 | 92 |
| 128_1 | 15 | 10.1 | 0.23 | 0.13 | CTcatatcagggCAGT | 2063 | 128 |
| 151_1 | 9 | 14.4 | 0.18 | 0.15 | GTCatggattacaaCT | 2324 | 151 |
| 164_1 | 16 | 22.0 | 0.57 | 0.60 | TCTGtttatgtcacTG | 2781 | 164 |
| 166_1 | 13 | 11.9 | 0.17 | 0.11 | TGgtctgtttatGTCA | 2784 | 166 |
| 169_1 | 0 | 9.3 | 0.22 | 0.11 | TTcagcaaatatTCGT | 2995 | 169 |
| 171_1 | 11 | 12.9 | 0.28 | 0.20 | TCTattgttaggtATC | 3053 | 171 |
| 222_1 | 16 | 19.7 | 0.68 | 0.64 | TGacttgtaattgTGG | 5467 | 222 |
| 245_1 | 14 | 6.1 | 0.26 | 0.08 | TCggttatgttaTCAT | 6470 | 245 |
| 246_1 | 28 | 7.3 | 0.10 | 0.20 | CActttatctggTCGG | 6482 | 246 |
| 252_1 | 19 | 8.0 | 0.29 | 0.12 | TCAtattgctaccATA | 6618 | 252 |
| 272_1 | 3 | 9.7 | 0.25 | 0.14 | TACTgtagaacatgGC | 7133 | 272 |
| 314_1 | 13 | 9.6 | 0.31 | 0.15 | GAgtttggattagCTG | 7764 | 314 |
| 344_1 | 11 | 8.0 | 0.14 | 0.06 | GTTagccctcagaTTG | 8039 | 344 |
| 349_1 | 12 | 12.5 | 0.18 | 0.14 | ACAagtggtatctTCT | 8228 | 349 |
| 415_1 | 11 | 9.6 | 0.26 | 0.12 | AAttgagtgaatCCAA | 9120 | 415 |
| 493_1 | 15 | 16.5 | 0.48 | 0.34 | CTTatgatacaacTTA | 10384 | 493 |
| 512_1 | 43 | 14.1 | 0.31 | 0.68 | GCacaacccagaggAA | 10735 | 512 |
| 519_1 | 9 | 12.2 | 0.45 | 0.26 | TAgatttgtgagGTAA | 11055 | 519 |
| 533_1 | 11 | 13.6 | 0.29 | 0.21 | TAGattgtttagtGCA | 11228 | 533 |
| 534_1 | 9 | 6.5 | 0.09 | 0.03 | GTagattgtttaGTGC | 11229 | 534 |
| 582_1 | 0 | 12.3 | 0.33 | 0.23 | AATCatgttggtacAT | 12092 | 582 |
| 619_1 | 8 | 10.4 | 0.32 | 0.18 | TAtgacactgcaTCTT | 15317 | 619 |
| 620_1 | 12 | 24.6 | 1.10 | 1.08 | GTAtgacactgcaTCT | 15318 | 620 |
| 638_1 | 2 | 5.4 | 0.00 | 0.00 | TAACatcagacaacTC | 15695 | 638 |
| 645_1 | 20 | 29.6 | 1.10 | 1.50 | GAtccttatattCTGG | 15854 | 645 |
| 651_1 | 0 | 11.2 | 0.14 | 0.09 | GCAaatcaactccATC | 15896 | 651 |
| 658_1 | 11 | 13.8 | 0.48 | 0.32 | TCaatagtgtagggCA | 16093 | 658 |

TABLE 12-continued

Max inhibition as % of saline and EC50 in THP1 cell line.

| CMP ID NO | Max Inhibition (% residual PD-L1 expression; % of saline) | | EC50 (µM) | | Compound CMP | Start on SEQ ID NO: 1 | SEQ ID NO |
|---|---|---|---|---|---|---|---|
| | Avg | SD | Avg | SD | | | |
| 659_1 | 0 | 8.2 | 0.11 | 0.06 | TTCaatagtgtaggGC | 16094 | 659 |
| 733_1 | 0 | 69.6 | 11.03 | 26.95 | CAGagttaataatAAG | 19327 | 733 |
| 734_1 | 36 | 16.8 | 2.84 | 2.12 | GTTCaagcacaacgAA | 19493 | 734 |

Figure 2:
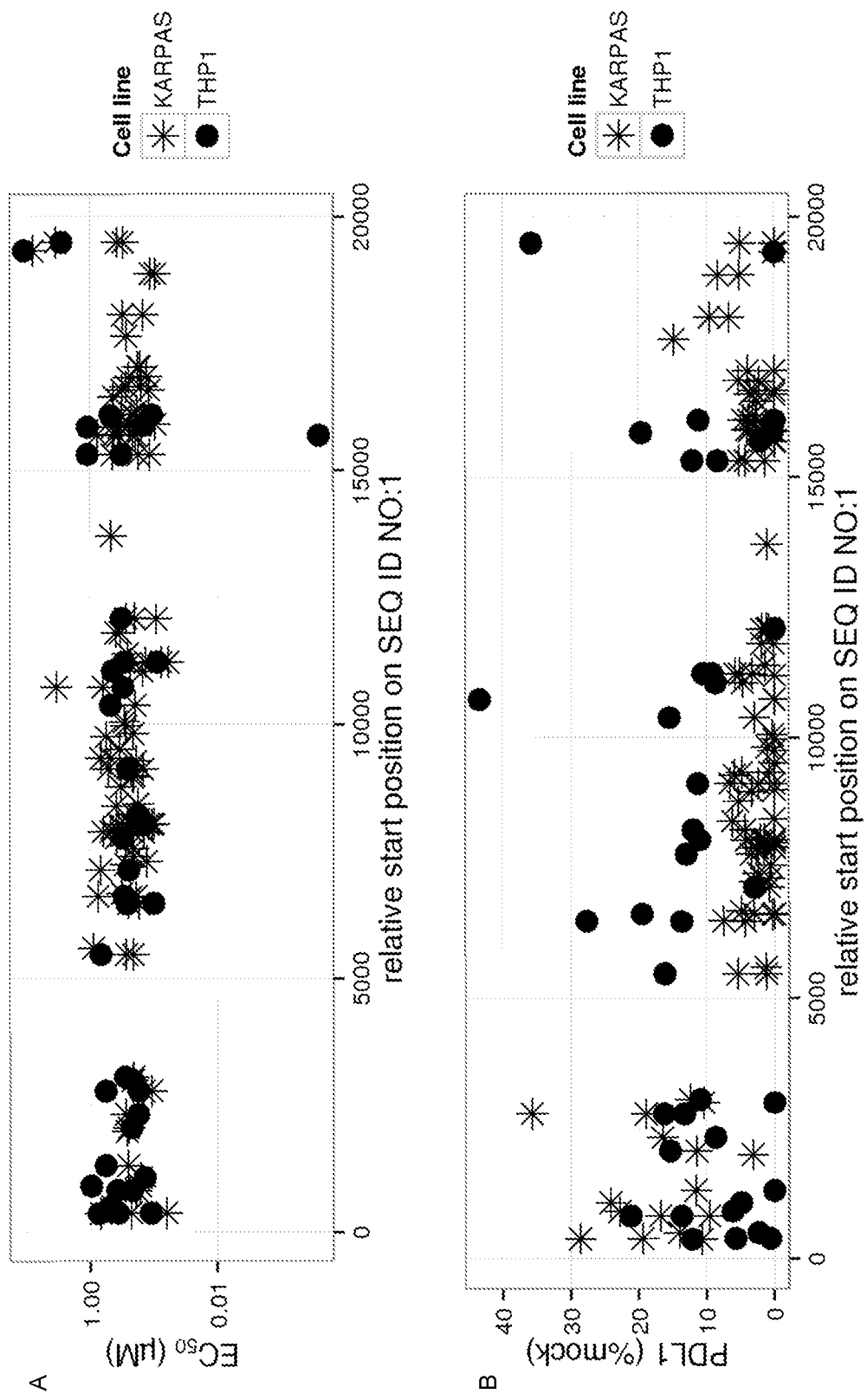
FIG. 2: Graph showing EC50 (A) and PD-L1 knock down as % of saline (B) for the compounds tested in Example 2, in relation to their position on the target nucleic acid. The cell line in which the compound were tested are THP1(●) and Karpas (*).

The results in table 7 and 8 are also shown in FIG. 2 in relation to their position where they target the PD-L1 pre mRNA of SEQ ID NO: 1.

From this it can be seen that almost all of the compounds have EC50 values below 1 µM and a target knock down below 25% of the PD-L1 expression level in the control cells (treated with saline).

Example 3—In Vitro Potency and Efficacy and In Vivo PD-L1 Reduction in Poly(I:C) Induced Mice Using Naked and GalNAc Conjugated PD-L1 Antisense Oligonucleotides Efficacy and potency testing was performed in an in vitro experiment in in dose-response studies in MCP-11 cells using the oligonucleotides in table 6. The same oligonucleotides as well as GalNAc conjugated versions (Table 8 CMP ID NO 755_2-765_2) were tested in vivo in poly(I:C) induced C57BL/6J female mice for their ability to reduce PD-L1 mRNA and protein expression In Vitro Assay MCP-11 cells (originally purchased from ATCC) suspended in DMEM (Sigma cat. no. D0819) supplemented with 10% horse serum, 2 mM L-glutamine, 0.025 mg/ml gentamicin and 1 mM sodium pyruvate were added at a density of 8000 cells/well to the oligonucleotides (10 µl) in 96-well round bottom plates and cultured for 3 days in a final volume of 200 µl/well in a humidified incubator at 37° C. with 5% $CO_2$. Oligonucleotides were screened in dose-range concentrations (50 µM, 15.8 µM, 5.0 µM, 1.58 µM, 0.5 µM, 0.158 µM, 0.05 µM and 0.0158 µM).

Total mRNA was extracted using the PureLink Pro 96 RNA Purification kit (Ambion), according to the manufacturer's instructions. cDNA was synthesized using M-MLT Reverse Transcriptase, random decamers RETROscript, RNase inhibitor (Ambion) and 100 mM dNTP set (Invitrogen, PCR Grade) according to the manufacturer's instruction. For gene expressions analysis, qPCR was performed using TaqMan Fast Advanced Master Mix (2x) (Ambion) in a duplex set up with TaqMan primer assays for the PD-L1 (Thermo Fisher Scientific; FAM-MGB Mm00452054-m1) and Gusb (Thermo Fisher Scientific; VIC-MGB-PL Mm01197698-m1). The relative PD-L1 mRNA expression level is shown in table 9 as % of residual PD-L1 expression in % of PBS control samples (PBS-treated cells). EC50 calculations were performed in GraphPad Prism6. The EC50 and maximum PD-L1 knockdown level is shown in table 13 as % of control (PBS) cells.

In Vivo Assay

C57BL/6J female mice (20-23 g; 5 mice per group) were injected s.c. with 5 mg/kg unconjugated oligonucleotides to mouse PD-L1 or 2.8 mg/kg GalNAc-conjugated oligonucleotides to mouse PD-L1. Three days later, the mice were injected i.v. with 10 mg/kg poly(I:C) (LWM, Invivogen). The mice were sacrificed 5 h after poly(I:C) injection and liver samples were placed in RNAlater (Thermo Fisher Scientific) for RNA extraction or frozen at dry ice for protein extraction.

Total mRNA was extracted from homogenized liver samples using the PureLink Pro 96 RNA Purification kit (Ambion), according to the manufacturer's instructions. cDNA was synthesized using M-MLT Reverse Transcriptase, random decamers RETROscript, RNase inhibitor (Ambion) and 100 mM dNTP set (Invitrogen, PCR Grade) according to the manufacturer's instruction. For gene expressions analysis, qPCR was performed using TaqMan® Fast Advanced Master Mix TaqMan Fast Advanced Master Mix (2x) (Ambion) in a duplex set up with TaqMan primer assays for the PD-L1 mRNA (Thermo Fisher Scientific; FAM-MGB Mm00452054-m1) and TBP (Thermo Fisher Scientific; VIC-MGB-PL Mm00446971_m1). The relative PD-L1 mRNA expression level is shown in table 13 as % of control samples from mice injected with saline and poly(I:C).

Figure 9:
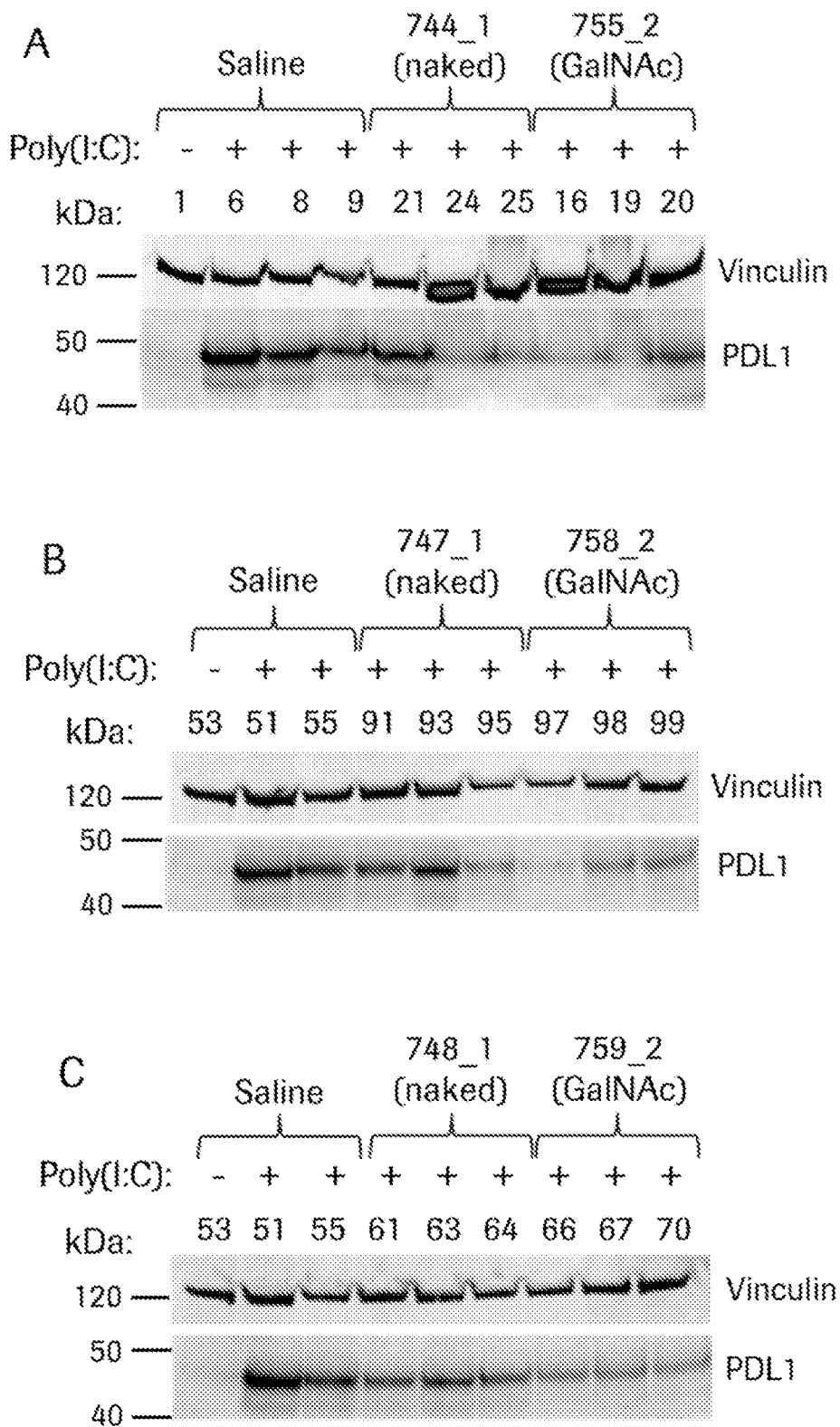
FIG. 9: Western blot detecting PD-L1 protein expression in liver from poly(IC) induced animals following treatment with saline and the indicated CMP ID NO's. Each blot shows a naked oligonucleotide versus a GalNAc conjugated version of the same oligonucleotide, blot A) CMP ID NO 744_1 and 755_2, B) CMP ID NO 747_1 and 758_2, C) CMP ID NO 748_1 and 759_2, D) CMP ID NO 752_1 and 763_2 and E) CMP ID NO 753_1 and 764_2. The upper band is the vinculin loading control, the lower band is the PD-L1 protein. The first lane in each blot show saline treated mice without Poly(IC) induction. These mice express very little PD-L protein.

Liver homogenates were prepared by homogenizing liver samples in 2 ml per 100 mg tissue T-PER® Tissue Protein Extraction Reagent (Thermo Fisher Scientific) mixed with 1x Halt Protease Inhibitor Cocktail, EDTA-Free (Thermo Fisher Scientific). Protein concentrations in liver homogenates were measured using Coomassie Plus (Bradford) Assay Reagent (Thermo Scientific) according to the manufacturer's instructions. Liver homogenates (40 µg protein) were separated on 4-12% Bis-Tris Plus polyacrylamide gels (Thermo Fisher Scientific) in 1xMOPS running buffer and transferred to nitrocellulose membranes using iBLOT Dry blotting system (Thermo Fisher Scientific) according to the manufacturer's instructions. Each blot was cut in to two parts horizontally at the 64 kDa band. Following blocking in TBS containing 5% skim milk and 0.05% Tween20, the membranes were incubated overnight at 4° C. with rabbit monoclonal anti-vinculin (Abcam cat. no. ab129002) diluted 1:10000 (upper membranes) or goat polyclonal anti-mPD-L1 (R&D Systems cat. no. AF1019) diluted 1:1000 (lower membranes) in TBS containing 5% skim milk and 0.05% Tween20. The membranes were washed in TBS containing 0.05% Tween20 and exposed for 1 h at room temperature to HRP-conjugated swine anti-rabbit IgG (DAKO) diluted 1:3000 (upper membranes) or HRP-conjugated rabbit anti-goat IgG (DAKO) diluted 1:2000 in TBS containing 5% skim milk and 0.05% Tween20. Following washing of the membranes, the reactivity was detected using ECL select (Amersham GE Healthcare). For each group of mice treated with oligonucleotides, the intensity of the PD-L1 bands in relation to vinculin bands were evaluated by comparison with the PD-L1/vinculin band intensities of mice injected with saline and poly(I:C) (control). Results are shown in table 13, and western blots with pairs of naked and conjugated oligonucleotides are shown in FIG. 9 A-E.

tigated in hepatocytes and non-parenchymal cells isolated from poly(I:C) induced mice.

C57BL/6J female mice (n=3 per group) were injected s.c. with 5 mg/kg unconjugated oligonucleotide (748_1) or 7 mg/kg GalNAc-conjugated oligonucleotides (759_2) targeting mouse PD-L1 mRNA. Two days later, the mice were injected i.p. with 15 mg/kg poly(I:C) (LWM, Invivogen). The mice were anesthesized 18-20 h after poly(I:C) injection and the liver was perfused at a flow rate of 7 ml per min

TABLE 13

In vitro and in vivo efficacy of oligonucleotides to mouse PD-L1

| CMP ID NO | Compound CMP | Max Inhibition (% of PBS) | EC50 (µM) | PD-L1 mRNA (% of control) | PD-L1 protein (relative to control) | SEQ ID NO |
|---|---|---|---|---|---|---|
| 744_1 | AGTttacattttcTGC | 9.1 | 0.56 | 86 | ++ | 744 |
| 746_1 | CACctttaaaaccCCA | 5.0 | 0.46 | 181 | nd | 746 |
| 747_1 | TCCtttataatcaCAC | 4.4 | 0.52 | 104 | ++ | 747 |
| 748_1 | ACGgtattttcacAGG | 1.8 | 0.26 | 102 | +++ | 748 |
| 749_1 | GACactacaatgaGGA | 7.6 | 1.21 | 104 | nd | 749 |
| 750_1 | TGGtttttaggacTGT | 12.4 | 0.74 | 84 | nd | 750 |
| 751_1 | CGAcaaattctatCCT | 9.9 | 0.69 | 112 | nd | 751 |
| 752_1 | TGAatacaatgcTAC | 10.5 | 1.11 | 142 | +++ | 752 |
| 753_1 | TCGttgggtaaatTTA | 5.7 | 0.53 | 116 | +++ | 753 |
| 754_1 | TGCtttataaatgGTG | 5.2 | 0.35 | 98 | nd | 754 |
| 755_2 | 5'-GN2-C6-caAGTttacattttcTGC | nd | nd | 58 | + | 744 |
| 757_2 | 5'-GN2-C6-caCACctttaaaaccCCA | nd | nd | 62 | nd | 746 |
| 758_2 | 5'-GN2-C6-caTCCtttataatcaCAC | nd | nd | 53 | + | 747 |
| 759_2 | 5'-GN2-C6-caACGgtattttcacAGG | nd | nd | 66 | + | 748 |
| 760_2 | 5'-GN2-C6-caGACactacaatgaGGA | nd | nd | 101 | nd | 749 |
| 761_2 | 5'-GN2-C6-caTGGtttttaggacTGT | nd | nd | 99 | nd | 750 |
| 762_2 | 5'-GN2-C6-caCGAcaaattctatCCT | nd | nd | 84 | nd | 751 |
| 763_2 | 5'-GN2-C6-caTGAatacaatgcTAC | nd | nd | 93 | +++ | 752 |
| 764_2 | 5'-GN2-C6-caTCGttgggtaaatTTA | nd | nd | 53 | + | 753 |
| 765_2 | 5'-GN2-C6-caTGCtttataaatgGTG | nd | nd | 106 | nd | 754 |

+++: similar to PD-L1/vinculin band intensity of control;
++: weaker than PD-L1/vinculin band intensity of control;
+: much weaker than PD-L1/vinculin band intensity of control;
nd = not determined.

From the data in table 13 it can be seen that GalNAc conjugation of the oligonucleotides clearly improves the in vivo PD-L1 reduction. The reduction of mRNA generally correlates with a reduction in PD-L1 protein. Except for CMP ID NO: 754_1, a low in vitro EC50 value generally reflects a good in vivo PD-L1 mRNA reduction once the oligonucleotide is conjugated to GalNAc.

Example 4—In Vivo PK/PD in Sorted Hepatocytes and Non-Parenchymal Cells from Poly(I:C) Induced Mice The distribution of naked and GalNAc conjugated oligonucleotides as well as PD-L1 mRNA reduction was investhrough the vena cava using Hank's balanced salt solution containing 15 mM Hepes and 0.38 mM EGTA for 5 min followed by collagenase solution (Hank's balanced salt solution containing 0.17 mg/ml Collagenase type 2 (Worthington 4176), 0.03% BSA, 3.2 mM $CaCl_2$ and 1.6 g/l $NaHCO_3$) for 12 min. Following perfusion, the liver was removed and the liver capsule was opened, the liver suspension was filtered through 70 µm cell strainer using William E medium and an aliquot of the cell suspension (=mixed liver cells) was removed for later analysis. The rest of the cell suspension was centrifuged for 3 min at 50×g. The supernatant was collected for later purification of non-parenchymal cells. The pellet was resuspended in 25 ml William E medium (Sigma cat. no. W1878 complemented with 1× Pen/Strep, 2 mM L-glutamine and 10% FBS (ATCC #30-2030)), mixed with 25 ml William E medium containing 90% percoll and the hepatocytes were precipitated by centrifugation at 50×g for 10 min. Following 2× washing in William E medium, the precipitated hepatocytes were resuspended in Williams E medium. The supernatant containing non-parenchymal cells was centrifuged at 500×g 7 min and the cells were resuspended in 4 ml RPMI medium and centrifugated through two layers of percoll (25% and 50% percoll) at 1800×g for 30 min. Following collection of the non-parenchymal cells between the two percoll layers, the cells were washed and resuspended in RPMI medium.

Total mRNA was extracted from purified hepatocytes, non-parenchymal cells and total liver suspension (non-fractionated liver cells) using the PureLink Pro 96 RNA Purification kit (Ambion), according to the manufacturer's instructions. cDNA was synthesized using M-MLT Reverse Transcriptase, random decamers RETROscript, RNase inhibitor (Ambion) and 100 mM dNTP set (Invitrogen, PCR Grade) according to the manufacturer's instruction. For gene expressions analysis, qPCR was performed using TaqMan Fast Advanced Master Mix (2×) (Ambion) in a duplex set up with TaqMan primer assays for the PD-L1 (Thermo Fisher Scientific; FAM-MGB Mm00452054-m1) and TBP (Thermo Fisher Scientific; VIC-MGB-PL Mm00446971_m1). The relative PD-L1 mRNA expression level is shown in table 10 as % of control samples from mice injected with saline and poly(I:C).

Oligonucleotide content analysis was performed using ELISA employing a biotinylated capture probe with the sequence 5'-TACCGT-s-Bio-3' and a digoxigenin conjugated detection probe with the sequence 5'-DIG-C12-S1-CCTGTG-3'. The probes consisted of only LNA with a phosphodiester backbone. Liver samples (approximately 50 mg) were homogenized in 1.4 mL MagNa pure lysis buffer (Roche Cat. No 03604721001) in a 2 mL Eppendorf tube containing one 5 mm stainless steel bead. Samples were homogenized on Retsch MM400 homogenizer (Merck Eurolab) until a uniform lysate was obtained. The samples were incubated for 30 min at room temperature. Standards were generated by spiking the unconjugated antisense oligonucleotide compound (CMP ID NO 748_1) in defined concentrations into an untreated liver sample and processing them as the samples. Spike-in concentrations are chosen to match the expected sample oligo content (within ~10-fold).

The homogenized samples were diluted a minimum of 10 times in 5×SSCT buffer (750 mM NaCl, and 75 mM sodium citrate, containing 0.05% (v/v) Tween-20, pH 7.0) and a dilution series of 6 times 2 fold dilutions using capture-detection solution (35 nM capture probe and 35 nM detection probe in 5×SSCT buffer) were made and incubated for 30 min at room temperature. The samples were transferred to a 96 well streptavidin coated plate (Nunc Cat. No. 436014) with 100 µL in each well. The plates were incubated for 1 hour at room temperature with gentle agitation. Wash three times with 2×SSCT buffer and add 100 µL anti-DIG-AP Fab fragment (Roche Applied Science, Cat. No. 11 093 274 910) diluted 1:4000 in PBST (Phosphate buffered saline, containing 0.05% (v/v) Tween-20, pH 7.2, freshly made) was added to each well and incubated for 1 hour at room temperature under gentle agitation. Wash three times with 2×SSCT buffer and add 100 µL of alkaline phosphatase (AP) substrate solution (Blue Phos Substrate, KPL product code 50-88-00, freshly prepared). The intensity of the color was measured spectrophotometrically at 615 nm after 30 minutes incubation with gentle agitation. Raw data were exported from the readers (Gen5 2.0 software) to excel format and further analyzed in excel. Standard curves were generated using GraphPad Prism 6 software and a logistic 4PL regression model.

TABLE 14

PD-L1 expression and oligo content in total liver suspension, hepatocytes and non-parenchymal cells from poly(I:C) mice treated with unconjugated and GalNAc-conjugated oligonucleotides, n = 3.

| Cell type | CMP ID no | PD-L1 expression (% of saline- poly(I:C)) | | oligo content (ng/$10^5$ cells) | |
|---|---|---|---|---|---|
| | | Avg | SD | Avg | SD |
| Total liver | 748_1 | 31 | 12.4 | 2.3 | 0.3 |
| | 759_2 | 28 | 5.3 | 8.3 | 1.1 |
| Hepatocytes | 748_1 | 33 | 8.0 | 5.1 | 3.7 |
| | 759_2 | 7 | 1.0 | 43.8 | 18.9 |
| Non-parenchymal cells | 748_1 | 31 | 10.1 | 2.2 | 0.7 |
| | 759_2 | 66 | 1.6 | 1.7 | 0.9 |

The results show that naked (CMP ID NO: 748_1) and conjugated (CMP ID NO: 759_2) oligonucleotide reduce PD-L1 mRNA equally well in total liver cells. In isolated hepatocytes, the effect of the conjugated oligonucleotide is almost 5 fold stronger than the effect of the naked oligonucleotide, while naked oligonucleotides showed two fold stronger effect than GalNAc-conjugated oligonucleotides in non-parenchymal cells. In hepatocytes and non-parenchymal cells the reduction of PD-L1 mRNA expression correlates to some extent with the oligonucleotide content in these cell types.

Example 5—In Vivo PD-L1 Knock Down in AAV/HBV Mice Using Naked and GalNAc Conjugated PD-L1 Antisense Oligonucleotides In the present study AAV/HBV mice were treated with naked or conjugated to GalNAc PD-L1 antisense oligonucleotides, and the PD-L1 mRNA expression and HBV gene expression was evaluated in the liver.

Female HLA-A2/DR1 mice 5-8 weeks old (5 animals pr. group) were pretreated at week −1 vehicle (saline), naked PD-L1 antisense oligonucleotides (CMP ID NO 752_1 at 5 mg/kg s.c.) and GalNAc PD-L1 antisense oligonucleotides (CMP ID NO 763_2 at 7 mg/kg s.c.), these doses correspond to equimolar concentrations of the oligonucleotides. The mice were transduced by $5 \times 10^{10}$ vg AAV-HBV at week 0 (for further details see description AAV/HBV mouse model in the Materials and Methods section). From W1 post AAV-HBV transduction to W4, mice received 4 additional s.c. injections of PD-L1 oligonucleotides or vehicle (saline solution), given one week apart.

Blood samples were taken one week before transduction and one week after each injection.

Mice were sacrificed two weeks after the last injections and their liver were removed following PBS perfusion. The liver was cut in smaller pieces and directly frozen.

To measure HBV gene expression, DNA was extracted from serum with Qiagen Biorobot using the QIAamp One for all nucleic acid kit, Cat. #965672, serum was diluted 1:20 dilution in PBS a total of 100 µl was lysed in 200 ul Buffer AL. DNA was eluted from the kit in 100 µl.

For the Real-Time qPCR the TaqMan Gene Expression Master Mix (cat. #4369016, Applied Biosystems) was used together with a primer mix prepared by adding 1:1:0.5 of the following primers F3_core, R3_core, P3_core (Integrated DNA Technologies, all reconstituted at 100 uM each)

```
Forward (F3_core):
                                         (SEQ ID NO: 784)
CTG TGC TTT GGG TGG CTT T Reverse (R3_core):
                                         (SEQ ID NO: 785)
AAG GAA AGA ACT CAG AAG GCA AAA Probe (P3_core):
                                         (SEQ ID NO: 786)
56-FAM-AGC TCC AAA/ZEN/TTC TTT ATA AGG GTC GAT GTC
CAT G-3IABkFQ
```

A standard curve using HBV plasmid (Genotype D, GTD) was prepared using 10-fold dilutions starting with $1\times10^9$ copies/µl down to 1 copy/µl and used in 5 µl per reaction.

For each reaction 10 µl Gene Expression Master Mix, 4.5 µl water, 0.5 µl Primer mix and 5 µl sample or standard was added and the qPCR was run.

For the analysis the copy number/ml/well was calculated using the standard curve. The results are shown in table 15.

PD-L1 mRNA expression was measured using qPCR.

mRNA was extracted from frozen liver pieces that were added to 2 ml tubes containing ceramic beads (Lysing Matrix D tubes, 116913500, mpbio) and 1 ml of Trizol.

The liver piece was homogenized using the Precellys Tissue Disruptor. 200 µl Chloroform was added to the homogenate, vortexed and centrifuged at 4° C. for 20 min at 10000 rpm. The RNA containing clear phase (around 500 ul) was transferred into a fresh tube and the same volume of 70% EtOH was added. After mixing well the solution was transferred onto a RNeasy spin column and RNA was further extracted following the RNeasy Kit's manual RNeasy Mini Kit, cat. #74104, Qiagen (including the RNA digestion RNase-free DNase Set, cat. #79254). Elution in 50 µl H$_2$O. The final RNA concentration was measured and adjusted to 100 ng/ul for all samples.

The qPCR was conducted on 7.5 µl RNA using the Taqman RNA-to-ct 1-step Kit, cat. #4392938, Thermo Fisher according to the manufactures instructions. The fprimer mixed used contained PD-L1_1-3 (Primer number Mm00452054_m1, Mm03048247_m1 and Mm03048248_m1) and endogenous controls (ATCB Mm00607939_s1, CANX Mm00500330_m1, YWHAZ Mm03950126_s1 and GUSB Mm01197698_m1)

Data were analysed using the 2^–ddct method. The mean of all four endogenous controls was used to calculate dct values. The PD-L1 expression relative to mean of the endogenous controls and in % of saline

TABLE 15

PD-L1 mRNA expression and HBV DNA in AAV/HBV mice treated with unconjugated and GalNAc-conjugated oligonucleotides, n = 5.

|  | CMP ID no | PD-L1 mRNA expression (% of saline) Avg | PD-L1 mRNA expression (% of saline) SD | HBV DNA expression (% of saline) Avg | HBV DNA expression (% of saline) SD |
|---|---|---|---|---|---|
| Naked | 752_1 | 55 | 35 | 72 | 16 |
| GalNAc conjugated | 763_2 | 34 | 3 | 79 | 9 |

From these results it can be seen that both naked and GalNAc conjugated oligonucleotides are capable of reducing PD-L1 mRNA expression in the liver of an AAV/HBV mouse, with the GalNAc conjugated oligonucleotide being somewhat better. Both oligonucleotides also resulted in some reduction in HBV DNA in the serum.

Example 6—In Vivo Effect on T Cell Response in AAV/HBV Mice

In the present study AAV/HBV mice from Pasteur were treated with an antibody or antisense oligonucleotides targeting PD-L1. The antisense oligonucleotides were either naked or conjugated to GalNAc. During the treatment the animals were immunized with a DNA vaccine against HBs and HBc antigens (see Materials and Methods section) to ensure efficient T cell priming by the antigen presenting cells. It was evaluated how the treatment affected the cell population in liver and spleen, as well as the PD-L1 expression on these populations and whether a HBV specific T cell response could be identified.

Treatment Protocol:

Female HLA-A2/DR1 mice were treated according to the protocols below. The study was conducted in two separate sub-studies, with slight differences in the administration regimens as indicated in Table 16 and 17 below.

DNA vaccine and anti-PD-L1 antibody was administered as described in the materials and method section. The antisense oligonucleotides used were CMP ID NO 748_1 (naked) at 5 mg/kg and CMP ID NO: 759_2 (GalNAc conjugated) at 7 mg/kg, both where administered as subcutaneous injections (s.c.).

TABLE 16

AAV/HBV mouse treatment protocol with DNA vaccine and DNA vaccine + anti-PD-L1 antibody, 6 mice in each group

| Day | Vehicle (Group 10) | DNA vaccine (Group 11) | DNA vaccine + anti-PDL-1 Ab (Group 13) |
|---|---|---|---|
| 0 |  | AAV/HBV |  |
| 29* |  | Animal randomization |  |
| 34 | Saline + Isotype | — | Ab |
| 41 | Saline + Isotype | — | Ab |
| 48 | Saline + Isotype | — | Ab |
| 50 | — | CaTx | CaTx |
| 55* | PBS + Isotype | DNA | DNA + Ab |
| 62 | Saline + Isotype | — | Ab |
| 69 | PBS + Isotype | DNA | DNA + Ab |
| 76* | Saline + Isotype | — | Ab |
| 83 | Saline + Isotype | — | Ab |
| 97* |  | Sacrifice |  |

Isotype = mouse IgG control Ab,
CaTx = cardiotoxine,
DNA = DNA vaccine,
Ab = anti-PD-L1 Ab and
*= serum collection

TABLE 17

AAV/HBV mouse treatment protocol with DNA vaccine and DNA vaccine + naked or conjugated PD-L1 oligonucleotide (ASO), 7 mice in each group

| Day | Vehicle (Group 1) | DNA vaccine (Group 2) | DNA vaccine + PDL-1 ASO (Group 7) | DNA vaccine + GN-PDL-1 ASO (Group 8) |
|---|---|---|---|---|
| 0 |  | AAV/HBV |  |  |
| 29* |  | Animal randomization |  |  |
| 39 | Saline | Saline |  |  |
| 41 |  | Saline | ASO | GN-ASO |
| 46 | Saline | Saline |  |  |
| 49 |  | Saline | ASO | GN-ASO |

TABLE 17-continued

AAV/HBV mouse treatment protocol with DNA vaccine
and DNA vaccine + naked or conjugated PD-L1
oligonucleotide (ASO), 7 mice in each group

| Day | Vehicle (Group 1) | DNA vaccine (Group 2) | DNA vaccine + PDL-1 ASO (Group 7) | DNA vaccine + GN-PDL-1 ASO (Group 8) |
|---|---|---|---|---|
| 53 | Saline | Saline | | |
| 55 | CaTx | CaTx | CaTx | CaTx |
| 56 | | Saline | ASO | GN-ASO |
| 59 | PBS + Saline | DNA + PBS | DNA | DNA |
| 62* | | Saline | ASO | GN-ASO |
| 67 | Saline | Saline | | |
| 70 | | Saline | ASO | GN-ASO |
| 74 | PBS + Saline | DNA + PBS | DNA | DNA |
| 77 | | Saline | ASO | GN-ASO |
| 81 | Saline | Saline | | |
| 84* | | Saline | ASO | GN-ASO |
| 88 | Saline | Saline | | |
| 91 | | Saline | ASO | GN-ASO |
| 102 | | | Sacrifice | |

DNA = DNA vaccine,
CaTx = cardiotoxine,
Ab = anti-PD-L1 Ab,
ASO = naked PDL-1 oligonucleotide,
GN-ASO = GalNAc-PDL-1 oligonucleotide and
*= serum collection At the time of sacrifice blood, spleen and liver mononuclear cells of each mouse from each group were collected and depleted of red blood cells (Lysing Buffer, BD biosciences, 555899). The liver mononuclear cells required a specific preparation as described in the materials and method section.

Cell Populations:

In the liver the cell population was analyzed by surface labeling on liver mononuclear cells (see materials and methods) using cytometry.

Figure 10:
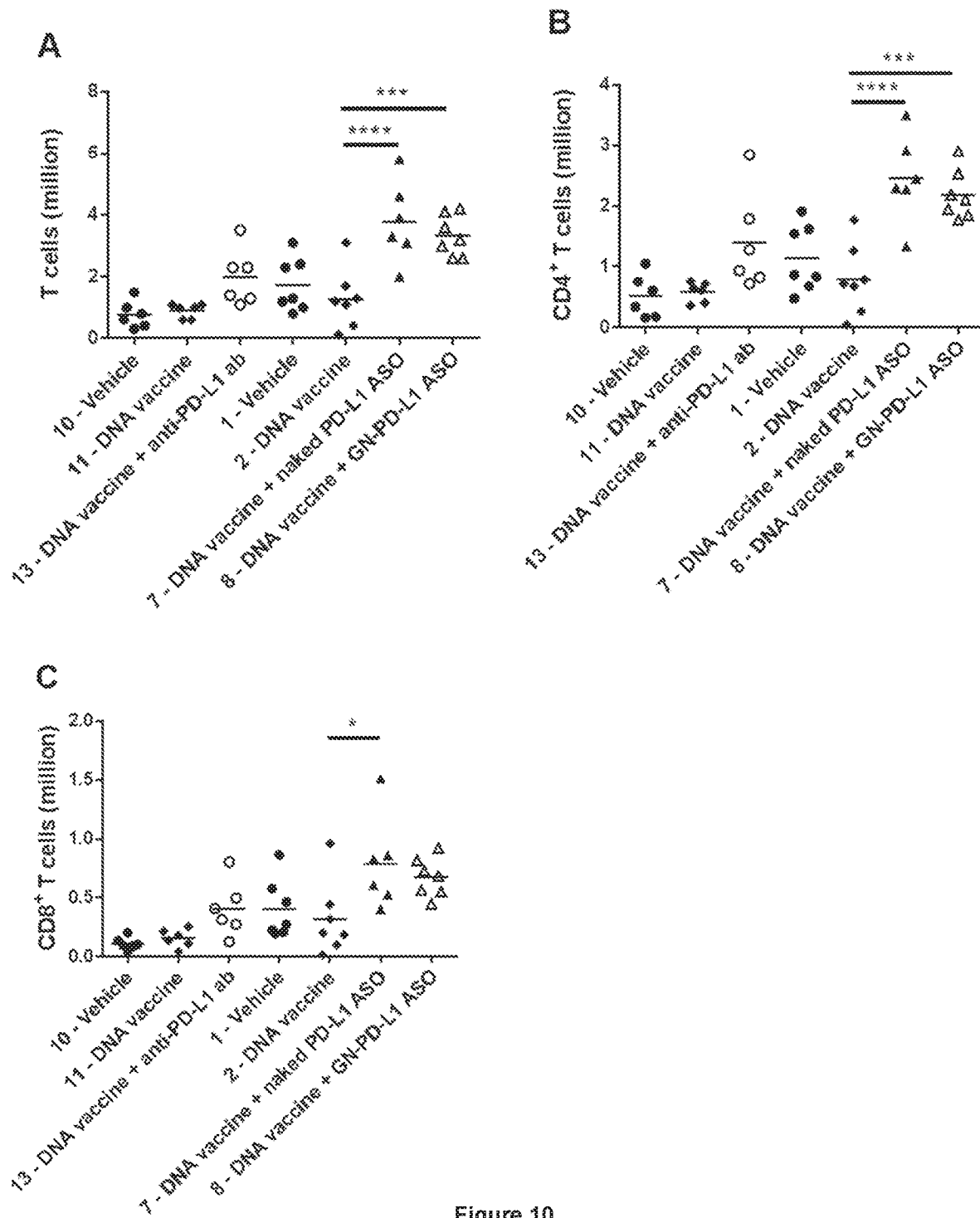
FIG. 10: Population of mononuclear cells in the liver after treatment with ● vehicle (group 10 and 1), ♦ DNA vaccine (group 11 and 2), ○ anti-PD-L1 antibody (group 12), ▲ naked PD-L1 ASO+DNA vaccine (group 7) or Δ GalNAc conjugated PD-L1 ASO+DNA vaccine (group 8), for each group the individual animals are represented and the average is indicated by the vertical line for each group (see table 18). Statistical significance between the DNA vaccine group and the three treatment groups has been assessed and if present it is indicated by * between the groups (*=P<0.05, *=P<0.001 and **=P<0.0001). A) represents the number of T cells in the liver following treatment. B) represents the fraction of CD4+ T cells and C) represents the fraction of CD8+ T cells.
Figure 10:
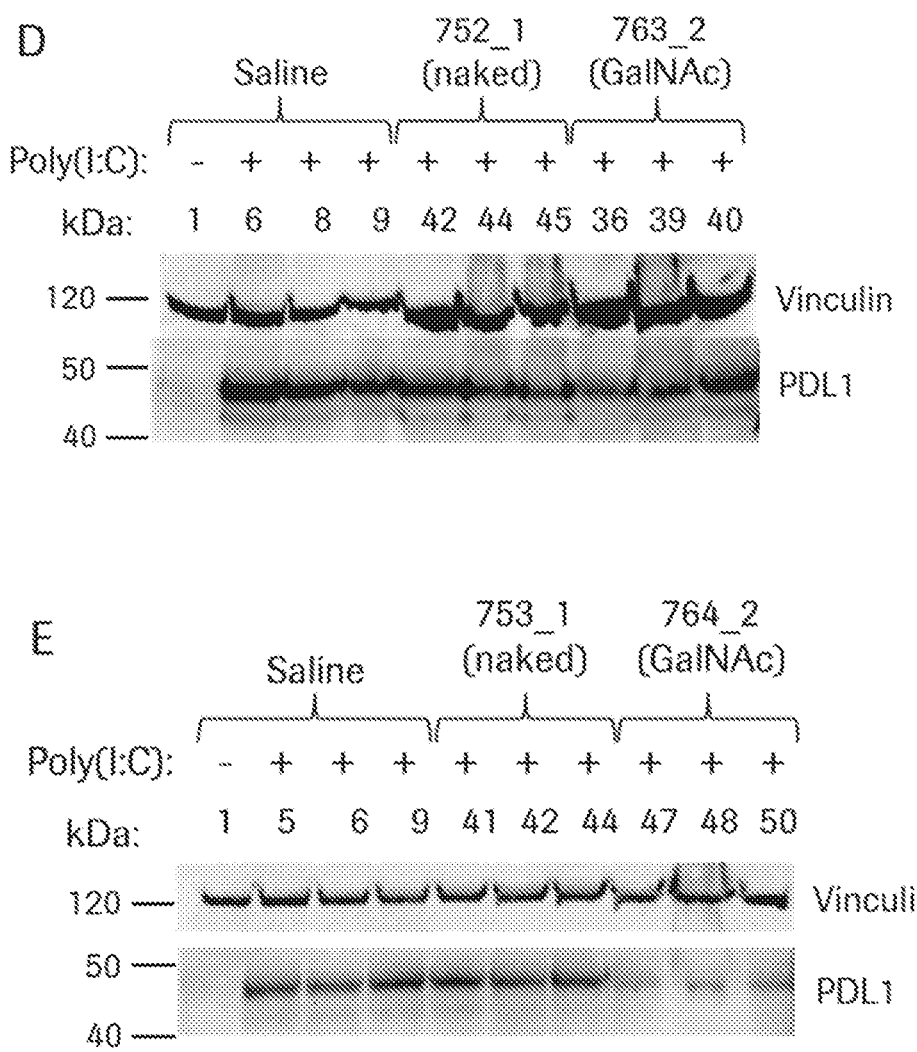

No significant changes were noticed in the frequencies of NK cells in the spleen and liver of treated mice compared to control groups (i.e. vehicle and DNA-immunized groups). Table 18 show that in the liver, groups treated with naked PD-L1 oligonucleotide (CMP ID NO 748_1) and GalNAc conjugated PD-L1 oligonucleotide (CMP ID NO: 759_2) had a significant increase in T cell numbers compared to either control groups (i.e. vehicle and DNA-immunized groups) also presented in FIG. 10 A. This increase was due to an increase in both CD4+ and CD8+ T cell populations (Table 18 and FIGS. 10B and 10C, respectively).

TABLE 18

T-cells in the liver following treatment in millions of cells

| | T-cells (millinons) | | CD4+ T-cells (millions) | | CD8+ T-cells (millions) | |
|---|---|---|---|---|---|---|
| | Avg | Std | Avg | Std | Avg | Std |
| Vehicle (Group 1) | 0.77 | 0.44 | 0.51 | 0.35 | 0.11 | 0.05 |
| DNA vaccine (Group 2) | 0.90 | 0.24 | 0.58 | 0.16 | 0.16 | 0.08 |
| DNA vaccine + anti-PD-L1 Ab (Group 13) | 1.98 | 0.90 | 1.40 | 0.81 | 0.41 | 0.23 |
| Vehicle (Group 10) | 1.73 | 0.87 | 1.13 | 0.55 | 0.40 | 0.25 |
| DNA vaccine (Group 11) | 1.27 | 0.97 | 0.79 | 0.58 | 0.32 | 0.32 |
| DNA vaccine + PD-L1 ASO (Group 7) | 3.78 | 1.31 | 2.46 | 0.72 | 0.79 | 0.39 |
| DNA vaccine + GN-PD-L1 ASO (Group 8) | 3.33 | 0.66 | 2.18 | 0.40 | 0.67 | 0.17 |

PD-L1 Expression:

The expression of PD-L1 protein was evaluated on macrophages, B and T cells from spleen and liver at time of sacrifice. The presence of PD-L1 antibody in the surface labeling antibody mix (see materials and methods) allowed quantification of PD-L1 expressing cells by cytometry.

In spleen, no significant difference between the treatments was observed in the % of macrophages, B cells and CD4+ T cells expressing PD-L1. The % of the CD8+ T cells expressing PD-L1 was lower in mice treated with naked PD-L1 oligonucleotide (CMP ID NO 748_1) and GalNAc conjugated PD-L1 oligonucleotide (CMP ID NO: 759_2) when compared to the other treatments (data not shown).

Figure 11:
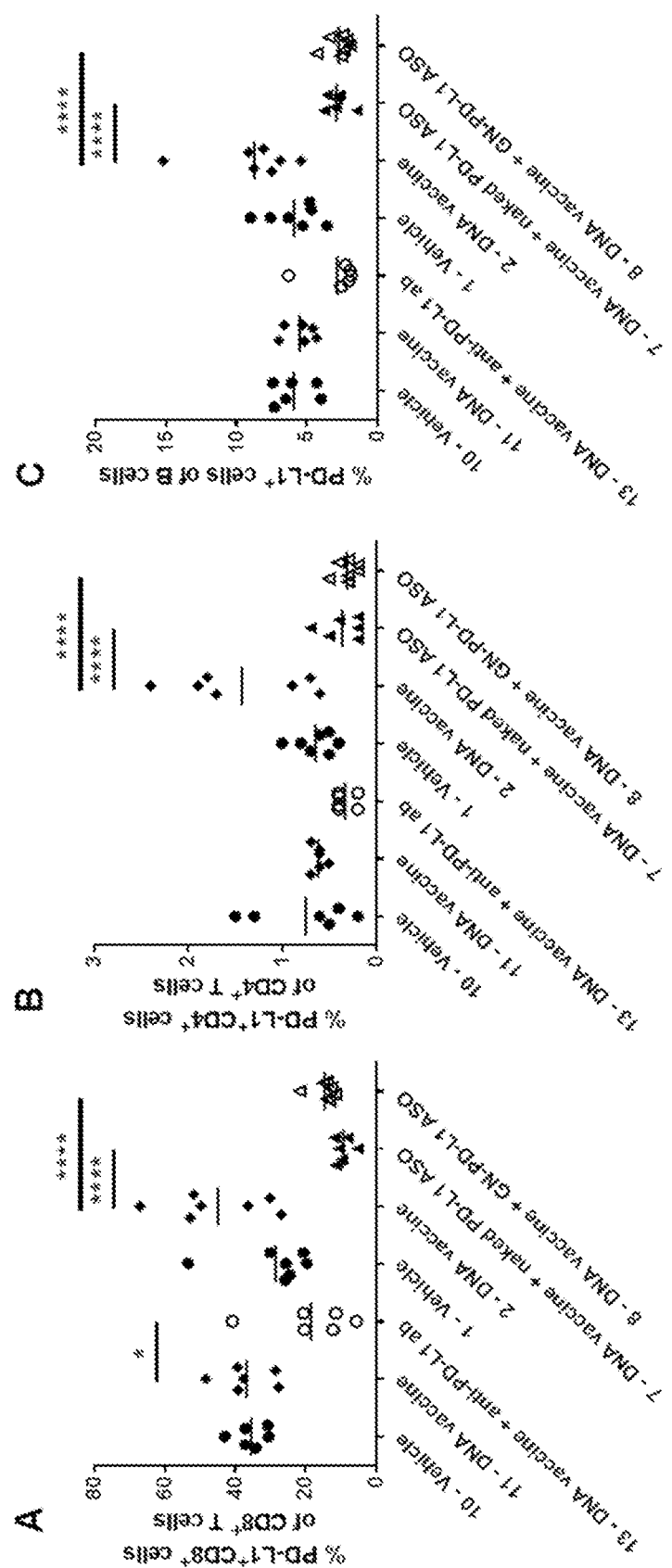
FIG. 11: Modulation of PD-L1 positive cells in the liver after treatment with ● vehicle (group 10 and 1), ♦ DNA vaccine (group 11 and 2), ○ anti-PD-L1 antibody (group 12), ▲ naked PD-L1 ASO+DNA vaccine (group 7) or Δ GalNAc conjugated PD-L1 ASO+DNA vaccine (group 8), for each group the individual animals are represented and the average is indicated by the vertical line for each group (see table 19). Statistical significance between the DNA vaccine group and the three treatment groups has been assessed and if present it is indicated by * between the groups (*=P<0.05 and ****=P<0.0001). A) represents the percentage of CD8+ T cells which express PD-L1 in the liver following treatment. B) represents the percentage of CD4+ T cells which express PD-L1 in the liver following treatment and C) represents the percentage of B cells which express PD-L1 in the liver following treatment.

In liver, PD-L1 was expressed mainly on CD8+ T cells with a mean frequency of 32% and 41% in the control groups (the two vehicle and DNA vaccination groups combined, respectively, FIG. 11A). Treatment with naked PD-L1 oligonucleotide or GalNAc PD-L1 oligonucleotide resulted in a decrease of the frequency of CD8+ T cells expressing PD-L1 (see table 19 FIG. 11A). Significant differences in the % of cells expressing PD-L1 were also noticed for B cells and CD4+ T-cells after ASO treatment, although these cell types express significantly less PD-L1 than the CD8+ T cells (see table 19 and FIGS. 11B and C). Treatment with anti-PD-L1 Ab, also resulted in an apparent decrease in the PD-L1 expression in all cell types. It is, however, possible that this decrease is due to partly blockage of the PD-L1 epitope by the anti-PD-L1 antibody used for treatment, so that the PD-L1 detection antibody in the surface labeling antibody mix is prevented from binding to PD-L1. Therefore what appears to be a PD-L1 down regulation by the anti-PD-L1 antibody used for treatment may be the result of epitope competition between the treatment antibody and the detection antibody.

TABLE 19

% of liver cell population with PD-L1 expression

| | % of CD8+ T-cells | | % of CD4+ T-cells | | % of B-cells | |
|---|---|---|---|---|---|---|
| | Avg | Std | Avg | Std | Avg | Std |
| Vehicle (Group 10) | 35.5 | 4.7 | 0.75 | 0.52 | 5.9 | 1.5 |
| DNA vaccine (Group 11) | 36.8 | 7.7 | 0.61 | 0.08 | 5.5 | 1.1 |
| DNA vaccine + anti-PD-L1 Ab (Group 13) | 18.6 | 12.3 | 0.33 | 0.10 | 2.9 | 1.7 |
| Vehicle (Group 1) | 28.5 | 11.5 | 0.64 | 0.21 | 5.9 | 1.7 |
| DNA vaccine (Group 2) | 44.9 | 14.4 | 1.43 | 0.69 | 8.7 | 3.1 |
| DNA vaccine + PD-L1 ASO (Group 7) | 9.6 | 2.4 | 0.37 | 0.21 | 2.9 | 0.8 |
| DNA vaccine + GN-PD-L1 ASO Group 8) | 14.6 | 3.3 | 0.31 | 0.11 | 2.8 | 0.8 |

HBV Specific T Cell Response:

NK cells and CD4+ and CD8+ T cells producing pro-inflammatory cytokines were detected using the intracellular cytokine staining assays (see Materials and Methods section) detecting IFNγ and TNFα production.

In the spleen no NK cells and few CD4+ T cells secreting IFNγ- and TNFα were detectable (frequency <0.1%) at sacrifice. IFNγ-producing CD8+ T cells targeting the two HBV antigens were detected in mice treated with naked PD-L1 oligonucleotide or GalNAc PD-L1 oligonucleotide as well as in mice from this study which received only DNA vaccine (data not shown).

Figure 12:
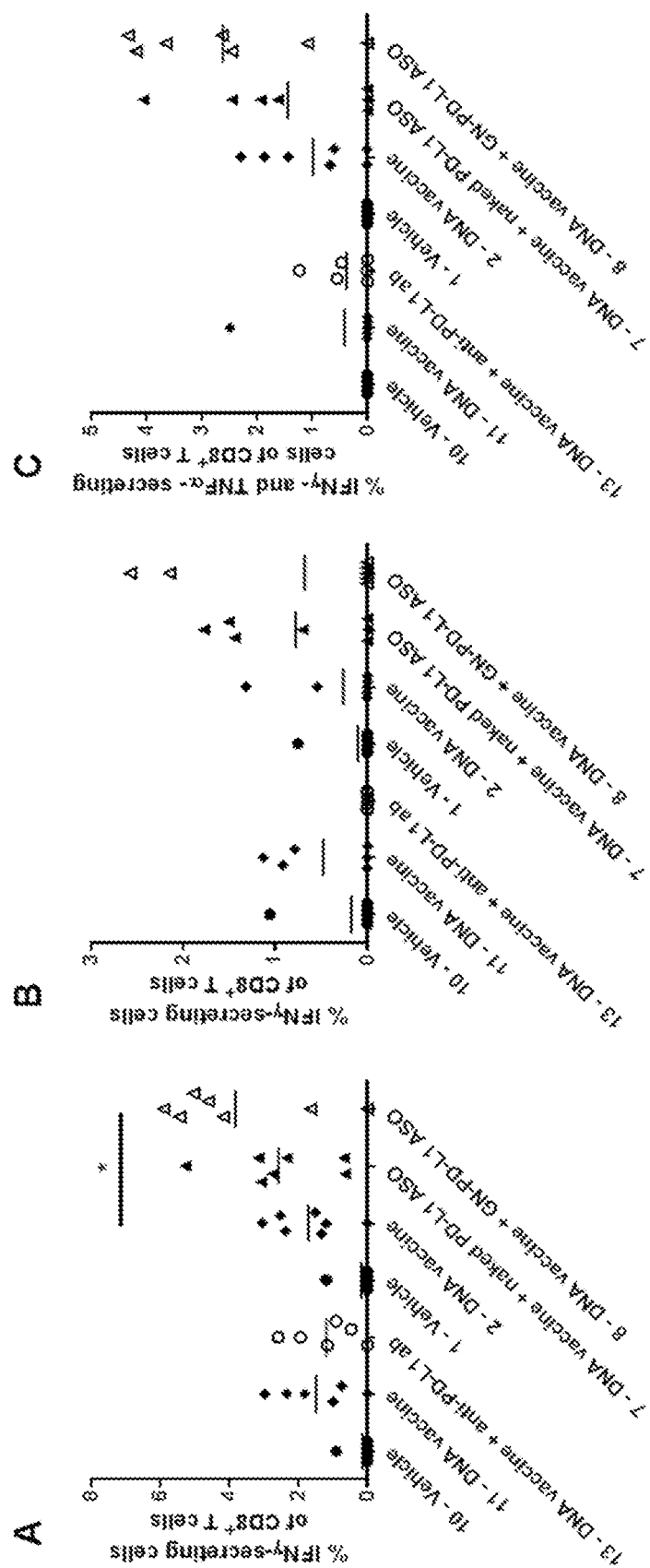
FIG. 12: HBV antigen specific CD8+ cytokine secreting cells in the liver after treatment with ● vehicle (group 10 and 1), ♦ DNA vaccine (group 11 and 2), ○ anti-PD-L1 antibody (group 12), ▲ naked PD-L1 ASO+DNA vaccine (group 7) or Δ GalNAc conjugated PD-L1 ASO+DNA vaccine (group 8), for each group the individual animals are represented and the average is indicated by the vertical line for each group (see table 20). Statistical significance between the DNA vaccine group and the three treatment groups has been assessed and if present it is indicated by * between the groups (*=P<0.05). A) represents the percentage of IFN-γ secreting CD8+ T cells in the liver which are specific towards HBV PreS2+S antigen following treatment. B) represents the percentage of IFN-γ secreting CD8+ T cells in the liver which are specific towards HBV core antigen following treatment and C) represents the percentage of IFN-γ and TNF-α secreting CD8+ T cells in the liver which are specific towards HBV PreS2+S antigen following treatment.

In the livers of DNA-immunized HBV-carrier mice, no IFNγ-producing NK cells were detected at sacrifice, whereas IFNγ-secreting CD4+ T cells specific for Core or for S2+S were detected in the liver of a few DNA-immunized mice at a low frequency (<0.4%, data not shown). HBV S2+S-specific CD8+ T cells producing IFNγ were detected in the majority of DNA-immunized mice. The frequency of IFNγ-secreting CD8+ T cells increased in mice treated with combination of DNA vaccine and naked PD-L1 oligonucleotide or GalNAc PD-L1 oligonucleotide, whereas treatment with anti-PD-L1 antibody did not add any apparent additional effect to the DNA vaccination (FIG. 12). IFNγ-producing CD8+ T cells targeting the envelope and core antigens were detected in most DNA-immunized groups (except anti-PD-L1 antibody) (FIG. 12B). Most of the S2-S specific T cells produced both IFNγ and TNFα (FIG. 12C). The results are also shown in Table 20.

TABLE 20

% of HBV antigen (S2-S or core) specific CD8+ T cells from total IFNγ or IFNγ + TNFα cell population

|  | PreS2-S specific T cells (% of IFNγ cells) | | Core specific T cells (% of IFNγ cells) | | S2-S specific T cells (% of IFNγ + TNFα) | |
| --- | --- | --- | --- | --- | --- | --- |
|  | Avg | Std | Avg | Std | Avg | Std |
| Vehicle (Group 10) | 0.15 | 0.37 | 0.18 | 0.43 | 0.00 | 0.00 |
| DNA vaccine (Group 11) | 1.48 | 1.10 | 0.47 | 0.53 | 0.42 | 1.02 |
| DNA vaccine + anti-PDL-1 Ab | 1.18 | 0.95 | 0 | 0 | 0.38 | 0.49 |
| Vehicle (Group 1) | 0.17 | 0.45 | 0.11 | 0.28 | 0.00 | 0.00 |
| DNA vaccine (Group 2) | 1.70 | 1.02 | 0.27 | 0.51 | 0.98 | 0.90 |
| DNA vaccine + PDL-1 ASO | 2.56 | 1.60 | 0.78 | 0.80 | 1.44 | 1.55 |
| DNA vaccine + GN-PDL-1 ASO | 3.83 | 2.18 | 0.68 | 1.16 | 2.62 | 1.62 |

Example 7—In Vivo Effect on HBV Antigen and HBV DNA in the Serum of AAV/HBV Mice In the present study AAV/HBV mice from Shanghai (see Materials and Methods section) were treated with the GalNAc conjugated PD-L1 antisense oligonucleotide CMP ID NO 759_2.

It was evaluated how the treatment affected the HBe and HBs antigens and HBV DNA levels in the serum compared to vehicle treated animals.

Figure 13:
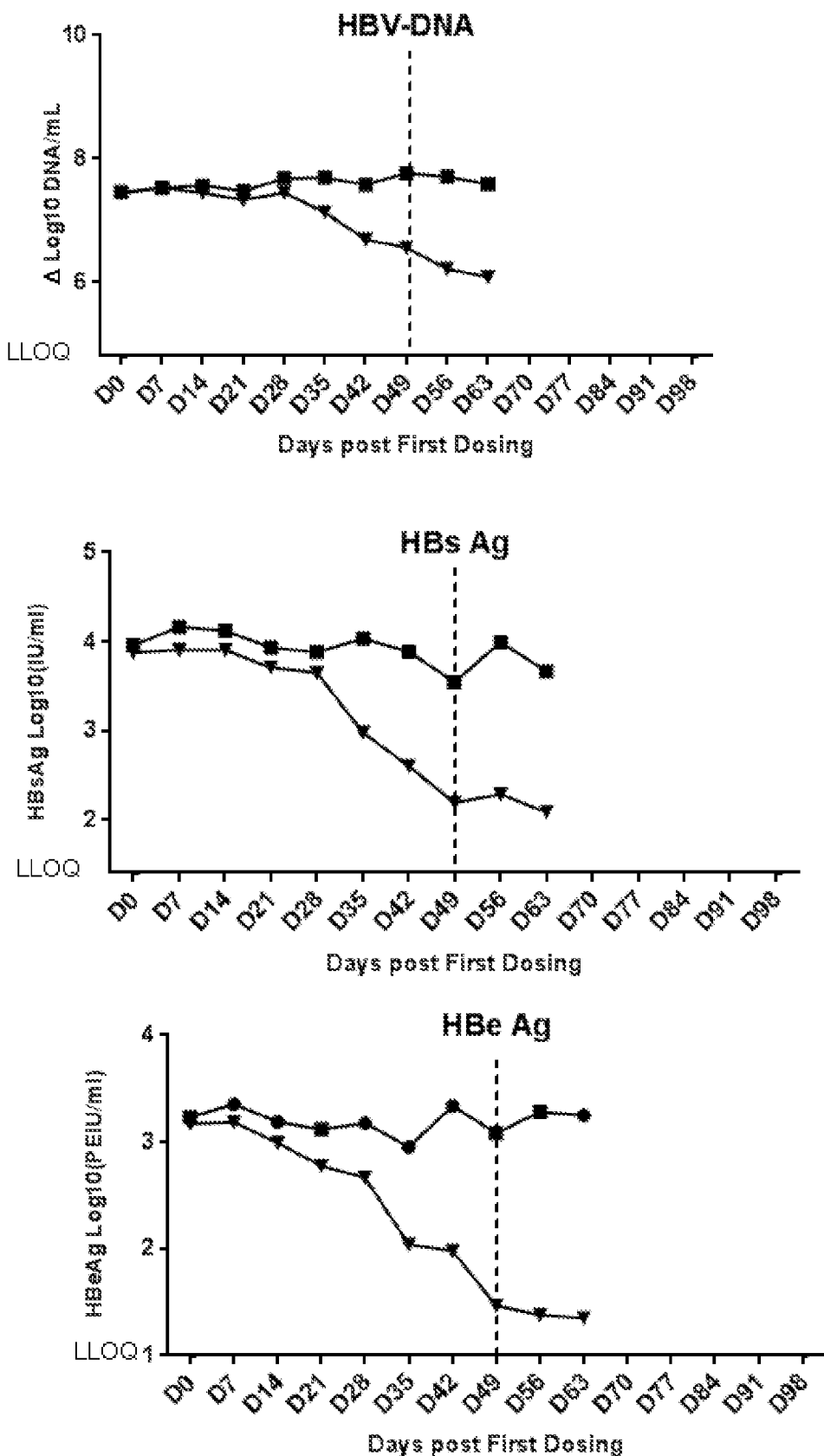
FIG. 13: HBV-DNA, HBsAg and HBeAg in AAV/HBV mice following treatment with GalNAc conjugated PD-L1 antisense CMP NO: 7592 (▼) compared to vehicle (■). The vertical line indicates the end of treatment.

Treatment Protocol:

Male C57BL/6 mice infected with recombinant adeno-associated virus (AAV) carrying the HBV genome (AAV/HBV) as described under the Shanghai model in the materials and method section were used in this study. The mice (6 mice pr. group) were injected once a week for 8 weeks with the antisense oligonucleotide CMP ID NO: 759_2 at 5 mg/kg or vehicle (saline) both where administered as subcutaneous injections (s.c.). Blood samples were collected each week during treatment as well as 6 weeks post treatment. HBV DNA, HBsAg and HBeAg levels were measured in the serum samples as described below. The results for the first 10 weeks are shown in table 21 and in FIG. 13. The study was still ongoing at the time of filing the application therefore data for the remaining 4 weeks have not been obtained.

HBsAg and HBeAg Detection:

Serum HBsAg and HBeAg levels were determined in the serum of infected AAV-HBV mouse using the HBsAg chemoluminescence immunoassay (CLIA) and the HBeAg CLIA kit (Autobio diagnostics Co. Ltd., Zhengzhou, China, Cat. no. CL0310-2 and CL0312-2 respectively), according to the manufacturer's protocol. Briefly, 50 µl of serum was transferred to the respective antibody coated microtiter plate and 50 µl of enzyme conjugate reagent was added. The plate was incubated for 60 min on a shaker at room temperature before all wells were washed six times with washing buffer using an automatic washer. 25 µl of substrate A and then 25 µl of substrate B was added to each well. The plate was incubated for 10 min at RT before luminescence was measured using an Envision luminescence reader. HBsAg is given in the unit IU/ml; where 1 ng HBsAg=1.14 IU. HBeAg is given in the unit NCU/ml serum.

HBV DNA Extraction and qPCR:

Initially mice serum was diluted by a factor of 10 (1:10) with Phosphate buffered saline (PBS). DNA was extracted using the MagNA Pure 96 (Roche) robot. 50 µl of the diluted serum was mixed in a processing cartridge with 200 ul MagNA Pure 96 external lysis buffer (Roche, Cat. no. 06374913001) and incubated for 10 minutes. DNA was then extracted using the "MagNA Pure 96 DNA and Viral Nucleic Acid Small Volume Kit" (Roche, Cat. no. 06543588001) and the "Viral NA Plasma SV external lysis 2.0" protocol. DNA elution volume was 50 µl.

Quantification of extracted HBV DNA was performed using a Taqman qPCR machine (ViiA7, life technologies). Each DNA sample was tested in duplicate in the PCR. 5 µl of DNA sample was added to 15 µl of PCR mastermix containing 10 µl TaqMan Gene Expression Master Mix (Applied Biosystems, Cat. no. 4369016), 0.5 µl PrimeTime XL qPCR Primer/Probe (IDT) and 4.5 µl distilled water in a 384 well plate and the PCR was performed using the following settings: UDG Incubation (2 min, 50° C.), Enzyme Activation (10 min, 95° C.) and PCR (40 cycles with 15 sec, 95° for Denaturing and 1 min, 60° C. for annealing and extension). DNA copy numbers were calculated from $C_t$ values based on a HBV plasmid DNA standard curve by the ViiA7 software.

Sequences for TaqMan Primers and Probes (IDT):

Forward core primer (F3_core): CTG TGC CTT GGG TGG CTT T (SEQ ID NO: 784)

Reverse primer (R3_core): AAG GAA AGA AGT CAG AAG GCA AAA (SEQ ID NO: 785)

Taqman probe (P3_core): 56-FAM/AGC TCC AAA/ZEN/TTC TTT ATA AGG GTC GAT GTC CAT G/3IABkFQ (SEQ ID NO: 786).

TABLE 21

HBV-DNA, HBsAg and HBeAg levels in serum from AAV/HBV mice following treatment with GalNAc conjugated PD-L1 antisense oligonucleotide.

| | Saline | | | | | | CMP ID NO: 759_2 at 5 mg/kg | | | | | |
|---|---|---|---|---|---|---|---|---|---|---|---|---|
| | HBV-DNA | | HBsAg | | HBeAg | | HBV-DNA | | HBsAg | | HBeAg | |
| Day | Avg | Std | Avg | Std | Avg | Std | Avg | Std | Avg | Std | Avg | Std |
| 0  | 7.46 | 0.35 | 3.96 | 0.48 | 3.23 | 0.14 | 7.44 | 0.29 | 3.87 | 0.40 | 3.17 | 0.13 |
| 7  | 7.53 | 0.23 | 4.17 | 0.45 | 3.35 | 0.10 | 7.53 | 0.20 | 3.91 | 0.42 | 3.19 | 0.18 |
| 14 | 7.57 | 0.24 | 4.12 | 0.49 | 3.19 | 0.11 | 7.45 | 0.22 | 3.90 | 0.50 | 2.99 | 0.27 |
| 21 | 7.47 | 0.27 | 3.93 | 0.51 | 3.12 | 0.05 | 7.33 | 0.47 | 3.71 | 0.76 | 2.78 | 0.26 |
| 28 | 7.68 | 0.26 | 3.88 | 0.67 | 3.18 | 0.13 | 7.45 | 0.46 | 3.65 | 0.93 | 2.67 | 0.38 |
| 35 | 7.69 | 0.21 | 4.03 | 0.54 | 2.95 | 0.08 | 7.13 | 0.75 | 2.98 | 1.05 | 2.04 | 0.38 |
| 42 | 7.58 | 0.23 | 3.89 | 0.65 | 3.34 | 0.10 | 6.69 | 0.89 | 2.60 | 1.05 | 1.98 | 0.45 |
| 49 | 7.77 | 0.17 | 3.54 | 1.06 | 3.08 | 0.26 | 6.56 | 1.26 | 2.19 | 0.70 | 1.47 | 0.37 |
| 56 | 7.71 | 0.24 | 3.99 | 0.86 | 3.28 | 0.05 | 6.21 | 1.48 | 2.28 | 0.84 | 1.38 | 0.30 |
| 63 | 7.59 | 0.28 | 3.67 | 1.07 | 3.25 | 0.13 | 6.08 | 1.39 | 2.08 | 0.71 | 1.35 | 0.30 |

From this study it can be seen that GalNAc conjugated PD-L1 antisense oligonucleotide CMP NO 759_2 has a significant effect on the reduction of HBV-DNA, HBsAg and HBeAg levels in serum after 6 weeks of treatment, and effect that is sustained for at least 2 weeks after the treatment has ended.

Example 8—In Vitro PD-L1 Knock Down in Human Primary Hepatocytes Using GalNAc Conjugated PD-L1 Oligonucleotides The ability of GalNAc conjugated PD-L1 antisense oligonucleotide compounds to reduce the PD-L1 transcript in primary human hepatocytes was investigated using genomics.

Cell Culture

Cryopreserved human hepatocytes were suspended in WME supplemented with 10% fetal calf serum, penicillin (100 U/ml), streptomycin (0.1 mg/ml) and L-glutamine (0.292 mg/ml) at a density of approx. $5 \times 10^6$ cells/ml and seeded into collagen-coated 24-well plates (Becton Dickinson AG, Allschwil, Switzerland) at a density of $2 \times 10^5$ cells/well. Cells were pre-cultured for 4 h allowing for attachment to cell culture plates before start of treatment with oligonucleotides at a final concentration of 100 µM. The oligonucleotides used are shown in table 21 and table 8, vehicle was PBS. Seeding medium was replaced by 315 µl of serum free WME (supplemented with penicillin (100 U/ml), streptomycin (0.1 mg/ml), L-glutamine (0.292 mg/ml)) and 35 µl of 1 mM oligonucleotide stock solutions in PBS were added to the cell culture and left on the cells for 24 hours or 66 hours.

Library Preparation

Transcript expression profiling was performed using Illumina Stranded mRNA chemistry on the Illumina sequencing platform with a sequencing strategy of 2×51 bp paired end reads and a minimum read depth of 30M per specimen (Q squared EA). Cells were lysed in the wells by adding 350 µl of Qiagen RLT buffer and were accessioned in a randomization scheme. mRNA was purified using the Qiagen RNeasy Mini Kit. mRNA was quantitated and integrity was assessed using an Agilent Bioanalyzer. Upon initial quality assessment of the isolated RNA, it was observed that all samples met the input quality metric of 100 ng with RIN scores >7.0.

Sequencing libraries were generated for all samples using the Illumina TruSeq Stranded mRNA Library Preparation, starting with 100 ng of total RNA. Final cDNA libraries were analyzed for size distribution and using an Agilent Bioanalyzer (DNA 1000 kit), quantitated by qPCR (KAPA Library Quant Kit) and normalized to 2 nM in preparation for sequencing. The Standard Cluster Generation Kit v5 was used to bind the cDNA libraries to the flow cell surface and the cBot isothermally to amplify the attached cDNA constructs up to clonal clusters of ~1000 copies each. The DNA sequence was determined by sequencing-by-synthesis technology using the TruSeq SBS Kit.

Data Processing

Illumina paired-end sequencing reads of length 2×51 bp were mapped on the human reference genome hg19 using the GSNAP short read alignment program. SAM-format alignments were converted into sorted alignment BAM-format files using the SAMTOOLS program. Gene read counts were estimated for PD-L1 based on the exon annotation from NCBI RefSeq, specified by the corresponding GTF file for hg19. A normalization step accounting for the different library size of each sample was applied using the DESeq2 R package.

The reduction in PD-L1 transcript after incubation with GalNAc conjugated PD-L1 antisense oligonucleotide compounds are shown in table 22.

TABLE 22

PD-L1 transcript reduction in human primary hepatocytes following treatment with GalNAc conjugated oligonucleotides, n = 4

| Compound | PD-L1 expression level 24 h (library size adjusted counts) | PD-L1 expression level 66 h (library size adjusted counts) |
|---|---|---|
| Vehicle | 259 | 156 |
|  | 159 | 168 |
|  | 192 | 136 |
|  | 202 | 211 |
| 767_2 | 7 | 7 |
|  | 11 | 14 |
|  | 22 | 9 |
|  | 28 | 15 |
| 766_2 | 16 | 13 |
|  | 15 | 10 |
|  | 17 | 11 |
|  | 29 | 13 |
| 769_2 | 15 | 21 |
|  | 18 | 18 |
|  | 25 | 18 |
|  | 26 | 25 |
| 768_2 | 41 | 25 |
|  | 27 | 48 |

TABLE 22-continued

PD-L1 transcript reduction in human primary hepatocytes following treatment with GalNAc conjugated oligonucleotides, n = 4

| Compound | PD-L1 expression level 24 h (library size adjusted counts) | PD-L1 expression level 66 h (library size adjusted counts) |
|---|---|---|
| | 31 | 25 |
| | 34 | 22 |
| 770_2 | 21 | 16 |
| | 44 | 62 |
| | 67 | 51 |
| | 38 | 63 |

All five GalNAc conjugated antisense compounds showed significant PD-L1 transcript reduction after 24 and 66 hour incubation when compared to samples treated with vehicle.

Example 9—EC50 of Conjugated and Naked PD-L1 Antisense Oligonucleotides in HBV Infected ASGPR-HepaRG Cells The potency of two naked and the equivalent GalNAc conjugated PD-L1 antisense oligonucleotides were compared in HBV infected ASGPR-HepaRG cells.

Cell Line

HepaRG cells (Biopredic International, Saint-Gregoire, France) were cultured in Williams E medium (supplemented with 10% HepaRG growth supplement (Biopredic). From this cell line a HepaRG cell line stably overexpressing human ASGPR1 and ASGPR2 was generated using a lentiviral method. Proliferating HepaRG cells were transduced at MOI 300 with a lentivirus produced on demand by Sirion biotech (CLV-CMV-ASGPR1-T2a_ASGPR2-IRES-Puro) coding for Human ASGPR1 and 2 under the control of a CMV promoter and a puromycin resistance gene. Transduced cells were selected for 11 days with 1 µg/ml puromycin and then maintained in the same concentration of antibiotic to ensure stable expression of the transgenes. ASGPR1/2 overexpression was confirmed both at mRNA level by RT-qPCR (ASGPR1: 8560 fold vs non-transduced, ASGPR2: 2389 fold vs non transduced), and at protein level by flow cytometry analysis.

The cells were differentiated using 1.8% DMSO for at least 2 weeks before infection. HBV genotype D was derived from HepG2.2.15 cell culture supernatant and was concentrated using PEG precipitation. To evaluate activity of test compounds against HBV, differentiated ASGPR-HepaRG cells in 96 well plates were infected with HBV at an MOI of 20 to 30 for 20 h, before the cells were washed 4 times with PBS to remove the HBV inoculum.

Oligonucleotide Potency

The following oligonucleotides

| Naked PD-L1 ASO | Equivalent GalNAc conjugated PD-L1 ASO |
|---|---|
| CPM ID NO: 640_1 | CPM ID NO: 768_2 |
| CPM ID NO: 466_1 | CPM ID NO: 769_2 | were added to the HBV infected ASGPR-HepaRG cells on day 7 and day 10 post infection using serial dilutions from 25 µM to 0.4 nM (1:4 dilutions in PBS). Cells were harvested on day 13 post infection.

Total mRNA was extracted using the MagNA Pure 96 Cellular RNA Large Volume Kit on the MagNA Pure 96 System (Roche Diagnostics) according to the manufacturer's instructions. For gene expression analysis, RT-qPCR was performed as described in Example 5.

Data were analysed using the $2^{-\Delta\Delta ct}$ method. ActinB was used as the endogenous control to calculate dct values. The PD-L1 expression is relative to the endogenous controls and to the saline vehicle.

EC50 calculations were performed in GraphPad Prism6 and is shown in table 23.

TABLE 23

EC50 in ASGPR-HepaRG HBV infected cells, n = 4.

| CMP ID NO | EC50 (µM) |
|---|---|
| 640_1 | 2.25 |
| 768_2 | 0.10 |
| 466_1 | 5.82 |
| 769_2 | 0.13 |

These data clearly shows that GalNAc conjugation of the PD-L1 antisense oligonucleotides improves the EC50 values significantly.

Example 10—Stimulation T Cell Function in PBMCs Derived from Chronic HBV Patients It was investigated whether naked PD-L1 antisense compounds could increase the T cells function of chronically infected HBV (CHB) patients after ex-vivo HBV antigen stimulation of the peripheral blood mononuclear cells (PBMCs).

Frozen PBMCs from three chronic HBV infected patients were thawed and seeded at a density of 200'000 cells/well in 100 µl medium (RPM11640+GlutaMax+8% Human Serum+25 mM Hepes+1% PenStrep). The next day, cells were stimulated with 1 µM PepMix HBV Large Envelope Protein or 1 µM PepMix HBV Core Protein (see table 9) with or without 5 µM of CMP ID NO: 466_1 or CMP ID NO: 640_1 in 100 µl medium containing 100 µg/ml IL-12 and 5 ng/ml IL-7 (Concanavalin stimulation was only applied at day 8). Four days later PD-L1 antisense oligonucleotide treatment was renewed with medium containing 50 IU IL-2. At day 8 after the first stimulation the cells were re-stimulated with PepMix or 5 µg/ml Concanavalin A plus PD-L1 antisense oligonucleotide for 24 h. For the last 5 h of the stimulation, 0.1 µl Brefeldin A, 0.1 µl Monensin and 3 µl anti-human CD-107 (APC) were added.

After 24 h the cells were washed with Stain Buffer (PBS+1% BSA+0.09% Sodium Azide+EDTA) and surface staining was applied for 30 min at 4° C. [anti-human CD3 (BV 605), anti-human CD4 (FITC), anti-human CD8 (BV711), anti-human PDL1 (BV421), anti-human PD1 (PerCP-Cy5.5) and Live and Dead stain (BV510) (BD Biosciences)]. Cells were fixed in BD Fixation Buffer for 15 min at 4° C. The next morning, cells were permeabilized with BD Perm/Wash Buffer for 15 min at 4° C. and intracellular staining was done for 30 min at 4° C. [anti-human INFγ (PE)]. After washing in Perm/Wash Buffer cells were dissolved in 250 µl stain buffer.

FACS measurement was performed on a BD Fortessa (BD Biosciences). For the analysis, the whole cell population was first gated on live cells (Live and Death stain, BV510), and then on CD3+(BV605) cells. The CD3+ cells were then graphed as CD107a+ (APC) vs IFNγ+ (PE).

The results are shown in table 24.

TABLE 24

Effect of PD-L1 ASO treatment on CD3+ T cell from PBMCs isolated from three chronically HBV infected patients.

| | No antigen stimulation | | | Envelope antigen | | | Core antigen | | |
|---|---|---|---|---|---|---|---|---|---|
| | Saline | CMP 466_1 | CMP 640_1 | Saline | CMP 466_1 | CMP 640_1 | Saline | CMP 466_1 | CMP 640_1 |
| INFγ-/ CD107+ | 1.16 | 4.95 | 4.81 | 4.7 | 9.12 | 8.62 | 3.84 | 9.66 | 7.31 |
| | 2.7 | 3.59 | 2.74 | 2.57 | 3.69 | 3.2 | 3.25 | 3.34 | 2.92 |
| | 3 | 3.87 | 3.98 | 4.59 | 12.5 | 10.9 | 9.23 | 6.11 | 6.88 |
| INFγ+/ CD107+ | 0.12 | 1.03 | 1.15 | 3.19 | 17.3 | 18.9 | 2.38 | 15.1 | 5.75 |
| | 0.49 | 3.12 | 1.75 | 2.73 | 7 | 5.34 | 1.63 | 2.35 | 1.9 |
| | 0.24 | 1.13 | 1.5 | 1.6 | 8.16 | 3.06 | 1.68 | 1.9 | 1.91 |
| INFγ+/ CD107- | 0.33 | 1.43 | 1.08 | 5.11 | 7.74 | 9.47 | 3.14 | 7.76 | 2.83 |
| | 0.61 | 2.9 | 2.26 | 7.84 | 5.79 | 5.78 | 2.33 | 2.82 | 2.95 |
| | 0.17 | 1.57 | 1.72 | 1.22 | 2.58 | 0.99 | 0.1 | 0.61 | 1.04 |

From these data it can be seen that the antigen stimulation by itself is capable of inducing T cell activation (increase % of CD3+ cells expressing INFγ and/or CD107a) in the PBMCs of CHB patients (n=3). The addition of PD-L1 antisense oligonucleotide CMP 466_1 or 640_1 resulted in an additional increase of CD3+ T cell response. This increase was mainly observed in the HBV envelop stimulated group.

The invention claimed is:

1. An antisense oligonucleotide of formula CTAattgtagtagtaCTC (SEQ ID NO: 466), wherein capital letters represent beta-D-oxy LNA nucleosides, lowercase letters represent DNA nucleosides, all LNA C are 5-methyl cytosine and all internucleoside linkages are phosphorothioate internucleoside linkages.

2. An antisense oligonucleotide conjugate comprising the oligonucleotide of claim 1 and a conjugate moiety covalently attached to said oligonucleotide.

3. The antisense oligonucleotide conjugate of claim 2, wherein a linker is present between the oligonucleotide and the conjugate moiety.

4. The antisense oligonucleotide conjugate of claim 3, wherein the conjugate moiety is an asialoglycoprotein receptor targeting moiety.

5. The antisense oligonucleotide conjugate of claim 4, wherein the asialoglycoprotein receptor targeting moiety is a tri-valent N-acetylgalactosamine (GalNAc) moiety.

6. The antisense oligonucleotide conjugate of claim 3, wherein the linker is a physiologically labile linker.

7. The antisense oligonucleotide conjugate of claim 6, wherein the physiologically labile linker is a nuclease susceptible linker.

8. The antisense oligonucleotide conjugate of claim 6, wherein the physiologically labile linker comprises a cytidine-adenosine dinucleotide.

9. The antisense oligonucleotide conjugate of claim 2, wherein a linker is present between the oligonucleotide and the conjugate moiety; further wherein the conjugate moiety is an asialoglycoprotein receptor targeting moiety that is a tri-valent N-acetylgalactosamine (GalNAc) moiety; wherein the linker is a physiologically labile linker; further wherein the physiologically labile linker comprises a cytidine-adenosine dinucleotide.

10. A pharmaceutical composition comprising the antisense oligonucleotide conjugate of claim 2 and a pharmaceutically acceptable diluent, solvent, carrier, salt and/or adjuvant.

11. The pharmaceutical composition according to claim 10 wherein the pharmaceutically acceptable diluent is sterile phosphate buffered saline.

12. The pharmaceutical composition according to claim 10, wherein the pharmaceutically acceptable salt is sodium.

13. The pharmaceutical composition according to claim 10, wherein the pharmaceutically acceptable salt is potassium.

14. An in vivo or in vitro method for modulating PD-L1 expression in a target cell which is expressing PD-L1, said method comprising administering the antisense oligonucleotide conjugate of claim 2 in an effective amount to said cell.

15. A method for restoration of immune response against a virus, said method comprising administering a therapeutically or prophylactically effective amount of the antisense oligonucleotide conjugate of claim 2 to a subject infected with a virus.

16. The method according to claim 15, wherein the virus is HBV.

17. A method for restoration of immune response against a parasite, said method comprising administering a therapeutically or prophylactically effective amount of the oligonucleotide conjugate of claim 2 to a subject infected with a parasite.

18. The method according to claim 15, wherein the restoration of the immune response is an increase in the liver of CD8+ T cells specific to one or more HBV antigens when compared to a control.

19. A method for treating or preventing HBV infection comprising administering a therapeutically or prophylactically effective amount of the antisense oligonucleotide conjugate of claim 2 to a subject suffering from or susceptible to HBV infection.

20. A pharmaceutically acceptable salt of the antisense oligonucleotide conjugate of claim 2.

21. A pharmaceutically acceptable sodium salt of the antisense oligonucleotide conjugate of claim 2.

22. A pharmaceutically acceptable potassium salt of the antisense oligonucleotide conjugate of claim 2.

* * * * *

SEQUENCE LISTING

<160> NUMBER OF SEQ ID NOS: 786

<210> SEQ ID NO 1
<211> LENGTH: 20064
<212> TYPE: DNA
<213> ORGANISM: homo sapiens

<400> SEQUENCE: 1

```
ggcgcaacgc tgagcagctg gcgcgtcccg cgcggcccca gttctgcgca gcttcccgag      60
gctccgcacc agccgcgctt ctgtccgcct gcaggtaggg agcgttgttc ctccgcgggt     120
gcccacggcc cagtatctct ggctagctcg ctgggcactt taggacggag ggtctctaca     180
cccttctttt gggatggaga gaggagaagg gaaagggaac gcgatggtct aggggggcagt    240 agagccaatt acctgttggg gttaataaga acaggcaatg catctggcct tcctccaggc     300
gcgattcagt tttgctctaa aaataattta tacctctaaa aataaataag ataggtagta     360
taggataggt agtcattctt atgcgactgt gtgttcagaa tatagctctg atgctaggct     420
ggaggtctgg acacgggtcc aagtccaccg ccagctgctt gctagtaaca tgacttgtgt     480
aagttatccc agctgcagca tctaagtaag tctcttcctg cgctaagcag gtccaggatc     540
cctgaacgga atttatttgc tctgtccatt ctgagaaccc aaaggagtcc taaaagagga     600
atggaggagc ctaagaataa aaatagtata ataaaacatt tcttagacac attgaccttg     660
gcctatgtca aagttcagtc tgggtttgtc ttataacaca aggagtaaaa gtaccattgt     720
tctacctctt tttttaatac ttgaaaaaaa tttactgtgg atgcttttct atgaattaaa     780
taaccttcta aaaaatgttt tcattgctgc attcgattag attgggtaac taatgaaat     840 taattcctca ctgttgggta taaggttat ttacagtggt tctgtcttag ccattcactg      900
aactcattgc atatatatct ctggaatatt gctgattgtt tccttcaagt aaacttagaa     960
gtgtaactac ttagtcaaag agcctgaata ttttaaaggc cttttgaaga aaactgaaaa    1020
tgctttccag aaaggatgta tcagttgaca atgacagtcg tcaacagtat ttaaggagaa    1080
ctatgatact ctgaagaaaa acttagcctt tctcagtaaa agtaggtagg cagaggccac    1140
atgacagcag ttagagtgtg gtcttcaagg aagtcacaga aatactgtgg ggaattgaaa    1200
```

-continued

```
ccccatgtgg aaaatgtaca agagtgtctc agtgtgactg agaaggaggt tgggcatggg   1260
gtttcatgga gtttaataaa gtttggtcac ttagtagagg tttaataaat caactgtctt   1320
aatctttgat cctacttaag aattttttt ttgttttgt agagatgggg ctcttgttat     1380
gttgcccagg ctgttctcga actcctagcc tcaggcgatc ctccctcctc aggctccaga   1440
agtcctggga ttactggcgg gagccaccat gcaggcctct tgctcctact tttgagaaag   1500
gaagtttaac cggttttttt tgtctttttt ttttttttt tgagacagag tctcactctg     1560
ttgcccatgc tggagtgcag tggtgcaatc tcagctcact gcctcccggg ttcaagtgat   1620
tctcctgcct cagcctcccg agtagctggg actacaggca cctgccacca cgcccagcta   1680 attttttgtat ttttagtaga aatggggttt caccatattg gccaggctga tctcgaactc   1740
ctgacctcag gtgatccgcc tgcctcggcc tcccaaagtg ctgggattac aggcatgagc   1800
cactgctcct ggctgcttaa cttttttctct atctcatcct cctacccatc ctacccttgg   1860
aagatagaga agtagtatta gttccatagt gttatactgg gcttcccca gggacaaacc     1920 cacttcccca acctgaatga gccatcactt cttccccagt ttacatttca ttgctcttta   1980
aatgtctcca ttcggatatg ggaattcaca tatggtcata attcttacct gaagaagatg   2040
tcagtcttct tctcttagac caactgccct gatatgaggt ttagaggtta aagaacatgt   2100
gtgtatttac atgatctttg tattctgcct tttcgtccct cactaatgac agctgcaccc   2160
caaggaaatg gagctgtgga agagagggtt tgataagaaa ttaagtaaat attggatcta   2220
atccatcacc ctccaggaag cctttattac tcctaaaaat ttcaaccaaa ttcattaaag   2280
gacaagaact ccaccagagt aggccataaa cattggcaaa attagttgta atccatgact   2340
agatttaatg tcccttgtt ttattcccat atggttataa tgctttgctt ggcattaggg     2400
gtattttaag ttttcttctg cctagtaagt gaatttgtgt ttataataca ataatcataa   2460
aatatcacat taatatttta taactgtaca gttataaaat attttataag taatatttat   2520
attttataag taatatttta taactgtaca gttaactctg gcccaaggaa aagatagtct   2580
gatagatgct gcagccccat tttagcaaat gtgacctcac aggcctgaat gccatcgcta   2640
ttccacatct acaggataga cggaaaggaa agaaataaaa aaataggtac ctaacactgg   2700
caagaggatg atgactcatg ttatttcact taacctttt atcttttaac atgaaggact     2760
catacaggtt gataagaaac cagtgacata aacagaccaa aaaatgatca gatctttcaa   2820
attagcaaaa aaataatatt tttaaacaa tgggtgaaaa tacagtgtaa cagtaccaat     2880
tatcaacatg tgttgagaac cagaaaaatg ttcttttct ttgatcagca acactatttg     2940
ggaaaatcta tcctcagggc ctagcctggg gccctggcac acagtaggca ctcaacgaat   3000
atttgctgaa cacacaaata cttatgatat tttaaaaaat tggcaacaat ctgataccta   3060
acaatagagg gattaaatat tatggaactg ttaaataaga tgcttatgaa taccatgcag   3120
taagatgggc aatatttatg ccataagctt taatgaaaca aatgggtatt aaatgtatga   3180
taaggttata aattacttt taaaagatta cagggaaaaa aattgaaaga tatacactga   3240 aatgttttt gctcacagtg gtgacaaggt ttctcagcac tggcactgtt gacgttttag   3300
gctgtatgtc tttgctgtgg gaggctggcc tgtgcactgc agggtgtttg gcagcactct   3360
tggcctctgc ccctagatag caatagcagt cctccctcaa ccagcccaat tttgacaacc   3420
aaaaatgttt ccaggcatca ccagatgctc cctgggtgag agtgatgaaa tagtagggga   3480 ttttccccctt cttttcttat tttctgtaat tccattatat tactttaata ataaagaaaa   3540
```

```
aaacataaaa aataaacgaa tgttattatt ctacgtcagt ttggatgttt ggactccatt    3600
ttggggttct ttccattata tcacttggtc tgctaaacat tctacggttt ggtaaggtga    3660
agtgattcat gaaattttgg ttttattttt ttcctgatac taaaaataaa acattctttc    3720
acttggaaat ttggacacag aacaccaaaa aaaatcccata atctcatctc tcttttttctg  3780 tcttttcctt cctttttttcc ctttaaaaac aataaagagt gaaacctacc tgttctccct   3840
ctaatttaat tcctaaatat aatcactgtc aatatcttgg acatttcctg tgtctaaaca    3900
cacacacaca ctttttttttt tcagcaaaag tggatttctg ctacatgtag tgttctgcaa   3960
cttactttct atgtgtttac aaaatcagta catgtacata tgctgaattc agtccttaat    4020
ggtattatat tttgtgaata taccaaaatt tgtttaacca cttagacaat ctaggatatt    4080
ctcagtttgc tgttatgagc aatgctcttc ctttacatat acagacatat atatatatat    4140
gtgtgtgtgt gtgttttttgt tttagtagga tagatttcta ggagagggtg aaaggtctta   4200
tgacatccgc atttacgatt gtaataggaa gtatcaaagt gcccctaaa gaaaaaaatc     4260 ctcccattag tgggtaagaa agcctatttg ttcatatctt cacaaacact aaatattaga    4320
aatatttaca attgtggtca agctcataag tgaaaatggt atttcatatc ttatattttt    4380
tattgtgaga ttgaacatct ttcatatgtt tacatgtcac ctgtatttct tattctctga    4440
actatatgtt atgaccttttc acttttttttc ctcatgggtt atgtgtagtt tgtatagttg  4500
tcttattgat tgttaggagc tatttatata ttaggaacat taatctcctg tcttatatat    4560
acgtggcatc gattagttga tcatttgtga gttcatgtct gtatacaaag attggagagg    4620
cactaagagg gaaaacttac ctcttttctta tcaaagtttg taaatatatg tataacagaa   4680
gagggagaaa atattaataa atgcacagat tggctgaaat agagtataaa tcttttactc    4740
ccctacttca acataaactg caaaaggaga gtgacttttc tttcactctg acttccgtat    4800
tcctcatgct taaaatagtg cctagcacag aagaggtgct caatcagtgt ttgctaaacg    4860
aaataattag tcacatttca agcaggatga ctaaatgaag aatagaatct aggcagatac    4920
tctggaagag tggctgtgag tcattcatat cttagtatga attagtcaaa tccaactctc    4980
tccccttccc actccccact gttagtagaa gaatctgttt attgagagaa tagatttata   5040
atttagaata agtgagaggg gcagaagagg agattttgaa ggatggcacc tgaaggagga    5100
ctagcatggc tgagacagtg aagtggaagc cttgaatagc taaagggtaa gatgaaagta    5160
tttagctgta gggggaaaaa gcattgacag gttggaaaag taaaagtcag attctccttg    5220
ctctgaaatt ttgtacaggg caggttctac taggtatgtt acaatgcaga aaaaacatga    5280
aataattgag aggaatttgg tgcaatatta tcttcttggc ttcttttgag tgggcagatt    5340
tttttcacgg cctgtaacta taataaattt gaaacttctc atcttttagt aacttttttc    5400
acttaagttt atgtggctgt gggcaatgga atgaagatat tgaacttcca attccctgtt    5460
gggtttccac aattacaagt caatcatgac tggttattag aagactattt cagttagaac    5520
caccaagtcc catattgtca tattgtatgt ttaattatta agtgaagcag tcttcttttc    5580
gtgttttcca taattagggc attccagaaa gatgaggata tttgctgtct ttatattcat    5640
gacctactgg catttgctga acggtaagac accaaatcct tccattaggt tctatatttt    5700
aaatatttta accatgagtt taaaactaaa atgatcattt aaaatgcatg caattttctt    5760
atagagagaa cattctattc tttcttctac tttacacaat ggcaaagtct tctttctact    5820
ttacgcaatg ataaagttac ctgtgtcatt ttgtaaaaat atagagaata tagacaaatt    5880
gaaagacaca aaataatcta ttacccatttt cccagggtta actactgaaa atatctgggg   5940
```

```
aaatggcctg tatgtataca tttatttgtt tgctttcaac aaggccaaga tcctttgatc     6000
tttcagtctt ggttgctctg tgacatgcct ttcctgatga ggatactta aggaagaatt     6060 gtaagataca tggaaaatgt caggctaaca cagtactggc atcaccctgt gctctttcct    6120
gaactccata ccaatgtact tcttgccaga aaactgatca aaagtttagg gaagtaaaaa    6180
gagatgactg ttagaatcta ccattccctc tatgtaggaa gcaaataggt gtcctgtcaa    6240
aggacattct ggggatgtct acatgaaacc aagtctccct ggttgtaagg actccatctc    6300
catataatat ttatacagta atatatgttt ataaattgtg ggggcaactt gtttagctaa    6360
ttttattatt ctgctattgg gacactgtgt ctcagcatga gatatagtgt cccaaaacat    6420
atttcaagcc cattggataa aatatgtgtt tagcaagttc ttaaatataa tgataacata    6480
accgaccaga taaagtgatt tataaacgct gtgccaattt tgtaaatgtt tcgaggaatt    6540
ttcccttttc tgaagattgt ccttctttct ttttagcatt tactgtcacg gttcccaagg    6600
acctatatgt ggtagagtat ggtagcaata tgacaattga atgcaaattc ccagtagaaa    6660
aacaattaga cctggctgca ctaattgtct attgggaaat ggaggataag aacattattc    6720
aatttgtgca tggagaggaa gacctgaagg ttcagcatag tagctacaga cagagggccc    6780
ggctgttgaa ggaccagctc tccctgggaa atgctgcact tcagatcaca gatgtgaaat    6840
tgcaggatgc aggggtgtac cgctgcatga tcagctatgg tggtgccgac tacaagcgaa    6900
ttactgtgaa agtcaatggt aagaattatt atagatgaga ggcctgatct ttattgaaaa    6960
catattccaa gtgttgaaga cttttcattc ttgtaagtcc atacttattt tcaaacagaa    7020
cagcatagtc tgttcattca ttcattcaat tcatgaattc attcacataa ttatccaatt    7080
tcttgagcac ctatttgata gtcactggaa atccagagac aaacaacaca gagccatgtt    7140
ctacagtatg tacagttttc caaaagaat ttctagtctt tactttttta ttacaaatgg     7200
aatacgtata cttgcaaata attcagatac tgtggaagag atcaaatgaa ttgcaaaagt    7260
gtccctcctc ccttcaccac tatctcccat ggcatgcaga gagagtaacc attatttgtg    7320
tgtccctcca gaaattttt tattcaacta ctattttttt attttattag gtccgtcagt     7380
tttccttttt tgagcctctc tatatcaaat gcaaataaat atattcagaa caaacccac     7440 tgtaaggttc acattaaaaa agacttgaag tcaccctatg aagacaaaaa ataatcacat    7500
taagtgtgaa agaacctatt cttccagtac aggataagcc atacttactg ggcatatatt    7560
catcttgaaa atctatactg atgttgtctt ggggaattga aaaggaacta ggagtgttag    7620
ttcctcggta ttgacccaca gttatgttat caggtcactt gagttcaaag ttttgtgttg    7680
gcactagcta agtaaaggaa aacacctctg ctttcattgt tgagtttcac agaattgaga    7740
gctgaaagga tcccaggcag gagcagctaa tccaaactcc cacaaagaac aaaaatcccc    7800
cagaggatct tctgttctta tatttcctgc aatggcgtcc ctgtcatatc ccacaatggc    7860
ctccctgcca tttggatatc ccttccatat cctgttgaaa ttactcccta atagtaagct    7920
gaaatctgcc cctctagttg tagtcttggg attatttcat ttacatgatg accttttaat    7980
atttgactag aattaaatca tctcccttg gtctttccat tcctgggcta actaccatca     8040
atctgagggc taacaataca agtagaaaaa gtatacattt gtcactgatc actgatcaat    8100
tattaatcaa tgatcactga taactataaa ctcaaaaaca aaatcatgtg gggattaaga    8160
gaaatgtatc agttttatgt tgtatttctg gtccctgata ctggctcagg taatgccact    8220
attgtcaaga agataccact tgtaaagtag atttaatttt cattatattt taccatatgc    8280
```

```
ttctccattc atgacatctc ttgagatgtt gtggtttata ctttcagttt ttctccagtc    8340
catccgcaaa tatcaggcat ctactgtgtt ccaagatatt aaagaaatca tcatgactta    8400
gcctcatcaa cagcattgct agatctggga tggaaaggaa gagtataatc ctggcagtca    8460
ggaagaaggc agcataaagt ataagttcct gcttccaaaa aaggtctctc atcagcctgt    8520
agggagtgtg tagggaaggg acagctgtcc ttgtagtagg gaagggtttt attcaggtcg    8580
tctgggctcc ataatatccc ttgtgtatct gcagtctcct ttgccatgga tcaacacaat    8640
aggaaatctt ccggcactga tggttttttcc aaggggagt tcttcctgga gcaaagcaaa    8700
tgaccaacca ggtttgagga cctgatttgt ttgacaattc cattttgtat tgtaaattac    8760
ttaattggca ttctactccc aatccatctt gtcatttgca tacagtggtt ttgggattga    8820
gttcagctat accaaaagtc tgaaccttct gcacttagaa caaggcaacc accaagcttc    8880
acttgcactg aggccgtgtc tccaatggaa atgaggcagc tggcttgcag gagcttccca    8940
actcagggaa gtagaactcc tgagtcacct ccatatgcaa atgatttcac agtaatgctg    9000
ttgaacttca cttcccatca cagcaaatgt gtggtaacat agcttcccca caggagttta    9060
ctcaccatgg tattttaaag gtgaaacatt tcaaaactga aatttgaaag aatttagttt    9120
tggattcact caattatcac tatcacttcg ggtgttattg cacctttctt gtttgtgagt    9180
ttaaatgcca gactctcagg ccactaactt tcaattaaaa gtgttttttct ttaatcgctg    9240
aacctaacag cagggaaaac gaaatgttca ttcagacttt cagaaccttc aatgagatta    9300
ggcagctgaa agatcaaagt gttgcatagt tgtcccgata aagctatttg gatcatatgg    9360
accaaatcga ctgctgtcat tccccaccaa ccccatctct ccccaaaatt cccagccctg    9420
tttaagtgtt ctctgtagca tttatctcta tctagtatat tgtgtagcat atcatatcat    9480
acttttctgt tttgtttatt gtctctctcc tcctagaata taaactccac aagcacaaag    9540
atttgggcct gttttataat attgttgcat ccccagggcc tgatatacag cagagtggtg    9600
gtacgaaaag agcacacaaa aaaatatttg ttgagtcaat gaatgaatga tttcctcaaa    9660
taggattagc ctaaaatttt tggaaacatga acagatttgg atatgtgaaa atttatttcc    9720
agactgttca tcaggaactg ttagcagctt ctaaagggta cactggagca gcagtagtaa    9780
aaggaggaag aggagcagct ctgctactgc tactatcgag tactactaca attagcactt    9840
gcttattctg tgtgttaggc cctgtactga acactctgtc taaattagtt catttcctcc    9900
tggaaatgac tctaggggt aagtgcttca tcatgtaaga tgagtatttt tcacattttg    9960
ttgtgtctga aatctgagtg tgtctttcaa tgatggaatc tttgattcca tgataagtgg   10020
tattattccc attttaagga tgaggaaact gaggtccaaa gaaattaagt aatttgccca   10080
aattcacccca gcctagaaaa tgataaagct agttctaaac ccaagcagat tagctctgaa   10140
gtctgggccc ttaataacca cttttattg cctatatttg tacctctggt gtacgtatca   10200
agttatatgt tgacttcaaa actatcatga ccttttcttg gttttgattg tccaacatta   10260
gtatagtgtt ctgggtctgc aaaaattttg attactcatc tcatctgtaa aacattttga   10320
actcgtgtgt ttgtgcatgc acatttgtgt gtaattataa aaattttact ttctgttaat   10380
atataagttg tatcataaga aactgccgtt tttgaagagc aaaaaaaggt tgaatgttac   10440
cagttacatc tggttcaacc taatagacat ttgtacaaaa acagacattt taagaggttg   10500
aaataaaaat ttaataaaca atattttcag ttttttactaa ttgtgatgct tcactatcat   10560
tagctaatat gtcaaggcat aatatacctt agggtgaact ttatcattaa caaaggtgga   10620
tggtgtcaat aatcttgagg tttgtgtttt tttatataac actgcgaggt ctaattaagt   10680
```

```
acttactgtt taccacctca tacagtggcc gataaaaagt gtcacttctg ctgtttcctc   10740
tgggttgtgc ttgaattatt agtattatct tcagtcctca gtttctttgt gggaaacttt   10800
ttaattagtt gtttaatttt gtaagatggt tagtttagtc aaaattagat aagagaattt   10860
gaaaatccgt agctacccca aagcaaccta cacataagaa ctattatttt tgtgttttga   10920
aatcataatt ttattgattt ccagtgtttc cactggtagt ggtttcattg atataggagt   10980
atcaaaacat cactcattat ttatttcagt ttcatttgat cctagccgtt ttgtattaac   11040
tctctgtgaa gaaattacct cacaaatcta ttgctgtcct tggtaaagga atggagaatt   11100
aaggctctag atcattagtg gttacactat agtattagaa gtaaaaaaaa gattatacca   11160
acaaaataag aacatgttaa tgtacttgta atgaataaac atgaataaag ctcttatgct   11220
atataggtgc actaaacaat ctactagaat tgtcagcaaa ctacgtatct taatcctgaa   11280
agggtcccaa accaatgatc taaaattgaa tcaaactttc ttccttgagc ataattactt   11340
aaatgattta ttaaaatagc cagcatttaa aagcttaaaa tgtaaatatc ataatgtggt   11400
atcctagata gcatcccaga acagaaaaag gatattaggg aaaaactgga ggaatggaat   11460
aaattatgca gtttagttat taataatgta ctaacgtcct tagttatgac gattgtacca   11520
tggtaatgta agatactaac aatagaggaa accgggtaag gagtatacag taactctata   11580
ctatctttgc aactttttg taaatttaaa acttctaaaa taaagaacaa atttaaacat    11640
taaaaagtat caccaggaac atatatcact gtttacagat gaaatactat gtattttcat   11700
atctaatttc tgatcattga cttcaaatca gaaaagtgaa tgacacctca aaatcaggtt   11760
ttctgtttac tgaagtctaa gaaaagaaag cataccagct ggagagattc atgtttataa   11820
agacagattt ataacaacaa aaataaaata tccaagaata aatttaagaa gaagcacttt   11880
actgagaaac atatgaaaac ctgaacaaat ggagagggat attttgtatt tgaatagaaa   11940
gacttctggt ttaaagataa ttctctttaa attattttt gtagaaattt aaggggtaca    12000
agagcagtgt tgtcacatgg atatattaca tagtggtgaa gtctggggtt ttagtgtaaa   12060
ttaatcttta cattttgttt gagcccaata aatgtaccaa catgattttt atagaaagat   12120
agtcattcct attaatccaa acttgtccca actttgaatt gaattgaggc agagctagca   12180
ggtgttcccc acggctgagg catctgaaca ttaagcatat ccctctgaga accagcctgc   12240
attgatactc tttctaatgt ggacagcatc aagctatgta cgtagttctg tgctcagcaa   12300
aagccctgac ttcttttgt ttatgtccta gccccataca acaaaatcaa ccaaagaatt    12360
ttggttgtgg atccagtcac ctctgaacat gaactgacat gtcaggctga gggctacccc   12420
aaggccgaag tcatctggac aagcagtgac catcaagtcc tgagtggtaa gaccaccacc   12480
accaattcca agagagagga gaagcttttc aatgtgacca gcacactgag aatcaacaca   12540
acaactaatg agattttcta ctgcactttt aggagattag atcctgagga aaaccataca   12600
gctgaattgg tcatcccagg taatattctg aatgtgtcca ttaaaatatg tctaacactg   12660
tcccctagca cctagcatga tgtctgccta tcatagtcat tcagtgattg ttgaataaat   12720
gaatgaatga ataacactat gtttacaaaa tatatcctaa ttcctcacct ccattcatcc   12780
aaaccatatt gttacttaat aaacattcag cagatatttta tggaatatac cttttgttcc   12840
atgcattgta gtactcattg gatacacata gaataataag actcagttca cactcttcag   12900
gaaacagata aaaactaag aaacaaacaa aaacaggca atccaacacc atgtgggaaa      12960
tgctttcata gccgggaaac ctggggaata cctgagagga atactcaatt caggccttgt   13020
```

```
ttcaggaatc caaatcctgg cacatcagag ctgcttccct ctttccaggg tggcaggaaa    13080
taaatggaac atattttct atcttatgcc aaacatgagg gacccttct ccccggtgcc     13140 tctcccaagg tagtctacaa tatttcaact ctagcagtct gcttagtgca tagaacatga   13200
ggctgtgtgt ccctgggcaa attactagac ttctgtgtgc ttcactttcc ctgtaggatt   13260
ataatctact gagcaagctt attgtaaggg tcagattagc aacagtgtat gaaaatgatt   13320
tgagaccatt gcctgcacaa attcaactat ttttttttat ctcactactc tacagaagta   13380
ggtagggtgg gagacagagt ctgatgagag gctcagaatg tgaaagaaag tgaggcgagt   13440
gagcatgata tttaatataa acacaaagat attctgagaa gagctgctca ctgcccctc    13500 ccccaataca tgttgatagg aaaatgccac gtacttcagc aaaaacaact gaaaaattag   13560
atagaaaagt caatcaatag gaaaagataa tccaggacgg tgttgtgaac agaaagaggg   13620
ggaaaaaact ttagaaaatg atggggatgc tcttactggg gtacgagtcc tcaggtattg   13680
aactggcttt cagtaaaagc tagattagtg ggttcctgcc atttacaagc tgttttatga   13740
caacttactt gttgggtggc ctacagtaac tcacctaact gcactgagtc tgtttcctca   13800
tctgtaaatt gggattttt ttttaaatac ctggcatgcc taactcataa agttgttctg    13860
aaactgaaat aaaacatacg tgaacaggca ttgtaaactg taagttacgg aaaaagctgg   13920
ctgttgttgt gtctttaaag tttcacctgg gtagtcaaag atggatcatg ggtctcagtg    13980
gagagctgag ccaggcagga gctgactaag ggtgagaggt gggagttagc agcctctgaa   14040
catctgtgta ccatgggacc ccctttcctc ctgcatggta ccccagacaa ggagcctagt   14100
aagagatact aatggcttgt tgtccagaga tgttcaaact gcagagaaag ataagacaac   14160
aagcattggc ctccaatcat gatgacagat aggaggaggt gggagctcct tagcagtgct   14220
ggttggcctt ccatgttcta ctgtgggcca tctctgccat gtactgtagg ctactagctt   14280
ctatattaaa gaatgcaaga ggggccagga gcggaggctc atgcctgtaa tctcagcact   14340
ttgggaggcc aaggtgggca gatcacttga ggtcaggagt ttgtgaccag cctgccaac    14400 atggtgaaac tctgccttta ctaaaaatat aaaaattagc tgggtgtggt ggtgtgcacc   14460
tgtaatccca gctactcggg agactgaggc acaagaattg cttgaacctg ggaggcggaa   14520
gttgcagtga gcccagattg cgccactgca ctccaccctg ggcaacagag aaagactctg   14580
cctcaaaaaa aaaaaaaaaa agcaagagga agtgaaataa tcaaggccgc catttaatag   14640
tgagcagcca ctccatgtgg tactgtgcaa gcacattata aatattagcc tcacaagaaa   14700
tgtattagca tttgtatttt gtacactggt taagtatctt gcccaagacc tcaaaactgg   14760
ttaagggcag cagaatttag ccccagcacc acctttcaa agcctgggct tctcacactt    14820
ctccatgctg ttcccatttt aacacaggta tctcgccatt ccagccactc aaactttggc   14880
atttaagaaa attatcctaa agctaaacta aacttcaagg atgaccattc tcctgacccc   14940
ttcccatcaa aatttatct ttagtcagtt tgttttcgtt ttgttttgtt tttcagaact    15000
acctctggca catcctccaa atgaaaggac tcacttggta attctgggag ccatcttatt   15060
atgccttggt gtagcactga cattcatctt ccgtttaaga aaaggtagta tttccttaat   15120
tgcagtggtc tccactgggg gtgaggaagg ggtgagaatt ggatcatggc tgcaaggaaa   15180
cccgacttaa cctctgcaag gtggtgcaaa ggcattccac tgttcaacag caattatatt   15240
gaagctgagt gggatcactg ggtgaagatg aagcgtaagg ggtgaggggc aggagaatgg   15300
gtatggatga aggtagaaga tgcagtgtca tacagttttt ttctatcatg aaaataacca   15360
cagacttaca gaagagaaag agctaaaatg cccgtcattt tcagttgcat tttagtcttg   15420
```

```
cattagttgc aaccagctgg tttctgggta ccctaagtaa taaaaatagt tcctctgtag    15480
aactgtagta tgtttaccat agagtatttt gcaaaatttt tggtagagga tgttacataa    15540
tttgcatgtg ttcatttctc catttacctg tgggaacaat taaaatccag gaaaatgagt    15600
atattcaaat aatttcctcc catttaagat gagtcagagt aaataattcc tccaatactt    15660
agagaagtat accaagagat ccagtgatgg tatagagttg tctgatgtta aatagggaag    15720
tagaatatgg aaggggattc caatagtcgt tgaaaaattc cccataaccc cttacatggg    15780
ggaaagtagt gttaactgag agagtagaga taagctgttt ccaaaaatta tattcttaac    15840
aggactgaga tagccagaat ataaggatca agtttcaatg acagtaagat cctgagatgg    15900
agttgatttg cacaaagaaa taattgttgc cagcatgcat tttgaatatt tctctggaaa    15960
aaaagattag ttggcagtag aaatggatag aaatcaatag atattaaaat acctcagaat    16020
ttggttcatc tctgggaaaa gatgaaaaat aaaagtgtat actcctcaag aacatctagg    16080
atcaaaagca tgtgccctac actattgaat taattaacct cataagttgg gacctgtgga    16140
ataaggatgt ccaccagact tcctagggat tacaaatgtt tcacagaact tgaaatttaa    16200
acttgggtca ctgtatggga tgtagagctg tgctatatgg aaataaaaat gatttctttt    16260
tctcaaggga gaatgatgga tgtgaaaaaa tgtggcatcc aagatacaaa ctcaaagaag    16320
caaagtggta agaatatcag aaggaattgg gaagtaaaag tcaaggaaa caaaaagcta    16380 aagcaataac aaagagaaat ccatcagtca taatctcctc tccttttaaa gaatgctggt    16440 tccccttttgc ctcacagcta acacaagaac tcctccaccg tctgaggagg tttaggagca    16500
gggaagggga aggagtcagc ttcatttgct aatcttctgt tgccctgcac cctagcagct    16560
ccttgcagca ggggacaagg atgacttagg tggatggata attaattgat tctaaaatat    16620
tgtgtgtcag tattgtaata ctatgttaat tgcaccatgc acggtatctc atttaatccc    16680 ccacccccttg ccattaccaa agagagagag agagagagag agagaaatac tagaatttat    16740 cctcattta cagtagagaa aacagagggt caagaagata atgtaaagtg cccaagaaca    16800
cacagctgat cacaaaaatc aagcttgggg gccattagcc taaccacaga cccttactct    16860
taacccatct gcttcaatcc attttgctac aaatgtttac atttataagc agggcagaaa    16920
aacctcatcc aggttattga actaagaaga aagttatatt aaggtttcta atttttttaa    16980
tgtagttaga aaccaaactt aacaatgagc ccaagtttaa agcagtctaa ttaacctgga    17040
caagctcagg caagtttcat tctgtggccc atagcatcat ctgtgttgta aagctaagta    17100
gcaaatgttg tttgggtcat gctgggggac aagccatccc aatttgctca ggactgaggg    17160
gttttccagg atatcatgta aggataattg ggtacaaata taacctgctg ctttctctca    17220
tttcaaattt atcatttatc atatcagcaa ctatgagtta tgtttttat tagatttctt    17280 gttactttttt ccccagacca cttcccatga aattaatata ctattatcac tctccagata    17340
cacatttgga ggagacgtaa tccagcattg gaacttctga tcttcaagca gggattctca    17400
acctgtggtt tagggggttca tcggggctga gcgtgacaag aggaaggaat gggcccgtgg    17460
gatgcaggca atgtgggact taaaaggccc aagcactgaa aatggaacct ggcgaaagca    17520
gaggaggaga atgaagaaag atggagtcaa acagggagcc tggagggaga ccttgatact    17580
ttcaaatgcc tgaggggctc atcgacgcct gtgacaggga gaaggatac ttctgaacaa    17640 ggagcctcca agcaaatcat ccattgctca tcctaggaag acgggttgag aatccctaat    17700
ttgagggtca gttcctgcag aagtgcccctt tgcctccact caatgcctca atttgttttc    17760
```

```
tgcatgactg agagtctcag tgttggaacg ggacagtatt tatgtatgag ttttccctat   17820
ttattttgag tctgtgaggt cttcttgtca tgtgagtgtg gttgtgaatg atttcttttg   17880
aagatatatt gtagtagatg ttacaatttt gtcgccaaac taaacttgct gcttaatgat   17940
ttgctcacat ctagtaaaac atggagtatt tgtaaggtgc ttggtctcct ctataactac   18000
aagtatacat tggaagcata aagatcaaac cgttggttgc ataggatgtc acctttattt   18060
aacccattaa tactctggtt gacctaatct tattctcaga cctcaagtgt ctgtgcagta   18120
tctgttccat ttaaatatca gctttacaat tatgtggtag cctacacaca taatctcatt   18180
tcatcgctgt aaccaccctg ttgtgataac cactattatt ttacccatcg tacagctgag   18240
gaagcaaaca gattaagtaa cttgcccaaa ccagtaaata gcagacctca gactgccacc   18300
cactgtcctt ttataataca atttacagct atattttact ttaagcaatt ctttattca   18360
aaaaccattt attaagtgcc cttgcaatat caatcgctgt gccaggcatt gaatctacag   18420
atgtgagcaa gacaaagtac ctgtcctcaa ggagctcata gtataatgag gagattaaca   18480
agaaaatgta ttattacaat ttagtccagt gtcatagcat aaggatgatg cgagggaaa   18540
acccgagcag tgttgccaag aggaggaaat aggccaatgt ggtctgggac ggttggatat   18600
acttaaacat cttaataatc agagtaattt tcatttacaa agagaggtcg gtacttaaaa   18660
taaccctgaa aaataacact ggaattcctt ttctagcatt atatttattc ctgatttgcc   18720
tttgccatat aatctaatgc ttgtttatat agtgtctggt attgtttaac agttctgtct   18780
tttctattta aatgccacta aattttaaat tcatacctt ccatgattca aaattcaaaa   18840
gatcccatgg gagatggttg gaaaatctcc acttcatcct ccaagccatt caagtttcct   18900
ttccagaagc aactgctact gcctttcatt catatgttct tctaaagata gtctacattt   18960
ggaaatgtat gttaaaagca cgtatttta aaatttttt cctaaatagt aacacattgt   19020
atgtctgctg tgtactttgc tattttatt tattttagtg tttcttatat agcagatgga   19080
atgaatttga agttcccagg gctgaggatc catgccttct ttgtttctaa gttatctttc   19140
ccatagcttt tcattatctt tcatatgatc cagtatatgt taaatatgtc ctacatatac   19200
atttagacaa ccaccatttg ttaagtattt gctctaggac agagtttgga tttgtttatg   19260
tttgctcaaa aggagaccca tgggctctcc agggtgcact gagtcaatct agtcctaaaa   19320
agcaatctta ttattaactc tgtatgacag aatcatgtct ggaacttttg ttttctgctt   19380
tctgtcaagt ataaacttca ctttgatgct gtacttgcaa aatcacattt tctttctgga   19440
aattccggca gtgtaccttg actgctagct accctgtgcc agaaaagcct cattcgttgt   19500
gcttgaaccc ttgaatgcca ccagctgtca tcactacaca gccctcctaa gaggcttcct   19560
ggaggtttcg agattcagat gccctgggag atcccagagt ttcctttccc tcttggccat   19620
attctggtgt caatgacaag gagtaccttg gctttgccac atgtcaaggc tgaagaaaca   19680
gtgtctccaa cagagctcct tgtgttatct gtttgtacat gtgcatttgt acagtaattg   19740
gtgtgacagt gttctttgtg tgaattacag gcaagaattg tggctgagca aggcacatag   19800
tctactcagt ctattcctaa gtcctaactc ctccttgtgg tgttggattt gtaaggcact   19860
ttatcccttt tgtctcatgt ttcatcgtaa atggcatagg cagagatgat acctaattct   19920
gcatttgatt gtcactttt gtacctgcat taatttaata aaatattctt atttatttg    19980
ttacttggta caccagcatg tccatttct tgtttatttt gtgtttaata aaatgttcag   20040
tttaacatcc cagtgggagaa agtt                                          20064
```

<210> SEQ ID NO 2
<211> LENGTH: 20261
<212> TYPE: DNA
<213> ORGANISM: macaca fascicularis

<400> SEQUENCE: 2

```
gtaaaatcaa ggtgcgttca gatgttggct tgttgtaaat ttctgtttat attaataaca      60
taccaaatgt ggatttgttt taatcttcgg aactctttcc ggtgaaaacc tcatttacaa     120
gaaaactgga ctgacaggtt tcactttctg tttcatttct atacatagct ttattcctag     180
gacaccaaca ccactcgcta cccaaactga agcttcccc gattccgccg aaggtcagga     240
aagtccaatg ccgggcaaac tggatttgct gccttgcgca gaggtgggcg ggaccccgcc     300
tccgggccgg gcgccaagtt gagcagctgg cacgcctcgc gaagcccag tcctgaagcc     360
ccagtcctgc gctgcttccc gaggctccgc accagccgcg cttctctctg cctgcaggta     420
gggagcgttg ttcctccgca ggtgcccacg gcccagcatc tctggctaac tcgctgggca     480
ccttaggacg gaggatctct acacccttc tttgggatgg agagaggag agggaaaggg     540
aaggcgatgg tctaggggc agtagagcca attacctgtt ggggttaata agaacaggca     600
atgcatctgg gcttcctcca ggcgcaattc agttttgctc taaaataat ttatacctct     660
aaaaataat aaggtgggta gtataggata ggtagtcatt cttatgcgac cgtgtgttca     720
gaatatagct ctgatgctag gctggaagtc tggacacggg tcctagtcca ccgtcagctg     780
cttgctagta atatgacttg tgtaagtcat cccagctgca gcagataagt aagtctcttc     840
ctgcgctaag cacgtccagg acccctgaac ggaatttatt tgctctgtcc attctgaaaa     900
cccaaaggag tcctaaaaga ggaatggagg agcctaagaa taaaaatagt ataataaaac     960
atttcttaga catgttgacc ttggcctatg tcaaagttca gtctgggttt gtcttataac    1020
ataaggagta aaagtaccat tgttctacct cttttttaa tacttgaaaa aaaatttact    1080
gtagatgctt ttctattaat taaataacct tctaaaaaat gttttagtg ctgcattcga    1140
ttaggttgga taactaaatg aaattaattc ctcactgttg ggtataaagg ttatttacag    1200
tggttctgtc ttagctattc actgaacatc attacataga tatctctgga atattgctga    1260
ttgtttccgt caataaactt agaagtgtaa ctacttagtc aaagagactg aatattttaa    1320
aggcattttg aagaaaactg aaaatgcttt ccagaaagga tgtatcagtt gacaatgatg    1380
gttgtcaaca gtatttaagg agaactatga tactctgaag aaaaacttag cctttctcag    1440
tagaagcagg taggcagagg ccacatgaca gcagttagag tgtggtcttc aaggaagtca    1500
cagaaatact gtggggaatt gaaaccccaa gtggaaaatg tacaagagtg tctcagtgtg    1560
actgagaagg aggttgggct tggggtttaa cttaagaatt ttttctttt tcttttgtgg    1620
agatagggct tttgttatgt tacccaggct ggtcttgaac tcctagcctc aggcgatcct    1680
cccgcctcag gctgcagaag tcctgggatt actggccgga ccaccatgc aggcctcttg    1740
ctcctacttt tgagaaagga agcttaacct ttttttttg tttgtttgtt tttgtttttt    1800
gtttttttg agacgagtct cactctgttg cccaagctgg agtgcagtgg tgccatctca    1860
gctcacggca acctctgcct cctgggttca agtgattctc ctgcctcagc ctcccgagta    1920
gctgggacta caggcaccca ccaccacgcc cggctaattt ttgtatttt agtagagatg    1980
gggtttcacc atattggtca ggctgatctc gaactcctga ctcaggtgat ccacctgcct    2040
cagcctccca aagtgctggg attacaggcg tgagccaccg cgcctggcca cttgactttt    2100
tctctatctc ttccttctac ccatcctacc cttggaagat agagaagtaa tatcagttcc    2160
```

```
atcgtgttat actgggcttc ccccagggac aaacccactt ccccaacctg aatgagccat    2220
cacttcttcc ccagtttaca tttcattgct ctttgaatgt ctccgttcgg atatgggaat    2280
tcacatgtgg tcataattct tacctgaaga agactgacgt cttcttctct tagaccaact    2340
gccctgatgt gaggtttaga ggttaaagaa catgtgtgta tttacatgat ctttgtattc    2400
tgccttttcg tccctcacta atgacagctg aaccccaagg aaatagagct gtggaggaga    2460
gggtttgatg agaaagtagg taaatattgg atctaatcca tcatcttcca ggaaacctcc    2520
attacttcta aaaatttcaa ccaaattcgt taaaggacaa gaactccacc agagtagggc    2580
cataaacatt ggcaaaatta gttgtaatct atgactagat ttaatgtccc tttgttttat    2640
tcacatatgg ttataatgct ttgcttggaa ttaggggtat tttaagtttt cttctgccta    2700
gtaagtgtat ttgtgcttat aatacaataa ttataaaata tcacattaat attttataac    2760
tgtacagtta actctggccc aaggaaaaga tagtccggta gatgctgcag cctgattttg    2820
tatctaaccc tggcaagagg ataatgactc atgttatttc acttacccct tttatctttt    2880
aacatgaagg gctcatatag gtcaataaga aaccagtgat ataaacagac caaaaaatga    2940
tcagatcttt cacattagca aaaaaaaata ttttttaaac aatacccaac tgggtgaaaa    3000
tacagtgtaa cagtaccaaa tatcaacatg tgtcaagaac cagaaaaatg tttgttttct    3060
ttgatcagca acactatttg aggaaatcta tcctcagggc ctagcctggg gcctggcaca    3120
cagtaggcac tgaacaaata tttgctgaac acacacatac ttatgatatt tttaaaattg    3180
gcaacaatcc aatacccaat aatagaggaa ttaaatatta tagaactgtt caataagatg    3240
cttacgaata tcatgcagta agatgggcaa tatttatatc ataagcttaa atgaaacaaa    3300
tgggtattaa aggtatggta aggttataaa ttactttta agagattaaa gggaaaagac    3360
tgaaagatat atactgaaat gctcacagtg gtgacaaggt tccccagcct tggcactatt    3420
gacattttgg gctatgtctt tgctgtggga ggctggcctg tgctctgcag gaggtttggc    3480
agcactcttg gtttctaccc ctagatagca gtagcaaccc tccctcaacc agcccaattt    3540
tgacaaccaa aaatgtttcc aggcatcacc agattctccc tgggtgagag tgatgaaaca    3600
gtaggtgatt ttccccttct tttctcattt tctgtaattt tgtcacatta cgttaataat    3660
aaggaaaaaa cataaaaaat agatgaattt attattctac ctcagtttgg atgtttggac    3720
tcccttggg ggttctttcc attatatcac ttggtctgct aaacagtcta tggtttggca    3780
aggtgaaatg attcatgaaa ttttgttttt atttttttacc tgatactaaa agtaaaacat    3840
tcattcgctt gaaatttgg acacagaaca ccaaaaaaaa tccataatct catctctctt    3900
tttctgtctt ttccttcctt ttttcccttt aaaaacaaga gtgaaaacct accggttctc    3960
cctccaattt aattcctaaa tataatcact gttaacatct tggacatttc ctgtgtctaa    4020
acacacatac tcactttttc ttttttttag caaaaagtgg atttctgcta catgtagtgt    4080
tccgcaactt cctacatgtt tacaaaatca gtacatttac atatgctgaa ttcagtcctt    4140
aatggtatta tattttgtga atataacaaa atttatttaa ccacttagac aatctaagat    4200
attctcagtt tgctgttatg agcaatgctc ttcctttaca tatacatata tatgtgtgtg    4260
tgtgtgtgtg tgtgtgtgtg tgtgtgtgtg ttttagtagg atagatttct aggagagggc    4320
gaaatgtcat atgacatcca catttacaat tgtaatagga agtatcaaag tgcccctaa    4380
aaaaaaaaat tcctcccatt agtgtgtgag aaagcctatt tgttcatatc ttcacaaaca    4440
ctaaatatta gaaatattta caattgtgtt caagctaaga agtgaaaaat ggtatttcat    4500
atcttataat ttttgttgtg agattgaaca tatttcctat gtttacatgt cacctgtatt    4560
```

```
tcttattctc tgaactatac gttatgacct ttcacttatt ttcctcatgg gttatgtgta    4620
gtttgtgtag ttgtcttatt gattgttagg agctatttat atattaggaa cattaatctc    4680
ctgtcttata tgtatgtggc attgattagt tgatcatttg tgagttcatg tctgtataca    4740
aagattagag aggcagtaag agggaaaact tacctctttc ttatcaaagt ttgtaaatat    4800
atgtataaca gaagagagag aaaacattaa taaatgctga aataaagtat aaattttta    4860 ctccactact tcaacataaa ctacaaaagg agagtgactt ttctttcatg ctgacttcca    4920
tattccccat gcctaaaata gtgcctagca cagaagaggt gctcaatcag tgtttgctaa    4980
atgaaagaat tagtaacatt tcaagcagga tgactaaatg aagaatagaa tctaggcaga    5040
tactctggaa gagtgactgt gagtcattca tggtcttggt atgaattagt caaatccagc    5100
tttctcccct tcccactccc cactgttagt agaataatct gtttattgag agaatagatt    5160
tataatttag aataagaggg gcagaagagg agattttgaa ggatggcacc tgaaggagga    5220
ctagcatggc tgagatagtg aagtggaagt cttggaaagc taaagggtaa gatgaaagta    5280
tttagccgta gggggaaaaa gcattgacag gttggaaatg taaaagtcag attctccttg    5340
ctttgaaatt ttgtacaggg caggttctac taggtatgtt acaatgcaga aaaaacatga    5400
aatagttgag aggaatttgg tgaaatatta tcttcctggc ttcttttgag tgagcagatt    5460
tttttcaggg cctgtaacta taataaattt gaaacttctc atcttttagt aacttttttc    5520
acttaagttt atgtggctgt gggcaatgga atgaaggtat tgaacttcct attccctgct    5580
gggtttccac aattacaagt caatcatgac tggttattag aagactattt caattagaac    5640
caccaagtcc cataatgtca tattgtgtgt ttaattatta agtaaagcag tcttcttttt    5700
gtgttttcca taattagcac attccagaaa gatgaggata tttgctgtct ttatattcac    5760
gatctactgg catttgctga atggtaagac accaaatcct tccattaggt tctatatttt    5820
aaatatttta accatgagtt taaaactaaa atgataattt aaaatgcatg caattttctt    5880
atagagagaa tattctcttc tttcttctac tttacacaat gacaaagtct ttcttctgct    5940
ttacacaatg ataaagttcc ctgtgtcatt gtgtaaaaat atagagaata tagacaaatt    6000
gaaagacaca aaataatcta ttacccattt cccagggtta actactgaaa atatctgggg    6060
aaatggcctg tatgtatata tttatttgtt tgttttcaac aaggccagga tctttcaatc    6120
tttcaatctt ggttgctctg tgacatgcct ttcctgatga gaatactcta aggaagaatt    6180
gtaggataca tggaaaatgt cagggtaaca cagtactggc accaccctgc ggtcctttct    6240
gaactccata ccaatgtact tcttgccaga aaactgatca aaagtttagg gaagtaaaaa    6300
gagatgttag aatctaccat tccctctatg taggaagcaa ataggtgtcc agtcaaagga    6360
cattctgggg atgtctacat gaaaccaagt ctcctggttg taagtactcc atctccatat    6420
aatatttcta cagtaatata tgtttataaa ttgtgggggc aacttgttta gctaatttta    6480
ttattctgtt attgggacac tatgtctctg catgagacat agtgtcccaa acatatttc    6540 aagcccattg gataaaatat gtatttagca agttcttaaa tataatgata acataactga    6600
ccagataagg tgattttaa atgctgtgcc aactttataa atgttttgag gaattttccc    6660
ttttctgaag gttattcttc tttctttta gcatttactg tcacggttcc caaggaccta    6720
tatgtggtag agtatggcag caatatgaca attgaatgca aattcccagt agaaaaacaa    6780
ttagacctga cttcactaat tgtctattgg gaaatggagg ataagaacat tattcaattt    6840
gtgcatggag aggaagacct gaaggttcag catagtaact acagacagag ggcccagctg    6900
```

-continued

```
ttgaaggacc agctctccct gggaaatgct gcacttcgga tcacagatgt gaaattgcag    6960
gatgcagggg tttaccgctg catgatcagc tatggtggtg ccgactacaa gcggattacc    7020
gtgaaagtca atggtaagaa ttattataga tgagaggcct gatctttata gaaaacatat    7080
tctaagtgtt gaagactttt cattcttata agtccatact tattttcaaa cagaatagca    7140
tagtctcttc attcattcat tcagttcatg aattcattca cgtaagtctc caattagcat    7200
ttcttgagca cctatatgat agtcattgga aatccagaga caacacagag ccatgttcta    7260
cggtatgtac agttttccaa aaataattcc tagtctttac ttttttatta taaatgtaat    7320
acatatactt gcaaagaatt cagatactat ggaagagatc aaatgaattg caaaagtgtc    7380
cctcctccct tcaccactat ctcccatgag ataaccaaga cactccaa gagagtaacc      7440
attatttgtg tgtccctcca gaacctttt tattcaacta ccatttttt attttattag      7500
gtctgtcagt tttccttttt tgagcctctc tatatcaaat gctaataaat atattcagat    7560
caaaccccac tgtaaggttc atattaaaaa agacttgaag tctccctatg aagacaaaaa    7620
ataatcatat taagtgtaaa agaacttatt cttccagtac agtataaact atactcactg    7680
ggcatatatt catcttgaaa atctatactg atgttgtctt ggggaattga agaggaacta    7740
ggagtgtcaa ttcctgggaa ctgacccaca gttatgtcat caggtcactt gagttcgaag    7800
ttttgtgttg gcactagcta agtaaaggaa aacacctctg ctttcattgt tgagtttcat    7860
agaattgaga gctgaaagga tcccaggcag gagcgactaa tccaaactcc cacaaagaac    7920
aaaaatcccc cagaggatct tctgttcata tatttcctgc agtggcatcc ctgtcatatc    7980
ccacaatggc atccctgcca tttggactcc ccttccatat cctgttgaaa ttactcccta    8040
atagtaagct gaaatctgcc cctctagttg tagttttgga attatttcat ttccatgatg    8100
accttttaat atttgactag aattaaatca tctcccttg gtatttccat tcctggacta     8160
actaccatca atctgagggc taacaataca agtagaaaaa gtctacactt gtcattgatc    8220
actgatcaat gattaatcaa tgatcactga taattataaa ctcaaaaaca aaatcatgta    8280
gggattaaga gaaatgtatc agttttatgt tgtatttctg gtccctgatt ctggctcaaa    8340
taatgctact attgtcaaga agatatcact tgtaaagtag atttaatttt cattatattt    8400
taccatgtgc ttctccattc acggcatttc ttgagatgtt gtggtttata ctttcagttt    8460
ttctccagtc catcagcaaa tatcaggcat ctactgtgtt ccaagatatt aaagaaatca    8520
tcatgactta gcctcatcaa cagcattgct agatctggga tggaaaagaa gagtataatc    8580
ctggcagtca ggaagaaggc tgcataaagt ataagtttct gcttccaaag aagatctctc    8640
atcagcctgt agggagtgta tagggagggg acagctgtcc ttgtagtagc aaagggtttt    8700
attcaggtca tctgggctcc ataatatccc ttgtgtatct gcagtctcct ttgccatgga    8760
tcaacacaat aggaaatctt ccggcactga tggttttcc aagggggagt tcttcaggga     8820
gcaaagcaaa tgaccaacca ggtttgagga cctgatttga caattccatt ttgtatttta    8880
aattagttaa tttgcattct agtcccaatc catcttgtca tttgcagaca gtggttttgg    8940
ggttgagttg agctatacca aaagtctgaa ccttctgcac ttagaacaag gaaggcaacc    9000
accaagcttc acttgcactg aggcagtgtc tccaatggaa acgaggtagc tggcttgcag    9060
aagcttttcca actcagggaa gtagaactcc tgagtcacct ccatatgcaa ataatttcac    9120
agtactgctg ttgaacttca cttcccatca cagcaaatgt gtggtaacat agctttgcca    9180
caggagttta ctcaccatgg gatttaaaag gtgaaacatt tcaaaactga aatttgaaag    9240
aatttagttt tggattcact caattatcat gatcactttg ggtgttattg caccttcat    9300
```

| | |
|---|---|
| gtttgtgagt ttaaatacca gactctcagg cctctaactt tcaattaaaa gtgttttcct | 9360 |
| ttaatcactg aacctaatag tagggaaaac gaaatgttca ttcagacttt caggaccttc | 9420 |
| aatgagatga ggcagctgaa agatcaaagt gttgcatagt tatcccagta aagctatttg | 9480 |
| gatcgtatgg accagatcaa ctgctgtcat tccccaccaa ccccatcttt ccccaaaatt | 9540 |
| cccagccctg tttaagtgtt ctctgtagca tttatctcta tctagtatat tgtgtagcat | 9600 |
| atcatatcat acttttctat tttgtttatt gtctctctcc tcctagaata taaactccac | 9660 |
| aagcacagag atttgggtct gttttttaat attgttgtat ccccagggct tgacgtaaag | 9720 |
| cagagtggta gtatgacaaa agcacacaaa aaaatatttg ttgagtcaat gaatgaatga | 9780 |
| tttcctcaaa taggattagc ctaaaatttt ggaaacatga acagacttgg atatatgaaa | 9840 |
| atttatttcc aaaactgttc atcaggaact gttagcacct tctaaagggt acactgaagc | 9900 |
| agcagtagta aaggaggag gaggagaagc agctctgcta ctactattat cgagtactac | 9960 |
| tacaactatc gagtactact acaactatcg agtactacta caattagcac ttgcttattc | 10020 |
| tgtgtgttag gtcctgtact gaacattctg cctaaattag ttcatttcct cctggaaatg | 10080 |
| actctgtggg gtaggtgctt catcatgtaa gatgagtatt tttcacactt cactgtctct | 10140 |
| gaaatctgag tgtgtctttc aatgatggaa tctttgattt catgataagt ggtattattc | 10200 |
| ccattttaag gatgaggaaa ctggggtcca aagaaattaa gtaatttgcc caaattcacc | 10260 |
| tagcctcgta aatgataaag ctagttctaa atccaagcag attggctctg aagtctgggc | 10320 |
| ccttaataac cacttattgc ctgtatttgc acctctggtg tatgtatcaa gttatatatt | 10380 |
| ggcttcaaaa ctatcatgac cttttcttga ttttgattgt tcaatattag tatagtgttc | 10440 |
| tagatctagt agaccagggg tctgcaaaaa atttttgatta ctcacctcat ctgtaaaaca | 10500 |
| ttttaaactt gtgtgtctgt gcaggcacat ttgtgtgtaa ttataaaaaa tttactatct | 10560 |
| attaatatat aggttgtacc gtaagaaaaa ttgccatttt tgaagagcaa aaaaggttga | 10620 |
| atattaccag tttcatctgg ttcaacctaa tagacatttg tacaaaaaca gacattttaa | 10680 |
| gaggatgaaa taaaaattta ataaacaata ttttcaattt ttactaattg tgacgcttca | 10740 |
| ctattgttag ctaatatgtc aaggcatgat ataccttagg gtggaattta tcattaacaa | 10800 |
| aggtggatag tgtcaataat cttgaggttt gtgtttttttt atataacact gtgaggtcta | 10860 |
| attaagtact taattgttta caacctcata cagtcgccaa taataagtgt cacttctgct | 10920 |
| gtttcctctg ggttgtgctt gaattattag tattatcttc aatcctcagt ttctttgtgg | 10980 |
| aaaacttttt aattagttgt ttaattttgt aagatggtta gtttagtcaa aattagataa | 11040 |
| gagaatctga aaatccataa ttaccccaaa gcaacccact cataagaact attattttg | 11100 |
| tgttttgaaa tcataatttt attgatttcc agtgtttcca ctggtagtgg tttcattgat | 11160 |
| gtaggagtat caaaacatca ctaattattt atttcagttt tgtttgatcc tagctgtttt | 11220 |
| gtgttaactt tgaagaaatt acatcacaga tctattgttg tccttggtaa aggaatggag | 11280 |
| agttaaggct ctagatcatt agtggttatg ctgtagtatt aggagtaaaa aaaaagatta | 11340 |
| tatcaacaaa ataagaacat gttaatgtac ttgtaataga taaacatgaa taaagctctt | 11400 |
| atgctatata gatgcactga acaatctact agaattgtca gcaaacggta tcttaatcct | 11460 |
| aaaagggtcc caaaccaatg atctaaaatt gaatcaaact ttcttccttg agcataatta | 11520 |
| tttaagtgat ttattaaaat agccagcatt taaaagctta aaatataagt atcataatgt | 11580 |
| ggtatcctag atagatccca gaacagagaa aggatattag ggaaaaactg gaggaatgga | 11640 |

```
ataaattatg cagtttagtt attaataatg tactaatgtc cttagttatg accattgtac    11700
catggtaaag taagatacta acaatagagg aaattgggta aggggtatat gtaactctat    11760
actatctttg caattttttt gtaaatttaa aacttctaaa ataaagaaca aatttgaaca    11820
ttaaaaagtg tcgccaggaa catgtatcac tgtttacaga tgaaacagta tgtatttta    11880
tatctaattt ctgatcattg gcttcaaatc agaaaagtga atgacacatc aagatcaggt    11940
tttctgttta ctaaataaag tctaagaaaa caaagcatac cagctggaga gattcatgtt    12000
tataaagaca gatttataac aacaaaaata aaatatccaa gaataaattt aagaagaaat    12060
agggcactat gtaaaaagta tagcactta ctgagaaaca tatgaaaacc tgaatacatg    12120
gagagaggta ttttatattt gaatagaaag attgctggtt taaagataat tctctttaaa    12180
tttttttgt agaaatttaa gaggtacaag agcagtttg tcacacggat atattacata    12240
gtggtgaagt ctggggtttt agtgtaaatt aatctttaca ttttgtttga gcccaataaa    12300
tgtaccaaca tgattttat agcaagatag tcattcctat taacccaaac ttgtcccaac    12360
tttgaactga actgaggcag agctagcagg tgttccccac tgctgaggca tctgaacatt    12420
aagcgtatcc ctctgagaac cagcctgcat tgatcctctt tctaatgtag acagcatcaa    12480
gctatatatc tagttctgtg ctcagcaaaa gccctgactt cttttttgctt atgtcctagc    12540
tccatacaac aaaatcaacc aaagaatttt ggttgtcgat ccagtcacct ctgaacatga    12600
actaacatgt caggctgagg gctaccccaa ggccgaagtc atttggacaa gcagtgacca    12660
tcaagtcctg agtggtaaga ccaccaccac caattccaag agagaggaga gcttttaaa    12720
tgtgaccagc acactgagaa tcaacacaac agctaatgag attttctact gcattttag    12780
gagattagat cctgaggaaa accatacagc tgaattggtc atcccaggta atattctgaa    12840
tgtgtccatt aaaatatgtc taacactgtc ccctagcacc tagtatgatg tctgcctatc    12900
atagtcattc agtgtttgtt gaataaatga attaatgaat aacattatat ttacaaaatg    12960
tatcctaatt cctcacttcc attcatccaa atcatattgt tacttaataa acattcacca    13020
aatatttatt gaatatgcct tttgttccat gcattgtagt actcatttga cacacataga    13080
ataataagac tcacgttcac actcttcagg aaacagataa aaaacaaatg aacaaacaaa    13140
aaacaggcaa tccaatacca tgtgggaaat gctttcatac catgtgggaa acctggggga    13200
atacctgaga ggaatattca attcaggcca tgtttcagga atccaaatcc tggcacatca    13260
gagccgcctc cttcttacta gggtttctgt ggcaggaaat aaatggaacg tattttcta    13320
tcttatgcca acaggaggg accctttctc ccctgtgcct ctcccaaggt agtctacaat    13380
atttcaacgc tagcagtctg tttagtgcac aggacatgag gctgtgtatc cctgggcaaa    13440
ttgctacact tctgtgtgct tcactttctc tgtaggatta taacctactg agcaaggtta    13500
ttgtggggt caaattagca acagtgtatg aaaatgattt gagaccagtg cctgcacaaa    13560
ttcaactatt tttttttatc tcactactct atagaagtag gtaggatggg agacagagtc    13620
tgatgggagg ctcagaatgt gaaagtaagt gaggtgagtg agcatgatat ttcatataaa    13680
cacaaagata ctctgagaag agcttctcac ttcccccgcc cccaatagat gttgacagga    13740
aaatgccatg tacttcagca aaaacagctg aaaaattaga cataaaagtc aatcaatagg    13800
aaaagataat ccaggatggt cttgtgaaca gaaagaggga aaaaaaaagt ttagaaaatg    13860
atggggatgc tcttactggg gtatgagtcc tcaggtattc aactggcttt cagaaaaagc    13920
tagactagtg ggttcctgcc atttaaaagc tgttttatga caacttactt gttgggtggc    13980
ctacagtaac tcacttaact gtgctgagtc tgtttcctca tctgtaaatt ggggattttt    14040
```

```
taaaataact ggcatgccta actcataaag ttgttctgaa actgaaataa aacatatatg   14100
aacaggcatt gtaaactgta agttacgaaa aaagctggct gttgttgtgt ctttaaagct   14160
tcacctgggt agttagagat ggatcatggg tctcagtgga gagctgagcc aggcaggagc   14220
tgactaaggg taagaggtgg gagttagcaa tctctgaaca tctgtgtgcc atgggacccc   14280
ttttcctcct gcatggtacc ccagacaagg agcctagtaa gagatactaa tgacttgttg   14340
tccagagatg ttcaaactgc agagaaagat aagacaacaa gcattggcct ccaatcatga   14400
tgacagatag gaggaggtgg gagctcctta gcagtgctgg ttggttttcc atgttctact   14460
gtgggccatc tctgccatgt actgtaggct actaacttct atattaaaaa atgcaagagg   14520
ggccgggagt ggaggctcat gcctgtaatc tcagcacttt gggaggccaa ggtgggcaga   14580
tcacttgagg tcaggagttt gtaaccagcc tggccaacat ggtgaatctc tgcctctact   14640
aaaaatacaa aaattagcca gatgtggtgg cgtgcacccg taatcccagc tactcgggaa   14700
gctgaggcac gagaattgct tgaacctggg aggcggaggt tgcagtgagc caagattgtg   14760
ccactgccct ccagcctggg caacagagaa agactttgcc tcaaaaataa ataaataaat   14820
aaataaataa ataaataaat aaatggaagt gaaataatca aggccaccat ttaatactga   14880
gtagccactc catgtggtac tgtgctaagc acattataaa atattagcct cacaagaaat   14940
gtattagcat ttgtattttg tacactggtt aagtatcttg cccaagacct caaaactggt   15000
taaggggcag cagaatttaa ccccagcgcc acctttcaa agtctgggct cttacactt   15060 ctccatgctg ttcccatttt aacagatgta tctcgccatt ccagccactc aaactttggc   15120
atttaagaaa attatcctaa agctaaacta aacttcaagg atgactattc tcctgatgac   15180
cccttcccat caaaatttta tctttagtca gtttgttttt gttttgtttt gtttttcaga   15240
actacctctg gcgcttcctc caaatgaaag gactcacttg gtaattctgg gagccatctt   15300
tttactcctt ggtgtagcac tgacattcat cttctattta agaaaaggta gtatttcctt   15360
aattgcagtg gtctccactg gggatgagga gggggtgaga attggatcga tcatggctgc   15420
aaggaaacct gacttaacct ctgcagggtg gtgcaaaggc attccactat tcaacagtaa   15480
ttatattgaa gctgcatggg atcactgggt gaagatgagg tgtaaggggt gagggacagg   15540
agaatgggta tggatggagg tagaagatgc agtgtcatac aatttttttc tatcatgaaa   15600
ataaccacag acttactgta aagaaggagc taaaatgcct gtcattttca gttgcatttt   15660
agttttgcat tagttgcacc cagctggttt ctgggtactc taagtaataa aaatagttcc   15720
tctgtagaac tgtagtattt tcaccataga gtattttgta aaattattgg tagaggatgt   15780
tacataattt gcatgtgttc ctttctccat ttacctgtgg gaacaattaa aatccaggaa   15840
aatgagtata ttcaaataat ttcctcccat ttatgatgat tcagagtaaa taattcctct   15900
gatacttaga gaagtatacc aagagatcca gtgattgtat agagttgtct gatgttaaat   15960
agggaagtag aatatggaag ggaattccaa tagtcgttga aaaattcccc acaacccctt   16020
acatggggga aagtggtgtt aactgagata gtagagataa gctgttacca aaaattatgt   16080
tcttaacagg attgagatag ccagaatata aggatcaagt ttcaatgaca gtaagatcct   16140
gagatgcagt tgatttgcac aaagaaataa ttgttgccag cttgcatttt gaatatttct   16200
ctggaaaaag agattagttg gcagtagaaa tgaatagaaa tcaatagata ttaaaatacc   16260
tcagaatttg attcatctct gggaaaagat gaaaaataaa agtgtatagt cctcaagaaa   16320
atctgggatc aaaagcatgg gccttaccct attgaattaa ttaacctcag aagttgggaa   16380
```

```
ctgtggaata aggatgtcca ccagacttcc tagggattac aaatgtttca tagaacttga    16440
aatttaaact tgggtcactg tatgggatgt agagctgtgc tatatggaaa taaaaatgat    16500
ttcttttcct caagggagaa tgatggatat gaaaaaatgt ggcattcgag ttacaaactc    16560
aaagaagcaa cgtggtaaga atatcagaag gaattgggaa gtagaaggca aaggaaacaa    16620
aaagctaaag caataacaaa gagaaatcca ttagtcataa tctcctctcc ttttaaagaa    16680
tgctggttcc cctttgcctc acaactaata caagaacttc tccaccatct caggaagttt    16740
agggatggcc ttcaagagta gagagtaggg agcagctctg tggagagagg agaggagcag    16800
ggaaggggaa ggagtcagct tctctttgct aatctgttgc cctgcaccct agcagctccc    16860
tgcagcaggg gacaaggttg acttaggtgg atggataatt aattgattct aaaatattgt    16920
gtgtcagtat tgtatattgt aatactatgt taactgcgcc atgcacggta tctcatttaa    16980
tcccccaccc cttgccatta ccaaaaagag agagagaaaa atactagaat tatcctcatt    17040
ttacagtaga gaaaacagag ggtcaagaag ataaagtaaa gtgcccaaga acacacaact    17100
gatcacaaat atcaagcttg gggtccatta gcctaaccac agaccttac  tcttaaccca    17160 tctgcttcaa tccattttgc tacaaatgtt tacatttata tgcagggcag aaaagtctca    17220
tccagtttat tgaactaaga agaaagttat attaaggtgt ctaatttttt ttaatgtagt    17280
tagaaaccaa acttaacaat gagcccaagt ttaaagcagt ctaattaact tgacaagctc    17340
aggcaagttt cattctgtgg cctgtagcat catctgtgtt gtaaagctaa gtagcaaatg    17400
ttatttgggt catcctgggg ggaaagtcat cccaatttgc tcaagactga ggggtttttc    17460
aggatatcat gtaaggataa ttgggtacaa atataacctg cttctttctc tcatttcaaa    17520
tttatcattt atcatctcag caactatgag ttatgttttt tattagattt cttgttactt    17580
tttccccaga ccgctcccca tgaaattaat atactattat cactctccag atacacaatt    17640
ggaggagacg taatccagca ttggaacttc tgatcttcaa gcagggattc tcagcctgtg    17700 gtttggggt tcgtcaggc tgagcatgac cagaggaatg aatgggcccg tgggatgcat     17760
gcagtatggg acttaaaagg cccaagcact gaaaatggaa cctggcgaaa gcagaggagg    17820
agaatgaaga aaaatggagt tgaacaggga gcgtggaggg agaccttgat actttcaaat    17880
gcctgagggg ctcatcggtg catgtgacag ggagaaagga tacttctgaa caaggagcct    17940
ccaagcaaat catccactgc tcatcttagg aaaacgggtt gagaatccct aatttgaggg    18000
tcagttcctg cagaagtgcc ctttgcctcc actcaatgcc tcaatttgtt ttctgcgtga    18060
ctgagggtcc cagtgttgga acagtattta tgtatgagat tttcctattt attttgagtc    18120
tgtgaggtct tcttgtcatg ggagtgtggt tgtgaatgat ttcttttgaa gatatattgt    18180
agtagatgtt acaattttgt cgccaaacta aacttgatgc ttaatgactt gctcacatct    18240
agtaaaacat ggagtatttg taaggtgctt ggtctcctct ataactacaa gtacacattg    18300
gaagcataaa gatcaaaccg ttgatttgta taggatgtca cctttattta acccattaat    18360
actctgattg acttaatctt attctcagac ctcaagtgtc tgtgcagtat ctgttccatt    18420
taaatatcag cttttataatt atgtggtacc atacacacat aatctccttt catcgctgta   18480
accaccctgt tgtgatgacc actattattt tacccattgt acagctgagg aagcaaacag    18540
attaagtaac ttgccaaaac cagtaaatag cagagctcag actgccaccc actgtccttt    18600
tataatacaa tttacagcta tatttacttt aagcaattc atttattcaa aacccattta     18660
ttaagtgccc ttgcaatatc aatcactgta ccaggcattg aatctacaga tgtgagcaag    18720
agaaagtacc tgtcctcaag gagcttggag tataataagg agattaataa gaaaatatat    18780
```

```
tattacaatc tagtccagtg tcatagcata aggatgatgt gaggagaaaa gctgagcagt   18840
gttgccaaga ggaggaaata ggccaatgtg gtctgggaca gttgaatgta tttaaacatc   18900
ttaataatca aagtaatttt catttacaaa gagaagtcag tacttaaaat aaccctgaaa   18960
aataacactg gaattccttt tctagcatta tatttatccc tgatttgcct ttgccataca   19020
atctaatgct tgtttatata gtgtctgata ttgtttaaca gttctgtctt ttctattcaa   19080
atgctattaa attttaaatt cataccttttc catgattcaa aattcaaaag atcccatggg   19140
agatggtttg aaaatctcca cttcatcctc caagccattc aagtttcctt tccagaagca   19200
actgctactg cctttttattc atatgttctt ctaaagatag tctacatttg gaaatgtatg   19260
ttaaaagcat atattttttaa attttttttcc ctaaatagta acacattata tgtctgctgt   19320
gcactttgct atttttattt attgtagtgt ttcttatgta gcagatggaa tgaatttgaa   19380
gctcccaagg gtcaggacac atgccttctt tgtttctaag ttatctttcc catagctttt   19440
cataatcttt catatgattt agtacatgtt aaatatgtgc tacatataca tttagacaac   19500
cagcatttgt taagtatttg ctctaggact gagtttggat ttatgtttgc tcaaaaggag   19560
acccatgggc tctccagggt gcactgagtc aatctagtcc taaaaagcaa tcttattatt   19620
aactctgtat gacagaatca tatctggaac ttttgttttc tgctttctgt caagtataaa   19680
cttcactttg atgctgtact tgcaaaatca catttttcttt ctggaaattc cagtagtgta   19740
ccttgactgc tagttaccct gtgccagaaa agcctcattc gttgtgcttg aacccttttaa   19800 tgccaccagc tgtcatcact acacaggcct cctaagaggc ttcctggagg ttttgagatt   19860
cagatgccct gagagatccc agagtttcct ttccctcttg gccacattct ggtgtcagtg   19920
acaaggaata ccttcgcttt gccacccgtc aaggttgaag aaacagcgtc tccaacagag   19980
ctccttgtgt tatctgtttg tacatgtgca tttgtacagt aatttgtgtg acagtgttct   20040
ttgtgtgaat tacaggcaag aactgtggct gagcaaggca catagtctac tcagtctatt   20100
cctaactcct cctttttggtg ttggatttgt aaggcacttt atccctttttg tctcatgttt   20160 catcgtaaat ggcataggca gagatgatat ctaattctgc atttgattgt cactttttgt   20220
acctgcatta atttaataaa atatccttat ttatttttgtt a                     20261
```

```
<210> SEQ ID NO 3
<211> LENGTH: 20340
<212> TYPE: DNA
<213> ORGANISM: macaca fascicularis
<220> FEATURE:
<221> NAME/KEY: misc_feature
<222> LOCATION: (1658)..(1881)
<223> OTHER INFORMATION: n is a, c, g, or t
<220> FEATURE:
<221> NAME/KEY: misc_feature
<222> LOCATION: (2742)..(2745)
<223> OTHER INFORMATION: n is a, c, g, or t
<220> FEATURE:
<221> NAME/KEY: misc_feature
<222> LOCATION: (2747)..(2747)
<223> OTHER INFORMATION: n is a, c, g, or t
<220> FEATURE:
<221> NAME/KEY: misc_feature
<222> LOCATION: (2749)..(2749)
<223> OTHER INFORMATION: n is a, c, g, or t
<220> FEATURE:
<221> NAME/KEY: misc_feature
<222> LOCATION: (4764)..(4802)
<223> OTHER INFORMATION: n is a, c, g, or t
<220> FEATURE:
<221> NAME/KEY: misc_feature
<222> LOCATION: (8775)..(8778)
```

```
<223> OTHER INFORMATION: n is a, c, g, or t
<220> FEATURE:
<221> NAME/KEY: misc_feature
<222> LOCATION: (8980)..(8984)
<223> OTHER INFORMATION: n is a, c, g, or t
<220> FEATURE:
<221> NAME/KEY: misc_feature
<222> LOCATION: (9161)..(9293)
<223> OTHER INFORMATION: n is a, c, g, or t
<220> FEATURE:
<221> NAME/KEY: misc_feature
<222> LOCATION: (9344)..(9348)
<223> OTHER INFORMATION: n is a, c, g, or t
<220> FEATURE:
<221> NAME/KEY: misc_feature
<222> LOCATION: (9840)..(9874)
<223> OTHER INFORMATION: n is a, c, g, or t
<220> FEATURE:
<221> NAME/KEY: misc_feature
<222> LOCATION: (9958)..(9973)
<223> OTHER INFORMATION: n is a, c, g, or t
<220> FEATURE:
<221> NAME/KEY: misc_feature
<222> LOCATION: (10437)..(10452)
<223> OTHER INFORMATION: n is a, c, g, or t
<220> FEATURE:
<221> NAME/KEY: misc_feature
<222> LOCATION: (10603)..(10603)
<223> OTHER INFORMATION: n is a, c, g, or t
<220> FEATURE:
<221> NAME/KEY: misc_feature
<222> LOCATION: (10830)..(10830)
<223> OTHER INFORMATION: n is a, c, g, or t
<220> FEATURE:
<221> NAME/KEY: misc_feature
<222> LOCATION: (10989)..(11006)
<223> OTHER INFORMATION: n is a, c, g, or t
<220> FEATURE:
<221> NAME/KEY: misc_feature
<222> LOCATION: (11105)..(11122)
<223> OTHER INFORMATION: n is a, c, g, or t
<220> FEATURE:
<221> NAME/KEY: misc_feature
<222> LOCATION: (11457)..(11457)
<223> OTHER INFORMATION: n is a, c, g, or t
<220> FEATURE:
<221> NAME/KEY: misc_feature
<222> LOCATION: (13710)..(13710)
<223> OTHER INFORMATION: n is a, c, g, or t
<220> FEATURE:
<221> NAME/KEY: misc_feature
<222> LOCATION: (14015)..(14049)
<223> OTHER INFORMATION: n is a, c, g, or t
<220> FEATURE:
<221> NAME/KEY: misc_feature
<222> LOCATION: (14518)..(14585)
<223> OTHER INFORMATION: n is a, c, g, or t
<220> FEATURE:
<221> NAME/KEY: misc_feature
<222> LOCATION: (14689)..(14699)
<223> OTHER INFORMATION: n is a, c, g, or t
<220> FEATURE:
<221> NAME/KEY: misc_feature
<222> LOCATION: (14707)..(14767)
<223> OTHER INFORMATION: n is a, c, g, or t
<220> FEATURE:
<221> NAME/KEY: misc_feature
<222> LOCATION: (14837)..(14865)
<223> OTHER INFORMATION: n is a, c, g, or t
<220> FEATURE:
<221> NAME/KEY: misc_feature
<222> LOCATION: (15703)..(15741)
<223> OTHER INFORMATION: n is a, c, g, or t
<220> FEATURE:
<221> NAME/KEY: misc_feature
<222> LOCATION: (17403)..(17415)
<223> OTHER INFORMATION: n is a, c, g, or t
<220> FEATURE:
<221> NAME/KEY: misc_feature
```

<222> LOCATION: (19122)..(19135)
<223> OTHER INFORMATION: n is a, c, g, or t

<400> SEQUENCE: 3

| | | | | | |
|---|---|---|---|---|---|
| ctgaaagctt | ccccgattcc | gccgaaggtc | aggaaagtcc | aatgccgggc | aaactggatt | 60 |
| tgctgccttg | cgcagaggtg | ggcgggaccc | cgcctccggg | ccgggcgcca | agttgagcag | 120 |
| ctggcacgcc | tcgcgaagcc | ccagtcctga | agccccagtc | ctgcgctgct | tcccgaggct | 180 |
| ccgcaccagc | cgcgcttctc | tctgcctgca | ggtagggagc | gttgttcctc | cgcaggtgcc | 240 |
| cacggcccag | catctctggc | taactcgctg | ggcaccttag | gacggaggat | ctctacaccc | 300 |
| tttctttggg | atggagagag | gaggagggaa | agggaaggcg | atggtctagg | gggcagtaga | 360 |
| gccaattacc | tgttggggtt | aataagaaca | ggcaatgcat | ctgggcttcc | tccagcgcaa | 420 |
| ttcagttttg | ctctaaaaat | aatttatacc | tctaaaaata | aataaggtgg | gtagtatagg | 480 |
| ataggtagtc | attcttatgc | gaccgtgtgt | tcagaatata | gctctgatgc | taggctggaa | 540 |
| gtctggacac | gggtcctagt | ccaccgtcag | ctgcttgcta | gtaatatgac | ttgtgtaagt | 600 |
| catcccagct | gcagcagata | agtaagtctc | ttcctgcgct | aagcacgtcc | aggacccctg | 660 |
| aacggaattt | atttgctctg | tccattctga | aaacccaaag | gagtcctaaa | agaggaatgg | 720 |
| aggagcctaa | gaataaaaat | agtataataa | aacatttctt | agacaggttg | accttggcct | 780 |
| atgtcaaagt | tcagtctggg | tttgtcttat | aacataagga | gtaaaagtac | cattgttcta | 840 |
| cctctttttt | taatacttga | aaaaaaattt | actgtagatg | cttttctatt | aattaaataa | 900 |
| ccttctaaaa | aatgttttta | gtgctgcatt | cgattaggtt | ggataactaa | atgaaattaa | 960 |
| ttcctcactg | ttgggtataa | aggttattta | cagtggttct | gtcttagcta | ttcactgaac | 1020 |
| atcattacat | agatatctct | ggaatattgc | tgattgtttc | cgtcaataaa | cttagaagtg | 1080 |
| taactactta | gtcaaagaga | ctgaatatt | taaaggcatt | ttgaagaaaa | ctgaaaatgc | 1140 |
| tttccagaaa | ggatgtatca | gttgacaatg | atggttgtca | acagtattta | aggaaactag | 1200 |
| tgatactctg | aagaaaaact | tagcctttct | cagtagaagc | aggtaggcag | aggccacatg | 1260 |
| acagcagtta | gagtgtggtc | ttcaaggaag | tcacagaaat | actgtgggga | attgaaaccc | 1320 |
| caagtggaaa | atgtacaaga | gtgtctcagt | gtgactgaga | aggaggttgg | gcttggggtt | 1380 |
| taacttaaga | attttttctt | ttcttttgtg | gagatagggc | ttttgttatg | ttacccaggc | 1440 |
| tggtcttgaa | ctcctagcct | caggcgatcc | tcccgcctca | ggctgcagaa | gtcctgggat | 1500 |
| tactggccgg | agccaccatg | caggcctctt | gctcctactt | tgagaaagg | aagcttaacc | 1560 |
| tttttttttt | gtttgttttt | gttttttgtt | tttttgtag | acgagtctca | ctctgttgcc | 1620 |
| caagctggag | tgcagtggtg | ccatctcagc | tcacagcnnn | nnnnnnnnn | nnnnnnnnnn | 1680 |
| nnnnnnnnnn | nnnnnnnnnn | nnnnnnnnnn | nnnnnnnnnn | nnnnnnnnnn | nnnnnnnnnn | 1740 |
| nnnnnnnnnn | nnnnnnnnnn | nnnnnnnnnn | nnnnnnnnnn | nnnnnnnnnn | nnnnnnnnnn | 1800 |
| nnnnnnnnnn | nnnnnnnnnn | nnnnnnnnnn | nnnnnnnnnn | nnnnnnnnnn | nnnnnnnnnn | 1860 |
| nnnnnnnnnn | nnnnnnnnnn | ngactttttc | tctatctctt | ccttctaccc | atcctaccct | 1920 |
| tggaagatag | agaagtaata | tcagttccat | cgtgttatac | tgggcttccc | ccagggacaa | 1980 |
| acccacttcc | ccaacctgaa | tgagccatca | cttcttcccc | agtttacatt | tcattgctct | 2040 |
| ttgaatgtct | ccgttcggat | atgggaattc | acatgtggtc | ataattctta | cctgaagaag | 2100 |
| actgacgtct | tcttctctta | gaccaactgc | cctgatgtga | ggtttagagg | ttaaagaaca | 2160 |
| tgtgtgtatt | tacatgatct | ttgtattctg | ccttttcgtc | cctcactaat | gacagctgaa | 2220 |

```
ccccaaggaa atagagctgt ggaggagagg gtttgatgag aaagtaggta aatattggat      2280
ctaatccatc atcttccagg aaacctccat tacttctaaa aatttcaacc aaattcgtta      2340
aaggacaaga actccaccag agtagggcca taaacattgg caaaattagt tgtaatctat      2400
gactagattt aatgtcccct tgttttattc acatatggtt ataatgcttt gcttggaatt      2460
aggggtattt taagttttct tctgcctagt aagtgtattt gtgcttataa tacaataatt      2520
ataaaatatc acattaatat tttataactg tacagttaac tctggcccaa ggaaaagata      2580
gtccggtaga tgctgcagcc tgattttgta tctaaccctg gcaagaggat aatgactcat      2640
gttatttcac ttacccttttt tatcttttaa catgaagggc tcatataggt caataagaaa      2700
ccagtgatat aaacagacca aaaaatgatc agatctttca cnnnnanana aaaaaaatat      2760
ttttaaacaa tacccaactg ggtgaaaata caatgtaaca gtaccaaata tcaacatgtg      2820
tcaagaacca gaaaaatgtt tgttttcttt gatcagcaac actatttgag gaaatctatc      2880
ctcagggcct agcctggggc ctggcacaca gtaggcactg aacaaatatt tgctgaacac      2940
acacatactt atgatatttt taaaattggc aacaatccaa tacccaataa tagaggaatt      3000
aaatattata gaactgttca ataagatgct tacgaatatc atgcagtaag atgggcaata      3060
tttatatcat aagcttaaat gaaacaaatg ggtattaaag gtatggtaag gttataaatt      3120
acttttttaag agattaaagg gaaaagactg aaagatatat actgaaatgc tcacagtggt      3180
gacaaggttc cccagccttg gcactattga cattttgggc tatgtctttg ctgtgggagg      3240
ctggcctgtg ctctgcagga ggtttggcag cactcttggt ttctacccct agatagcagt      3300
agcaaccctc cctcaaccag cccaattttg acaaccaaaa atgtttccag gcatcaccag      3360
attctccctg ggtgagagtg atgaaacagt aggtgatttt cccccttcttt tctcatttttc      3420
tgtaattttg tcacattacg ttaataataa ggaaaaaaca taaaaaatag atgaatttat      3480
tattctacct cagtttggat gtttggactc ccttttgggg ttctttccat tatatcactt      3540
ggtctgctaa acagtctatg gtttggcaag gtgaaatgat tcatgaaatt ttgttttttat      3600
tttttacctg atactaaaag taaaacattc attcgcttga aaatttggac acagaacacc      3660
aaaaaaaatc cataatctca tctctctttt tctgtctttt ccttccttttt ttccctttaa      3720
aaacaagagt gaaaacctac cggttctccc tccaatttaa ttcctaaata taatcactgt      3780
taacatcttg gacatttcct gtgtctaaac acacatactc acttttttctt ttttttagca      3840
aaaagtggat ttctgctaca tgtagtgttc cgcaacttcc tacatgttta caaaatcagt      3900
acatttacat acgctgaatt cagtccttaa tggtattata ttttgtgaat ataacaaaat      3960
ttatttaacc acttagacaa tctaagatat tctcagtttg ctgttatgag caatgctctt      4020
cctttcacata tacatatata tgtgtgtgtg tgtgtgtgtg tgtgtgtgtt      4080
ttagtaggat agatttctag gagagggcga aatgtcatat gacatccaca tttacaattg      4140
taataggaag tatcaaagtg ccccctaaaa aaaaaaattc ctcccattag tgtgtgagaa      4200
agcctatttg ttcatatctt cacaaacact aaatattaga aatatttaca attgtgttca      4260
agctaagaag tgaaaaatgg tatttcatat cttataattt ttgttgtgag attgaacata      4320
tttcctatgt ttacatgtca cctgtatttc ttattctctg aactatacgt tatgaccttt      4380
cacttatttt cctcatgggt tatgtgtagt ttgtgtagtt gtcttattga ttgttaggag      4440
ctatttatat attaggaaca ttaatctcct gtcttatatg tatgtggcat tgattagttg      4500
atcatttgtg agttcatgtc tgtatacaaa gattagagag gcagtaagag ggaaaactta      4560
cctctttctt atcaaagttt gtaaatatat gtataacaga agagagagaa aacattaata      4620
```

```
aatgctgaaa taaagtataa attttactc cactacttca acataaacta caaaaggaga    4680 gtgactttc tttcatgctg acttccatat tccccatgcc taaaatagtg cctagcacag    4740
aagaggtgct caatcagtgt ttgnnnnnnn nnnnnnnnnn nnnnnnnnnn nnnnnnnnnn    4800
nnaaatgaag aatagaatct aggcagatac tctggaagag tgactgtgag tcattcatgg    4860
tcttggtatg aattagtcaa atccagcttt ctccccttcc cactcccac tgttagtaga    4920 ataatctgtt tattgagaga atagatttat aatttagaat aagaggggca gaagaggaga    4980
ttttgaagga tggcacctga aggaggacta gcatggctga gatagtgaag tggaagtctt    5040
ggaaagctaa agggtaagat gaaagtattt agccgtaggg ggaaaaagca ttgacaggtt    5100
ggaaatgtaa aagtcagatt ctccttgctt tgaaattttg tacagggcag gttctactag    5160
gtatgttaca atgcagaaaa aacatgaaat agttgagagg aatttggtga aatattatct    5220
tcctggcttc ttttgagtga gcagatttt ttcagggcct gtaactataa taaatttgaa    5280
acttctcatc ttttagtaac ttttttcact taagtttatg tggctgtggg caatggaatg    5340
aaggtattga acttcctatt ccctgctggg tttccacaat tacaagtcaa tcatgactgg    5400
ttattagaag actatttcaa ttagaaccac caagtcccat aatgtcatat tgtgtgttta    5460
attattaagt aaagcagtct tcttttgtg ttttccataa ttagcacatt ccagaaagat    5520
gaggatattt gctgtcttta tattcacgat ctactggcat ttgctgaatg gtaagacacc    5580
aaatccttcc attaggttct atattttaaa tattttaacc atgagtttaa aactaaaatg    5640
ataatttaaa atgcatgcaa ttttcttata gagagaatat tctcttcttt cttctacttt    5700
acacaatgac aaagtctttc ttctgcttta cacaatgata aagctccctg tgtcattgtg    5760
taaaaatata gagaatatag acaaattgaa agacacaaaa taatctatta cccatttccc    5820
agggttaact actgaaaata tctggggaaa tggcctgtat gtatatattt atttgtttgt    5880
tttcaacaag gccaggatct ttcaatcttt caatcttggt tgctctgtga catgcctttc    5940
ctgatgagaa tactctaagg aagaattgta ggatacatgg aaaatgtcag ggtaacacag    6000
tactggcacc accctgcggt cctttctgaa ctccatacca atgtacttct tgccagaaaa    6060
ctgatcaaaa gtttagggaa gtaaaaagag atgttagaat ctaccattcc ctctatgtag    6120
gaagcaaata ggtgtccagt caaaggacat tctggggatg tctacatgaa accaagtctc    6180
ctggttgtaa gtactccatc tccatataat atttctacag taatatatgt ttataaattg    6240
tgggggcaac ttgtttagct aattttatta ttctgttatt gggacactat gtctctgcat    6300
gagacatagt gtcccaaaac atatttcaag cccattggat aaaatatgta tttagcaagt    6360
tcttaaatat aatgataaca taactgacca gataaggtga ttttaaatg ctgtgccaac    6420 tttataaatg ttttgaggaa ttttcccttt tctgaaggtt attcttcttt cttttagca    6480 tttactgtca cggttcccaa ggacctatat gtggtagagt atggcagcaa tatgacaatt    6540
gaatgcaaat tcccagtaga aaacaatta gacctgactt cactaattgt ctattgggaa    6600
atggaggata agaacattat tcaatttgtg catggagagg aagacctgaa ggttcagcat    6660
agtaactaca gacagagggc ccagctgttg aaggaccagc ctccctggg aaatgctgca    6720 cttcggatca cagatgtgaa attgcaggat gcaggggttt accgctgcat gatcagctat    6780
ggtggtgccg actacaagcg gattaccgtg aaagtcaatg gtaagaatta ttatagatga    6840
gaggcctgat ctttatagaa aacatattct aagtgttgaa gacttttcat tcttataagt    6900
ccatacttat tttcaaacag aatagcatag tctcttcatt cattcattca gttcatgaat    6960
```

```
tcattcacgt aagtctccaa ttagcatttc ttgagcacct atatgatagt cattggaaat    7020
ccagagacaa cacagagcca tgttctacgg tatgtacagt tttccaaaaa taattcctag    7080
tctttacttt tttattataa atgtaataca tatacttgca aagaattcag atactatgga    7140
agagatcaaa tgaattgcaa aagtgtccct cctcccttca ccactatctc ccatgagata    7200
accaagagac actccaagag agtaaccatt atttgtgtgt ccctccagaa cctttttat    7260
tcaactacca ttttttatt ttattaggtc tgtcagtttt ccttttttga gcctctctat    7320
atcaaatgct aataaatata ttcagatcaa accccactgt aaggttcata ttaaaaaga    7380
cttgaagtct ccctatgaag acaaaaaata atcatattaa gtgtaaaaga acttattctt    7440
ccagtacagt ataaactata ctcactgggc atatattcat cttgaaaatc tatactgatg    7500
ttgtcttggg gaattgaaga ggaactagga gtgtcaattc ctgggaactg acccacagtt    7560
atgtcatcag gtcacttgag ttcgaagttt tgtgttagca ctagctaagt aaaggaaaac    7620
acctctgctt tcattgttga gtttcataga attgagagct gaaaggatcc caggcaggag    7680
cgactaatcc aaactcccac aaagaacaaa atcccccag aggatcttct gttcatatat     7740
ttcctgcagt ggcatccctg tcatatccca caatggcatc cctgccattt ggactcccct    7800
tccatatcct gttgaaatta ctccctaata gtaagctgaa atctgcccct ctagttgtag    7860
ttttggaatt atttcatttc catgatgacc ttttaatatt tgactagaat taaatcatct    7920
cccccttggta tttccattcc tggactaact accatcaatc tgagggctaa caatacaagt    7980
agaaaaagtc tacacttgtc attgatcact gatcaatgat taatcaatga tcactgataa    8040
ttataaactc aaaaacaaaa tcatgtaggg attaagagaa atgtatcagt tttatgttgt    8100
atttctggtc cctgattctg gctcaaataa tgctactatt gtcaagaaga tatcacttgt    8160
aaagtagatt taattttcat tatattttac catgtgcttc tccattcacg gcatttcttg    8220
agatgttgtg gttatactt tcagttttc tccagtccat cagcaaatat caggcatcta     8280
ctgtgttcca agatattaaa gaaatcatca tgacttagcc tcatcaacag cattgctaga    8340
tctgggatgg aaaagaagag tataatcctg gcagtcagga agaaggctgc ataaagtata    8400
agtttctgct tccaaagaag atctctcatc agcctgtagg gagtgtatag ggaggggaca    8460
gctgtccttg tagtagcaaa gggttttatt caggtcatct gggctccata atatcccttg    8520
tgtatctgca gtctccttg ccatggatca acacaatagg aaatcttccg gcactgatgg     8580
ttttccaag ggggagttct tcagggagca aagcaaatga ccaaccaggt ttgaggacct     8640
gatttgacaa ttccattttg tattttaaat tagttaattt gcattctagt cccaatccat    8700
cttgtcatt gcagacagtg gttttgggt tgagttgagc tataccaaaa gtctgaacct     8760
tctgcactta gaacnnnnaa ggcaaccacc aagcttcact tgcactgagg cagtgtctcc    8820
aatggaaacg aggtagctgg cttgcagaag ctttccaact cagggaagta gaactcctga    8880
gtcacctcca tatgcaaata atttcacagt actgctgttg aacttcactt cccatcacag    8940
caaatgtgtg gtaacatagc tttgccacag gagtttactn nnnccatgg gatttttaaag    9000
gtgaaacatt tcaaaactga aatttgaaag aatttagttt tggattcact caattatcat    9060
gatcactttg ggtgttattg cacctttcat gtttgtgagt ttaaatacca gactctcagg    9120
cctctaactt tcaattaaaa gtgttttct ttaatcactg nnnnnnnnnn nnnnnnnnnn     9180
nnnnnnnnnn nnnnnnnnnn nnnnnnnnnn nnnnnnnnnn nnnnnnnnnn nnnnnnnnnn    9240
nnnnnnnnnn nnnnnnnnnn nnnnnnnnnn nnnnnnnnnn nnnnnnnnnn nnnctgtcat    9300
tccccaccaa ccccatcttt ccccaaaatt cccagccctg tttnnnnggt ttttctttaa    9360
```

```
tcactgaacc taatagtagg gaaaacgaaa tgttcattca gactttcagg accttcaatg   9420
agatgaggca gctgaaagat caaagtagtt gcatagttat cccagtaaag ctatttggat   9480
cgtatggacc agatcaactg ctgtcattcc ccaccaaccc catctttccc caaaattccc   9540
agccctgttt aagtgttctc tgtagcattt atctctatct agtatattgt gtagcatatc   9600
atatcatact tttctatttt gtttattgtc tctctcctcc tagaatataa actccacaag   9660
cacagagatt tgggtctgtt ttttaatatt gttgtatccc cagggcttga cgtaaagcag   9720
agtggtagta tgacaaaagc acacaaaaaa tatttgttga gtcaatgaat gaatgatttc   9780
ctcaaatagg attagcctaa aatttggaaa catgaacaga cttggatata tgaaaatttn   9840
nnnnnnnnnn nnnnnnnnnn nnnnnnnnnn nnnnttctaa agggtacact gaagcagcag   9900
tagtaaaagg aggaggagga gaagcagctc tgctactact attatcgagt actactannn   9960
nnnnnnnnnn nnnctacaac tatcgagtac tactacaatt agcacttgct tattctgtgt  10020
gttaggtcct gtactgaaca ttctgcctaa attagttcat ttcctcctgg aaatgactct  10080
gtggggtagg tgcttcatca tgtaagatga gtattttttca cacttcactg tctctgaaat  10140
ctgagtgtgt cttcaatga tggaatcttt gatttcatga taagtggtat tattcccatt  10200
ttaaggatga ggaaactggg gtccaaagaa attaagtaat ttgcccaaat tcacctagcc  10260
tcgtaaatga taaagctagt tctaaatcca agcagattgg ctctgaagtc tgggcccttta  10320 ataaccactt attgcctgta tttgcacctc tggtgtatgt atcaagttat atattggctt  10380
caaaactatc atgacctttt cttgattttg attgttcaat attagtatag tgttctnnnn  10440
nnnnnnnnnn nngggtctgc aaaaaatttt gattactcac ctcatctgta aacatttta   10500 aacttgtgtg tctgtgcagg cacatttgtg tgtaattata aaaaatttac tatctattaa  10560
tatataggtt gtaccgtaag aaaaattgcc attttttgaag agncaaaaaa ggttgaatat  10620
taccagtttc atctggttca acctaataga catttgtaca aaaacagaca ttttaagagg  10680
atgaaataaa aatttaataa acaatatttt caatttttac taattgtgac gcttcactat  10740
tgttagctaa tatgtcaagg catgatatac cttagggtgg aatttatcat taacaaaggt  10800
ggatagtgtc aataatcttg aggtttgtgn ttttttatat aacactgtga ggtctaatta  10860
agtacttaat tgtttacaac ctcatacagt cgccaataat aagtgtcact tctgctgttt  10920
cctctgggtt gtgcttgaat tattagtatt atcttcaatc ctcagtttct ttgtggaaaa  10980 cttttttaann nnnnnnnnnn nnnnnnaaga tggttagttt agtcaaaatt agataagaga  11040
atctgaaaat ccataattac cccaaagcaa cccactcata agaactatta ttttttgtgtt 11100 ttggnnnnnn nnnnnnnnnn nntttccagt gtttccactg gtagtggttt cattgatgta  11160
ggagtatcaa aacatcacta attatttatt tcagttttgt ttgatcctag ctgttttgtg  11220
ttaactttga agaaattaca tcacagatct attgttgtcc ttggtaaagg aatggagagt  11280
taaggctcta gatcattagt ggttatgctg tagtattagg agtaaaaaaa agattatatc  11340
aacaaaataa gaacatgtta atgtacttgt aatagataaa catgaataaa gctcttatgc  11400
tatatagatg cactgaacaa tctactagaa ttgtcagcaa acggtatctt aatcctnaaa  11460
agggtcccaa accaatgatc taaaattgaa tcaaactttc ttccttgagc ataattattt  11520 aagtgatttta ttaaaatagc cagcatttaa aagcttaaaa tataagtatc ataatgtggt  11580
atcctagata gatcccagaa cagagaaagg atattaggga aaaactggag gaatggaata  11640
aattatgcag tttagttatt aataatgtac taatgtcctt agttatgacc attgtaccat  11700
```

```
ggtaaagtaa gatactaaca atagaggaaa ttgggtaagg ggtatatgta actctatact    11760
atctttgcaa ttttttttgta aatttaaaac ttctaaaata aagaacaaat ttgaacatta    11820
aaaagtgtcg ccaggaacat gtatcactgt ttacagatga aacagtatgt atttttatat    11880
ctaatttctg atcattggct tcaaatcaga aaagtgaatg acacatcaag atcaggtttt    11940
ctgtttacta aataaagtct aagaaaacaa agcataccag ctggagagat tcatgtttat    12000
aaagacagat ttataacaac aaaataaaat atccaagaat aaatttaaga agaaataggg    12060
cactatgtaa aaagtatagc actttactga gaaacatatg aaaacctgaa tacatggaga    12120
gaggtatttt atatttgaat agaaagattg ctggtttaaa gataattctc tttaaatttt    12180
ttttgttaga aatttaagag gtacaagagc agttttgtca cacggatata ttacatagtg    12240
gtgaagtctg gggttttagt gtaaattaat ctttacattt tgtttgagcc caataaatgt    12300
accaacatga tttttatagc aagatagtca ttcctattaa cccaaacttg tcccaacttt    12360
gaactgaact gaggcagagc tagcaggtgt tcccactgc tgaggcatct gaacattaag    12420
cgtatccctc tgagaaccag cctgcattga tcctctttct aatgtagaca gcatcaagct    12480
atatatctag ttctgtgctc agcaaaagcc ctgacttctt tttgcttatg tcctagctcc    12540
atacaacaaa atcaaccaaa gaattttggt tgtcgatcca gtcacctctg aacatgaact    12600
aacatgtcag gctgagggct accccaaggc cgaagtcatt tggacaagca gtgaccatca    12660
agtcctgagt ggtaagacca ccaccaccaa ttccaagaga gaggagaagc ttttaaatgt    12720
gaccagcaca ctgagaatca acacaacagc taatgagatt ttctactgca ttttttaggag   12780 attagatcct gaggaaaacc atacagctga attggtcatc ccaggtaata ttctgaatgt    12840
gtccattaaa atatgtctaa cactgtcccc tagcacctag tatgatgtct gcctatcata    12900
gtcattcagt gtttgttgaa taaatgaatt aatgaataac attatattta caaaatgtat    12960
cctaattcct cacttccatt catccaaatc atattgttac ttaataaaca ttcaccaaat    13020
atttattgaa tatgccttttt gttccatgca ttgtagtact catttgacac acatagaata    13080
ataagactca cgttcacact cttcaggaaa cagataaaaa acaaatgaac aaacaaaaaa    13140
caggcaatcc aataccatgt gggaaatgct ttcataccat gtgggaaacc tgggggaata    13200
cctgagagga atattcaatt caggccatgt ttcaggaatc caaatcctgg cacatcagag    13260
ccgcctcctt cttactaggg tttctgtggc aggaaataaa tggaacgtat ttttctatct    13320
tatgccaaac aggagggacc ctttctcccc tgtgcctctc ccaaggtagt ctacaatatt    13380
tcaacgctag cagtctgttt agtgcacagg acatgaggct gtgtatccct gggcaaattg    13440
ctacacttct gtgtgcttca ctttctctgt aggattataa cctactgagc aaggttattg    13500
tgggggtcaa attagcaaca gtgtatgaaa atgatttgag accagtgcct gcacaaattc    13560
aactattttt ttttatctca ctactctata gaagtaggta ggatgggaga cagagtctga    13620
tgggaggctc agaatgtgaa agtaagtgag gtgagtgagc atgatatttc atataaacac    13680
aaagatactc tgagaagagc ttctcacttn ccccgccccc aatagatgtt gacaggaaaa    13740
tgccacgtac ttcagcaaaa acagctgaaa aattagacat aaaagtcaat caataggaaa    13800
agataatcca ggatggtctt gtgaacagaa agaggaaaaa aaagtttag aaaatgatgg     13860 ggatgctctt actggggtat gagtcctcag gtattcaact ggctttcaga aaaagctaga    13920
ctagtgggtt cctgccattt aaaagctgtt ttatgacaac ttacttgttg ggtggcctac    13980
agtaactcac ttaactgtgc tgagtctgtt tcctnnnnnn nnnnnnnnnn nnnnnnnnnn    14040
nnnnnnnnna tgcctaactc ataaagttgt tctgaaactg aaataaaaca tatatgaaca    14100
```

```
ggcattgtaa actgtaagtt acggaaaaag ctggctgttg ttgtgtcttt aaagcttcac    14160
ctgggtagtt agagatggat catgggtctc agtggagagc tgagccaggc aggagctgac    14220
taagggtaag aggtgggaat tagcaatctc tgaacatctg tgtgccatgg gaccccttt    14280 cctcctgcat ggtacccag acaaggagcc tagtaagaga tactaatgac ttgttgtcca    14340
gagatgttca aactgcagag aaagataaga caacaagcat tggcctccaa tcatgatgac    14400
agatagagga ggtgggagct ccttagcagt gctggttggt tttccatgtt ctactgtggg    14460
ccatctctgc catgtactgt aggctactaa cttctatatt aaaaaatgca agaggggnnn    14520
nnnnnnnnnn nnnnnnnnnn nnnnnnnnnn nnnnnnnnnn nnnnnnnnnn nnnnnnnnnn    14580
nnnnntcagg agtttgtaac cagcctggcc aacatggtga atctctgcct ctactaaaaa    14640
tacaaaaatt agccagatgt ggtggcgtgc acccgtaatc ccagctacnn nnnnnnnna    14700 ggcacgnnnn nnnnnnnnnn nnnnnnnnnn nnnnnnnnnn nnnnnnnnnn nnnnnnnnnn    14760
nnnnnnnagc atgggcaaca gagaaagact ttgcctcaaa aataaataaa aaataaataa    14820
ataaataaat aaataannnn nnnnnnnnnn nnnnnnnnnn nnnnncattt aatactgagt    14880
agccactcca tgtggtactg tgctaagcac attataaaat attagcctca caagaaatgt    14940
attagcattt gtattttgta cactggttaa gtatcttgcc caagacctca aaactggtta    15000
aggggcagca gaatttaacc ccagcgccac cttttcaaag tctgggcttc ttacacttct    15060
ccatgctgtt cccattttaa cagatgtatc tcgccattcc agccactcaa actttggcat    15120
ttaagaaaat tatcctaaag ctaaactaaa cttcaaggat gactattctc ctcatgaccc    15180
cttcccatca aaatttatc tttagtcagt ttgttttgt tttgttttgt ttttcagaac    15240
tacctctggc gcttcctcca aatgaaagga ctcacttggt aattctggga gccatctttt    15300
tactccttgg tgtagcactg acattcatct tctatttaag aaaaggtagt atttccttaa    15360
ttgcagtggt ctccactggg gatgaggagg gggtgagaat tggatcgatc atggctgcaa    15420
ggaaacctga cttaacctct gcagggtggt gcaaaggcat tccactattc aacagtaatt    15480
atattgaagc tgcatgggat cactgggtga agatggggtg taaggggtga gggacaggag    15540
aatgggtatg gatggaggta aagatgcag tgtcataca ttttttttcta tcatgaaaat    15600 aaccacagac ttactgtaaa gaaggagcta aaatgcctgt cattttcagt tgcattttag    15660
ttttgcatta gttgcaccca gctggtttct gggtactcta acnnnnnnnn nnnnnnnnnn    15720
nnnnnnnnnn nnnnnnnnnn nccatagagt attttgtaaa attattggca gaggatgtac    15780
ataatttgca tgtgttcctt tctccatttta cctgtgggaa caattaaaat ccaggaaaat    15840
gagtatattc aaataatttc ctcccatttta tgatgattca gagtaaataa ttcctctgat    15900
acttagagaa gtataccaag agatccagtg attgtataga gttgtctgat gttaaatagg    15960
gaagtagaat atggaaggga ttccaatagt cgttgaaaaa ttccccacaa ccccttacat    16020
gggggaaagt ggtgttaact gagatagtag agataagctg ttaccaaaaa ttatgttctt    16080
aacaggattg agatagccag aatataagga tcaagtttca atgacagtaa gatcctgaga    16140
tgcagttgat ttgcacaaag aaataattgt tgccagcttg cattttgaat attctctgg    16200 aaaaagagat tagttggcag tagaaatgaa tagaaatcaa tagatattaa aatacctcag    16260
aatttgattc atctctggga aaagatgaaa aataaaagtg tatagtcctc aagaaaatct    16320
gggatcaaaa gcatgggcct tacccctattg aattaattaa cctcagaagt tgggaactgt    16380
ggaataagga tgtccaccag acttcctagg gattacaaat gtttcataga acttgaaatt    16440
```

```
taaacttggg tcactgtatg ggatgtagag ctgtgctata tggaaataaa aatgatttct    16500 tttctcaag  ggagaatgat  ggatatgaaa  aaatgtggca  ttcgagttac  aaactcaaag    16560
aagcaacgtg gtaagaatat cagaaggaat tgggaagtag aaggcaaagg aaacaaaaag    16620
ctaaagcaat aacaaagaga aatccattag tcataatctc ctctcctttt aaagaatgct    16680
ggttcccctt tgcctcacaa ctaatacaag aacttctcca ccatctcagg aagtttaggg    16740
atggccttca agagtagaga gtagggagca gctctgtgga gagaggagag gagcagggaa    16800
ggggaaggag tcagcttctc tttgctaatc tgttgccctg caccctagca gctccctgca    16860 gcagggggaca aggttgactt aggtggatgg ataattaatt gattctaaaa tattgtgtgt    16920
cagtattgta tattgtaata ctatgttaac tgcgccatgc acggtatctc atttaatccc    16980
ccaccccttg ccattaccaa aaagagagag agaaaaatac tagaattatc ctcattttac    17040
agtagagaaa acagagggtc aagaagataa agtaaagtgc ccaagaacac acaactgatc    17100
acaaatatca agcttggggt ccattagcct aaccacagac ccttactctt aacccatctg    17160
cttcaatcca ttttgctaca aatgtttaca ttatatgcag ggcagaaaag tctcatccag    17220
tttattgaac taagaagaaa gttatattaa ggtgtctaat ttttttttaat gtagttagaa    17280 accaaactta acaatgagcc caagtttaaa gcagtctaat taacttgaca agctcaggca    17340
agtttcattc tgtggcctgt agcatcatct gtgttgtaaa gctaagtagc aaatgttatt    17400
tgnnnnnnnn nnnnnggtca tcctgggggg aaagtcatcc caatttgctc aagactgagg    17460 ggttttttcag gatatcatgt aaggataatt gggtacaaat ataacctgct tctttctctc    17520
atttcaaatt tatcatttat catctcagca actatgagtt atgttttta  ttagatttct    17580 tgttactttt tccccagacc gctccccatg aaattaatat actattatca ctctccagat    17640
acacaattgg aggagacgta atccagcatt ggaacttctg atcttcaagc agggattctc    17700
agcctgtggt ttgggggttc gtcagggctg agcatgacca gaggaatgaa tgggcccgtg    17760
ggatgcatgc agtatgggac ttaaaaggcc caagcactga aaatggaacc tggcgaaagc    17820
agaggaggag aatgaagaaa aatggagttg aacagggagc gtggagggag accttgatac    17880
tttcaaatgc ctgaggggct catccggtgca tgtgacaggg agaaaggata cttctgaaca    17940
aggagcctcc aagcaaatca tccactgctc atcttaggaa aacgggttga gaatccctaa    18000
tttgagggtc agttcctgca gaagtgccct ttgcctccac tcaatgcctc aatttgtttt    18060
ctgcgtgact gagggtccca gtgttggaac agtatttatg tatgagattt tcctatttat    18120
tttgagtctg tgaggtcttc ttgtcatggg agtgtggttg tgaatgattt cttttgaaga    18180
tatattgtag tagatgttac aattttgtcg ccaaactaaa cttgatgctt aatgacttgc    18240
tcacatctag taaaacatgg agtatttgta aggtgcttgg tctcctctat aactacaagt    18300
acacattgga agcataaaga tcaaaccgtt gatttgtata ggatgtcacc tttatttaac    18360
ccattaatac tctgattgac ttaatcttat tctcagacct caagtgtctg tgcagtatct    18420
gttccattta aatatcagct ttataattat gtggtaccat acacacataa tctcctttca    18480
tcgctgtaac caccctgttg tgatgaccac tattatttta cccattgtac agctgaggaa    18540
gcaaacagat taagtaactt gccaaaacca gtaaatagca gagctcagac tgccaccccac    18600 tgtccttttta taatacaatt tacagctata ttttactta  agcaattcat ttattcaaaa    18660
cccatttatt aagtgcccctt gcaatatcaa tcactgtacc aggcattgaa tctacagatg    18720
tgagcaagag aaagtacctg tcctcaagga gcttggagta taataaggag attaataaga    18780
aaatatatta ttacaatcta gtccagtgtc atagcataag gatgatgtga ggagaaaagc    18840
```

```
tgagcagtgt tgccaagagg aggaaatagg ccaatgtggt ctgggacagt tgaatgtatt    18900
taaacatctt aataatcaaa gtaattttca tttacaaaga gaagtcagta cttaaaataa    18960
ccctgaaaaa taacactgga attccttttc tagcattata tttatccctg atttgccttt    19020
gccatacaat ctaatgcttg tttatatagt gtctgatatt gttaacagt  tctgtctttt    19080 ctattcaatg ctattaattt taaattcata cctttccatg annnnnnnnn nnnnngatcc    19140
catgggagat ggtttgaaaa tctccacttc atcctccaag ccattcaagt ttcctttcca    19200
gaagcaactg ctactgcctt ttattcatat gttcttctaa agatagtcta catttggaaa    19260
tgtatgttaa aagcatatat ttttaaattt ttttccctaa atagtaacac attatatgtc    19320
tgctgtgcac tttgctattt ttatttattg tagtgtttct tatgtagcag atggaatgaa    19380
tttgaagctc ccaaaggtca ggacacatgc cttctttgtt tctaagttat ctttcccata    19440
gcttttcata atctttcata tgatttagta catgttaaat atgtgctaca tatacattta    19500
gacaaccagc atttgttaag tatttgctct aggactgagt ttggatttat gtttgctcaa    19560
aaggagaccc atgggctctc cagggtgcac tgagtcaatc tagtcctaaa aagcaatctt    19620
attattaact ctgtatgaca gaatcatatc tggaactttt gttttctgct ttctgtcaag    19680
tataaacttc actttgatgc tgtacttgca aaatcacatt ttctttctgg aaattccagt    19740
agtgtacctt gactgctagt taccctgtgc cagaaaagcc tcattcgttg tgcttgaacc    19800
ctttaatgcc accagctgtc atcactacac aggcctccta agaggcttcc tggaggtttt    19860
gagattcaga tgccctgaga gatcccagag tttcctttcc ctcttggcca cattctggtg    19920
tcagtgacaa ggaataccct cgctttgcca cccgtcaagg ttgaagaaac agcgtctcca    19980
acagagctcc ttgtgttatc tgtttgtaca tgtgcatttg tacagtaatt tgtgtgacag    20040
tgttctttgt gtgaattaca ggcaagaact gtggctgagc aaggcacata gtctactcag    20100
tctattccta actcctccct ttggtgttgg atttgtaagg cactttatcc ctttttgtctc   20160 atgtttcatc gtaaatggca taggcagaga tgatatctaa ttctgcattt gattgtcact    20220
ttttgtacct gcattaattt aataaaatat ccttatttat tttgttactt ggtacaccag    20280
catgtccatt ttcttgttta ttttgtgttt cataaaatgc ttagtttaac atcccggtgg    20340
```

<210> SEQ ID NO 4
<211> LENGTH: 20641
<212> TYPE: DNA
<213> ORGANISM: mus musculus

<400> SEQUENCE: 4

```
gcctcatgcc aggctgcact tgcacgtcgc gggccagtct cctcgcctgc aggtaaggga      60
gcatcttctc gcggaatccg cttgcagggc actttaaaga gccagaatcc ctagacctttt   120 ttaggacgga aagggaacc ggtttcctgg aaagttaag aactcagaat ccgcagtttt      180
gtgtgtttat ggatcttgtg ggtaggtagc tgggtcagaa gagatgaatt aattggtcct    240
agcgcgactt gactgtttgc tagcaatgac tgggtctttc cacttgaagc atctccggag    300
gtcccttcct ctgtcgaggt ctaggatgct ggagcttaag attttcattc tatctgccca    360
gagaacctaa aggattttg gaagaaaatg tcccaaacag ttcttagata cagtgaccta     420
ggctatgtta agtttaggt tggggttgtc ataagaggtg aaagtacaat attctatctt     480 ttttttaaaaa taaattatta caggtgcttt cctatgaatt acttagccag tttttttta    540 attgctatat tccattgtgc tgggttatta aagggcatca ctctcccact gaggaatgca    600
```

```
caggttagta atagtgcctt actagctcag tcatccactg accatctgtg tatgtgactg    660
tctggaatat ggctaggtat ttcatttaga taaactctta tatgtataag tacttcatta    720
tgtttgagtg tctgaaaggc ctttgtgtag aaaaaaaaaa aacaacaacc tgagaataca    780
ttccagaaag tatccgcagc tgatgatgat agtgaccaag cggtgtttaa ggagaacttt    840
atacagggaa atattcacc tttcccagct gagcatcata gataggaaga catgatagtg     900
gttatatgct gctctaagga gggatggaga agggatggat ttgagcacag ggttcaggat    960
catttgatag aatttgaaaa ctgggtaaat tttcactctt ttgagaaagg aagtttgcat   1020
ctgcttcccc tccccgcccc aggcactctt ccccccccca tcccccccg tgccccccc     1080
ccccatggga agataaagaa gtggcgttcc aagatcttca tctggacttc ccctgggaca   1140
aacctatttc cccatcttga atgagcgtca cttctttact ttaaactctg ttctgtgaaa   1200
ggctctcagc tcttgtctgg gaatttgtga aaggttacag tttcttgccg gagggaggga   1260
gaaggtgacc ctggactctt agcccatgta agaggtgcag gtttagaggt caaaggccat   1320
gctgatttac atggtccctg aatttcccct tttgatctac tgctcacacc tgcaccctga   1380
gagccaggga gggaggata tgatactgaa gaaggtgact atcagaccca acccatcacc    1440
tttcagactt tatactaagc tttaaagcag actcataagc aatagataac tgttccaact   1500
gagtctgcca tcaacgtagg aaaaattagg tacagtcttc agtggatatc atgtacctca   1560
ttgtgactgt ctagtactcg gcttggccat ttctcccagg gcctcattgc aacagtcact   1620
gtgtcctcac aggcctggat gtcatcctgc ctcatctgct tgggcagatg aactggagag   1680
atatgattaa taatgagtca tttgattttg ctcttttgt aaatgtcctt ggtttggttt    1740
ggtttgttta ttttttgttt tgttgttgtt gtttgttttt attttcatgc tcttgttgtt   1800
gtttgagaca gagtctcact atgtagccca ggctagcctc ttcccccagt ctctcagatg   1860
ctgttgcatc tgccctttc taacatcaat gattcataat aatcagcaag aaggctatga    1920
ccttaacagt caaaataagt aatcaggtaa ttattgagag ctaaatattt atttaaacaa   1980
atcaagttgc attttccaag aattgaatgg ggggatctaa aaagtaatgt ttgtgctgca   2040
caaagatgta gtggtatcag ttgccatagt cttctctccct agatccgcag atctccttag  2100
ggaaatctat aattcaagcc taaacttgga cctggtacac aactggtact cgcccaaaca   2160
ttggccaagc acacatat ttgtgactct gaaaaaggg acaacacata acagcaaagg      2220
cgctccgtgt tagggggcctg ttaaatacaa gacttgggga aattatgcca taatcttaca  2280
ttttaaaaat ggctattaca tgtgtgagac aacgggggct ggagagatac ctcagaggta   2340
ctaggcacac atatggcaag cagatgtaca agcaggcaaa acattcttaa aaaacaaaaa   2400
caaaaccca aaacagattt cttctctatat tatttatatg gggttctgcc tgcgtgtaca   2460
cctgaagggc agaggagagc accaggtctc ataggtggtt ggttgtaagc taccatatgg   2520
ttgctaggaa ttaaactcag gactttggta agagcagcca gtgctcttaa cctctgagcc   2580
atccctccag tcccagacaa aacactctta cacataaaat aaatcaatct ttaaaagtgt   2640
agaggaaaat ggctgaacag aaactattga cagacatgct gagagtggtc accgtttctc   2700
cagcttggca ctggtggtgc tgtaggccat ctcagtgtct gtcacttgg ggcggggcgg    2760
gggggcggag gggggggaagg cggcagggca gggtcttggc agcatctcgg gcctctatt   2820
catcacatca gtaacagctc tccttcgtcc caagcaagct ttggcaacca aataaatatg   2880
ttagccaata ttaccaaacg gtccctagag gagaatgtgt gtaatgtgcc tacattcgtt   2940
tttataacaa caccaacaat atccaaccat aaaaataaac tgaaatggtc actctacctc   3000
```

-continued

```
agtgacaacg tctgagctcc gtttcagggt ccctcacaag aaattcgata ggtgtaatga    3060
tttattttc ctaataagta aaatgattat tcactcattt gaaaattgga cacacacaca     3120
aaaaaatgaa gaaaaaattt gctatttcat ctctcctttt ctatctcttt ccctttaaaa    3180
aaagtataaa tgtgggctaa agagatggct cagcagttaa gagcactggc tgctcttccg    3240
gaggtactga gttcaaactg caccaaccac atggtggctc acaaccatct gtaatgggat    3300
ctgatgccct cttctggtgt gtctagagac agtgacagtg tactcacata cataaaataa    3360
gtaaaaaaaa aaaaaacaaa acttttttt aagtataaat gtgtaagaac ttacctgtct     3420
tccctataaa agccacaatt accttgcag ataatcactg tcaggcagtg tcttcaagag     3480
aagtggggtt gttctacgac acaagaatat ttttgtttat atactaccct ctaagctcct    3540
tcctacttct ctgcaaactc atccctgtg catatactga aatctatccg tcacggtatt     3600
ttgagtatac acagttatcc gtcacggtat tttgagtata cacagttta ttagctaata     3660
catgggtat ttcaagtctg ggactgttgt tggctgtgtc atctctgtta catatgactt     3720
atattttcta agatgaattt ccaagacagg aatagagaga tcatacgaca tgcacagtta    3780
aagtttaag agattacaaa attgacctt aagaagctat acaatttcac atcctttcca      3840
ggaaaggtca agaaatccct gtatcttcac taatgctacc tatgaggagt ctgtaatttt    3900
ggtagagcag aaggtccaaa tggtatcaca gatcctccat ggacttctt atcgagagcg     3960
ttctttccgc ttttattgat tatccttcga gctatgtgag actctcatcc gtcttcctct    4020
tgaccgatgt atagttttct cactgagttc agaggctagg atgcagaagc cgtcctcgtc    4080
agctttatac acctttcaga ttgactgtga atgagcacac aggtcagaga gacggtaagg    4140
gaagacctac tctcccatga acgttgtaaa catgcgaata acacagaagc agaaaatgta    4200
aactattaga ctggctggaa tgtagcgctc acctttgagc ccactccttt agacaccggt    4260
ttcatggaag aatggctcct gtttcccacc tgctgcttca gcagtgccc aaatagtgcc     4320
agattcagag gagatactca gtgtttgccg agtgaattag gaaagtgttc agcggagggg    4380
acactagcat tcagacatcc agaccttaga gtaaccgggc cagatggaag tctccttcct    4440
tcccatagct gttaccactg tactgtcttt actggggaaa agatttatca tgtggaatag    4500
gtgcgaggca gaggtgagat tttaatgggg aggaagcatt gaaaagtgaa agtgaaaatt    4560
ggatgctctt tgctttgaag cttgcctaa agcaggtttt agcttcaaa tacgtttcaa      4620
tgttgaaaga acgcatgata catatggagg ggggcctggg gggggtcctt ggctgagttt    4680
gaatgtacat taacaatctg gggggctaat aactcaatgt aaagctgctg atcccatcat    4740
actgacttct ttccacttgg ttctacatgg ctttgagtta caaatgaaa gcattgaatt     4800
ttgaactgtt cagctgtgtt tccacacttg caaatcggtt gttggccagc cctcagaatt    4860
gcttcagtta cagctggctc gtctgctctt tccagactgg cttttagggc ttatgtatat    4920
atgagaagga cacatttact agtgtctcct tgctctgcta ttgaaattaa gcagacctct    4980
ctgtgtttcc cgttactaga tagttcccaa acatgagga tatttgctgg cattatattc     5040
acagcctgct gtcacttgct acggggtaag tcaccaaatc ttttcagtgg gttctatatt    5100
ttcaatattt tagctatgaa ttaaaaatgg aagtaatttg tggggtgtgt atgtgtgtgt    5160
atatgtgtgt gtagaggggg gtctgtgtgt atgtgcagtt gctaggcaca cataaagcgt    5220
tcataggaca acctagagct tagtcctcac cttctacctt gtttgagaca aggtctctta    5280
tttgttgtac attgctgagt cctgtagttc ggctagctca gaacctcctg ggggctctcc    5340
```

-continued

```
tgtctccacc tcccagtcca ctgagattgt aggcacatgc tactgcacct ggcttctacc    5400
tggtctctgg ggatttgaac ttgggtccat gggctacaca gcaagtcgtt tacttactgg    5460
gcaatcactc catcccctaa gataattata aggaatatac cttgcttatc caaacacatt    5520
ctcattctcc tttgccataa ataagttact tggcaaatat attgtatgta tttttaataa    5580
ataaataaaa tcttaaaaat aaataaaatt atttgtgaag acaaaaaaaa taagttactt    5640
ggaaaggatg aaggaaaata ctggagcttt gggtgtggtt tagtagtaga cacttggct     5700
gatgtaaaaa aaagcccta ggtgcaatcc caacaccaga aacaaatgaa ggaatgaaca     5760
acaaccgccc ccaccccca ggggatgaat ataaaaatat caggtaatac agaactaaca     5820
ggtgatccgt ttcctatgaa taactactga acattcccag ggaggtggcc cactgataat    5880
atatttttat ttattggttc cttttaaaca agactgggaa tatattatct agcttgcatc    5940
accaccacca cccccaccc ccgccccatg aagttatttc aaagaagaat tttagtgttc     6000
atgtgattcc ctaaataaaa tgatagtaac cttttaccca ggttttcaga tgtgtttgga    6060
ggagttttct gtcttctgag ggctggtcct ctttccttttt cagcgtttac tatcacggct   6120
ccaaaggact tgtacgtggt ggagtatggc agcaacgtca cgatggagtg cagattccct    6180
gtagaacggg agctggacct gcttgcgtta gtggtgtact gggaaaagga agatgagcaa    6240
gtgattcagt ttgtggcagg agaggaggac cttaagcctc agcacagcaa cttcaggggg    6300
agagcctcgc tgccaaagga ccagcttttg aagggaaatg ctgcccttca gatcacagac    6360
gtcaagctgc aggacgcagg cgtttactgc tgcataatca gctacggtgg tgcggactac    6420
aagcgaatca cgctgaaagt caatggtaag aattaccctg gatggggaag gcttcatccg    6480
tatttaaaac agctccctaa tgttgagagc tcttcattct tgagagttcg cacgcacttc    6540
tcacagaaca acagcagcct gttcttctcg ctcgtttgtt cattcgttcg ttcacacact    6600
tcaccagtga aaaagcctag cactgtgtgt ttgatagtaa cttgagattc agtaccagat    6660
aatactcagc catgctttgc agtcagtacc atgatcttgc aaaggtgaaa tgccaggtgt    6720
ttgtttctta tcataaatgc aatatataat atattacata gatgtataga tataactgtg    6780
taacatgcaa taagatataa tatgcatata tttcatataa cataatgtat aatatataat    6840
gtataataat atatactaca atatatagtt atatgcatag ttatatattg catttatgat    6900
aaaaagcaaa cacctggcat ttcactttg caagcttttt gaattacttg taaatatata     6960
tacatgcaaa catacataca cacacatgtt ttttacaag taatttgaat gtcatggaaa     7020
gaaatagaat cataaaaatg tccctcctcc ctaactacca tcttctaagc ataaatatac    7080
agtaactact atttgtacat ccctccatga cttttttgatt ggattactgt ttatatttaa   7140
tctatcaggc ttagcacatt ttcttttcctt tgaatacctc catacaaaat tcaatgtgtg   7200
tttatatata tatgtatata tatagttata tcatatcata tatcatacaa agtttatat    7260
atgtatacat atataaacac acatatctac acatacatac acattttta tatatataca    7320
caatatataa tgtatatgtg tgtgtgtgtg catataccctc tatatctatc tatctatcta   7380
tctatctatc tatctatcta tctatctatc tatagcttct actgtaaggg tcactttta    7440
aaaaattaag gttaatctat gaaggatgag aagtgaagat cttaagtgta gaagaagccg    7500
ttcttccaca gagatggtac aggctacact cagcaggcat gcattcattt tcagggcctg   7560
catctctggg agtgctgagg aggaactatg agtgtaagtt cctgggtaac gagccacaga   7620
aatgtcatca ggtcccttga gttcacggtt ctggttgga actaactaag ggaaggaaaa    7680
caccttgcta accacccctg ctttcactgt tgggttgcat agacctgaga gcttcactca   7740
```

```
tcgcaggcgt gcacacagcc agcccagttg cccaccagga ctggaaatcc ccaaggctct   7800
cctcttcaca tacctcccac agtggtgtcc ctcgaatcag gtccctttcg tggtctgcgg   7860
aaacttcacc ttgatggaca ctgagccgaa ccccgtcttc tccaggcaga cgttgcagat   7920
ggtctgcctg ctccttttcg gttttcataa taactttaaa actatttggc tagaatcaga   7980
tagtctcctt cgatcttttt actcctaaac tagtgtgaag ctcaatatta tacataggaa   8040
aaattcacat tcctcataag ggatcacggc agttattaac gcaatcttat gtagagatta   8100
ggaaaaatgt gtccattcga cagtttatta atgggtctgt gatggtgggt cgcttagagc   8160
ttatgaagat gccacttgcc ttatttcggt gcttggctct aacttccatt acctttact    8220
tacaattctt catttgtgac actcatgaaa ggagactcgg gatatggttg ttaatatctt   8280
gagcagctgt tagtacatca gcaaatatga ggctcctgtt tggttccaag atttttaaag   8340
acattgtgaa gctggaaggc catgagcagt caaagttgct ggacctgggg cactggaagg   8400
agctcaaggc gggcagtcag gaagaaggga gcagggtgta agcctctgtg acaagaggtc   8460
tctcatggct tgttaggagt aggtgactct ggtaaggagg aatttactct agattatgtg   8520
ctcagtgata tctctgatac caaagacaat cttttggagc gcacggcttc tccacggagg   8580
gacctgtgat gcggcaaagc tggtatccaa gcagtcttga aggcctgctt gactattttg   8640
ttttcttaca gaaatcacta cgtcgatatt ttactcccag ttcaccttgc catttgcatg   8700
cacgttagct ggtctaggcc aagagtctga accttggttg tggctcaaat ctgtaatctc   8760
agctatgtgg gaagctgagg caggagaatc gcgcaattag gacttgtctg agctacgaac   8820
atatagcagg ttcaagagca gcctgggcaa tttggcaaga tccgttctca aagacataca   8880
tacatacata tatttggcaa gatccgttct caaagacata catacataca tacatttggc   8940
aagatccgtt ctcaaagaca tacatacatg catgcatgca taaatacatg tataaatgaa   9000
tataaaatta aaataggaac aggactgagg acatgcccag tgatgtacag gaccctggtt   9060
tcagtttcta gcaccatggt cgctggcatg caaaagcttt ccatgtcaag gaagtagaac   9120
tcctgaattc tgtgctatgc aaatgacttc acagcaaggt tccttcccat cactgcaagt   9180
gtgtggtggt gaagcagccc tacagggagt tcactcgcca tggggtttta aaggtgaatt   9240
atttcaaaac tgaaatctga aagagtgtag ttttggatta actcagtttt tattatctct   9300
ttggataatg ttctaccttc aaaggtttac agaagaccct caggcatcag gcttttaatt   9360
gaaaaatatt cagctttaat cactgacctc aatatcagaa agaatgaag tgtccattta    9420
gtagtcctcg gaccgtagat ggcattaagc agctgtaaga aacacgctca tcacatggtt   9480
caacaattaa ggattgccat ggtgcacccg atcccccagc tctgtttaaa ccttttctct   9540
gtcatctatg cctatctaag atgtctcagc atatcatgct tattgtctct ttccttctct   9600
tgaacacaag ctctaggggt aggggctttg gtcagtttta ttgttggacc tgttggcctt   9660
gacgtattat gaaggggcag tgtaataaga aagaaaaacc gtgtttgttg atggaatggt   9720
ttaaaaaaaa attagcttaa aatgtatgct atacgaacgg gcatgaatct gggagatttt   9780
agactgttcc ttgtgagccg taggaacttt cttgtttctg tgttcacagt cctccgcagc   9840
tgtgctcatg gtcctccaca tctgcctaac aacagcaggg gtagatgtta taattaacac   9900
tcacagaaca cctgatatgt gagaggttgt gccctgggct tcttgctcat atgaattcat   9960
ttcatcttta acataactct tcgggggagg cacttgccca tgaccatggc ttgttttctt  10020
tcctatcgac tatctttcaa atcggaatgt gtctttccct aggtgacatc tcagattcaa  10080
```

```
tgttacacag cactgctgtg cccattttca ggcattaaaa atgcgatccg cctaaattcc   10140
accccgataa aattatgcag ccaggttcgg aacccaacta gcccatctct aaaaatctat   10200
gcccttccta gcctcgcttt gttgcctgtc tttgtacctc tggagtgggt atcaaggaac   10260
agaatggctt taaacatgat ttgaactttt cctggttttt gatcacagca gtaacagagt   10320
gttctagaga taagccagag gtttgaaaac aaacagaact tgtctttgag gtgttataaa   10380
catgtgtgtg attataaagg atatatctgg tgccaatagg tatagcttat attataagaa   10440
atggccattg tgaagatcag aaggagataa ctcactgatt tcaggtggtt gattcaatct   10500
aacacatgat atattctgaa actgtacaaa aaagatattc aaaagaagaa acacatggaa   10560
caaagagtat atggaaattc tgacaactca gaatcagtgt atgttaagat gaagttcatg   10620
attaacaaat ggagatggtc gcagtcatcc tgaagcttat tttagccaat gctttatcac   10680
atccaactca atcttcgttt ttttttttc agatggatct tcccattttt aattaacctt   10740
atcatgatag ccctagtaa ggcatgtcct gacatttctt ttcttttttt ttatagctta   10800
tgtttctttt tttaaaaatt tttttactac atattttcct caattacatt tccaatgcta   10860
tcccaaaagt cccccatacc ctcctccccc actcccctac ccacccactc ccactttttg   10920
gccctggggt tcccctgtac tgggggatat aaagtctgcg tgtccaatgg gcctctcttt   10980
ccagtgatgg cctactaggc catcttttga tacatatgca gcttgagtca agagctccgg   11040
ggtactggtt agttcatagt gttgttccac ctatagggtt gcagatccct ttagttcctt   11100
gggtgctttc tctagcttct ccattgggag ccctgtgatc catccaatag ctgactgtga   11160
gcatccactt ctgtgtttgc taggtcccgg ccaagtctca aagagacag ctatttcagg   11220 gtcctttcag catatgcttg ctagtgtatg caatggtgtc atcgtttgga ggctaattat   11280
gggatggctc cctggatatg gcagtctcta aatggtccat cctttgtct cagctccaaa   11340 ctttgtctct gtaactcctt tcaatcttcg tttttaatgt ccgaaaatga ctggtaacgt   11400
cactgcttac atttcccttt gctttgtgtt gaattgtgag ctttatcttt gatctggagt   11460
ttctttaaga agactttgta atgtgcttat ttttaaagat ggtgaattca attaaagata   11520
gacaagaggg acgggtctgt atttcatctg gtagagtgct tacctgccat tcatgaagtt   11580
ctggttcgat ccccggcaca gcatagaacc acatgcggtg gcaactcagt tgcctgtgac   11640
cccagcactc aggagctaga ggcaggttac ctttgactac acagcaagtt caaggctagc   11700
ctggtctaca tgcaactctt cctcaaaggg aaaacaaaac aaaaatagac aggagaattg   11760
gaaacatcca tagaacccca aatatgaatc aatagactcc cctcttcctg tgtcagacat   11820
tcagactcag tgacagccgt caccgtttat gaggcatgac tgattttaca gatcctagag   11880
caagcgtgca caattctggt gtttcctgcc tgcgtcctca cacacacgct caccttaggg   11940
acggaggcag cggaggtcta gtcagtttca gacgaatcca ctcatcagct gctcaccatg   12000
gtcttctagg tgaagcagaa ctctccttcc atcagcaccc gtgaaaaaca aaagtggaaa   12060
gcagatattt cactccgaat gctttatcat tggcagtgat ttcaaattta aaccactaat   12120
ttcccagaag aattaggtca cgggccatgt ggcattagac cctattgtgg tgacattatt   12180
tcctgatgtg cctatttaat aatgtatagt ggtctcatct ttatttagtt ggtcttgaat   12240
gtgataaata caagactggg caagtgttca tcaaagctgt tacttgaaat tgtaattata   12300
cctattttgt tggtggtgtt ttttcttggt tcatggacaa ccaaacacat tacggctttg   12360
ctttgtctta gctactctgt gtcaagttcc tgtgaaaata ccgtattaca gtgctcttat   12420
tacatctttg gtaatgaagt agtcacctaa gccctatcc tgggctctct atggctcact   12480
```

```
aaagaatcgt aagttggata atgattgctg aagaaataga tatgttttat ttacattgag   12540
gtagaaagac ctgtggtttc taggtaacag tttacttaac ttagttgcta catctagttt   12600
gcactcagta aacaccctgg tgtggttttt acaacaacaa ggttgttcct gaagcccaaa   12660
catggcccag atttgaatag aagacctgag gcagactaac actcactccc tgctgccaaa   12720
gtagcagagc cggggacata tttctccaat agccagcccg agttgatgct ctttgtaagc   12780
agacaccaca aagccacacg gctagcccta agatgggaga gccctgacct ctctttgctt   12840
ctgacctagc cccataccgc aaaatcaacc agagaatttc cgtggatcca gccacttctg   12900
agcatgaact aatatgtcag gccgagggtt atccagaagc tgaggtaatc tggacaaaca   12960
gtgaccacca acccgtgagt gggaagagaa gtgtcaccac ttcccggaca gaggggatgc   13020
ttctcaatgt gaccagcagt ctgagggtca acgccacagc gaatgatgtt ttctactgta   13080
cgttttggag atcacagcca gggcaaaacc acacagcgga gctgatcatc ccaggtgagt   13140
tgcctaactc gtccccggat tcctagcacg atggccatcc gccatagtca tttagcagta   13200
gttggccgag tgtatgaata catgaaactt acattggcta gacgtattct agttcctctt   13260
tctcttgcgt gcaagccata atgctacttg gtcaacactc agcaagaatt aagtgtttgc   13320
tcctgacaga cagtatgtta gtcattgagt attcgtggct ggataggaca taagttactc   13380
tgctccagga aacaggtgac agtcgcatgt aggagatgct cttgtaactt gggcaccacg   13440
ggcaacgtga gagcaagctt atgcttcagg aatgtaaacc tttgtcacat caaagctgcc   13500
ctcttccctc ccgggctgct gtagtagaaa gcaaatgcat tgccttttt tgtatcttat    13560 attcaacagg aagaatcctt tcttcccata ctcctcttca gggcattccc tgatacttca   13620
actccaggaa gtctgcctgt gcatagaaca cgaggctgat gcctatgggc aaccgactag   13680
ctgggttgta actcaccagg ccagggcatt gtagggatag aatgagctgc acgaaaatga   13740
ttgtaggaaa atcgtttgag aattcagctg tctttaaaat tcatttacct tacagaaata   13800
gggccacagg agacagtttg gtgagaggct cagagcatta tatgaatatg aacccagagg   13860
tactcactct gaggagggtt gcttctgcct ccatcgacac ccctttccca atgtatgtca   13920
acagtacatt gatgtctaga gatagctctg tgaagtttag agaagatata taaaactaca   13980
ttaaaaagtc aaccaatatg aaaaatgaag cccaggatgg gcgtggagcc aaaaggagca   14040
cacaagtttg gaaaaatgta aaataaaaag gaagacactc taactagaat tggacttttc   14100
cataaaagct atattgttgg tttcctacca ttaaatgttt tatggggctg gagacgttgt   14160
agctcagttg ggagagtact tgcctagcat ccacaatgct ctgaccccag cgccatataa   14220
acgtatatag ggctcaccta tagtctaaac actttggtgg tggaagccgg agggtcagtt   14280
caaggtcatc ctcagcttca tagcaagttc aaggccagta tggactgact acaagagacc   14340
ctgcctcaaa gacaaaacaa gcaaacatca tcataataaa acagcaaaaa gctgttctct   14400
ggccatttct ttgtaggaca tcctggagta acttaaccac tctgagtgtc tcttctcatc   14460
tgtaacttgg gttcatagtg ggaccaaaata ggagctgagt tacaacagga gatggaagtt  14520
agcaatctca gagcatccca gagccctggg acccattttt ctctttctca aaactccagg   14580
cagagaaaca gggagatgtt aatgactgga gtgcccaaga gtctcagaca tggaagaaac   14640
acaacccgca ctggtccaca tttgtgggag acagaagcgg cttagcagtg ccccgctttc   14700
ccatgttcgg gagttggcct tccacaccaa gtcagccatt actgtctata ttaatgagtg   14760
cacaaggaag ttactgcact aaggttacca tttaatattg cagtcacttt ctgtggcaac   14820
```

```
atgtcacagg cctggagttc ttctctgtgc tgctcccagt tcttaggag atctgtcttc   14880
ttcttccaac ccttacctgg acattaactt tcagtgatta agattaccct aagaccaaac   14940
tatatttcag gagtcatcat tcccctgact atggcgcagc aaagccttac cttccatcag   15000
cttctcttta tccttttcca gaactgcctg caacacatcc tccacagaac aggactcact   15060
gggtgcttct gggatccatc ctgttgttcc tcattgtagt gtccacggtc ctcctcttct   15120
tgagaaaaca aggtatttcc tccattgctg tactgcctgc agggaagtgc atgagggtcc   15180
cttcaccatt gccttgagca ggcagtgcca gagatggtac caccctgaca agaacagacc   15240
cacatcacag ggcgtcctac actgcacgct agctgaacct caccaggaaa cactgacttg   15300
aaaggtgctg ccctccattc cctgggcttg ctttcagtta cacagagtaa gttttaacag   15360
tgactctggt gtactgagtc ttccttaagt cctgttcaca ttgttgctct gcgacatctc   15420
ctaccttgga gctcggtgtt ggaccctgtt gtaatatgaa gaggtatcag ttggacaagg   15480
gcgtagggaa gctaaaagac ttagctttca aggcgtgggg gaggggagg gcattgtgag   15540
gttccctgtt cagcggttca gagtaaagct gggcagcaca caagtttaga caacaaggaa   15600
gatgctctaa ctggggttgg aggtcaatgg tgcagggata ggtagcaatg gaggctaaag   15660
aagaaagcca taaggtttct ttctacagac tctgaagaca gagcactgtg gtgcctattg   15720
gtctcaggtg aactcaagtc ttgtgttcct tacaccacct attgagctgg gttctggata   15780
ccctaagtgg aaaaacactt ctgtctaaaa agagctgtgg catctttacc acaaagcact   15840
tttttttttt gcaagatttc tgaagacgaa atgacacagt ttttaaaata atttccatat   15900
atttatttca gtacttaccc ataagaatga ctgaaatcta ggaaaatgaa tatattcaaa   15960
taatgccttc ctattgtaaa gtgacttaga gtaaaccttt tcaccaaata ctttgaaatg   16020
cataccaagt gagccaatga tgcatggact tgtgtgaagc caaatgggga aatagaatat   16080
gggagggaac atcaatcatc agagaggaat tccccatcac ccttttggag ggcgcgtgta   16140
tgggaaaagt gttgtaactg gggcggtagc gaccagctgc ttccaaagaa taagccctga   16200
gcagaaccaa gagggttgcc agggtgtgaa gattaagctt cagagacaca tctggcttag   16260
ggctagccta ggacttgcac aggaccgcag ttgttgccta atggcatctg ggatgattgg   16320
ctgaggatga ggaaagcaga gagtcagtta ggtggtaagc tagctcagga tgtgggacgt   16380
ttctgaggga agggtggaag acaaagtaga cagtcctaaa aaccatctga gaatgaaagt   16440
atgtacccta aattgttgaa taattaactt tgcggcgtgg gatctggaat aaggaagttc   16500
acgggctaaa agcctggtga ttaggggatt gatcggtgtc tcctaaaaac cttaagttga   16560
aaatcgagtc cctgtgggtt gtagtagcat cttgctataa ggaattaaga ttgatttctt   16620
cttctttagt gagaatgcta gatgtggaga aatgtggcgt tgaagataca agctcaaaaa   16680
accgaaatgg taagtgtgag taacgaggga ggggcaagcc gagggaatga gtgggacaga   16740
gcagccaagc agggtcctgc aagggctgca gttccagcgc tctgtaggct gaggcagggg   16800
gatagggagt tccaggccag caaccacaca gccaaaacaa aacaaacaaa acaaaaaaca   16860
aagcaaaagg aagagcagaa aaagctactg ttaccaacaa gagacatact ttagccgtga   16920
tctcctctcc ttccaaagga agctgttttgt ggggctgct ggttcctctg cctaaggatc   16980
gccacatctg agaaaactct gggtttgctg ctgcggtgtc tgtgtggtag ccctgcaacc   17040
agggacgctg ttgacttatt tgaatgggca tttgattaag caaatgattc tgctgtgtgg   17100
ttagctgtta actgtttcat gtgtatgata tggcatttca tttcatcatc ctgccccaa   17160
tcagataaat atgagaatca tctccattgt atagtaggga aaacagggct gagaagataa   17220
```

```
tgcgaggtgc ctaagaacac acagacttgc taccacagac gtccgttctt tgctaggtgc   17280
ttcaatctat gctgctacta atgtctgtat ttataagagt agaaaactct gcccgggcgt   17340
tggtggccca cgcctttaat cccagcactc gggaggcaga ggtagtcgga tttctgagtt   17400
tgaggccagc ctggtctaca gagtgagttc caggacagcc aggctacaca gagaaaccct   17460
gtctcgaaaa aaatcaaaaa agaaaaaaga acaagaaaac tctaactgaa ctatcttgta   17520
gtaaattaca gtgtgttcta attcatttta gtgttgttag aaaccaaaca gtaaggccag   17580
gcagaactaa agtggtttcg ctaacttggg cagacccaag caggttccct cctgtacatt   17640
accatttatt ctgctgagtc accctgagga accggcctgg cttgctcaag actgaggatt   17700
tctcagccat gaacactttc cattttaaaa ctagggcagt cccggacaag caaggatggt   17760
tagtcatcct tcatcatgta agggtagtca gacataggta gtatctgtct ctgtcttacg   17820
gcaacgttac tatctgctct agcaaacatc ccatttgttt atcttacata tcatacgttt   17880
cccccccaca tattccctgc ccctgtgaaa ttattatact atgatcactc tccagataca   17940
caattcgagg agacgtaagc agtgttgaac cctctgatcg tcgattggca gcttgtggtc   18000
tgtgaaagaa agggcccatg ggacatgagt ccaaagactc aagatggaac ctgagggaga   18060
gaaccaagaa agtgttggga gaggagcctg gaacaacgga cattttttcc agggagacac   18120
tgctaagcaa gttgcccatc agtcgtcttg ggaaatggat tgagggttcc tggcttagca   18180
gctggtcctt gcacagtgac cttttcctct gctcagtgcc gggatgagag atggagtcat   18240
gagtgttgaa gaataagtgc cttctattta ttttgagtct gtgtgttctc actttgggca   18300
tgtaattatg actggtgaat tctgacgaca tgatagatct taagatgtag tcaccaaact   18360
caactgctgc ttagcatcct ccgtaactac tgatacaagc agggaacaca gaggtcacct   18420
gcttggtttg acaggctctt gctgtctgac tcaaataatc tttatttttc agtcctcaag   18480
gctcttcgat agcagttgtt ctgtatcagc cttataggtg tcaggtatag cactcaacat   18540
ctcatctcat tacaatagca accctcatca ccatagcaac agctaacctc tgttatcctc   18600
acttcatagc caggaagctg agcgactaag tcacttgccc acagagtatc agctctcaga   18660
tttctgttct tcagccactg tcctttcagg atagaatttg tcgttaagaa attaatttaa   18720
aaactgatta ttgagtagca ttgtatatca atcacaacat gccttgtgca ctgtgctggc   18780
ctctgagcat aaagatgtac gccggagtac cggtcggaca tgtttatgtg tgttaaatac   18840
tcagagaaat gttcattaac aaggagcttg cattttagag acactggaaa gtaactccag   18900
ttcattgtct agcattacat ttacctcatt tgctatcctt gccatacagt ctcttgttct   18960
ccatgaagtg tcatgaatct tgttgaatag ttcttttatt ttttaaatgt ttctatttaa   19020
atgatattga catctgaggc gatagctcag ttggtaaaac cctttcctca caagtgtgaa   19080
accctgagtc ttatccctag aacccacata aaaaacagtt gcgtatgttt gtgcatgctt   19140
ttgatcccag cactagggag gcagaggcag gcagatcctg agctctcatt gaccacccag   19200
cctagcctac atggttagct ccaggcctac aggagctggc agagcctgaa aaacgatgcc   19260
tagacacaca cacacacaca cacacacaca cacacacaca cacacaccat gtactcatag   19320
acctaagtgc accctcctac acatgcacac acatacaatt caaacacaaa tcaacaggga   19380
attgtctcag aatggtcccc aagacaaaga agaagaaaaa caccaaacca gctctattcc   19440
ctcagcctat cctctctact ccttcctaga agcaactact attgttttg tatataaatt   19500 tacccaacga cagttaatat gtagaatata tattaaagtg tctgtcaata tatattatct   19560
```

-continued

```
ctttctttct tttcttcctttt ctttctttct ttctttcttt ctttctttct ttctttcttt    19620
ctttcttcct tccttccttc cttccttcct tccttccttc ctttctttct ttctttcttt    19680
ttttctgtct atctgtacct aaatggttgc tcactatgca ttttctgtgc tcttcgccct    19740
ttttatttaa tgtatggata tttatgctgc ttccagaatg gatctaaagc tcttgtttc    19800 taggttttct cccccatcct tctaggcatc tctcacactg tctaggccag acaccatgtc    19860
tgctgcctga atctgtagac accatttata aagcacgtac tcaccgagtt tgtatttggc    19920
ttgttctgtg tctgattaaa gggagaccat gagtccccag ggtacactga gttaccccag    19980
taccaagggg gagccttgtt tgtgtctcca tggcagaagc aggcctggag ccattttggt    20040
ttcttccttg acttctctca aacacagacg cctcacttgc tcattacagg ttctcctttg    20100
ggaatgtcag cattgctcct tgactgctgg ctgccctgga aggagcccat tagctctgtg    20160
tgagcccttg acagctactg cctctcctta ccacaggggc ctctaagata ctgttaccta    20220
gaggtcttga ggatctgtgt tctctggggg gaggaaagga ggaggaaccc agaactttct    20280
tacagttttc cttgttctgt cacatgtcaa gactgaagga acaggctggg ctacgtagtg    20340
agatcctgtc tcaaaggaaa gacgagcata gccgaacccc cggtggaacc ccctctgtta    20400
cctgttcaca caagcttatt gatgagtctc atgttaatgt cttgtttgta tgaagtttaa    20460
gaaaatatcg ggttgggcaa cacattctat ttattcattt tatttgaaat cttaatgcca    20520
tctcatggtg ttggattggt gtggcacttt attcttttgt gttgtgtata accataaatt    20580
ttattttgca tcagattgtc aatgtattgc attaatttaa taaatatttt tatttattaa    20640
a                                                                     20641
```

<210> SEQ ID NO 5
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 5
taattggctc tactgc                                                       16

<210> SEQ ID NO 6
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 6
tcgcataaga atgact                                                       16

<210> SEQ ID NO 7
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 7
tgaacacaca gtcgca                                                       16

<210> SEQ ID NO 8
<211> LENGTH: 16
<212> TYPE: DNA
<213> ORGANISM: Artificial Sequence -continued

```
<220> FEATURE:
<223> OTHER INFORMATION: Oligonucleotide motif

<400> SEQUENCE: 8
ctgaacacac agtcgc                                                   16

<210> SEQ ID NO 9
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 9
tctgaacaca cagtcg                                                   16

<210> SEQ ID NO 10
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 10
ttctgaacac acagtc                                                   16

<210> SEQ ID NO 11
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 11
acaagtcatg ttacta                                                   16

<210> SEQ ID NO 12
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 12
acacaagtca tgttac                                                   16

<210> SEQ ID NO 13
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 13
cttacttaga tgctgc                                                   16

<210> SEQ ID NO 14
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 14
acttacttag atgctg                                                   16
```

```
<210> SEQ ID NO 15
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 15
gacttactta gatgct                                                     16

<210> SEQ ID NO 16
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 16
agacttactt agatgc                                                     16

<210> SEQ ID NO 17
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 17
gcaggaagag acttac                                                     16

<210> SEQ ID NO 18
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 18
aataaattcc gttcagg                                                    17

<210> SEQ ID NO 19
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 19
gcaaataaat tccgtt                                                     16

<210> SEQ ID NO 20
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 20
agcaaataaa ttccgt                                                     16

<210> SEQ ID NO 21
<211> LENGTH: 17
<212> TYPE: DNA
<213> ORGANISM: Artificial Sequence
<220> FEATURE:
<223> OTHER INFORMATION: Oligonucleotide motif
```

```
-continued

<400> SEQUENCE: 21
cagagcaaat aaattcc                                              17

<210> SEQ ID NO 22
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 22
tggacagagc aaataaat                                             18

<210> SEQ ID NO 23
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 23
atggacagag caaata                                               16

<210> SEQ ID NO 24
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 24
cagaatggac agagca                                               16

<210> SEQ ID NO 25
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 25
ttctcagaat ggacag                                               16

<210> SEQ ID NO 26
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 26
ctgaactttg acatag                                               16

<210> SEQ ID NO 27
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 27
aagacaaacc cagactga                                             18

<210> SEQ ID NO 28
```

```
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 28
tataagacaa acccagac                                                   18

<210> SEQ ID NO 29
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 29
ttataagaca aacccaga                                                   18

<210> SEQ ID NO 30
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 30
tgttataaga caaaccc                                                    17

<210> SEQ ID NO 31
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 31
tagaacaatg gtacttt                                                    17

<210> SEQ ID NO 32
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 32
gtagaacaat ggtact                                                     16

<210> SEQ ID NO 33
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 33
aggtagaaca atggta                                                     16

<210> SEQ ID NO 34
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 34
```

```
aagaggtaga acaatgg                                                      17

<210> SEQ ID NO 35
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 35
gcatccacag taaatt                                                       16

<210> SEQ ID NO 36
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 36
gaaggttatt taattc                                                       16

<210> SEQ ID NO 37
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 37
ctaatcgaat gcagca                                                       16

<210> SEQ ID NO 38
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 38
tacccaatct aatcga                                                       16

<210> SEQ ID NO 39
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 39
tagttaccca atctaa                                                       16

<210> SEQ ID NO 40
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 40
catttagtta cccaat                                                       16

<210> SEQ ID NO 41
<211> LENGTH: 16
<212> TYPE: DNA
```

```
<213> ORGANISM: Artificial Sequence
<220> FEATURE:
<223> OTHER INFORMATION: Oligonucleotide motif

<400> SEQUENCE: 41
tcatttagtt acccaa                                                    16

<210> SEQ ID NO 42
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 42
ttcatttagt taccca                                                    16

<210> SEQ ID NO 43
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 43
gaattaattt catttagt                                                  18

<210> SEQ ID NO 44
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 44
cagtgaggaa ttaattt                                                   17

<210> SEQ ID NO 45
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 45
ccaacagtga ggaatt                                                    16

<210> SEQ ID NO 46
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 46
cccaacagtg aggaat                                                    16

<210> SEQ ID NO 47
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 47
tatacccaac agtgagg                                                   17
```

<210> SEQ ID NO 48
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 48
ttatacccaa cagtgag                                                 17

<210> SEQ ID NO 49
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 49
tttataccca acagtga                                                 17

<210> SEQ ID NO 50
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 50
cctttatacc caacag                                                  16

<210> SEQ ID NO 51
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 51
taacctttat acccaa                                                  16

<210> SEQ ID NO 52
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 52
aataaccttt ataccca                                                 17

<210> SEQ ID NO 53
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 53
gtaaataacc tttata                                                  16

<210> SEQ ID NO 54
<211> LENGTH: 18
<212> TYPE: DNA
<213> ORGANISM: Artificial Sequence
<220> FEATURE:

<223> OTHER INFORMATION: Oligonucleotide motif

<400> SEQUENCE: 54
actgtaaata acctttat                                                    18

<210> SEQ ID NO 55
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 55
atatatatgc aatgag                                                      16

<210> SEQ ID NO 56
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 56
agatatatat gcaatg                                                      16

<210> SEQ ID NO 57
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 57
gagatatata tgcaat                                                      16

<210> SEQ ID NO 58
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 58
ccagagatat atatgc                                                      16

<210> SEQ ID NO 59
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 59
caatattcca gagatat                                                     17

<210> SEQ ID NO 60
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 60
gcaatattcc agagata                                                     17

```
<210> SEQ ID NO 61
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 61
agcaatattc cagagat                                                  17

<210> SEQ ID NO 62
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 62
cagcaatatt ccagag                                                   16

<210> SEQ ID NO 63
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 63
aatcagcaat attccag                                                  17

<210> SEQ ID NO 64
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 64
acaatcagca atattcc                                                  17

<210> SEQ ID NO 65
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 65
actaagtagt tacacttct                                                19

<210> SEQ ID NO 66
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 66
ctaagtagtt acacttc                                                  17

<210> SEQ ID NO 67
<211> LENGTH: 18
<212> TYPE: DNA
<213> ORGANISM: Artificial Sequence
<220> FEATURE:
<223> OTHER INFORMATION: Oligonucleotide motif
```

```
<400> SEQUENCE: 67
gactaagtag ttacactt                                                 18

<210> SEQ ID NO 68
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 68
tgactaagta gttaca                                                   16

<210> SEQ ID NO 69
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 69
ctttgactaa gtagtta                                                  17

<210> SEQ ID NO 70
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 70
ctctttgact aagtag                                                   16

<210> SEQ ID NO 71
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 71
gctctttgac taagta                                                   16

<210> SEQ ID NO 72
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 72
ccttaaatac tgttgac                                                  17

<210> SEQ ID NO 73
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 73
cttaaatact gttgac                                                   16

<210> SEQ ID NO 74
<211> LENGTH: 16
```

```
<212> TYPE: DNA
<213> ORGANISM: Artificial Sequence
<220> FEATURE:
<223> OTHER INFORMATION: Oligonucleotide motif

<400> SEQUENCE: 74
tccttaaata ctgttg                                                    16

<210> SEQ ID NO 75
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 75
tctccttaaa tactgtt                                                   17

<210> SEQ ID NO 76
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 76
tatcatagtt ctcctt                                                    16

<210> SEQ ID NO 77
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 77
agtatcatag ttctcc                                                    16

<210> SEQ ID NO 78
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 78
gagtatcata gttctc                                                    16

<210> SEQ ID NO 79
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 79
agagtatcat agttct                                                    16

<210> SEQ ID NO 80
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 80
```
cagagtatca tagttc                                                    16

<210> SEQ ID NO 81
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 81
ttcagagtat catagt                                                    16

<210> SEQ ID NO 82
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 82
cttcagagta tcatag                                                    16

<210> SEQ ID NO 83
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 83
ttcttcagag tatcata                                                   17

<210> SEQ ID NO 84
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 84
tttcttcaga gtatcat                                                   17

<210> SEQ ID NO 85
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 85
gagaaaggct aagttt                                                    16

<210> SEQ ID NO 86
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 86
gacactcttg tacatt                                                    16

<210> SEQ ID NO 87
<211> LENGTH: 17
<212> TYPE: DNA
<213> ORGANISM: Artificial Sequence

```
<220> FEATURE:
<223> OTHER INFORMATION: Oligonucleotide motif

<400> SEQUENCE: 87
tgagacactc ttgtaca                                                17

<210> SEQ ID NO 88
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 88
tgagacactc ttgtac                                                 16

<210> SEQ ID NO 89
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 89
ctttattaaa ctccat                                                 16

<210> SEQ ID NO 90
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 90
accaaacttt attaaa                                                 16

<210> SEQ ID NO 91
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 91
aaacctctac taagtg                                                 16

<210> SEQ ID NO 92
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 92
agattaagac agttga                                                 16

<210> SEQ ID NO 93
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 93
aagtaggagc aagaggc                                                17
```

```
<210> SEQ ID NO 94
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 94
aaagtaggag caagagg                                                    17

<210> SEQ ID NO 95
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 95
gttaagcagc caggag                                                     16

<210> SEQ ID NO 96
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 96
agggtaggat gggtag                                                     16

<210> SEQ ID NO 97
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 97
aagggtagga tgggta                                                     16

<210> SEQ ID NO 98
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 98
caagggtagg atgggt                                                     16

<210> SEQ ID NO 99
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 99
ccaagggtag gatggg                                                     16

<210> SEQ ID NO 100
<211> LENGTH: 16
<212> TYPE: DNA
<213> ORGANISM: Artificial Sequence
<220> FEATURE:
<223> OTHER INFORMATION: Oligonucleotide motif
```

```
<400> SEQUENCE: 100
tccaagggta ggatgg                                                    16

<210> SEQ ID NO 101
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 101
cttccaaggg taggat                                                    16

<210> SEQ ID NO 102
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 102
atcttccaag ggtagga                                                   17

<210> SEQ ID NO 103
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 103
agaagtgatg gctcatt                                                   17

<210> SEQ ID NO 104
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 104
aagaagtgat ggctcat                                                   17

<210> SEQ ID NO 105
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 105
gaagaagtga tggctca                                                   17

<210> SEQ ID NO 106
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 106
atgaaatgta aactggg                                                   17

<210> SEQ ID NO 107
```

```
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 107
caatgaaatg taaactgg                                                    18

<210> SEQ ID NO 108
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 108
gcaatgaaat gtaaactg                                                    18

<210> SEQ ID NO 109
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 109
agcaatgaaa tgtaaact                                                    18

<210> SEQ ID NO 110
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 110
gagcaatgaa atgtaaac                                                    18

<210> SEQ ID NO 111
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 111
tgaattccca tatccga                                                     17

<210> SEQ ID NO 112
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 112
agaattatga ccatat                                                      16

<210> SEQ ID NO 113
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 113
```
aggtaagaat tatgacc    17

<210> SEQ ID NO 114
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 114
tcaggtaaga attatgac    18

<210> SEQ ID NO 115
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 115
cttcaggtaa gaattatg    18

<210> SEQ ID NO 116
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 116
tcttcaggta agaatta    17

<210> SEQ ID NO 117
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 117
cttcttcagg taagaat    17

<210> SEQ ID NO 118
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 118
tcttcttcag gtaagaa    17

<210> SEQ ID NO 119
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 119
tcttcttcag gtaaga    16

<210> SEQ ID NO 120
<211> LENGTH: 17
<212> TYPE: DNA

```
<213> ORGANISM: Artificial Sequence
<220> FEATURE:
<223> OTHER INFORMATION: Oligonucleotide motif

<400> SEQUENCE: 120
tggtctaaga gaagaag                                                   17

<210> SEQ ID NO 121
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 121
gttggtctaa gagaag                                                    16

<210> SEQ ID NO 122
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 122
agttggtcta agagaa                                                    16

<210> SEQ ID NO 123
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 123
cagttggtct aagagaa                                                   17

<210> SEQ ID NO 124
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 124
gcagttggtc taagagaa                                                  18

<210> SEQ ID NO 125
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 125
cagttggtct aagaga                                                    16

<210> SEQ ID NO 126
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 126
gcagttggtc taagaga                                                   17
```

<210> SEQ ID NO 127
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 127
gcagttggtc taagag                                                     16

<210> SEQ ID NO 128
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 128
ctcatatcag ggcagt                                                     16

<210> SEQ ID NO 129
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 129
cacacatgtt ctttaac                                                    17

<210> SEQ ID NO 130
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 130
taaatacaca catgttct                                                   18

<210> SEQ ID NO 131
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 131
gtaaatacac acatgttc                                                   18

<210> SEQ ID NO 132
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 132
tgtaaataca cacatgtt                                                   18

<210> SEQ ID NO 133
<211> LENGTH: 18
<212> TYPE: DNA
<213> ORGANISM: Artificial Sequence
<220> FEATURE:

```
<223> OTHER INFORMATION: Oligonucleotide motif

<400> SEQUENCE: 133
gatcatgtaa atacacac                                                 18

<210> SEQ ID NO 134
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 134
agatcatgta aatacaca                                                 18

<210> SEQ ID NO 135
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 135
caaagatcat gtaaatacac                                               20

<210> SEQ ID NO 136
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 136
acaaagatca tgtaaataca                                               20

<210> SEQ ID NO 137
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 137
gaatacaaag atcatgta                                                 18

<210> SEQ ID NO 138
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 138
agaatacaaa gatcatgt                                                 18

<210> SEQ ID NO 139
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 139
cagaatacaa agatcatg                                                 18
```

```
<210> SEQ ID NO 140
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 140
gcagaataca aagatca                                                 17

<210> SEQ ID NO 141
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 141
aggcagaata caaagat                                                 17

<210> SEQ ID NO 142
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 142
aaggcagaat acaaaga                                                 17

<210> SEQ ID NO 143
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 143
attagtgagg gacgaa                                                  16

<210> SEQ ID NO 144
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 144
cattagtgag ggacga                                                  16

<210> SEQ ID NO 145
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 145
gagggtgatg gattag                                                  16

<210> SEQ ID NO 146
<211> LENGTH: 16
<212> TYPE: DNA
<213> ORGANISM: Artificial Sequence
<220> FEATURE:
<223> OTHER INFORMATION: Oligonucleotide motif
```

```
<400> SEQUENCE: 146
ttaggagtaa taaagg                                                      16

<210> SEQ ID NO 147
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 147
ttaatgaatt tggttg                                                      16

<210> SEQ ID NO 148
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 148
ctttaatgaa tttggt                                                      16

<210> SEQ ID NO 149
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 149
catggattac aactaa                                                      16

<210> SEQ ID NO 150
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 150
tcatggatta caacta                                                      16

<210> SEQ ID NO 151
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 151
gtcatggatt acaact                                                      16

<210> SEQ ID NO 152
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 152
cattaaatct agtcat                                                      16

<210> SEQ ID NO 153
<211> LENGTH: 17
```

```
<212> TYPE: DNA
<213> ORGANISM: Artificial Sequence
<220> FEATURE:
<223> OTHER INFORMATION: Oligonucleotide motif

<400> SEQUENCE: 153
gacattaaat ctagtca                                                      17

<210> SEQ ID NO 154
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 154
agggacatta aatcta                                                       16

<210> SEQ ID NO 155
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 155
caaagcatta taacca                                                       16

<210> SEQ ID NO 156
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 156
acttactagg cagaag                                                       16

<210> SEQ ID NO 157
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 157
cagagttaac tgtaca                                                       16

<210> SEQ ID NO 158
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 158
ccagagttaa ctgtac                                                       16

<210> SEQ ID NO 159
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 159
```
gccagagtta actgta                                                   16

<210> SEQ ID NO 160
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 160
tgggccagag ttaact                                                   16

<210> SEQ ID NO 161
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 161
cagcatctat cagact                                                   16

<210> SEQ ID NO 162
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 162
tgaaataaca tgagtcat                                                 18

<210> SEQ ID NO 163
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 163
gtgaaataac atgagtc                                                  17

<210> SEQ ID NO 164
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 164
tctgtttatg tcactg                                                   16

<210> SEQ ID NO 165
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 165
gtctgtttat gtcact                                                   16

<210> SEQ ID NO 166
<211> LENGTH: 16
<212> TYPE: DNA
<213> ORGANISM: Artificial Sequence

```
<220> FEATURE:
<223> OTHER INFORMATION: Oligonucleotide motif

<400> SEQUENCE: 166
tggtctgttt atgtca                                                 16

<210> SEQ ID NO 167
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 167
ttggtctgtt tatgtc                                                 16

<210> SEQ ID NO 168
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 168
tcacccattg tttaaa                                                 16

<210> SEQ ID NO 169
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 169
ttcagcaaat attcgt                                                 16

<210> SEQ ID NO 170
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 170
gtgtgttcag caaatat                                                17

<210> SEQ ID NO 171
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 171
tctattgtta ggtatc                                                 16

<210> SEQ ID NO 172
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 172
attgcccatc ttactg                                                 16
```

<210> SEQ ID NO 173
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 173
tattgcccat cttact                                                      16

<210> SEQ ID NO 174
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 174
aaatattgcc catctt                                                      16

<210> SEQ ID NO 175
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 175
ataaccttat cataca                                                      16

<210> SEQ ID NO 176
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 176
tataacctta tcatac                                                      16

<210> SEQ ID NO 177
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 177
ttataacctt atcata                                                      16

<210> SEQ ID NO 178
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 178
tttataacct tatcat                                                      16

<210> SEQ ID NO 179
<211> LENGTH: 16
<212> TYPE: DNA
<213> ORGANISM: Artificial Sequence
<220> FEATURE:
<223> OTHER INFORMATION: Oligonucleotide motif

```
<400> SEQUENCE: 179
actgctattg ctatct                                                   16

<210> SEQ ID NO 180
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 180
aggactgcta ttgcta                                                   16

<210> SEQ ID NO 181
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 181
gaggactgct attgct                                                   16

<210> SEQ ID NO 182
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 182
acgtagaata ataaca                                                   16

<210> SEQ ID NO 183
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 183
ccaagtgata taatgg                                                   16

<210> SEQ ID NO 184
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 184
ttagcagacc aagtga                                                   16

<210> SEQ ID NO 185
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 185
gtttagcaga ccaagt                                                   16

<210> SEQ ID NO 186
```

```
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 186
tgacagtgat tatatt                                                     16

<210> SEQ ID NO 187
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 187
tgtccaagat attgac                                                     16

<210> SEQ ID NO 188
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 188
gaatatccta gattgt                                                     16

<210> SEQ ID NO 189
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 189
caaactgaga atatcc                                                     16

<210> SEQ ID NO 190
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 190
gcaaactgag aatatc                                                     16

<210> SEQ ID NO 191
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 191
tcctattaca atcgta                                                     16

<210> SEQ ID NO 192
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 192
```
ttcctattac aatcgt                                               16

<210> SEQ ID NO 193
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 193
actaatggga ggattt                                               16

<210> SEQ ID NO 194
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 194
tagttcagag aataag                                               16

<210> SEQ ID NO 195
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 195
taacatatag ttcaga                                               16

<210> SEQ ID NO 196
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 196
ataacatata gttcag                                               16

<210> SEQ ID NO 197
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 197
cataacatat agttca                                               16

<210> SEQ ID NO 198
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 198
tcataacata tagttc                                               16

<210> SEQ ID NO 199
<211> LENGTH: 16
<212> TYPE: DNA

```
<213> ORGANISM: Artificial Sequence
<220> FEATURE:
<223> OTHER INFORMATION: Oligonucleotide motif

<400> SEQUENCE: 199
tagctcctaa caatca                                                     16

<210> SEQ ID NO 200
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 200
ctccaatctt tgtata                                                     16

<210> SEQ ID NO 201
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 201
tctccaatct ttgtat                                                     16

<210> SEQ ID NO 202
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 202
tctatttcag ccaatc                                                     16

<210> SEQ ID NO 203
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 203
cggaagtcag agtgaa                                                     16

<210> SEQ ID NO 204
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 204
ttaagcatga ggaata                                                     16

<210> SEQ ID NO 205
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 205
tgattgagca cctctt                                                     16
```

<210> SEQ ID NO 206
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 206
gactaattat ttcgtt                                                  16

<210> SEQ ID NO 207
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 207
tgactaatta tttcgt                                                  16

<210> SEQ ID NO 208
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 208
gtgactaatt atttcg                                                  16

<210> SEQ ID NO 209
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 209
ctgcttgaaa tgtgac                                                  16

<210> SEQ ID NO 210
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 210
cctgcttgaa atgtga                                                  16

<210> SEQ ID NO 211
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 211
atcctgcttg aaatgt                                                  16

<210> SEQ ID NO 212
<211> LENGTH: 16
<212> TYPE: DNA
<213> ORGANISM: Artificial Sequence
<220> FEATURE:

<223> OTHER INFORMATION: Oligonucleotide motif

<400> SEQUENCE: 212
attataaatc tattct                                                     16

<210> SEQ ID NO 213
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 213
gctaaatact ttcatc                                                     16

<210> SEQ ID NO 214
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 214
cattgtaaca taccta                                                     16

<210> SEQ ID NO 215
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 215
gcattgtaac atacct                                                     16

<210> SEQ ID NO 216
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 216
taatattgca ccaaat                                                     16

<210> SEQ ID NO 217
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 217
gataatattg caccaa                                                     16

<210> SEQ ID NO 218
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 218
agataatatt gcacca                                                     16

```
<210> SEQ ID NO 219
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 219
gccaagaaga taatat                                                   16

<210> SEQ ID NO 220
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 220
cacagccaca taaact                                                   16

<210> SEQ ID NO 221
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 221
ttgtaattgt ggaaac                                                   16

<210> SEQ ID NO 222
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 222
tgacttgtaa ttgtgg                                                   16

<210> SEQ ID NO 223
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 223
tctaactgaa atagtc                                                   16

<210> SEQ ID NO 224
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 224
gtggttctaa ctgaaa                                                   16

<210> SEQ ID NO 225
<211> LENGTH: 16
<212> TYPE: DNA
<213> ORGANISM: Artificial Sequence
<220> FEATURE:
<223> OTHER INFORMATION: Oligonucleotide motif
```

```
<400> SEQUENCE: 225
caatatggga cttggt                                                    16

<210> SEQ ID NO 226
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 226
atgacaatat gggact                                                    16

<210> SEQ ID NO 227
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 227
tatgacaata tgggac                                                    16

<210> SEQ ID NO 228
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 228
atatgacaat atggga                                                    16

<210> SEQ ID NO 229
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 229
cttcacttaa taatta                                                    16

<210> SEQ ID NO 230
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 230
ctgcttcact taataa                                                    16

<210> SEQ ID NO 231
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 231
aagactgctt cactta                                                    16

<210> SEQ ID NO 232
<211> LENGTH: 16
```

```
<212> TYPE: DNA
<213> ORGANISM: Artificial Sequence
<220> FEATURE:
<223> OTHER INFORMATION: Oligonucleotide motif

<400> SEQUENCE: 232
gaatgcccta attatg                                                        16

<210> SEQ ID NO 233
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 233
tggaatgccc taatta                                                        16

<210> SEQ ID NO 234
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 234
gcaaatgcca gtaggt                                                        16

<210> SEQ ID NO 235
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 235
ctaatggaag gatttg                                                        16

<210> SEQ ID NO 236
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 236
aatatagaac ctaatg                                                        16

<210> SEQ ID NO 237
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 237
gaaagaatag aatgtt                                                        16

<210> SEQ ID NO 238
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 238
```
atgggtaata gattat                                                16

<210> SEQ ID NO 239
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 239
gaaagagcac agggtg                                                16

<210> SEQ ID NO 240
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 240
ctacatagag ggaatg                                                16

<210> SEQ ID NO 241
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 241
gcttcctaca tagagg                                                16

<210> SEQ ID NO 242
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 242
tgcttcctac atagag                                                16

<210> SEQ ID NO 243
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 243
tgggcttgaa atatgt                                                16

<210> SEQ ID NO 244
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 244
cattatattt aagaac                                                16

<210> SEQ ID NO 245
<211> LENGTH: 16
<212> TYPE: DNA
<213> ORGANISM: Artificial Sequence

```
<220> FEATURE:
<223> OTHER INFORMATION: Oligonucleotide motif

<400> SEQUENCE: 245
tcggttatgt tatcat                                                    16

<210> SEQ ID NO 246
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 246
cactttatct ggtcgg                                                    16

<210> SEQ ID NO 247
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 247
aaattggcac agcgtt                                                    16

<210> SEQ ID NO 248
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 248
accgtgacag taaatg                                                    16

<210> SEQ ID NO 249
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 249
tgggaaccgt gacagta                                                   17

<210> SEQ ID NO 250
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 250
ccacatatag gtcctt                                                    16

<210> SEQ ID NO 251
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 251
catattgcta ccatac                                                    16
```

<210> SEQ ID NO 252
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 252
tcatattgct accata					16

<210> SEQ ID NO 253
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 253
caattgtcat attgct					16

<210> SEQ ID NO 254
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 254
cattcaattg tcatattg					18

<210> SEQ ID NO 255
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 255
tttctactgg gaatttg					17

<210> SEQ ID NO 256
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 256
caattagtgc agccag					16

<210> SEQ ID NO 257
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 257
gaataatgtt cttatcc					17

<210> SEQ ID NO 258
<211> LENGTH: 20
<212> TYPE: DNA
<213> ORGANISM: Artificial Sequence
<220> FEATURE:
<223> OTHER INFORMATION: Oligonucleotide motif

```
<400> SEQUENCE: 258
cacaaattga ataatgttct                                                    20

<210> SEQ ID NO 259
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 259
catgcacaaa ttgaataat                                                     19

<210> SEQ ID NO 260
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 260
atcctgcaat ttcacat                                                       17

<210> SEQ ID NO 261
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 261
ccaccatagc tgatca                                                        16

<210> SEQ ID NO 262
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 262
accaccatag ctgatca                                                       17

<210> SEQ ID NO 263
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 263
caccaccata gctgatc                                                       17

<210> SEQ ID NO 264
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 264
tagtcggcac caccat                                                        16

<210> SEQ ID NO 265
```

```
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 265
cttgtagtcg gcaccac                                                      17

<210> SEQ ID NO 266
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 266
cttgtagtcg gcacca                                                       16

<210> SEQ ID NO 267
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 267
cgcttgtagt cggcac                                                       16

<210> SEQ ID NO 268
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 268
tcaataaaga tcaggc                                                       16

<210> SEQ ID NO 269
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 269
tggacttaca agaatg                                                       16

<210> SEQ ID NO 270
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 270
atggacttac aagaat                                                       16

<210> SEQ ID NO 271
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 271
```

-continued

```
gctcaagaaa ttggat                                              16

<210> SEQ ID NO 272
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 272
tactgtagaa catggc                                              16

<210> SEQ ID NO 273
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 273
gcaattcatt tgatct                                              16

<210> SEQ ID NO 274
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 274
tgaagggagg agggacac                                            18

<210> SEQ ID NO 275
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 275
agtggtgaag ggaggag                                             17

<210> SEQ ID NO 276
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 276
tagtggtgaa gggaggag                                            18

<210> SEQ ID NO 277
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 277
atagtggtga agggaggag                                           19

<210> SEQ ID NO 278
<211> LENGTH: 17
<212> TYPE: DNA
```

```
<213> ORGANISM: Artificial Sequence
<220> FEATURE:
<223> OTHER INFORMATION: Oligonucleotide motif

<400> SEQUENCE: 278
tagtggtgaa gggagga                                                  17

<210> SEQ ID NO 279
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 279
atagtggtga agggagga                                                 18

<210> SEQ ID NO 280
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 280
tagtggtgaa gggagg                                                   16

<210> SEQ ID NO 281
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 281
atagtggtga agggagg                                                  17

<210> SEQ ID NO 282
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 282
gatagtggtg aagggagg                                                 18

<210> SEQ ID NO 283
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 283
atagtggtga agggag                                                   16

<210> SEQ ID NO 284
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 284
gatagtggtg aagggag                                                  17
```

<210> SEQ ID NO 285
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 285
gagatagtgg tgaagg                                            16

<210> SEQ ID NO 286
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 286
catgggagat agtggt                                            16

<210> SEQ ID NO 287
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 287
acaaataatg gttactct                                          18

<210> SEQ ID NO 288
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 288
acacacaaat aatggtta                                          18

<210> SEQ ID NO 289
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 289
gagggacaca caaataat                                          18

<210> SEQ ID NO 290
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 290
atatagagag gctcaa                                            16

<210> SEQ ID NO 291
<211> LENGTH: 16
<212> TYPE: DNA
<213> ORGANISM: Artificial Sequence
<220> FEATURE:

<223> OTHER INFORMATION: Oligonucleotide motif

<400> SEQUENCE: 291
ttgatataga gaggct                                                    16

<210> SEQ ID NO 292
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 292
gcatttgata tagaga                                                    16

<210> SEQ ID NO 293
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 293
tttgcatttg atatag                                                    16

<210> SEQ ID NO 294
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 294
ctggaagaat aggttc                                                    16

<210> SEQ ID NO 295
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 295
actggaagaa taggtt                                                    16

<210> SEQ ID NO 296
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 296
tactggaaga ataggt                                                    16

<210> SEQ ID NO 297
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 297
tggcttatcc tgtact                                                    16

```
<210> SEQ ID NO 298
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 298
atggcttatc ctgtac                                                    16

<210> SEQ ID NO 299
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 299
tatggcttat cctgta                                                    16

<210> SEQ ID NO 300
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 300
gtatggctta tcctgt                                                    16

<210> SEQ ID NO 301
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 301
atgaatatat gcccagt                                                   17

<210> SEQ ID NO 302
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 302
gatgaatata tgccca                                                    16

<210> SEQ ID NO 303
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 303
caagatgaat atatgcc                                                   17

<210> SEQ ID NO 304
<211> LENGTH: 17
<212> TYPE: DNA
<213> ORGANISM: Artificial Sequence
<220> FEATURE:
<223> OTHER INFORMATION: Oligonucleotide motif
```

-continued

<400> SEQUENCE: 304
gacaacatca gtataga                                                  17

<210> SEQ ID NO 305
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 305
caagacaaca tcagta                                                   16

<210> SEQ ID NO 306
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 306
cactcctagt tccttt                                                   16

<210> SEQ ID NO 307
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 307
aacactccta gttcct                                                   16

<210> SEQ ID NO 308
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 308
taacactcct agttcc                                                   16

<210> SEQ ID NO 309
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 309
ctaacactcc tagttc                                                   16

<210> SEQ ID NO 310
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 310
tgataacata actgtg                                                   16

<210> SEQ ID NO 311
<211> LENGTH: 16

```
<212> TYPE: DNA
<213> ORGANISM: Artificial Sequence
<220> FEATURE:
<223> OTHER INFORMATION: Oligonucleotide motif

<400> SEQUENCE: 311
ctgataacat aactgt                                                        16

<210> SEQ ID NO 312
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 312
tttgaactca agtgac                                                        16

<210> SEQ ID NO 313
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 313
tcctttactt agctag                                                        16

<210> SEQ ID NO 314
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 314
gagtttggat tagctg                                                        16

<210> SEQ ID NO 315
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 315
tgggatatga caggga                                                        16

<210> SEQ ID NO 316
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 316
tgtgggatat gacagg                                                        16

<210> SEQ ID NO 317
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 317
```

```
atatggaagg gatatc                                               16

<210> SEQ ID NO 318
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 318
acaggatatg gaaggg                                               16

<210> SEQ ID NO 319
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 319
atttcaacag gatatgg                                              17

<210> SEQ ID NO 320
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 320
gagtaatttc aacagg                                               16

<210> SEQ ID NO 321
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 321
agggagtaat ttcaaca                                              17

<210> SEQ ID NO 322
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 322
attagggagt aatttca                                              17

<210> SEQ ID NO 323
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 323
cttactatta gggagt                                               16

<210> SEQ ID NO 324
<211> LENGTH: 16
<212> TYPE: DNA
<213> ORGANISM: Artificial Sequence
```

```
<220> FEATURE:
<223> OTHER INFORMATION: Oligonucleotide motif

<400> SEQUENCE: 324
cagcttacta ttaggg                                                   16

<210> SEQ ID NO 325
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 325
tcagcttact attagg                                                   16

<210> SEQ ID NO 326
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 326
atttcagctt actattag                                                 18

<210> SEQ ID NO 327
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 327
ttcagcttac tattag                                                   16

<210> SEQ ID NO 328
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 328
cagatttcag cttact                                                   16

<210> SEQ ID NO 329
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 329
gactacaact agaggg                                                   16

<210> SEQ ID NO 330
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 330
agactacaac tagagg                                                   16
```

```
<210> SEQ ID NO 331
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 331
aagactacaa ctagag                                                   16

<210> SEQ ID NO 332
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 332
atgatttaat tctagtcaaa                                               20

<210> SEQ ID NO 333
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 333
tttaattcta gtcaaa                                                   16

<210> SEQ ID NO 334
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 334
gatttaattc tagtca                                                   16

<210> SEQ ID NO 335
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 335
atgatttaat tctagtca                                                 18

<210> SEQ ID NO 336
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 336
gatgatttaa ttctagtca                                                19

<210> SEQ ID NO 337
<211> LENGTH: 16
<212> TYPE: DNA
<213> ORGANISM: Artificial Sequence
<220> FEATURE:
<223> OTHER INFORMATION: Oligonucleotide motif
```

```
<400> SEQUENCE: 337
gatttaattc tagtca                                                  16

<210> SEQ ID NO 338
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 338
gatgatttaa ttctagtc                                                18

<210> SEQ ID NO 339
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 339
tgatttaatt ctagtc                                                  16

<210> SEQ ID NO 340
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 340
gagatgattt aattcta                                                 17

<210> SEQ ID NO 341
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 341
gagatgattt aattct                                                  16

<210> SEQ ID NO 342
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 342
cagattgatg gtagtt                                                  16

<210> SEQ ID NO 343
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 343
ctcagattga tggtag                                                  16

<210> SEQ ID NO 344
```

```
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 344
gttagccctc agattg                                                    16

<210> SEQ ID NO 345
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 345
tgtattgtta gccctc                                                    16

<210> SEQ ID NO 346
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 346
acttgtattg ttagcc                                                    16

<210> SEQ ID NO 347
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 347
agccagtatc agggac                                                    16

<210> SEQ ID NO 348
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 348
ttgacaatag tggcat                                                    16

<210> SEQ ID NO 349
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 349
acaagtggta tcttct                                                    16

<210> SEQ ID NO 350
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 350
```

```
aatctacttt acaagt                                                   16

<210> SEQ ID NO 351
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 351
cacagtagat gcctgata                                                 18

<210> SEQ ID NO 352
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 352
gaacacagta gatgcc                                                   16

<210> SEQ ID NO 353
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 353
cttggaacac agtagat                                                  17

<210> SEQ ID NO 354
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 354
atatcttgga acacag                                                   16

<210> SEQ ID NO 355
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 355
tctttaatat cttggaac                                                 18

<210> SEQ ID NO 356
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 356
tgatttcttt aatatcttg                                                19

<210> SEQ ID NO 357
<211> LENGTH: 19
<212> TYPE: DNA
```

```
<213> ORGANISM: Artificial Sequence
<220> FEATURE:
<223> OTHER INFORMATION: Oligonucleotide motif

<400> SEQUENCE: 357
tgatgatttc tttaatatc                                               19

<210> SEQ ID NO 358
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 358
aggctaagtc atgatg                                                  16

<210> SEQ ID NO 359
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 359
ttgatgaggc taagtc                                                  16

<210> SEQ ID NO 360
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 360
ccaggattat actctt                                                  16

<210> SEQ ID NO 361
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 361
gccaggatta tactct                                                  16

<210> SEQ ID NO 362
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 362
ctgccaggat tatact                                                  16

<210> SEQ ID NO 363
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 363
cagaaactta tactttatg                                               19
```

<210> SEQ ID NO 364
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 364
aagcagaaac ttatact                                                   17

<210> SEQ ID NO 365
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 365
gaagcagaaa cttatact                                                  18

<210> SEQ ID NO 366
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 366
tggaagcaga aacttatact                                                20

<210> SEQ ID NO 367
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 367
tggaagcaga aacttatac                                                 19

<210> SEQ ID NO 368
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 368
aagcagaaac ttatac                                                    16

<210> SEQ ID NO 369
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 369
tggaagcaga aacttata                                                  18

<210> SEQ ID NO 370
<211> LENGTH: 16
<212> TYPE: DNA
<213> ORGANISM: Artificial Sequence
<220> FEATURE:

<223> OTHER INFORMATION: Oligonucleotide motif

<400> SEQUENCE: 370
aagggatatt atggag                                           16

<210> SEQ ID NO 371
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 371
tgccggaaga tttcct                                           16

<210> SEQ ID NO 372
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 372
atggattggg agtaga                                           16

<210> SEQ ID NO 373
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 373
agatggattg ggagta                                           16

<210> SEQ ID NO 374
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 374
aagatggatt gggagt                                           16

<210> SEQ ID NO 375
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 375
acaagatgga ttggga                                           16

<210> SEQ ID NO 376
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 376
agaaggttca gacttt                                           16

<210> SEQ ID NO 377
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 377
gcagaaggtt cagact                                                         16

<210> SEQ ID NO 378
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 378
tgcagaaggt tcagac                                                         16

<210> SEQ ID NO 379
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 379
agtgcagaag gttcag                                                         16

<210> SEQ ID NO 380
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 380
aagtgcagaa ggttca                                                         16

<210> SEQ ID NO 381
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 381
taagtgcaga aggttc                                                         16

<210> SEQ ID NO 382
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 382
tctaagtgca gaaggt                                                         16

<210> SEQ ID NO 383
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 383
ctcaggagtt ctacttc                                                17

<210> SEQ ID NO 384
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 384
ctcaggagtt ctactt                                                 16

<210> SEQ ID NO 385
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 385
atggaggtga ctcaggag                                               18

<210> SEQ ID NO 386
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 386
atggaggtga ctcagga                                                17

<210> SEQ ID NO 387
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 387
atggaggtga ctcagg                                                 16

<210> SEQ ID NO 388
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 388
tatggaggtg actcagg                                                17

<210> SEQ ID NO 389
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 389
atatggaggt gactcagg                                               18

<210> SEQ ID NO 390
<211> LENGTH: 16

```
<212> TYPE: DNA
<213> ORGANISM: Artificial Sequence
<220> FEATURE:
<223> OTHER INFORMATION: Oligonucleotide motif

<400> SEQUENCE: 390
tatggaggtg actcag                                                    16

<210> SEQ ID NO 391
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 391
atatggaggt gactcag                                                   17

<210> SEQ ID NO 392
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 392
catatggagg tgactcag                                                  18

<210> SEQ ID NO 393
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 393
atatggaggt gactca                                                    16

<210> SEQ ID NO 394
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 394
catatggagg tgactca                                                   17

<210> SEQ ID NO 395
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 395
catatggagg tgactc                                                    16

<210> SEQ ID NO 396
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 396
```

```
gcatatggag gtgactc                                              17

<210> SEQ ID NO 397
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 397
tgcatatgga ggtgactc                                             18

<210> SEQ ID NO 398
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 398
ttgcatatgg aggtgactc                                            19

<210> SEQ ID NO 399
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 399
tttgcatatg gaggtgactc                                           20

<210> SEQ ID NO 400
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 400
gcatatggag gtgact                                               16

<210> SEQ ID NO 401
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 401
tgcatatgga ggtgact                                              17

<210> SEQ ID NO 402
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 402
ttgcatatgg aggtgact                                             18

<210> SEQ ID NO 403
<211> LENGTH: 19
<212> TYPE: DNA
<213> ORGANISM: Artificial Sequence
```

```
<220> FEATURE:
<223> OTHER INFORMATION: Oligonucleotide motif

<400> SEQUENCE: 403
tttgcatatg gaggtgact                                                    19

<210> SEQ ID NO 404
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 404
tgcatatgga ggtgac                                                       16

<210> SEQ ID NO 405
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 405
ttgcatatgg aggtgac                                                      17

<210> SEQ ID NO 406
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 406
tttgcatatg gaggtgac                                                     18

<210> SEQ ID NO 407
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 407
tttgcatatg gaggtga                                                      17

<210> SEQ ID NO 408
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 408
tttgcatatg gaggtg                                                       16

<210> SEQ ID NO 409
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 409
aagtgaagtt caacagc                                                      17
```

<210> SEQ ID NO 410
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 410
tgggaagtga agttca                                                      16

<210> SEQ ID NO 411
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 411
atgggaagtg aagttc                                                      16

<210> SEQ ID NO 412
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 412
gatgggaagt gaagtt                                                      16

<210> SEQ ID NO 413
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 413
ctgtgatggg aagtgaa                                                     17

<210> SEQ ID NO 414
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 414
attgagtgaa tccaaa                                                      16

<210> SEQ ID NO 415
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 415
aattgagtga atccaa                                                      16

<210> SEQ ID NO 416
<211> LENGTH: 17
<212> TYPE: DNA
<213> ORGANISM: Artificial Sequence
<220> FEATURE:
<223> OTHER INFORMATION: Oligonucleotide motif

```
<400> SEQUENCE: 416
gataattgag tgaatcc                                                    17

<210> SEQ ID NO 417
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 417
gtgataattg agtgaa                                                     16

<210> SEQ ID NO 418
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 418
aagaaaggtg caataa                                                     16

<210> SEQ ID NO 419
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 419
caagaaaggt gcaata                                                     16

<210> SEQ ID NO 420
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 420
acaagaaagg tgcaat                                                     16

<210> SEQ ID NO 421
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 421
atttaaactc acaaac                                                     16

<210> SEQ ID NO 422
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 422
ctgttaggtt cagcga                                                     16

<210> SEQ ID NO 423
```

```
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 423
tctgaatgaa catttcg                                                  17

<210> SEQ ID NO 424
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 424
ctcattgaag gttctg                                                   16

<210> SEQ ID NO 425
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 425
ctaatctcat tgaagg                                                   16

<210> SEQ ID NO 426
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 426
cctaatctca ttgaag                                                   16

<210> SEQ ID NO 427
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 427
actttgatct ttcagc                                                   16

<210> SEQ ID NO 428
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 428
actatgcaac actttg                                                   16

<210> SEQ ID NO 429
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 429
```

| | |
|---|---|
| caaatagctt tatcgg | 16 |

<210> SEQ ID NO 430
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 430

| | |
|---|---|
| ccaaatagct ttatcg | 16 |

<210> SEQ ID NO 431
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 431

| | |
|---|---|
| tccaaatagc tttatc | 16 |

<210> SEQ ID NO 432
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 432

| | |
|---|---|
| gatccaaata gcttta | 16 |

<210> SEQ ID NO 433
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 433

| | |
|---|---|
| atgatccaaa tagctt | 16 |

<210> SEQ ID NO 434
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 434

| | |
|---|---|
| tatgatccaa atagct | 16 |

<210> SEQ ID NO 435
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 435

| | |
|---|---|
| taaacagggc tgggaat | 17 |

<210> SEQ ID NO 436
<211> LENGTH: 16
<212> TYPE: DNA

```
<213> ORGANISM: Artificial Sequence
<220> FEATURE:
<223> OTHER INFORMATION: Oligonucleotide motif

<400> SEQUENCE: 436
acttaaacag ggctgg                                                    16

<210> SEQ ID NO 437
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 437
acacttaaac agggct                                                    16

<210> SEQ ID NO 438
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 438
gaacacttaa acaggg                                                    16

<210> SEQ ID NO 439
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 439
agagaacact taaacag                                                   17

<210> SEQ ID NO 440
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 440
ctacagagaa cactta                                                    16

<210> SEQ ID NO 441
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 441
atgctacaga gaacact                                                   17

<210> SEQ ID NO 442
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 442
ataaatgcta cagagaaca                                                 19
```

```
<210> SEQ ID NO 443
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 443
agataaatgc tacagaga                                                   18

<210> SEQ ID NO 444
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 444
tagagataaa tgctaca                                                    17

<210> SEQ ID NO 445
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 445
tagatagaga taaatgct                                                   18

<210> SEQ ID NO 446
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 446
caatatacta gatagaga                                                   18

<210> SEQ ID NO 447
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 447
tacacaatat actagatag                                                  19

<210> SEQ ID NO 448
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 448
ctacacaata tactag                                                     16

<210> SEQ ID NO 449
<211> LENGTH: 16
<212> TYPE: DNA
<213> ORGANISM: Artificial Sequence
<220> FEATURE:
```

<223> OTHER INFORMATION: Oligonucleotide motif

<400> SEQUENCE: 449
gctacacaat atacta                                               16

<210> SEQ ID NO 450
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 450
atatgctaca caatatac                                             18

<210> SEQ ID NO 451
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 451
tgatatgcta cacaat                                               16

<210> SEQ ID NO 452
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 452
atgatatgat atgctac                                              17

<210> SEQ ID NO 453
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 453
gaggagagag acaataaa                                             18

<210> SEQ ID NO 454
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 454
ctaggaggag agagaca                                              17

<210> SEQ ID NO 455
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 455
tattctagga ggagaga                                              17

```
<210> SEQ ID NO 456
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 456
ttatattcta ggaggag                                                    17

<210> SEQ ID NO 457
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 457
gtttatattc taggag                                                     16

<210> SEQ ID NO 458
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 458
tggagtttat attctagg                                                   18

<210> SEQ ID NO 459
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 459
cgtaccacca ctctgc                                                     16

<210> SEQ ID NO 460
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 460
tgaggaaatc attcattc                                                   18

<210> SEQ ID NO 461
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 461
tttgaggaaa tcattcat                                                   18

<210> SEQ ID NO 462
<211> LENGTH: 16
<212> TYPE: DNA
<213> ORGANISM: Artificial Sequence
<220> FEATURE:
<223> OTHER INFORMATION: Oligonucleotide motif
```

```
<400> SEQUENCE: 462
aggctaatcc tatttg                                                    16

<210> SEQ ID NO 463
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 463
tttaggctaa tcctat                                                    16

<210> SEQ ID NO 464
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 464
tgctccagtg taccct                                                    16

<210> SEQ ID NO 465
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 465
tagtagtact cgatag                                                    16

<210> SEQ ID NO 466
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 466
ctaattgtag tagtactc                                                  18

<210> SEQ ID NO 467
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 467
tgctaattgt agtagt                                                    16

<210> SEQ ID NO 468
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 468
agtgctaatt gtagta                                                    16

<210> SEQ ID NO 469
<211> LENGTH: 16
```

```
<212> TYPE: DNA
<213> ORGANISM: Artificial Sequence
<220> FEATURE:
<223> OTHER INFORMATION: Oligonucleotide motif

<400> SEQUENCE: 469
gcaagtgcta attgta                                                   16

<210> SEQ ID NO 470
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 470
gaggaaatga actaattta                                                19

<210> SEQ ID NO 471
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 471
caggaggaaa tgaacta                                                  17

<210> SEQ ID NO 472
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 472
ccctagagtc atttcc                                                   16

<210> SEQ ID NO 473
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 473
atcttacatg atgaagc                                                  17

<210> SEQ ID NO 474
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 474
gacacactca gatttcag                                                 18

<210> SEQ ID NO 475
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 475
```
agacacactc agatttcag                                                 19

<210> SEQ ID NO 476
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 476
aagacacact cagatttcag                                                20

<210> SEQ ID NO 477
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 477
agacacactc agatttca                                                  18

<210> SEQ ID NO 478
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 478
aagacacact cagatttca                                                 19

<210> SEQ ID NO 479
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 479
aaagacacac tcagatttca                                                20

<210> SEQ ID NO 480
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 480
gaaagacaca ctcagatttc                                                20

<210> SEQ ID NO 481
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 481
aagacacact cagatttc                                                  18

<210> SEQ ID NO 482
<211> LENGTH: 19
<212> TYPE: DNA
<213> ORGANISM: Artificial Sequence

```
<220> FEATURE:
<223> OTHER INFORMATION: Oligonucleotide motif

<400> SEQUENCE: 482
aaagacacac tcagatttc                                              19

<210> SEQ ID NO 483
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 483
tgaaagacac actcagattt                                             20

<210> SEQ ID NO 484
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 484
tgaaagacac actcagatt                                              19

<210> SEQ ID NO 485
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 485
tgaaagacac actcagat                                               18

<210> SEQ ID NO 486
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 486
attgaaagac acactca                                                17

<210> SEQ ID NO 487
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 487
tcattgaaag acacact                                                17

<210> SEQ ID NO 488
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 488
ttccatcatt gaaaga                                                 16
```

```
<210> SEQ ID NO 489
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 489
ataataccac ttatcat                                                    17

<210> SEQ ID NO 490
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 490
ttacttaatt tctttgga                                                   18

<210> SEQ ID NO 491
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 491
ttagaactag ctttatca                                                   18

<210> SEQ ID NO 492
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 492
gaggtacaaa tatagg                                                     16

<210> SEQ ID NO 493
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 493
cttatgatac aactta                                                     16

<210> SEQ ID NO 494
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 494
tcttatgata caactt                                                     16

<210> SEQ ID NO 495
<211> LENGTH: 16
<212> TYPE: DNA
<213> ORGANISM: Artificial Sequence
<220> FEATURE:
<223> OTHER INFORMATION: Oligonucleotide motif
```

```
<400> SEQUENCE: 495
ttcttatgat acaact                                                        16

<210> SEQ ID NO 496
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 496
cagtttctta tgatac                                                        16

<210> SEQ ID NO 497
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 497
gcagtttctt atgata                                                        16

<210> SEQ ID NO 498
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 498
tacaaatgtc tattaggtt                                                     19

<210> SEQ ID NO 499
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 499
tgtacaaatg tctattag                                                      18

<210> SEQ ID NO 500
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 500
agcatcacaa ttagta                                                        16

<210> SEQ ID NO 501
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 501
ctaatgatag tgaagc                                                        16

<210> SEQ ID NO 502
```

```
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 502
agctaatgat agtgaa                                                       16

<210> SEQ ID NO 503
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 503
atgccttgac atatta                                                       16

<210> SEQ ID NO 504
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 504
ctcaagatta ttgacac                                                      17

<210> SEQ ID NO 505
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 505
acctcaagat tattga                                                       16

<210> SEQ ID NO 506
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 506
aacctcaaga ttattg                                                       16

<210> SEQ ID NO 507
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 507
cacaaacctc aagattatt                                                    19

<210> SEQ ID NO 508
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 508
```
gtacttaatt agacct                                                    16

<210> SEQ ID NO 509
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 509
agtacttaat tagacc                                                    16

<210> SEQ ID NO 510
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 510
gtatgaggtg gtaaac                                                    16

<210> SEQ ID NO 511
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 511
aggaaacagc agaagtg                                                   17

<210> SEQ ID NO 512
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 512
gcacaaccca gaggaa                                                    16

<210> SEQ ID NO 513
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 513
caagcacaac ccagag                                                    16

<210> SEQ ID NO 514
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 514
ttcaagcaca acccag                                                    16

<210> SEQ ID NO 515
<211> LENGTH: 16
<212> TYPE: DNA

```
<213> ORGANISM: Artificial Sequence
<220> FEATURE:
<223> OTHER INFORMATION: Oligonucleotide motif

<400> SEQUENCE: 515
aattcaagca caaccc                                                         16

<210> SEQ ID NO 516
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 516
taataattca agcacaacc                                                      19

<210> SEQ ID NO 517
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 517
actaataatt caagcac                                                        17

<210> SEQ ID NO 518
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 518
ataatactaa taattcaagc                                                     20

<210> SEQ ID NO 519
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 519
tagatttgtg aggtaa                                                         16

<210> SEQ ID NO 520
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 520
agccttaatt ctccat                                                         16

<210> SEQ ID NO 521
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 521
aatgatctag agcctta                                                        17
```

<210> SEQ ID NO 522
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 522
ctaatgatct agagcc                                                    16

<210> SEQ ID NO 523
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 523
actaatgatc tagagc                                                    16

<210> SEQ ID NO 524
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 524
cattaacatg ttcttatt                                                  18

<210> SEQ ID NO 525
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 525
acaagtacat taacatgttc                                                20

<210> SEQ ID NO 526
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 526
ttacaagtac attaacatg                                                 19

<210> SEQ ID NO 527
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 527
gctttattca tgtttat                                                   17

<210> SEQ ID NO 528
<211> LENGTH: 16
<212> TYPE: DNA
<213> ORGANISM: Artificial Sequence
<220> FEATURE:

<223> OTHER INFORMATION: Oligonucleotide motif

<400> SEQUENCE: 528
gctttattca tgttta                                                   16

<210> SEQ ID NO 529
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 529
agagctttat tcatgttt                                                 18

<210> SEQ ID NO 530
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 530
ataagagctt tattcatg                                                 18

<210> SEQ ID NO 531
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 531
cataagagct ttattca                                                  17

<210> SEQ ID NO 532
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 532
agcataagag ctttat                                                   16

<210> SEQ ID NO 533
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 533
tagattgttt agtgca                                                   16

<210> SEQ ID NO 534
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 534
gtagattgtt tagtgc                                                   16

```
<210> SEQ ID NO 535
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 535
gacaattcta gtagatt                                                    17

<210> SEQ ID NO 536
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 536
ctgacaattc tagtag                                                     16

<210> SEQ ID NO 537
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 537
gctgacaatt ctagta                                                     16

<210> SEQ ID NO 538
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 538
aggattaaga tacgta                                                     16

<210> SEQ ID NO 539
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 539
caggattaag atacgt                                                     16

<210> SEQ ID NO 540
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 540
tcaggattaa gatacg                                                     16

<210> SEQ ID NO 541
<211> LENGTH: 16
<212> TYPE: DNA
<213> ORGANISM: Artificial Sequence
<220> FEATURE:
<223> OTHER INFORMATION: Oligonucleotide motif
```

```
<400> SEQUENCE: 541
ttcaggatta agatac                                              16

<210> SEQ ID NO 542
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 542
aggaagaaag tttgattc                                            18

<210> SEQ ID NO 543
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 543
tcaaggaaga aagtttga                                            18

<210> SEQ ID NO 544
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 544
ctcaaggaag aaagtttg                                            18

<210> SEQ ID NO 545
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 545
tgctcaagga agaaagt                                             17

<210> SEQ ID NO 546
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 546
aattatgctc aaggaaga                                            18

<210> SEQ ID NO 547
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 547
taggatacca cattatga                                            18

<210> SEQ ID NO 548
<211> LENGTH: 20
```

<212> TYPE: DNA
<213> ORGANISM: Artificial Sequence
<220> FEATURE:
<223> OTHER INFORMATION: Oligonucleotide motif

<400> SEQUENCE: 548
cataatttat tccattcctc                                                   20

<210> SEQ ID NO 549
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 549
tgcataattt attccat                                                      17

<210> SEQ ID NO 550
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 550
actgcataat ttattcc                                                      17

<210> SEQ ID NO 551
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 551
ctaaactgca taatttatt                                                    19

<210> SEQ ID NO 552
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 552
ataactaaac tgcata                                                       16

<210> SEQ ID NO 553
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 553
ttattaataa ctaaactgc                                                    19

<210> SEQ ID NO 554
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 554
tagtacatta ttaataact                                                          19

<210> SEQ ID NO 555
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 555
cataactaag gacgtt                                                             16

<210> SEQ ID NO 556
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 556
tcataactaa ggacgt                                                             16

<210> SEQ ID NO 557
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 557
cgtcataact aaggac                                                             16

<210> SEQ ID NO 558
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 558
tcgtcataac taagga                                                             16

<210> SEQ ID NO 559
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 559
atcgtcataa ctaagg                                                             16

<210> SEQ ID NO 560
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 560
gttagtatct tacatt                                                             16

<210> SEQ ID NO 561
<211> LENGTH: 16
<212> TYPE: DNA
<213> ORGANISM: Artificial Sequence

```
<220> FEATURE:
<223> OTHER INFORMATION: Oligonucleotide motif

<400> SEQUENCE: 561
ctctattgtt agtatc                                                      16

<210> SEQ ID NO 562
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 562
agtatagagt tactgt                                                      16

<210> SEQ ID NO 563
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 563
ttcctggtga tactttt                                                     16

<210> SEQ ID NO 564
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 564
gttcctggtg atactt                                                      16

<210> SEQ ID NO 565
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 565
tgttcctggt gatact                                                      16

<210> SEQ ID NO 566
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 566
ataaacatga atctctcc                                                    18

<210> SEQ ID NO 567
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 567
ctttataaac atgaatctc                                                   19
```

<210> SEQ ID NO 568
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 568
ctgtctttat aaacatg                                                    17

<210> SEQ ID NO 569
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 569
ttgttataaa tctgtctt                                                   18

<210> SEQ ID NO 570
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 570
ttaaatttat tcttggata                                                  19

<210> SEQ ID NO 571
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 571
cttaaattta ttcttgga                                                   18

<210> SEQ ID NO 572
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 572
cttcttaaat ttattcttg                                                  19

<210> SEQ ID NO 573
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 573
tatgtttctc agtaaag                                                    17

<210> SEQ ID NO 574
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 574
gaattatctt taaacca                                                    17

<210> SEQ ID NO 575
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 575
cccttaaatt tctaca                                                     16

<210> SEQ ID NO 576
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 576
acactgctct tgtacc                                                     16

<210> SEQ ID NO 577
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 577
tgacaacact gctctt                                                     16

<210> SEQ ID NO 578
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 578
tacatttatt gggctc                                                     16

<210> SEQ ID NO 579
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 579
gtacatttat tgggct                                                     16

<210> SEQ ID NO 580
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 580
ttggtacatt tattgg                                                     16

<210> SEQ ID NO 581

```
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 581
catgttggta catttat                                                    17

<210> SEQ ID NO 582
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 582
aatcatgttg gtacat                                                     16

<210> SEQ ID NO 583
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 583
aaatcatgtt ggtaca                                                     16

<210> SEQ ID NO 584
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 584
gacaagtttg gattaa                                                     16

<210> SEQ ID NO 585
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 585
aatgttcaga tgcctc                                                     16

<210> SEQ ID NO 586
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 586
gcttaatgtt cagatg                                                     16

<210> SEQ ID NO 587
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 587
```

-continued cgtacatagc ttgatg                                                    16

<210> SEQ ID NO 588
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 588
gtgaggaatt aggata                                                    16

<210> SEQ ID NO 589
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 589
gtaacaatat ggtttg                                                    16

<210> SEQ ID NO 590
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 590
gaaatattgt agacta                                                    16

<210> SEQ ID NO 591
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 591
ttgaaatatt gtagac                                                    16

<210> SEQ ID NO 592
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 592
aagtctagta atttgc                                                    16

<210> SEQ ID NO 593
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 593
gctcagtaga ttataa                                                    16

<210> SEQ ID NO 594
<211> LENGTH: 16
<212> TYPE: DNA

```
<213> ORGANISM: Artificial Sequence
<220> FEATURE:
<223> OTHER INFORMATION: Oligonucleotide motif

<400> SEQUENCE: 594
catacactgt tgctaa                                                        16

<210> SEQ ID NO 595
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 595
atggtctcaa atcatt                                                        16

<210> SEQ ID NO 596
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 596
caatggtctc aaatca                                                        16

<210> SEQ ID NO 597
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 597
ttcctattga ttgact                                                        16

<210> SEQ ID NO 598
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 598
tttctgttca caacac                                                        16

<210> SEQ ID NO 599
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 599
aggaacccac taatct                                                        16

<210> SEQ ID NO 600
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 600
taaatggcag gaaccc                                                        16
```

<210> SEQ ID NO 601
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 601
gtaaatggca ggaacc                                           16

<210> SEQ ID NO 602
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 602
ttgtaaatgg caggaa                                           16

<210> SEQ ID NO 603
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 603
ttatgagtta ggcatg                                           16

<210> SEQ ID NO 604
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 604
ccaggtgaaa ctttaa                                           16

<210> SEQ ID NO 605
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 605
cccttagtca gctcct                                           16

<210> SEQ ID NO 606
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 606
acccttagtc agctcc                                           16

<210> SEQ ID NO 607
<211> LENGTH: 16
<212> TYPE: DNA
<213> ORGANISM: Artificial Sequence
<220> FEATURE:

<223> OTHER INFORMATION: Oligonucleotide motif

<400> SEQUENCE: 607
cacccttagt cagctc 16

<210> SEQ ID NO 608
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 608
tctcttacta ggctcc 16

<210> SEQ ID NO 609
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 609
cctatctgtc atcatg 16

<210> SEQ ID NO 610
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 610
tcctatctgt catcat 16

<210> SEQ ID NO 611
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 611
gagaagtgtg agaagc 16

<210> SEQ ID NO 612
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 612
catccttgaa gtttag 16

<210> SEQ ID NO 613
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 613
taataagatg gctccc 16

```
<210> SEQ ID NO 614
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 614
caaggcataa taagat                                                    16

<210> SEQ ID NO 615
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 615
ccaaggcata ataaga                                                    16

<210> SEQ ID NO 616
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 616
tgatccaatt ctcacc                                                    16

<210> SEQ ID NO 617
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 617
atgatccaat tctcac                                                    16

<210> SEQ ID NO 618
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 618
cgcttcatct tcaccc                                                    16

<210> SEQ ID NO 619
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 619
tatgacactg catctt                                                    16

<210> SEQ ID NO 620
<211> LENGTH: 16
<212> TYPE: DNA
<213> ORGANISM: Artificial Sequence
<220> FEATURE:
<223> OTHER INFORMATION: Oligonucleotide motif
```

<400> SEQUENCE: 620
gtatgacact gcatct                                                   16

<210> SEQ ID NO 621
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 621
tgtatgacac tgcatc                                                   16

<210> SEQ ID NO 622
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 622
ttctcttctg taagtc                                                   16

<210> SEQ ID NO 623
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 623
ttctacagag gaacta                                                   16

<210> SEQ ID NO 624
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 624
actacagttc tacaga                                                   16

<210> SEQ ID NO 625
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 625
ttcccacagg taaatg                                                   16

<210> SEQ ID NO 626
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 626
attatttgaa tatactcatt                                               20

<210> SEQ ID NO 627
<211> LENGTH: 17

```
<212> TYPE: DNA
<213> ORGANISM: Artificial Sequence
<220> FEATURE:
<223> OTHER INFORMATION: Oligonucleotide motif

<400> SEQUENCE: 627
tgggaggaaa ttatttg                                                    17

<210> SEQ ID NO 628
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 628
tgactcatct taaatg                                                     16

<210> SEQ ID NO 629
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 629
ctgactcatc ttaaat                                                     16

<210> SEQ ID NO 630
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 630
tttactctga ctcatc                                                     16

<210> SEQ ID NO 631
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 631
tattggagga attatt                                                     16

<210> SEQ ID NO 632
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 632
gtattggagg aattat                                                     16

<210> SEQ ID NO 633
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 633
```
tggtatactt ctctaagtat                                              20

<210> SEQ ID NO 634
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 634
gatctcttgg tatact                                                  16

<210> SEQ ID NO 635
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 635
cagacaactc tatacc                                                  16

<210> SEQ ID NO 636
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 636
aacatcagac aactcta                                                 17

<210> SEQ ID NO 637
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 637
tttaacatca gacaactc                                                18

<210> SEQ ID NO 638
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 638
taacatcaga caactc                                                  16

<210> SEQ ID NO 639
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 639
atttaacatc agacaa                                                  16

<210> SEQ ID NO 640
<211> LENGTH: 17
<212> TYPE: DNA
<213> ORGANISM: Artificial Sequence

```
<220> FEATURE:
<223> OTHER INFORMATION: Oligonucleotide motif

<400> SEQUENCE: 640
cctatttaac atcagac                                                  17

<210> SEQ ID NO 641
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 641
tccctattta acatca                                                   16

<210> SEQ ID NO 642
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 642
tcaacgacta ttggaat                                                  17

<210> SEQ ID NO 643
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 643
cttatattct ggctat                                                   16

<210> SEQ ID NO 644
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 644
atccttatat tctggc                                                   16

<210> SEQ ID NO 645
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 645
gatccttata ttctgg                                                   16

<210> SEQ ID NO 646
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 646
tgatccttat attctg                                                   16
```

<210> SEQ ID NO 647
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 647
attgaaactt gatcct                                                          16

<210> SEQ ID NO 648
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 648
actgtcattg aaactt                                                          16

<210> SEQ ID NO 649
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 649
tcttactgtc attgaa                                                          16

<210> SEQ ID NO 650
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 650
aggatcttac tgtcatt                                                         17

<210> SEQ ID NO 651
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 651
gcaaatcaac tccatc                                                          16

<210> SEQ ID NO 652
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 652
gtgcaaatca actcca                                                          16

<210> SEQ ID NO 653
<211> LENGTH: 17
<212> TYPE: DNA
<213> ORGANISM: Artificial Sequence
<220> FEATURE:
<223> OTHER INFORMATION: Oligonucleotide motif

```
<400> SEQUENCE: 653
caattatttc tttgtgc                                          17

<210> SEQ ID NO 654
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 654
tggcaacaat tatttctt                                         18

<210> SEQ ID NO 655
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 655
gctggcaaca attatt                                           16

<210> SEQ ID NO 656
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 656
atccatttct actgcc                                           16

<210> SEQ ID NO 657
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 657
taatatctat tgatttcta                                        19

<210> SEQ ID NO 658
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 658
tcaatagtgt agggca                                           16

<210> SEQ ID NO 659
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 659
ttcaatagtg tagggc                                           16

<210> SEQ ID NO 660
```

```
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 660
aggttaatta attcaatag                                                19

<210> SEQ ID NO 661
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 661
catttgtaat ccctag                                                   16

<210> SEQ ID NO 662
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 662
acatttgtaa tcccta                                                   16

<210> SEQ ID NO 663
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 663
aacatttgta atccct                                                   16

<210> SEQ ID NO 664
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 664
taaatttcaa gttctg                                                   16

<210> SEQ ID NO 665
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 665
gtttaaattt caagttct                                                 18

<210> SEQ ID NO 666
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 666
```

```
ccaagtttaa atttcaag                                                  18

<210> SEQ ID NO 667
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 667
acccaagttt aaatttc                                                   17

<210> SEQ ID NO 668
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 668
catacagtga cccaagttt                                                 19

<210> SEQ ID NO 669
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 669
acatcccata cagtga                                                    16

<210> SEQ ID NO 670
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 670
agcacagctc tacatc                                                    16

<210> SEQ ID NO 671
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 671
atatagcaca gctcta                                                    16

<210> SEQ ID NO 672
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 672
tccatatagc acagct                                                    16

<210> SEQ ID NO 673
<211> LENGTH: 16
<212> TYPE: DNA
```

```
<213> ORGANISM: Artificial Sequence
<220> FEATURE:
<223> OTHER INFORMATION: Oligonucleotide motif

<400> SEQUENCE: 673
atttccatat agcaca                                                    16

<210> SEQ ID NO 674
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 674
tttatttcca tatagca                                                   17

<210> SEQ ID NO 675
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 675
tttatttcca tatagc                                                    16

<210> SEQ ID NO 676
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 676
aaggagagga gattatg                                                   17

<210> SEQ ID NO 677
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 677
agttcttgtg ttagct                                                    16

<210> SEQ ID NO 678
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 678
gagttcttgt gttagc                                                    16

<210> SEQ ID NO 679
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 679
attaattatc catccac                                                   17
```

<210> SEQ ID NO 680
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 680
atcaattaat tatccatc                                                   18

<210> SEQ ID NO 681
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 681
agaatcaatt aattatcc                                                   18

<210> SEQ ID NO 682
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 682
tgagataccg tgcatg                                                     16

<210> SEQ ID NO 683
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 683
aatgagatac cgtgca                                                     16

<210> SEQ ID NO 684
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 684
ctgtggttag gctaat                                                     16

<210> SEQ ID NO 685
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 685
aagagtaagg gtctgtggtt                                                 20

<210> SEQ ID NO 686
<211> LENGTH: 16
<212> TYPE: DNA
<213> ORGANISM: Artificial Sequence
<220> FEATURE:

```
<223> OTHER INFORMATION: Oligonucleotide motif

<400> SEQUENCE: 686
gatgggttaa gagtaa                                                   16

<210> SEQ ID NO 687
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 687
agcagatggg ttaaga                                                   16

<210> SEQ ID NO 688
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 688
tgtaaacatt tgtagc                                                   16

<210> SEQ ID NO 689
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 689
cctgcttata aatgta                                                   16

<210> SEQ ID NO 690
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 690
tgccctgctt ataaat                                                   16

<210> SEQ ID NO 691
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 691
tcttcttagt tcaata                                                   16

<210> SEQ ID NO 692
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 692
tggtttctaa ctacat                                                   16
```

```
<210> SEQ ID NO 693
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 693
agtttggttt ctaacta                                                    17

<210> SEQ ID NO 694
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 694
gaatgaaact tgcctg                                                     16

<210> SEQ ID NO 695
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 695
attatcctta catgat                                                     16

<210> SEQ ID NO 696
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 696
gtacccaatt atcctt                                                     16

<210> SEQ ID NO 697
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 697
tgtacccaat tatcct                                                     16

<210> SEQ ID NO 698
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 698
ttgtacccaa ttatcc                                                     16

<210> SEQ ID NO 699
<211> LENGTH: 16
<212> TYPE: DNA
<213> ORGANISM: Artificial Sequence
<220> FEATURE:
<223> OTHER INFORMATION: Oligonucleotide motif
```

```
<400> SEQUENCE: 699
tttgtaccca attatc                                              16

<210> SEQ ID NO 700
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 700
agcagcaggt tatatt                                              16

<210> SEQ ID NO 701
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 701
tgggaagtgg tctggg                                              16

<210> SEQ ID NO 702
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 702
ctggagagtg ataata                                              16

<210> SEQ ID NO 703
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 703
aatgctggat tacgtc                                              16

<210> SEQ ID NO 704
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 704
caatgctgga ttacgt                                              16

<210> SEQ ID NO 705
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 705
ttgttcagaa gtatcc                                              16

<210> SEQ ID NO 706
<211> LENGTH: 16
```

```
<212> TYPE: DNA
<213> ORGANISM: Artificial Sequence
<220> FEATURE:
<223> OTHER INFORMATION: Oligonucleotide motif

<400> SEQUENCE: 706
gatgatttgc ttggag                                                    16

<210> SEQ ID NO 707
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 707
gaaatcattc acaacc                                                    16

<210> SEQ ID NO 708
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 708
ttgtaacatc tactac                                                    16

<210> SEQ ID NO 709
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 709
cattaagcag caagtt                                                    16

<210> SEQ ID NO 710
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 710
ttactagatg tgagca                                                    16

<210> SEQ ID NO 711
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 711
tttactagat gtgagc                                                    16

<210> SEQ ID NO 712
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 712
```

```
gaccaagcac cttaca                                              16

<210> SEQ ID NO 713
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 713
agaccaagca ccttac                                              16

<210> SEQ ID NO 714
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 714
atgggttaaa taaagg                                              16

<210> SEQ ID NO 715
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 715
tcaaccagag tattaa                                              16

<210> SEQ ID NO 716
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 716
gtcaaccaga gtatta                                              16

<210> SEQ ID NO 717
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 717
attgtaaagc tgatat                                              16

<210> SEQ ID NO 718
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 718
cacataattg taaagc                                              16

<210> SEQ ID NO 719
<211> LENGTH: 16
<212> TYPE: DNA
<213> ORGANISM: Artificial Sequence
```

```
<220> FEATURE:
<223> OTHER INFORMATION: Oligonucleotide motif

<400> SEQUENCE: 719
gaggtctgct atttac                                                  16

<210> SEQ ID NO 720
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 720
tgtagattca atgcct                                                  16

<210> SEQ ID NO 721
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 721
cctcattata ctatga                                                  16

<210> SEQ ID NO 722
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 722
ccttatgcta tgacac                                                  16

<210> SEQ ID NO 723
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 723
tccttatgct atgaca                                                  16

<210> SEQ ID NO 724
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 724
aagatgttta agtata                                                  16

<210> SEQ ID NO 725
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 725
ctgattatta agatgt                                                  16
```

```
<210> SEQ ID NO 726
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 726
tggaaaggta tgaatt                                                     16

<210> SEQ ID NO 727
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 727
acttgaatgg cttgga                                                     16

<210> SEQ ID NO 728
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 728
aacttgaatg gcttgg                                                     16

<210> SEQ ID NO 729
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 729
caatgtgtta ctattt                                                     16

<210> SEQ ID NO 730
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 730
acaatgtgtt actatt                                                     16

<210> SEQ ID NO 731
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 731
catctgctat ataaga                                                     16

<210> SEQ ID NO 732
<211> LENGTH: 16
<212> TYPE: DNA
<213> ORGANISM: Artificial Sequence
<220> FEATURE:
<223> OTHER INFORMATION: Oligonucleotide motif
```

```
<400> SEQUENCE: 732
cctagagcaa atactt                                                         16

<210> SEQ ID NO 733
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 733
cagagttaat aataag                                                         16

<210> SEQ ID NO 734
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 734
gttcaagcac aacgaa                                                         16

<210> SEQ ID NO 735
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 735
agggttcaag cacaac                                                         16

<210> SEQ ID NO 736
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 736
tgttggagac actgtt                                                         16

<210> SEQ ID NO 737
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 737
aaggaggagt taggac                                                         16

<210> SEQ ID NO 738
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 738
ctatgccatt tacgat                                                         16

<210> SEQ ID NO 739
```

```
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 739
tcaaatgcag aattag                                                       16

<210> SEQ ID NO 740
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 740
agtgacaatc aaatgc                                                       16

<210> SEQ ID NO 741
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 741
aagtgacaat caaatg                                                       16

<210> SEQ ID NO 742
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 742
gtgtaccaag taacaa                                                       16

<210> SEQ ID NO 743
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 743
tgggatgtta aactga                                                       16

<210> SEQ ID NO 744
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 744
agtttacatt ttctgc                                                       16

<210> SEQ ID NO 745
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 745
```

-continued

```
tatgtgaaga ggagag                                                    16

<210> SEQ ID NO 746
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 746
cacctttaaa acccca                                                    16

<210> SEQ ID NO 747
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 747
tcctttataa tcacac                                                    16

<210> SEQ ID NO 748
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 748
acggtatttt cacagg                                                    16

<210> SEQ ID NO 749
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 749
gacactacaa tgagga                                                    16

<210> SEQ ID NO 750
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 750
tggtttttag gactgt                                                    16

<210> SEQ ID NO 751
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 751
cgacaaattc tatcct                                                    16

<210> SEQ ID NO 752
<211> LENGTH: 16
<212> TYPE: DNA
```

<213> ORGANISM: Artificial Sequence
<220> FEATURE:
<223> OTHER INFORMATION: Oligonucleotide motif

<400> SEQUENCE: 752
tgatatacaa tgctac                                                    16

<210> SEQ ID NO 753
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 753
tcgttgggta aattta                                                    16

<210> SEQ ID NO 754
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 754
tgctttataa atggtg                                                    16

<210> SEQ ID NO 755
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 755
caagtttaca ttttctgc                                                  18

<210> SEQ ID NO 756
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 756
catatgtgaa gaggagag                                                  18

<210> SEQ ID NO 757
<211> LENGTH: 16
<212> TYPE: DNA
<213> ORGANISM: Artificial Sequence
<220> FEATURE:
<223> OTHER INFORMATION: Oligonucleotide motif

<400> SEQUENCE: 757
cacctttaaa acccca                                                    16

<210> SEQ ID NO 758
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 758
catcctttat aatcacac                                                  18

```
<210> SEQ ID NO 759
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 759
caacggtatt ttcacagg                                                 18

<210> SEQ ID NO 760
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 760
cagacactac aatgagga                                                 18

<210> SEQ ID NO 761
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 761
catggttttt aggactgt                                                 18

<210> SEQ ID NO 762
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 762
cacgacaaat tctatcct                                                 18

<210> SEQ ID NO 763
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 763
catgatatac aatgctac                                                 18

<210> SEQ ID NO 764
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 764
catcgttggg taaattta                                                 18

<210> SEQ ID NO 765
<211> LENGTH: 18
<212> TYPE: DNA
<213> ORGANISM: Artificial Sequence
<220> FEATURE:
```

```
<223> OTHER INFORMATION: Oligonucleotide motif

<400> SEQUENCE: 765
catgctttat aaatggtg                                                  18

<210> SEQ ID NO 766
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 766
caacaaataa tggttactct                                                20

<210> SEQ ID NO 767
<211> LENGTH: 18
<212> TYPE: DNA
<213> ORGANISM: Artificial Sequence
<220> FEATURE:
<223> OTHER INFORMATION: Oligonucleotide motif

<400> SEQUENCE: 767
cacagattga tggtagtt                                                  18

<210> SEQ ID NO 768
<211> LENGTH: 19
<212> TYPE: DNA
<213> ORGANISM: Artificial Sequence
<220> FEATURE:
<223> OTHER INFORMATION: Oligonucleotide motif

<400> SEQUENCE: 768
cacctattta acatcagac                                                 19

<210> SEQ ID NO 769
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 769
cactaattgt agtagtactc                                                20

<210> SEQ ID NO 770
<211> LENGTH: 20
<212> TYPE: DNA
<213> ORGANISM: Artificial Sequence
<220> FEATURE:
<223> OTHER INFORMATION: Oligonucleotide motif

<400> SEQUENCE: 770
caataaacat gaatctctcc                                                20

<210> SEQ ID NO 771
<211> LENGTH: 17
<212> TYPE: DNA
<213> ORGANISM: Artificial Sequence
<220> FEATURE:
<223> OTHER INFORMATION: Oligonucleotide motif

<400> SEQUENCE: 771
tgatttaatt ctagtca                                                   17
```

-continued

```
<210> SEQ ID NO 772
<211> LENGTH: 16
<212> TYPE: DNA
<213> ORGANISM: artificial sequence
<220> FEATURE:
<223> OTHER INFORMATION: Target sequence

<400> SEQUENCE: 772
gcagtagagc caatta                                                        16

<210> SEQ ID NO 773
<211> LENGTH: 10
<212> TYPE: PRT
<213> ORGANISM: artificial
<220> FEATURE:
<223> OTHER INFORMATION: HBV epitope

<400> SEQUENCE: 773

Phe Leu Pro Ser Asp Phe Phe Pro Ser Val
1               5                   10

<210> SEQ ID NO 774
<211> LENGTH: 15
<212> TYPE: PRT
<213> ORGANISM: Artificial
<220> FEATURE:
<223> OTHER INFORMATION: HBV epitope

<400> SEQUENCE: 774

Gly Arg Glu Thr Val Leu Glu Tyr Leu Val Ser Phe Gly Val Trp
1               5                   10                  15

<210> SEQ ID NO 775
<211> LENGTH: 15
<212> TYPE: PRT
<213> ORGANISM: Artificial
<220> FEATURE:
<223> OTHER INFORMATION: HBV epitope

<400> SEQUENCE: 775

Thr Thr Phe His Gln Thr Leu Gln Asp Pro Arg Val Arg Gly Leu
1               5                   10                  15

<210> SEQ ID NO 776
<211> LENGTH: 16
<212> TYPE: PRT
<213> ORGANISM: Artificial
<220> FEATURE:
<223> OTHER INFORMATION: HBV epitope

<400> SEQUENCE: 776

Gln Ala Gly Phe Phe Leu Leu Thr Arg Ile Leu Thr Ile Pro Gln Ser
1               5                   10                  15

<210> SEQ ID NO 777
<211> LENGTH: 9
<212> TYPE: PRT
<213> ORGANISM: Artificial
<220> FEATURE:
<223> OTHER INFORMATION: HBV epitope

<400> SEQUENCE: 777

Phe Leu Leu Thr Arg Ile Leu Thr Ile
1               5

<210> SEQ ID NO 778
<211> LENGTH: 15
```

```
<212> TYPE: PRT
<213> ORGANISM: Artificial
<220> FEATURE:
<223> OTHER INFORMATION: HBV epitope

<400> SEQUENCE: 778

Thr Ser Leu Asn Phe Leu Gly Gly Thr Thr Val Cys Leu Gly Gln
1               5                   10                  15

<210> SEQ ID NO 779
<211> LENGTH: 9
<212> TYPE: PRT
<213> ORGANISM: Artificial
<220> FEATURE:
<223> OTHER INFORMATION: HBV epitope

<400> SEQUENCE: 779

Phe Leu Gly Gly Thr Thr Val Cys Leu
1               5

<210> SEQ ID NO 780
<211> LENGTH: 9
<212> TYPE: PRT
<213> ORGANISM: Artificial
<220> FEATURE:
<223> OTHER INFORMATION: HBV epitope

<400> SEQUENCE: 780

Trp Leu Ser Leu Leu Val Pro Phe Val
1               5

<210> SEQ ID NO 781
<211> LENGTH: 21
<212> TYPE: PRT
<213> ORGANISM: Artificial
<220> FEATURE:
<223> OTHER INFORMATION: HBV epitope

<400> SEQUENCE: 781

Ser Leu Leu Val Pro Phe Val Gln Trp Phe Val Gly Leu Ser Pro Thr
1               5                   10                  15

Val Trp Leu Ser Val
            20

<210> SEQ ID NO 782
<211> LENGTH: 10
<212> TYPE: PRT
<213> ORGANISM: Artificial
<220> FEATURE:
<223> OTHER INFORMATION: HBV epitope

<400> SEQUENCE: 782

Gly Leu Ser Pro Thr Val Trp Leu Ser Val
1               5                   10

<210> SEQ ID NO 783
<211> LENGTH: 10
<212> TYPE: PRT
<213> ORGANISM: Artificial
<220> FEATURE:
<223> OTHER INFORMATION: HBV epitope

<400> SEQUENCE: 783

Ser Ile Leu Ser Pro Phe Leu Pro Leu Leu
1               5                   10
```

```
<210> SEQ ID NO 784
<211> LENGTH: 19
<212> TYPE: DNA
<213> ORGANISM: Artificial
<220> FEATURE:
<223> OTHER INFORMATION: Primer

<400> SEQUENCE: 784
ctgtgccttg ggtggcttt                                                  19

<210> SEQ ID NO 785
<211> LENGTH: 24
<212> TYPE: DNA
<213> ORGANISM: Artificial
<220> FEATURE:
<223> OTHER INFORMATION: Primer

<400> SEQUENCE: 785
aaggaaagaa gtcagaaggc aaaa                                            24

<210> SEQ ID NO 786
<211> LENGTH: 25
<212> TYPE: DNA
<213> ORGANISM: Artificial
<220> FEATURE:
<223> OTHER INFORMATION: primer

<400> SEQUENCE: 786
ttctttataa gggtcgatgt ccatg                                           25
```